(12) United States Patent
Billy et al.

(10) Patent No.: US 11,530,413 B2
(45) Date of Patent: Dec. 20, 2022

(54) COMPOSITIONS AND METHODS TO TREAT CANCER

(71) Applicant: NOVARTIS AG, Basel (CH)

(72) Inventors: Eric Billy, Basel (CH); Antoine De Weck, Basel (CH); Javad Golji, Cambridge, MA (US); Gregory Hoffman, Cambridge, MA (US); Francesco Hofmann, Basel (CH); Audrey Kauffmann, Basel (CH); Konstantinos John Mavrakis, Cambridge, MA (US); Earl Robert McDonald, III, Cambridge, MA (US); William Sellers, Cambridge, MA (US); Tobias Schmelzle, Basel (CH); Frank Peter Stegmeier, Cambridge, MA (US); Michael Ray Schlabach, Jr., Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/632,777

(22) PCT Filed: Jul. 20, 2018

(86) PCT No.: PCT/IB2018/055418
§ 371 (c)(1),
(2) Date: Jan. 21, 2020

(87) PCT Pub. No.: WO2019/016772
PCT Pub. Date: Jan. 24, 2019

(65) Prior Publication Data
US 2021/0155932 A1 May 27, 2021

Related U.S. Application Data

(60) Provisional application No. 62/535,539, filed on Jul. 21, 2017.

(51) Int. Cl.
| | | |
|---|---|---|
| *C12N 15/115* | (2010.01) | |
| *A61K 45/06* | (2006.01) | |
| *C12N 9/22* | (2006.01) | |
| *C12N 15/113* | (2010.01) | |
| *G01N 33/574* | (2006.01) | |
| *A61K 47/18* | (2017.01) | |

(52) U.S. Cl.
CPC ............ *C12N 15/115* (2013.01); *A61K 45/06* (2013.01); *A61K 47/18* (2013.01); *C12N 9/22* (2013.01); *C12N 15/113* (2013.01); *G01N 33/574* (2013.01); *C12N 2310/14* (2013.01); *C12N 2310/20* (2017.05); *G01N 2800/52* (2013.01)

(58) Field of Classification Search
None
See application file for complete search history.

(56) References Cited

U.S. PATENT DOCUMENTS

2017/0191057 A1* 7/2017 Jamieson ............ A61K 31/7064
2020/0377879 A1* 12/2020 Meyerson ............ A61K 31/712

FOREIGN PATENT DOCUMENTS

| WO | 2002068690 A1 | 9/2002 | |
|---|---|---|---|
| WO | 2005113764 A2 | 12/2005 | |
| WO | 2009045443 A2 | 4/2009 | |
| WO | WO 2017/182783 A2 * | 10/2017 | ............ A61K 31/00 |

OTHER PUBLICATIONS

Kawasaki et al., Modern Pathology (2008), 21(2), pp. 150-158.*
Aggarwal et al., Cell Cycle (2013), 12:20, pp. 3329-3335.*
Moles et al., Journal of Hematology & Oncology (2016), 9:121, pp. 1-11.*
Andersen et al., Danish Medical Journal (2016), 63(2), pp. 1-6.*
Rosenthal et al., Bioorganic & Medicinal Chemistry Letters (2013), 23, pp. 5600-5666.*
Lao, Victoria Valinluck et al: "Altered RECQ Helicase Expression in Sporadic Primary Colorectal Cancers", Translational Oncology, vol. 6, No. 4, Aug. 1, 2013, p. 458-IN10.
Lauper, Julia M. et al: "Spectrum and Risk of Neoplasia in Werner Syndrome: A Systematic Review", PLOS One, vol. 8, No. 4, Apr. 1, 2013, p. e59709.
Barretina, Jordi et al, "The Cancer Cell Line Encyclopedia enables predictive modelling of anticancer drug sensitivity", Nature, vol. 483, No. 7391, Sep. 29, 2012, p. 603-307.
McDonald, E. Robert et al: "Project DRIVE: A Compendium of Cancer Dependencies and Synthetic Lethal Relationships Uncovered by Large-Scale, Deep RNAi Screening", Cell, vol. 170, No. 3, Jul. 27, 2017, p. 577-592.e10.
Kazunobu Futami et al: "RECQL1 and WRN DNA repair helicases: potential therapeutic targets and proliferative markers against cancers", Frontiers in Genetics, vol. 5, No. 441, Jan. 1, 2015.

* cited by examiner

*Primary Examiner* — Brian J Davis
(74) *Attorney, Agent, or Firm* — David K. Cheung

(57) ABSTRACT

The disclosure provides novel personalized therapies, kits, transmittable forms of information and methods for use in treating patients having cancer, wherein the cancer is amenable to therapeutic treatment with an inhibitor, e.g., an inhibitor of any of the targets disclosed herein. Kits, methods of screening for candidate inhibitors, and associated methods of treatment are also provided.

6 Claims, 25 Drawing Sheets
Specification includes a Sequence Listing.

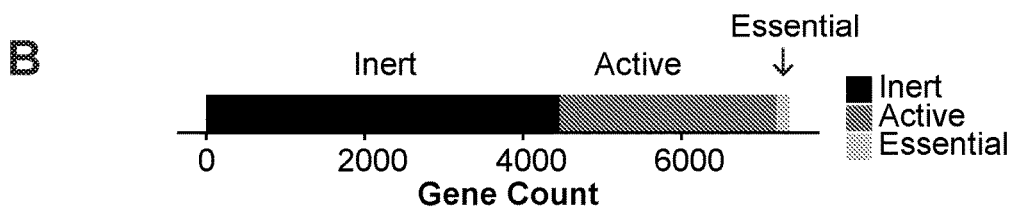
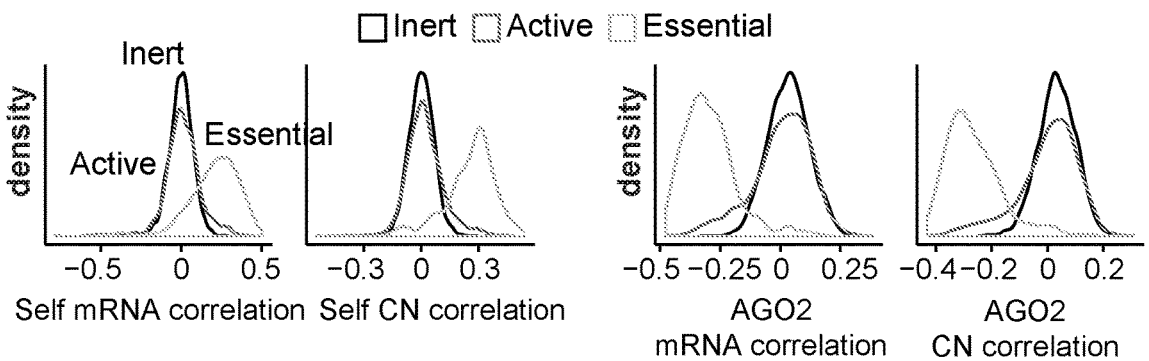
Fig. 1B-1
Fig. 1B-2
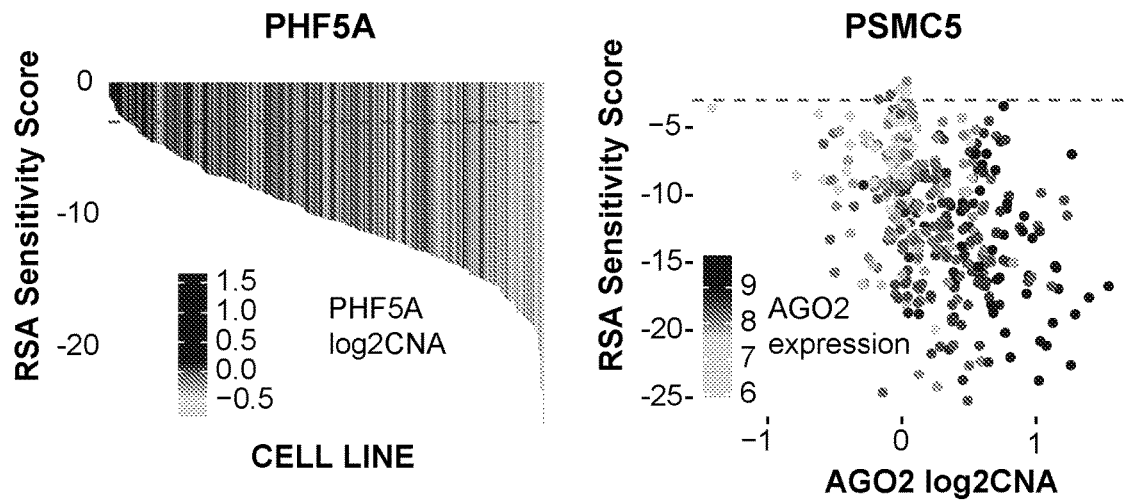
Fig. 1B-3

Fig. 7D

```
SEQUENCE LISTING

<160> NUMBER OF SEQ ID NOS: 27

<210> SEQ ID NO 1
<211> LENGTH: 19
<212> TYPE: RNA
<213> ORGANISM: Artificial Sequence
<220> FEATURE:
<223> OTHER INFORMATION: siRNA_1

<400> SEQUENCE: 1
ccguaugcag cacaagaaa                                                  19

<210> SEQ ID NO 2
<211> LENGTH: 19
<212> TYPE: RNA
<213> ORGANISM: Artificial Sequence
<220> FEATURE:
<223> OTHER INFORMATION: siRNA_2

<400> SEQUENCE: 2
guaugcagca caagaaaga                                                  19

<210> SEQ ID NO 3
<211> LENGTH: 89
<212> TYPE: DNA
<213> ORGANISM: Artificial Sequence
<220> FEATURE:
<223> OTHER INFORMATION: DRIVE_PCR_Rev_Primer_1

<400> SEQUENCE: 3
caagcagaag acggcatacg agatcactgt gtgactggag ttcagacgtg tgctcttccg     60
atctgaggtt cagagttcta cagtccgaa                                       89
```

```
<210> SEQ ID NO 4
<211> LENGTH: 89
<212> TYPE: DNA
<213> ORGANISM: Artificial Sequence
<220> FEATURE:
<223> OTHER INFORMATION: DRIVE_PCR_Rev_Primer_2

<400> SEQUENCE: 4
caagcagaag acggcatacg agatattggc gtgactggag ttcagacgtg tgctcttccg    60
atctgaggtt cagagttcta cagtccgaa                                      89

<210> SEQ ID NO 5
<211> LENGTH: 89
<212> TYPE: DNA
<213> ORGANISM: Artificial Sequence
<220> FEATURE:
<223> OTHER INFORMATION: DRIVE_PCR_Rev_Primer_3

<400> SEQUENCE: 5
caagcagaag acggcatacg agatgatctg gtgactggag ttcagacgtg tgctcttccg    60
atctgaggtt cagagttcta cagtccgaa                                      89

<210> SEQ ID NO 6
<211> LENGTH: 89
<212> TYPE: DNA
<213> ORGANISM: Artificial Sequence
<220> FEATURE:
<223> OTHER INFORMATION: DRIVE_PCR_Rev_Primer_4

<400> SEQUENCE: 6
caagcagaag acggcatacg agattcaagt gtgactggag ttcagacgtg tgctcttccg    60
atctgaggtt cagagttcta cagtccgaa                                      89

<210> SEQ ID NO 7
<211> LENGTH: 89
<212> TYPE: DNA
<213> ORGANISM: Artificial Sequence
<220> FEATURE:
<223> OTHER INFORMATION: DRIVE_PCR_Rev_Primer_5

<400> SEQUENCE: 7
caagcagaag acggcatacg agatctgatc gtgactggag ttcagacgtg tgctcttccg    60
atctgaggtt cagagttcta cagtccgaa                                      89

<210> SEQ ID NO 8
<211> LENGTH: 89
<212> TYPE: DNA
<213> ORGANISM: Artificial Sequence
<220> FEATURE:
<223> OTHER INFORMATION: DRIVE_PCR_Rev_Primer_6

<400> SEQUENCE: 8
caagcagaag acggcatacg agataagcta gtgactggag ttcagacgtg tgctcttccg    60
atctgaggtt cagagttcta cagtccgaa                                      89

<210> SEQ ID NO 9
<211> LENGTH: 89
<212> TYPE: DNA
<213> ORGANISM: Artificial Sequence
<220> FEATURE:
<223> OTHER INFORMATION: DRIVE_PCR_Rev_Primer_7
```

```
<400> SEQUENCE: 9
caagcagaag acggcatacg agatgtagcc gtgactggag ttcagacgtg tgctcttccg    60
atctgaggtt cagagttcta cagtccgaa                                      89

<210> SEQ ID NO 10
<211> LENGTH: 89
<212> TYPE: DNA
<213> ORGANISM: Artificial Sequence
<220> FEATURE:
<223> OTHER INFORMATION: DRIVE_PCR_Rev_Primer_8

<400> SEQUENCE: 10
caagcagaag acggcatacg agattacaag gtgactggag ttcagacgtg tgctcttccg    60
atctgaggtt cagagttcta cagtccgaa                                      89

<210> SEQ ID NO 11
<211> LENGTH: 89
<212> TYPE: DNA
<213> ORGANISM: Artificial Sequence
<220> FEATURE:
<223> OTHER INFORMATION: DRIVE_PCR_Rev_Primer_9

<400> SEQUENCE: 11
caagcagaag acggcatacg agatttgact gtgactggag ttcagacgtg tgctcttccg    60
atctgaggtt cagagttcta cagtccgaa                                      89

<210> SEQ ID NO 12
<211> LENGTH: 89
<212> TYPE: DNA
<213> ORGANISM: Artificial Sequence
<220> FEATURE:
<223> OTHER INFORMATION: DRIVE_PCR_Rev_Primer_10

<400> SEQUENCE: 12
caagcagaag acggcatacg agatggaact gtgactggag ttcagacgtg tgctcttccg    60
atctgaggtt cagagttcta cagtccgaa                                      89

<210> SEQ ID NO 13
<211> LENGTH: 89
<212> TYPE: DNA
<213> ORGANISM: Artificial Sequence
<220> FEATURE:
<223> OTHER INFORMATION: DRIVE_PCR_Rev_Primer_11

<400> SEQUENCE: 13
caagcagaag acggcatacg agattgacat gtgactggag ttcagacgtg tgctcttccg    60
atctgaggtt cagagttcta cagtccgaa                                      89

<210> SEQ ID NO 14
<211> LENGTH: 89
<212> TYPE: DNA
<213> ORGANISM: Artificial Sequence
<220> FEATURE:
<223> OTHER INFORMATION: DRIVE_PCR_Rev_Primer_12

<400> SEQUENCE: 14
caagcagaag acggcatacg agatggacgg gtgactggag ttcagacgtg tgctcttccg    60
atctgaggtt cagagttcta cagtccgaa                                      89
```

<210> SEQ ID NO 15
<211> LENGTH: 89
<212> TYPE: DNA
<213> ORGANISM: Artificial Sequence
<220> FEATURE:
<223> OTHER INFORMATION: DRIVE_PCR_Rev_Primer_13

<400> SEQUENCE: 15
caagcagaag acggcatacg agatctctac gtgactggag ttcagacgtg tgctcttccg     60
atctgaggtt cagagttcta cagtccgaa                                       89

<210> SEQ ID NO 16
<211> LENGTH: 89
<212> TYPE: DNA
<213> ORGANISM: Artificial Sequence
<220> FEATURE:
<223> OTHER INFORMATION: DRIVE_PCR_Rev_Primer_14

<400> SEQUENCE: 16
caagcagaag acggcatacg agatgcggac gtgactggag ttcagacgtg tgctcttccg     60
atctgaggtt cagagttcta cagtccgaa                                       89

<210> SEQ ID NO 17
<211> LENGTH: 89
<212> TYPE: DNA
<213> ORGANISM: Artificial Sequence
<220> FEATURE:
<223> OTHER INFORMATION: DRIVE_PCR_Rev_Primer_15

<400> SEQUENCE: 17
caagcagaag acggcatacg agattttcac gtgactggag ttcagacgtg tgctcttccg     60
atctgaggtt cagagttcta cagtccgaa                                       89

<210> SEQ ID NO 18
<211> LENGTH: 89
<212> TYPE: DNA
<213> ORGANISM: Artificial Sequence
<220> FEATURE:
<223> OTHER INFORMATION: DRIVE_PCR_Rev_Primer_16

<400> SEQUENCE: 18
caagcagaag acggcatacg agatggccac gtgactggag ttcagacgtg tgctcttccg     60
atctgaggtt cagagttcta cagtccgaa                                       89

<210> SEQ ID NO 19
<211> LENGTH: 89
<212> TYPE: DNA
<213> ORGANISM: Artificial Sequence
<220> FEATURE:
<223> OTHER INFORMATION: DRIVE_PCR_Rev_Primer_17

<400> SEQUENCE: 19
caagcagaag acggcatacg agatcgaaac gtgactggag ttcagacgtg tgctcttccg     60
atctgaggtt cagagttcta cagtccgaa                                       89

<210> SEQ ID NO 20
<211> LENGTH: 89
<212> TYPE: DNA
<213> ORGANISM: Artificial Sequence
<220> FEATURE:
<223> OTHER INFORMATION: DRIVE_PCR_Rev_Primer_18

```
<400> SEQUENCE: 20
caagcagaag acggcatacg agatcgtacg gtgactggag ttcagacgtg tgctcttccg    60
atctgaggtt cagagttcta cagtccgaa                                      89

<210> SEQ ID NO 21
<211> LENGTH: 89
<212> TYPE: DNA
<213> ORGANISM: Artificial Sequence
<220> FEATURE:
<223> OTHER INFORMATION: DRIVE_PCR_Rev_Primer_19

<400> SEQUENCE: 21
caagcagaag acggcatacg agatccactc gtgactggag ttcagacgtg tgctcttccg    60
atctgaggtt cagagttcta cagtccgaa                                      89

<210> SEQ ID NO 22
<211> LENGTH: 89
<212> TYPE: DNA
<213> ORGANISM: Artificial Sequence
<220> FEATURE:
<223> OTHER INFORMATION: DRIVE_PCR_Rev_Primer_20

<400> SEQUENCE: 22
caagcagaag acggcatacg agatatcagt gtgactggag ttcagacgtg tgctcttccg    60
atctgaggtt cagagttcta cagtccgaa                                      89

<210> SEQ ID NO 23
<211> LENGTH: 89
<212> TYPE: DNA
<213> ORGANISM: Artificial Sequence
<220> FEATURE:
<223> OTHER INFORMATION: DRIVE_PCR_Rev_Primer_21

<400> SEQUENCE: 23
caagcagaag acggcatacg agataggaat gtgactggag ttcagacgtg tgctcttccg    60
atctgaggtt cagagttcta cagtccgaa                                      89

<210> SEQ ID NO 24
<211> LENGTH: 89
<212> TYPE: DNA
<213> ORGANISM: Artificial Sequence
<220> FEATURE:
<223> OTHER INFORMATION: DRIVE_PCR_Rev_Primer_22

<400> SEQUENCE: 24
caagcagaag acggcatacg agatcttttg gtgactggag ttcagacgtg tgctcttccg    60
atctgaggtt cagagttcta cagtccgaa                                      89

<210> SEQ ID NO 25
<211> LENGTH: 89
<212> TYPE: DNA
<213> ORGANISM: Artificial Sequence
<220> FEATURE:
<223> OTHER INFORMATION: DRIVE_PCR_Rev_Primer_23

<400> SEQUENCE: 25
caagcagaag acggcatacg agattagttg gtgactggag ttcagacgtg tgctcttccg    60
atctgaggtt cagagttcta cagtccgaa                                      89
```

```
<210> SEQ ID NO 26
<211> LENGTH: 89
<212> TYPE: DNA
<213> ORGANISM: Artificial Sequence
<220> FEATURE:
<223> OTHER INFORMATION: DRIVE_PCR_Rev_Primer_24

<400> SEQUENCE: 26
caagcagaag acggcatacg agatccggtg gtgactggag ttcagacgtg tgctcttccg      60
atctgaggtt cagagttcta cagtccgaa                                       89

<210> SEQ ID NO 27
<211> LENGTH: 51
<212> TYPE: DNA
<213> ORGANISM: Artificial Sequence
<220> FEATURE:
<223> OTHER INFORMATION: DRIVE_PCR_Fwd_Universal_Primer

<400> SEQUENCE: 27
aatgatacgg cgaccaccga gatctacaca ttcgcaccag cacgctacgc a              51
```

COMPOSITIONS AND METHODS TO TREAT CANCER

CROSS-REFERENCE TO RELATED APPLICATIONS

This application is a U.S. National Phase application filed under 35 U.S.C. § 371 claiming benefit to International Patent Application No. PCT/IB2018/055418, filed on Jul. 20, 2018, which is entitled to priority under 35 U.S.C. § 119(e) to U.S. Provisional Application No. 62/535,539, filed Jul. 21, 2017, each of which is hereby incorporated by reference in its entirety.

BACKGROUND

Cancer is a leading cause of death in the world. Approximately 595,000 people per year die from cancer in the U. S. alone. The standard of care for many cancers includes surgery, radiotherapy, and/or cytotoxic chemotherapy, with few targeted agents currently approved. There is an increasing body of evidence suggesting that a patient's genetic profile can be indicative of a patient's responsiveness to a therapeutic treatment. Given the numerous therapies available to an individual having cancer, a determination of the genetic factors that influence, for example, response to a particular drug, could be used to provide a patient with a personalized treatment regimen. Currently, there are limited targeted therapies that have been approved for use in cancer. Therefore, there is an unmet need to develop targeted, personalized therapies for cancer.

SUMMARY

The present disclosure is based, at least in part, on the identification of targets associated with specific cancer types using a large-scale RNAi screen. These targets can include genes, e.g., oncogenes, presently identified to be associated with specific cancer types. In some embodiments, the targets were identified from a large-scale RNAi screen performed on 398 cancer cell lines. Accordingly, provided herein are, inter alia, methods and compositions comprising an inhibitor of one or more of the targets disclosed herein, e.g., an inhibitor of one or more of the targets disclosed in Tables 1 and 2. These inhibitors can be used to treat cancers, e.g., hematological cancers or solid tumors, associated with the expression or activity of their corresponding cancer targets. Additionally disclosed are methods and compositions for identifying and/or evaluating a subject having a cancer, e.g., by detecting a genetic alteration, the level and/or activity of one or more of the targets disclosed herein. In one embodiment, the present disclosure also provides methods for treating selected patient populations with one or more of the inhibitors disclosed herein. In one embodiment, the patient population is selected on the basis of having a cancer associated with any one of the targets disclosed herein. Thus, therapeutic and diagnostic targets for the treatment of cancer are disclosed.

Accordingly, in one aspect, the present disclosure provides a method for reducing, e.g., inhibiting, proliferation of cancer cells, e.g., hematological cancer cells or solid tumor cells. The methods may comprise administering to a subject in need thereof, an inhibitor, e.g., an inhibitor of any of the targets disclosed in Tables 1 or 2, in an amount that is effective to reduce, e.g., inhibit, proliferation of the cancer cells.

In an embodiment, the present disclosure provides an inhibitor, e.g., an inhibitor of any of the targets disclosed in Tables 1 or 2, for use in the treatment of cancer, e.g., hematological cancers or solid tumors. Also provided is a use of the inhibitors for the manufacture of a medicament for treating cancer, such as hematological cancers or solid tumors or any cancers disclosed herein.

In another aspect, the present disclosure provides a method of treating (e.g., inhibiting, reducing, ameliorating or preventing) a proliferative condition or disorder (e.g., a cancer) in a subject. The methods include administering to the subject an inhibitor (e.g., an inhibitor of any one of the targets disclosed in Tables 1 or 2), thereby treating the proliferative condition or disorder (e.g., the cancer).

In some embodiments of any of the methods or uses disclosed herein, the method or use comprises administering to a subject in need thereof, an inhibitor of any of the targets disclosed in Tables 1 or 2, in combination with a second therapeutic agent, e.g., 1, 2, 3, 4 or more therapeutic agents disclosed herein. In an embodiment, the second therapeutic agent is chosen from one or more of an anti-cancer agent, anti-allergic agents, anti-nausea agents (or anti-emetics), pain relievers, or cytoprotective agents, or a second therapeutic agent described herein.

Methods of Evaluating, Selecting and Monitoring a Patient

The disclosure also provides methods of evaluating, predicting, selecting, or monitoring, a subject who will receive, is about to receive, has received or is receiving a therapeutic treatment (e.g., a treatment with an inhibitor, e.g., an inhibitor of any of the targets disclosed in Tables 1 or 2).

In another aspect, disclosed herein are methods of evaluating or predicting the responsiveness of a subject having a cancer (e.g., any of the cancers disclosed in Tables 1 or 2), to a therapeutic treatment (e.g., a treatment with an inhibitor, e.g., an inhibitor of any of the targets disclosed in Tables 1 or 2). The method comprises:

evaluating the presence or absence of a genetic alteration (e.g., a genetic alteration as described in Table 2), e.g., gene amplification, copy number deletion, mutation or presence of microsatellites, wherein:
  (i) the presence of the alteration is indicative that the subject is likely to respond to the therapeutic treatment; or
  (ii) the absence of the alteration is indicative that the subject is less likely to respond to the therapeutic treatment;
for at least one time point, e.g., prior to administration of the therapeutic treatment, thereby evaluating the subject, or predicting the responsiveness of the subject to a therapeutic treatment.

In one embodiment, responsive to said evaluation or prediction, the method further comprises selecting the subject for administration in an amount effective to treat the cancer, an inhibitor (e.g., an inhibitor of any of the targets disclosed in Tables 1 or 2) to treat the cancer (e.g., any of the cancers disclosed in Tables 1 or 2) in the subject.

In one embodiment, responsive to said evaluation or prediction, the method further comprises administering an inhibitor (e.g., an inhibitor of any of the targets disclosed in Tables 1 or 2) in an amount effective to treat the cancer (e.g., any of the cancers disclosed in Tables 1 or 2) in the subject.

In one aspect, disclosed herein is a method of evaluating or predicting the responsiveness of a subject having a cancer (e.g., any of the cancers disclosed in Tables 1 or 2), to a therapeutic treatment (e.g., a treatment with an inhibitor, e.g., an inhibitor of any of the targets disclosed in Tables 1 or 2). The method comprises:

evaluating the expression level (e.g., high or low expression of, e.g., mRNA or protein) or activity, of a target (e.g., a target disclosed in Tables 1 or 2) or a target-associated molecule (e.g., a downstream effector disclosed in Table 2), comprising:

(i) measuring the expression level or activity of the target or a target-associated molecule (e.g., a downstream effector disclosed in Table 2) in the subject for at least one time point (e.g., prior to administration of the therapeutic treatment), e.g., using a method described herein, and (ii) (optionally) comparing the expression level or activity of the target or downstream target of the target ("sample value") at the at least one time point with a reference level or activity ("reference value"), wherein:

(a) a higher sample value compared to a reference value is indicative that the subject is likely to respond to the therapeutic treatment; or (b) a lower sample value compared to a reference value is indicative that the subject is less likely to respond to the therapeutic treatment;

thereby evaluating the subject, or predicting the responsiveness of the subject to a therapeutic treatment.

In one embodiment, the reference value is the expression level or activity of a target (e.g., a target disclosed in Tables 1 or 2) or a target-associated molecule (e.g., a downstream effector disclosed in Table 2), of a sample taken from a healthy, e.g., normal, subject.

In one embodiment, the reference value is the expression level or activity of a target (e.g., a target disclosed in Tables 1 or 2) or a target-associated molecule (e.g., a downstream effector disclosed in Table 2), of a sample taken from the subject at a different time period.

In one embodiment, responsive to said evaluation or prediction, the method further comprises selecting the subject for administration in an amount effective to treat the cancer, an inhibitor (e.g., an inhibitor of any of the targets disclosed in Tables 1 or 2) to treat the cancer (e.g., any of the cancers disclosed in Tables 1 or 2) in the subject.

In one embodiment, responsive to said valuation or prediction, the method further comprises administering an inhibitor (e.g., an inhibitor of any of the targets disclosed in Tables 1 or 2) in an amount effective to treat the cancer (e.g., any of the cancers disclosed in Tables 1 or 2) in the subject.

In one aspect, disclosed herein is a method of evaluating the effectiveness of a therapeutic treatment, e.g., a treatment with an inhibitor (e.g., an inhibitor of any of the targets disclosed in Tables 1 or 2), in a subject having a cancer (e.g., any of the cancers disclosed in Tables 1 or 2), comprising measuring the level (e.g., mRNA or protein), or activity (e.g., enzyme activity), of a target (e.g., a target of the inhibitor administered), in the subject (e.g., in a sample from the subject) for at least two time points, e.g., a first time point (e.g., prior to administration of the therapeutic treatment) and a second time point (e.g., after administration of the therapeutic treatment), e.g., using a method described herein, wherein:

(i) a decrease in the expression or activity of the target or a target-associated molecule (e.g., a downstream effector disclosed in Table 2), between the first time point and the second time point is indicative that the subject is responding to the therapeutic treatment; or (ii) an increase in the expression or activity of the target or a target-associated molecule (e.g., a downstream effector disclosed in Table 2), between the first time point and the second time point is indicative that the subject is less responsive to the therapeutic treatment, thereby evaluating the effectiveness of the therapeutic treatment in the subject.

In one embodiment, responsive to said evaluation, the method further comprises administering an inhibitor, e.g., the same inhibitor, at a higher dose, e.g., at a dose at least 1-fold, 2-fold, 3-fold, 4-fold, 5-fold, or 10-fold higher, compared to the first administration of the inhibitor to treat the disease. In one embodiment, responsive to said evaluation, the method further comprising administering a second therapy, e.g., a therapy disclosed herein, to the subject, thereby treating the cancer.

In one aspect, disclosed herein is a method of monitoring cancer relapse in a subject having a cancer, (e.g., any of the cancers disclosed in Tables 1 or 2), who has responded or partially responded to a therapeutic treatment (e.g., a treatment with an inhibitor, e.g., an inhibitor of any of the targets disclosed in Tables 1 or 2), comprising measuring the level (e.g., mRNA or protein), or activity (e.g., enzyme activity), of a target (e.g., a target of the inhibitor administered), in the subject (e.g., in a sample from the subject) for at least two time points, e.g., a first time point (e.g., prior to administration of the therapeutic treatment) and a second time point (e.g., after administration of the therapeutic treatment), e.g., using a method described herein, wherein:

(i) an increase in the expression or activity of the target or a target-associated molecule (e.g., a downstream effector disclosed in Table 2), between the first time point and the second time point is indicative that the cancer is relapsing; or (ii) the absence of an increase, e.g., a decrease, in the expression or activity of the target or a target-associated molecule (e.g., a downstream effector disclosed in Table 2), between the first time point and the second time point is indicative that the cancer is not relapsing.

In one embodiment, (i) an increase in the expression or activity of the target or a target-associated molecule (e.g., a downstream effector disclosed in Table 2), at a subsequent (e.g., second, third, fourth, fifth, sixth, or seventh or later) time point relative to a prior (e.g., first, second, third, fourth, fifth, or sixth or later) time point, among the at least two time points, indicates that the cancer is relapsing; and (ii) the absence of an increase in the expression or activity of the target or a target-associated molecule (e.g., a downstream effector disclosed in Table 2), at a subsequent (e.g., second, third, fourth, fifth, sixth, or seventh or later) time point relative to a prior (e.g., first, second, third, fourth, fifth, or sixth or later) time point, among the at least two time points, indicates that the cancer is not relapsing.

In one aspect, disclosed herein is a method of treating a subject having a cancer, e.g., a cancer disclosed in Tables 1 or 2, comprising in response to a determination that the subject, after having responded or partially responded to a first therapeutic treatment, (e.g., a treatment with an inhibitor, e.g., an inhibitor of any of the targets disclosed in Tables 1 or 2), has experienced, or has been identified as having experienced an increase in expression or activity of the target or a target-associated molecule (e.g., a downstream effector disclosed in Table 2), administering a second therapy, e.g., a second therapy disclosed herein, thereby treating the cancer.

According to an aspect of the invention, a kit is provided, wherein said kit is for predicting the sensitivity of a subject afflicted with a cancer associated with reduced, e.g., defective, activity of any of the targets disclosed in Tables 1 or 2, wherein the reduced activity of the target can be due to gene inactivation mechanisms (e.g., epigenetic mechanisms), for treatment with an inhibitor, e.g., an inhibitor for the target, comprising: i) reagents capable of: a) detecting human cancer cells harboring genetic abnormalities, e.g., one or more of mutations, deletions, insertions, translocations, or microsatellite instability, or other gene inactivation mechanisms (e.g. epigenetic mechanisms); or b) detecting expression level (e.g., mRNA or protein), or activity (e.g., enzyme activity), of a target (e.g., a target of the inhibitor administered) or a target-associated molecule (e.g., a downstream effector disclosed in Table 2) in human cancer cells from a subject; and ii) instructions for how to use said kit.

In yet another aspect, a method of treating a cancer in a selected patient population is provided, wherein the patient population is selected on the basis of having a cancer associated with any one of the targets disclosed in Tables 1 or 2. The method includes administering an inhibitor, e.g., an inhibitor of any one of the targets disclosed in Tables 1 or 2, in an amount sufficient to treat the cancer. In one embodiment, the cancer is a hematological cancer or a solid tumor or any of the cancers disclosed in Tables 1 or 2.

In another aspect, a composition comprising an inhibitor of one of the targets, e.g., any one of the targets, disclosed in Tables 1 or 2 for use in treatment of cancer in a selected patient population is provided, wherein the patient population is selected on the basis of having a cancer associated with any one of the targets disclosed in Tables 1 or 2. In one embodiment, the cancer is a hematological cancer or a solid tumor or any of the cancers disclosed in Tables 1 or 2.

Additional features or embodiments of the methods, compositions, combinations, and kits described herein include one or more of the following:

In some embodiments, an inhibitor of any of the targets disclosed in Tables 1 or 2, is a compound capable of reducing, e.g., inhibiting, expression of the target e.g., a gene product, e.g., a protein, encoded by the target. The inhibitor can be chosen from: an RNA inhibitor (e.g., an RNAi agent), a CRISPR, a TALEN, a zinc finger nuclease, a mRNA, an antibody or derivative thereof, a chimeric antigen receptor T cell (CART) or a low molecular weight compound.

In some embodiments, an inhibitor of any of the targets disclosed in Tables 1 or 2 can be a compound capable of reducing, e.g., inhibiting, a normal cellular function of the target, e.g., a gene product, e.g., a protein, encoded by the target.

In certain embodiments, the target of an inhibitor disclosed herein comprises one or more of the targets disclosed in Tables 1 or 2. In one embodiment, the target is chosen from MITF, MYB, FLI1, ASNS, WRN, SOX10, ALDH18A1, FOXA1, HNF1B, RUNX1, CBFB, TP63, CDK2, VPS4A, TCF4, CEBPA, GATA3, ARIDIB, PRKRA, HSPA8, IRF4, SPI1, MTHFD1, ADAR, and NFE2L2.

In certain embodiments, an inhibitor described herein, e.g., an inhibitor of any of the targets disclosed in Tables 1 or 2, can be used to treat a subject across cancer types, including but not restricted to any of the cancers disclosed in Tables 1 or 2. In some embodiments, the cancer is chosen from: hematopoietic cancer (e.g., ALL, AML, MM or DLBCL), skin cancer, lung cancer, colorectal cancer (CRC), stomach cancer, thyroid cancer, melanoma, uveal melanoma cancer, pancreatic cancer, endometrial cancer, Ewing's sarcoma, breast cancer, central nervous system (CNS, e.g., brain) cancer, kidney cancer, bladder cancer, esophageal cancer, upper aerodigestive cancer, neuroblastoma, ovarian cancer, liver cancer, and colon cancer.

In certain embodiments, the target is MITF. In some embodiments, the subject has a cancer, e.g., a cancer as described in Table 1 or 2. In one embodiment, the subject has a skin cancer or a uveal cancer. In some embodiments, the subject has or is identified as having MITF expression. In some embodiments, the subject has or is identified as having high MITF expression, e.g., in reference to a control, e.g., a normal, subject. In some embodiments, the subject has a skin cancer or a uveal melanoma cancer, which cancer has or is identified as having high MITF expression, e.g., in reference to a control, e.g., a normal, subject. In other embodiments, the subject with high MITF expression (e.g., a skin cancer or a uveal melanoma cancer with high MITF expression) is selected for treatment with a MITF inhibitor, e.g., one or more of MITF inhibitors described herein. In other embodiments, the subject with high MITF expression (e.g., a subject having a skin cancer or a uveal melanoma cancer with high MITF expression) is treated with a MITF inhibitor, e.g., one or more of MITF inhibitors described herein.

In certain embodiments, the target is MYB. In some embodiments, the subject has a cancer, e.g., a cancer as described in Table 1 or 2. In one embodiment, the subject has a hematopoietic cancer (e.g., ALL or AML) or colorectal cancer (CRC). In some embodiments, the subject has or is identified as having MYB expression. In some embodiments, the subjects has or is identified as having high MYB expression, e.g., in reference to a control, e.g., a normal, subject. In some embodiments, the subject has a hematopoietic cancer (e.g., ALL or AML) or colorectal cancer (CRC), which cancer has or is identified as having high MYB expression, e.g., in reference to a control, e.g., a normal, subject. In other embodiments, the subject with high MYB expression (e.g., a hematopoietic cancer (e.g., ALL or AML) or colorectal cancer (CRC) with high MYB expression) is selected for treatment with a MYB inhibitor, e.g., one or more of MYB inhibitors described herein. In other embodiments, the subject with high MYB expression (e.g., a subject having a hematopoietic cancer (e.g., ALL or AML) or colorectal cancer (CRC) with high MYB expression) is treated with a MYB inhibitor, e.g., one or more of MYB inhibitors described herein.

In certain embodiments, the target is FLI1. In some embodiments, the subject has a cancer, e.g., a cancer as described in Table 1 or 2. In one embodiment, the subject has a hematopoietic cancer (e.g., ALL, AML, MM or DLBCL) or Ewing's sarcoma. In some embodiments, the subject has or is identified as having FLI1 expression. In some embodiments, the subject has or is identified as having high FLI1 expression, e.g., in reference to a control, e.g., a normal, subject. In some embodiments, the subject has a hematopoietic cancer (e.g., ALL, AML, MM or DLBCL) or Ewing's sarcoma, which cancer has or is identified as having high FLI1 expression, e.g., in reference to a control, e.g., a normal, subject. In other embodiments, the subject with high FLI1 expression (e.g., a hematopoietic cancer (e.g., ALL, AML, MM or DLBCL) or Ewing's sarcoma with high FLI1 expression) is selected for treatment with a FLI1 inhibitor, e.g., one or more of FLI1 inhibitors described herein. In other embodiments, the subject with high FLI1 expression (e.g., a subject having a hematopoietic cancer (e.g., ALL, AML, MM or DLBCL) or Ewing's sarcoma with high FLI1 expression) is treated with a FLI1 inhibitor, e.g., one or more of FLI1 inhibitors described herein.

In certain embodiments, the target is ASNS. In some embodiments, the subject has a cancer, e.g., a cancer as described in Table 1 or 2. In one embodiment, the subject has a breast, colorectal, pancreatic or skin cancer. In some embodiments, the subject has or is identified as having ASNS expression. In some embodiments, the subject has or is identified as having high ASNS expression, e.g., in reference to a control, e.g., a normal, subject. In some embodiments, the subject has a breast, colorectal, pancreatic or skin cancer, which cancer has or is identified as having high ASNS expression, e.g., in reference to a control, e.g., a normal, subject. In other embodiments, the subject with high ASNS expression (e.g., a breast, colorectal, pancreatic or skin cancer with high ASNS expression) is selected for treatment with an ASNS modulator, e.g., an ASNS inhibitor, e.g., one or more of ASNS inhibitors described herein In other embodiments, the subject with high ASNS expression (e.g., a subject having a breast, colorectal, pancreatic or skin cancer with high ASNS expression) is treated with an ASNS modulator, e.g., an ASNS inhibitor, e.g., one or more of ASNS inhibitors described herein.

In some embodiments, the subject has or is identified as having low ASNS expression, e.g., in reference to a control, e.g., a normal, subject. In some embodiments, the subject has a breast, colorectal, pancreatic or skin cancer, which cancer has or is identified as having low ASNS expression, e.g., in reference to a control, e.g., a normal, subject. In some embodiments, the subject with low ASNS expression (e.g., a subject having a breast, colorectal, pancreatic or skin cancer with low ASNS expression) is treated with an ASNS modulator, e.g., an ASNS agonist, e.g., one or more ASNS agonists described herein. In some embodiments, the subject with low ASNS expression (e.g., a breast, colorectal, pancreatic or skin cancer with low ASNS expression) is selected for treatment with an ASNS modulator, e.g., an ASNS agonist, e.g., one or more ASNS agonists described herein.

In certain embodiments, the target is WRN. In some embodiments, the subject has a cancer, e.g., a cancer as described in Table 1 or 2. In some embodiments, the subject has or is identified as having a microsatellite instable (MSI+) cancer, e.g., in reference to a control, e.g., a normal, subject. In one embodiment, the subject has a colorectal (CRC), endometrial or stomach cancer. In some embodiments, the subject has a colorectal (CRC), endometrial or stomach cancer, which cancer has or is identified as having a microsatellite instability (MSI+), e.g., in reference to a control, e.g., a normal, subject. In other embodiments, the subject with a microsatellite instable (MSI+) cancer (e.g., a colorectal (CRC), endometrial or stomach cancer with a microsatellite instability (MSI+)) is selected for treatment with a WRN inhibitor, e.g., one or more of WRN inhibitors described herein. In other embodiments, the subject with a microsatellite instable (MSI+) cancer (e.g., a colorectal (CRC), endometrial or stomach cancer with a microsatellite instability (MSI+)) is treated with a WRN inhibitor, e.g., one or more of WRN inhibitors described herein.

In certain embodiments, the target is SOX10. In some embodiments, the subject has a cancer, e.g., a cancer as described in Table 1 or 2. In one embodiment, the subject has a melanoma (e.g., a skin or uveal melanoma) or a central nervous system (CNS) cancer. In some embodiments, the subject has or is identified as having SOX10 expression. In some embodiments, the subject has or is identified as having high SOX10 expression, e.g., in reference to a control, e.g., a normal, subject. In some embodiments, the subject has a melanoma (e.g., a skin or uveal melanoma) or a central nervous system (CNS) cancer, which cancer has or is identified as having high SOX10 expression, e.g., in reference to a control, e.g., a normal, subject. In other embodiments, the subject with high SOX10 expression (e.g., a melanoma (e.g., a skin or uveal melanoma) or a central nervous system (CNS) cancer with high SOX10 expression) is selected for treatment with a SOX10 inhibitor, e.g., one or more of SOX10 inhibitors described herein. In other embodiments, the subject with high SOX10 expression (e.g., a subject having a melanoma (e.g., a skin or uveal melanoma) or a central nervous system (CNS) cancer with high SOX10 expression) is treated with a SOX10 inhibitor, e.g., one or more of SOX10 inhibitors described herein.

In certain embodiments, the target is ALDH18A1. In some embodiments, the subject has a cancer, e.g., a cancer as described in Table 1 or 2. In one embodiment, the subject has a breast, lung, pancreatic or skin cancer. In some embodiments, the subject has or is identified as having ALDH18A1 expression. In some embodiments, the subject has or is identified as having high ALDH18A1 expression, e.g., in reference to a control, e.g., a normal, subject. In some embodiments, the subject has a breast, lung, pancreatic or skin cancer, which cancer has or is identified as having high ALDH18A1 expression, e.g., in reference to a control, e.g., a normal, subject. In other embodiments, the subject with high ALDH18A1 expression (e.g., a breast, lung, pancreatic or skin cancer with high ALDH18A1 expression) is selected for treatment with an ALDH18A1 modulator, e.g., an inhibitor, e.g., one or more of ALDH18A1 inhibitors described herein. In other embodiments, the subject with high ALDH18A1 expression (e.g., a subject having a breast, lung, pancreatic or skin cancer with high ALDH18A1 expression) is treated with an ALDH18A1 modulator, e.g., an inhibitor, e.g., one or more of ALDH18A1 inhibitors described herein.

In some embodiments, the subject has or is identified as having low ALDH18A1 expression, e.g., in reference to a control, e.g., a normal, subject. In some embodiments, the subject has a breast, lung, pancreatic or skin cancer, which cancer has or is identified as having low ALDH18A1 expression, e.g., in reference to a control, e.g., a normal, subject. In other embodiments, the subject with low ALDH18A1 expression (e.g., a breast, lung, pancreatic or skin cancer with low ALDH18A1 expression) is selected for treatment with an ALDH18A1 modulator, e.g., an ALDH18A1 agonist, e.g., one or more ALDH18A1 agonists described herein. In other embodiments, the subject with low ALDH18A1 expression (e.g., a subject having a breast, lung, pancreatic or skin cancer with low ALDH18A1 expression) is treated with an ALDH18A1 modulator, e.g., an agonist, e.g., one or more ALDH18A1 agonists described herein.

In certain embodiments, the target is FOXA1. In some embodiments, the subject has a cancer, e.g., a cancer as described in Table 1 or 2. In one embodiment, the subject has a breast, or prostate cancer. In some embodiments, the subject has or is identified as having FOXA1 expression. In some embodiments, the subject has or is identified as having high FOXA1 expression, e.g., in reference to a control, e.g., a normal, subject. In some embodiments, the subject has a breast, or prostate cancer, which cancer has or is identified as having high FOXA1 expression, e.g., in reference to a control, e.g., a normal, subject. In other embodiments, the subject with high FOXA1 expression (e.g., a breast, or prostate cancer with high FOXA1 expression) is selected for treatment with a FOXA1 inhibitor, e.g., one or more of FOXA1 inhibitors described herein. In other embodiments, the subject with high FOXA1 expression (e.g., a subject having a breast, or prostate cancer with high FOXA1 expression) is treated with a FOXA1 inhibitor, e.g., one or more of FOXA1 inhibitors described herein.

In certain embodiments, the target is HNF1B. In some embodiments, the subject has a cancer, e.g., a cancer as described in Table 1 or 2. In one embodiment, the subject has a kidney or a lung cancer. In some embodiments, the subject has or is identified as having HNF1B expression. In some embodiments, the subject has or is identified as having high HNF1B expression, e.g., in reference to a control, e.g., a normal, subject. In some embodiments, the subject has a kidney or a lung cancer, which cancer has or is identified as having high HNF1B expression, e.g., in reference to a control, e.g., a normal, subject. In other embodiments, the subject with high HNF1B expression (e.g., a kidney or a lung cancer with high HNF1B expression) is selected for treatment with a HNF1B inhibitor, e.g., one or more of HNF1B inhibitors described herein. In other embodiments, the subject with high HNF1B expression (e.g., a subject having a kidney or a lung cancer with high HNF1B expression) is treated with a HNF1B inhibitor, e.g., one or more of HNF1B inhibitors described herein.

In certain embodiments, the target is RUNX1. In some embodiments, the subject has a cancer, e.g., a cancer as described in Table 1 or 2. In one embodiment, the subject has a hematopoietic cancer (e.g., ALL or AML). In some embodiments, the subject has or is identified as having RUNX1 expression. In some embodiments, the subject has or is identified as having high RUNX1 expression, e.g., in reference to a control, e.g., a normal, subject. In some embodiments, the subject has a hematopoietic cancer (e.g., ALL or AML), which cancer has or is identified as having high RUNX1 expression, e.g., in reference to a control, e.g., a normal, subject. In other embodiments, the subject with high RUNX1 expression (e.g., has a hematopoietic cancer (e.g., ALL or AML) with high RUNX1 expression) is selected for treatment with a RUNX1 inhibitor, e.g., one or more of RUNX1 inhibitors described herein. In other embodiments, the subject with high RUNX1 expression (e.g., has a hematopoietic cancer (e.g., ALL or AML) with high RUNX1 expression) is treated with a RUNX1 inhibitor, e.g., one or more of RUNX1 inhibitors described herein.

In certain embodiments, the target is CBFB. In some embodiments, the subject has a cancer, e.g., a cancer as described in Table 1 or 2. In one embodiment, the subject has a hematopoietic cancer (e.g., ALL or AML). In some embodiments, the subject has or is identified as having RUNX1 or IKZF1 expression. In some embodiments, the subject has or is identified as having high RUNX1 or IKZF1 expression, e.g., in reference to a control, e.g., a normal, subject. In some embodiments, the subject has a hematopoietic cancer (e.g., ALL or AML), which cancer has or is identified as having high RUNX1 or IKZF1 expression, e.g., in reference to a control, e.g., a normal, subject. In other embodiments, the subject with high RUNX1 or IKZF1 expression (e.g., has a hematopoietic cancer (e.g., ALL or AML) with high RUNX1 or IKZF1 expression) is selected for treatment with a CBFB inhibitor, e.g., one or more of CBFB inhibitors described herein. In other embodiments, the subject with high RUNX1 or IKZF1 expression (e.g., has a hematopoietic cancer (e.g., ALL or AML) with high RUNX1 expression) is treated with a CBFB inhibitor, e.g., one or more of CBFB inhibitors described herein.

In certain embodiments, the target is TP63. In some embodiments, the subject has a cancer, e.g., a cancer as described in Table 1 or 2. In one embodiment, the subject has a squamous cancer (e.g., bladder, esophageal or upper aerodigestive cancer). In some embodiments, the subject has or is identified as having TP63 expression). In some embodiments, the subject has or is identified as having high TP63 expression, e.g., in reference to a control, e.g., a normal, subject. In some embodiments, the subject has a squamous cancer (e.g., bladder, esophageal or upper aerodigestive cancer), which cancer has or is identified as having high TP63 expression, e.g., in reference to a control, e.g., a normal, subject. In other embodiments, the subject with high TP63 expression (e.g., has a squamous cancer (e.g., bladder, esophageal or upper aerodigestive cancer) with high TP63 expression) is selected for treatment with a TP63 inhibitor, e.g., one or more of TP63 inhibitors described herein. In other embodiments, the subject with high TP63 expression (e.g., a squamous cancer (e.g., bladder, esophageal or upper aerodigestive cancer) with high TP63 expression) is treated with a TP63 inhibitor, e.g., one or more of TP63 inhibitors described herein.

In certain embodiments, the target is CDK2. In some embodiments, the subject has a cancer, e.g., a cancer as described in Table 1 or 2. In one embodiment, the subject has a breast, endometrial, ovarian or lung cancer. In some embodiments, the subject has or is identified as having CCNE1 expression. In some embodiments, the subject has or is identified as having high CCNE1 expression or gene amplification, e.g., in reference to a control, e.g., a normal, subject. In some embodiments, the subject has a breast, endometrial, ovarian or lung cancer, which cancer has or is identified as having high CCNE1 expression or gene amplification, e.g., in reference to a control, e.g., a normal, subject. In other embodiments, the subject with high CCNE1 expression or gene amplification (e.g., a breast, endometrial, ovarian or lung cancer with high CCNE1 expression or gene amplification) is selected for treatment with a CDK2 inhibitor, e.g., one or more of CDK2 inhibitors described herein. In other embodiments, the subject with high CCNE1 expression or gene amplification (e.g., a subject having a breast, endometrial, ovarian or lung cancer with high CCNE1 expression or gene amplification) is treated with a CDK2 inhibitor, e.g., one or more of CDK2 inhibitors described herein.

In certain embodiments, the target is VPS4A. In some embodiments, the subject has a cancer, e.g., a cancer as described in Table 1 or 2. In one embodiment, the subject has a breast, CRC, lung, stomach, pancreatic or upper aerodigestive cancer. In some embodiments, the subject has or is identified as having a copy number deletion of VPS4B, e.g., in reference to a control, e.g., a normal, subject. In some embodiments, the subject has a breast, CRC, lung, stomach, pancreatic or upper aerodigestive cancer, which cancer has or is identified as having a copy number deletion of VPS4B, e.g., in reference to a control, e.g., a normal, subject. In other embodiments, the subject having a copy number deletion of VPS4B (e.g., a breast, CRC, lung, stomach, pancreatic or upper aerodigestive cancer having a copy number deletion of VPS4B) is selected for treatment with a VPS4A inhibitor, e.g., one or more of VPS4A inhibitors described herein. In other embodiments, the subject having a copy number deletion of VPS4B (e.g., a subject having a breast, CRC, lung, stomach, pancreatic or upper aerodigestive cancer having a copy number deletion of VPS4B) is treated with a VPS4A inhibitor, e.g., one or more of VPS4A inhibitors described herein.

In certain embodiments, the target is TCF4. In some embodiments, the subject has a cancer, e.g., a cancer as described in Table 1 or 2. In one embodiment, the subject has a hematopoietic cancer or a neuroblastoma. In some embodiments, the subject has or is identified as having TCF4 expression. In some embodiments, the subject has or is identified as having high TCF4 expression, e.g., in reference to a control, e.g., a normal, subject. In some embodiments, the subject has a hematopoietic cancer or a neuroblastoma, which cancer has or is identified as having high TCF4 expression, e.g., in reference to a control, e.g., a normal, subject. In other embodiments, the subject with high TCF4 expression (e.g., a hematopoietic cancer or a neuroblastoma with high TCF4 expression) is selected for treatment with a TCF4 inhibitor, e.g., one or more of TCF4 inhibitors described herein. In other embodiments, the subject with high TCF4 expression (e.g., a subject having a hematopoietic cancer or a neuroblastoma with high TCF4 expression) is treated with a TCF4 inhibitor, e.g., one or more of TCF4 inhibitors described herein.

In certain embodiments, the target is CEBPA. In some embodiments, the subject has a cancer, e.g., a cancer as described in Table 1 or 2. In one embodiment, the subject has a liver cancer or AML. In some embodiments, the subject has or is identified as having CEBPA expression. In some embodiments, the subject has or is identified as having high CEBPA expression, e.g., in reference to a control, e.g., a normal, subject. In some embodiments, the subject has a liver cancer or AML, which cancer has or is identified as having high CEBPA expression, e.g., in reference to a control, e.g., a normal, subject. In other embodiments, the subject with high CEBPA expression (e.g., a liver cancer or AML with high CEBPA expression) is selected for treatment with a CEBPA inhibitor, e.g., one or more of CEBPA inhibitors described herein. In other embodiments, the subject with high CEBPA expression (e.g., a subject having a liver cancer or AML with high CEBPA expression) is treated with a CEBPA inhibitor, e.g., one or more of CEBPA inhibitors described herein.

In certain embodiments, the target is GATA3. In some embodiments, the subject has a cancer, e.g., a cancer as described in Table 1 or 2. In one embodiment, the subject has a breast cancer or neuroblastoma. In some embodiments, the subject has or is identified as having GATA3 expression. In some embodiments, the subject has or is identified as having high GATA3 expression, e.g., in reference to a control, e.g., a normal, subject. In some embodiments, the subject has a breast cancer or neuroblastoma, which cancer has or is identified as having high GATA3 expression, e.g., in reference to a control, e.g., a normal, subject. In other embodiments, the subject with high GATA3 expression (e.g., a breast cancer or neuroblastoma with high GATA3 expression) is selected for treatment with a GATA3 inhibitor, e.g., one or more of GATA3 inhibitors described herein. In other embodiments, the subject with high GATA3 expression (e.g., a subject having a breast cancer or neuroblastoma with high GATA3 expression) is treated with a GATA3 inhibitor, e.g., one or more of GATA3 inhibitors described herein.

In certain embodiments, the target is ARID1B. In some embodiments, the subject has a cancer, e.g., a cancer as described in Table 1 or 2. In some embodiments, the subject has or is identified as having an ARID1A mutation, e.g., in reference to a control, e.g., a normal, subject. In some embodiments, the subject has a cancer, which has or is identified as having an ARID1A mutation, e.g., in reference to a control, e.g., a normal, subject. In other embodiments, the subject with an ARID1A mutation (e.g., a cancer with an ARID1A mutation) is selected for treatment with an ARID1B inhibitor, e.g., one or more of ARID1B inhibitors described herein. In other embodiments, the subject with an ARID1A mutation (e.g., a subject having a cancer with an ARID1A mutation) is treated with an ARID1B inhibitor, e.g., one or more of ARID1B inhibitors described herein.

In certain embodiments, the target is PRKRA. In some embodiments, the subject has a cancer, e.g., a cancer as described in Table 1 or 2. In some embodiments, the subject has or is identified as having EIF2AK2 expression. In some embodiments, the subject has or is identified as having high EIF2AK2 expression, e.g., in reference to a control, e.g., a normal, subject. In some embodiments, the subject has a cancer, which has or is identified as having high PRKRA expression, e.g., in reference to a control, e.g., a normal, subject. In other embodiments, the subject with high EIF2AK2 expression (e.g., a cancer with high EIF2AK2 expression) is selected for treatment with a PRKRA inhibitor, e.g., one or more of PRKRA inhibitors described herein. In other embodiments, the subject with high EIF2AK2 expression (e.g., a subject having a cancer with high EIF2AK2 expression) is treated with a PRKRA inhibitor, e.g., one or more of PRKRA inhibitors described herein.

In certain embodiments, the target is HSPA8. In some embodiments, the subject has a cancer, e.g., a cancer as described in Table 1 or 2. In one embodiment, the subject has a colorectal cancer (CRC) or skin cancer. In some embodiments, the subject has or is identified as having HSP1A1 expression. In some embodiments, the subject has or is identified as having low HSP1A1 expression, e.g., in reference to a control, e.g., a normal, subject. In some embodiments, the subject has a colorectal cancer (CRC) or skin cancer, which cancer has or is identified as having low HSP1A1 expression, e.g., in reference to a control, e.g., a normal, subject. In other embodiments, the subject with low HSP1A1 expression (e.g., a colorectal cancer (CRC) or skin cancer with low HSP1A1 expression) is selected for treatment with a HSPA8 inhibitor, e.g., one or more of HSPA8 inhibitors described herein. In other embodiments, the subject with low HSP1A1 expression (e.g., a subject having a colorectal cancer (CRC) or skin cancer with low HSP1A1 expression) is treated with a HSPA8 inhibitor, e.g., one or more of HSPA8 inhibitors described herein.

In certain embodiments, the target is IRF4. In some embodiments, the subject has a cancer, e.g., a cancer as described in Table 1 or 2. In one embodiment, the subject has multiple myeloma (MM). In some embodiments, the subject has or is identified as having IRF4 expression. In some embodiments, the subject has or is identified as having high IRF4 expression, e.g., in reference to a control, e.g., a normal, subject. In some embodiments, the subject has multiple myeloma (MM), which cancer has or is identified as having high IRF4 expression, e.g., in reference to a control, e.g., a normal, subject. In other embodiments, the subject with high IRF4 expression (e.g., multiple myeloma (MM) with high IRF4 expression) is selected for treatment with an IRF4 inhibitor, e.g., one or more of IRF4 inhibitors described herein. In other embodiments, the subject with high IRF4 expression (e.g., a subject having multiple myeloma (MM) with high IRF4 expression) is treated with an IRF4 inhibitor, e.g., one or more of IRF4 inhibitors described herein.

In certain embodiments, the target is SPI1. In some embodiments, the subject has a cancer, e.g., a cancer as described in Table 1 or 2. In one embodiment, the subject has a hematopoietic cancer, (e.g., AML or ALL). In some embodiments, the subject has or is identified as having SPI1 expression. In some embodiments, the subject has or is identified as having high SPI1 expression, e.g., in reference to a control, e.g., a normal, subject. In some embodiments, the subject has a hematopoietic cancer, (e.g., AML or ALL), which cancer has or is identified as having high SPI1 expression, e.g., in reference to a control, e.g., a normal, subject. In other embodiments, the subject with high SPI1 expression (e.g., a hematopoietic cancer, (e.g., AML or ALL), with high SPI1 expression) is selected for treatment with a SPI1 inhibitor, e.g., one or more of SPI1 inhibitors described herein. In other embodiments, the subject with high SPI1 expression (e.g., a subject having a hematopoietic cancer, (e.g., AML or ALL) with high SPI1 expression) is treated with a SPI1 inhibitor, e.g., one or more of SPI1 inhibitors described herein.

In certain embodiments, the target is MTHFD1. In some embodiments, the subject has a cancer, e.g., a cancer as described in Table 1 or 2. In one embodiment, the subject has a breast cancer, colorectal cancer, lung cancer, pancreatic cancer or hematopoietic cancer (e.g., AML or ALL). In some embodiments, the subject has or is identified as having MTHFD1 expression. In some embodiments, the subject has or is identified as having high MTHFD1 expression, e.g., in reference to a control, e.g., a normal, subject. In some embodiments, the subject has a breast cancer, colorectal cancer, lung cancer, pancreatic cancer or hematopoietic cancer (e.g., AML or ALL), which cancer has or is identified as having high MTHFD1 expression, e.g., in reference to a control, e.g., a normal, subject. In other embodiments, the subject with high MTHFD1 expression (e.g., has a breast cancer, colorectal cancer, lung cancer, pancreatic cancer or hematopoietic cancer (e.g., AML or ALL), with high MTHFD1 expression) is selected for treatment with a MTHFD1 modulator, e.g., an MTHFD1 inhibitor, e.g., one or more of MTHFD1 inhibitors described herein. In other embodiments, the subject with high MTHFD1 expression (e.g., a subject having a breast cancer, colorectal cancer, lung cancer, pancreatic cancer or hematopoietic cancer (e.g., AML or ALL) with high MTHFD1 expression) is treated with a MTHFD1 modulator, e.g., an MTHFD1 inhibitor, e.g., one or more of MTHFD1 inhibitors described herein.

In some embodiments, the subject has or is identified as having low MTHFD1 expression, e.g., in reference to a control, e.g., a normal, subject. In some embodiments, the subject has a breast cancer, colorectal cancer, lung cancer, pancreatic cancer or hematopoietic cancer (e.g., AML or ALL), which cancer has or is identified as having low MTHFD1 expression, e.g., in reference to a control, e.g., a normal, subject. In other embodiments, the subject with low MTHFD1 expression (e.g., has a breast cancer, colorectal cancer, lung cancer, pancreatic cancer or hematopoietic cancer (e.g., AML or ALL), with low MTHFD1 expression) is selected for treatment with a MTHFD1 modulator, e.g., an MTHFD1 agonist, e.g., one or more MTHFD1 agonists described herein. In other embodiments, the subject with low MTHFD1 expression (e.g., a subject having a breast cancer, colorectal cancer, lung cancer, pancreatic cancer or hematopoietic cancer (e.g., AML or ALL) with low MTHFD1 expression) is treated with a MTHFD1 modulator, e.g., an MTHFD1 agonist, e.g., one or more MTHFD1 agonists described herein.

In certain embodiments, the target is ADAR. In some embodiments, the subject has a cancer, e.g., a cancer as described in Table 1 or 2. In one embodiment, the subject has a breast cancer, a lung cancer, an esophageal cancer, an upper aerodigestive cancer, a pancreatic cancer or a skin cancer. In some embodiments, the subject has or is identified as being positive for interferon stimulated gene (ISG) signature, e.g., in reference to a control, e.g., a normal, subject. In some embodiments, the subject has a breast cancer, a lung cancer, an esophageal cancer, an upper aerodigestive cancer, a pancreatic cancer or a skin cancer, which cancer has or is identified as being positive for interferon stimulated gene (ISG) signature, e.g., in reference to a control, e.g., a normal, subject. In other embodiments, the subject is positive for interferon stimulated gene (ISG) signature (e.g., a breast cancer, a lung cancer, an esophageal cancer, an upper aerodigestive cancer, a pancreatic cancer or a skin cancer positive for interferon stimulated gene (ISG) signature) and is selected for treatment with an ADAR inhibitor, e.g., one or more of ADAR inhibitors described herein. In other embodiments, the subject is positive for interferon stimulated gene (ISG) signature (e.g., a subject having a breast cancer, a lung cancer, an esophageal cancer, an upper aerodigestive cancer, a pancreatic cancer or a skin cancer positive for interferon stimulated gene (ISG) signature) and is treated with an ADAR inhibitor, e.g., one or more of ADAR inhibitors described herein.

In certain embodiments, the target is NFE2L2. In some embodiments, the subject has a cancer, e.g., a cancer as described in Table 1 or 2. In one embodiment, the subject has a lung cancer, an esophageal cancer or a kidney cancer. In some embodiments, the subject has or is identified as having a KEAP1 mutation, an NFE2L2 mutation, high SQSTM1 expression, or positive for an NFE2L2 gene signature, e.g., in reference to a control, e.g., a normal, subject. In some embodiments, the subject has a lung cancer, an esophageal cancer or a kidney cancer, which cancer has or is identified as having a KEAP1 mutation, an NFE2L2 mutation, high SQSTM1 expression, or positive for an NFE2L2 gene signature, e.g., in reference to a control, e.g., a normal, subject. In other embodiments, the subject having a KEAP1 mutation, an NFE2L2 mutation, high SQSTM1 expression, or positive for an NFE2L2 gene signature (e.g., a lung cancer, an esophageal cancer or a kidney cancer having a KEAP1 mutation, an NFE2L2 mutation, high SQSTM1 expression, or positive for an NFE2L2 gene signature) is selected for treatment with an NFE2L2 inhibitor, e.g., one or more of NFE2L2 inhibitors described herein. In other embodiments, the subject with high NFE2L2 expression (e.g., a subject having a lung cancer, an esophageal cancer or a kidney cancer having a KEAP1 mutation, an NFE2L2 mutation, high SQSTM1 expression or positive for an NFE2L2 gene signature) is treated with an NFE2L2 inhibitor, e.g., one or more of NFE2L2 inhibitors described herein.

Definitions

A "mutant," or "mutation" is any change in DNA or protein sequence that deviates from wild type sequence of the target, e.g., a target disclosed herein. This includes without limitation; single base nucleic acid changes or single amino acid changes, insertions, deletions and truncations of the wild type target gene (including all of its splice forms (i.e., transcript variants)) and its corresponding protein.

The term "inhibitor" refers to any compound capable of inhibiting the expression or activity of a target, e.g., a target disclosed in Tables 1 or 2, that is to say, in particular, any compound inhibiting the transcription of the gene, the maturation of RNA, the translation of mRNA, the posttranslational modification of the protein, the enzymatic activity of the protein, the interaction of same with a substrate, etc. The term also refers to any agent that inhibits or abrogates the normal cellular function of the target protein, either by ATP-competitive inhibition of the active site, allosteric modulation of the protein structure, disruption of protein-protein interactions, or by inhibiting the transcription, translation, or stability of the protein.

The term "antibody" or "antibody to a target" and the like as used herein refers to whole antibodies that interact with (e.g., by binding, steric hindrance, stabilizing/destabilizing, spatial distribution) a target epitope and inhibit signal transduction. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelised antibodies, or chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively. In particular, the term "antibody" specifically includes an IgG-scFv format.

The term "epitope binding domain" or "EBD" refers to portions of a binding molecule (e.g., an antibody or epitope-binding fragment or derivative thereof), that specifically interacts with (e.g., by binding, steric hindrance, stabilizing/destabilizing, spatial distribution) a binding site on a target epitope. EBD also refers to one or more fragments of an antibody that retain the ability to specifically interact with (e.g., by binding, steric hindrance, stabilizing/destabilizing, spatial distribution) a target epitope and inhibit signal transduction. Examples of antibody fragments include, but are not limited to, an scFv, a Fab fragment, a monovalent fragment consisting of the VL, VH, CL and CH1 domains; a F(ab).sub.2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR).

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883).

Such single chain antibodies are also intended to be encompassed within the terms "fragment", "epitope-binding fragment" or "antibody fragment". These fragments are obtained using conventional techniques known to those of skill in the art, and the fragments are screened for utility in the same manner as are intact antibodies.

As used herein, the term "Affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity. As used herein, the term "high affinity" for an IgG antibody or fragment thereof (e.g., a Fab fragment) refers to an antibody having a KD of $10^{-8}$ M or less, $10^{-9}$ M or less, or $10^{-10}$ M, or $10^{-10}$ M or less, or $10^{-11}$ M or less, or $10^{-12}$ M or less, or $10^{-13}$ M or less for a target antigen. However, high affinity binding can vary for other antibody isotypes. For example, high affinity binding for an IgM isotype refers to an antibody having a KD of $10^{-7}$ M or less, or $10^{-8}$ M or less.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

As used in the specification and claims, the singular forms "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely examples and that equivalents of such are known in the art.

As used herein the term "amino acid" refers to either natural and/or unnatural or synthetic amino acids, and both the D and L optical isomers, amino acid analogs, and peptidomimetics. A peptide of three or more amino acids is commonly called an oligopeptide if the peptide chain is short. If the peptide chain is long, the peptide is commonly called a polypeptide or a protein. The terms "biomarker" or "marker" are used interchangeably herein. A biomarker is a nucleic acid or polypeptide and the presence or absence of a mutation or differential expression of the polypeptide is used to determine sensitivity to any target inhibitor. For example, a target, e.g., a target disclosed in Tables 1 or 2, is a biomarker in a cancer cell when it is deficient, mutated, deleted, or decreased in post-translational modification, production, expression, level, stability and/or activity, as compared to the target in normal (non-cancerous) cell or control cell.

The term "cDNA" refers to complementary DNA, i.e. mRNA molecules present in a cell or organism made into cDNA with an enzyme such as reverse transcriptase. A "cDNA library" is a collection of all of the mRNA molecules present in a cell or organism, all turned into cDNA molecules with the enzyme reverse transcriptase, then inserted into "vectors" (other DNA molecules that can continue to replicate after addition of foreign DNA). Example vectors for libraries include bacteriophage (also known as "phage"), viruses that infect bacteria, for example, lambda phage. The library can then be probed for the specific cDNA (and thus mRNA) of interest.

The term "cell proliferative disorders" shall include dysregulation of normal physiological function characterized by abnormal cell growth and/or division or loss of function. Examples of "cell proliferative disorders" include but are not limited to hyperplasia, neoplasia, metaplasia, and various autoimmune disorders, e.g., those characterized by the dysregulation of T cell apoptosis.

"Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the present invention and a combination partner, are both administered to a patient simultaneously in the form of a single entity or dosage. The term "non-fixed combination" means that the active ingredients, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

A "gene" refers to a polynucleotide containing at least one open reading frame (ORF) that is capable of encoding a particular polypeptide or protein after being transcribed and translated. A polynucleotide sequence can be used to identify larger fragments or full-length coding sequences of the gene with which they are associated. Methods of isolating larger fragment sequences are known to those of skill in the art.

"Gene expression" or alternatively a "gene product" refers to the nucleic acids or amino acids (e.g., peptide or polypeptide) generated when a gene is transcribed and translated. As used herein, "expression" refers to the process by which DNA is transcribed into mRNA and/or the process by which the transcribed mRNA is subsequently translated into peptides, polypeptides or proteins. If the polynucleotide is derived from genomic DNA, expression may include splicing of the mRNA in a eukaryotic cell.

"Differentially expressed" as applied to a gene, refers to the differential production of the mRNA transcribed and/or translated from the gene or the protein product encoded by the gene. A differentially expressed gene may be overexpressed or underexpressed as compared to the expression level of a normal or control cell. However, as used herein, overexpression is an increase in gene expression and generally is at least 1.25 fold or, alternatively, at least 1.5 fold or, alternatively, at least 2 fold, or alternatively, at least 3 fold or alternatively, at least 4 fold expression over that detected in a normal or control counterpart cell or tissue. As used herein, underexpression, is a reduction of gene expression and generally is at least 1.25 fold, or alternatively, at least 1.5 fold, or alternatively, at least 2 fold or alternatively, at least 3 fold or alternatively, at least 4 fold expression under that detected in a normal or control counterpart cell or tissue. The term "differentially expressed" also refers to where expression in a cancer cell or cancerous tissue is detected but expression in a control cell or normal tissue (e.g. non-cancerous cell or tissue) is undetectable.

A high expression level of the gene can occur because of over expression of the gene or an increase in gene copy number. The gene can also be translated into increased protein levels because of deregulation or absence of a negative regulator. Lastly, high expression of the gene can occur due to increased stabilization or reduced degradation of the protein, resulting in accumulation of the protein.

A "gene expression profile" or "gene signature" refers to a pattern of expression of at least one biomarker that recurs in multiple samples and reflects a property shared by those samples, such as mutation, response to a particular treatment, or activation of a particular biological process or pathway in the cells. A gene expression profile differentiates between samples that share that common property and those that do not with better accuracy than would likely be achieved by assigning the samples to the two groups at random. A gene expression profile may be used to predict whether samples of unknown status share that common property or not. Some variation between the biomarker(s) and the typical profile is to be expected, but the overall similarity of biomarker(s) to the typical profile is such that it is statistically unlikely that the similarity would be observed by chance in samples not sharing the common property that the biomarker(s) reflects.

As used herein, the term "inhibit", "inhibiting", or "inhibit the growth" or "inhibiting the proliferation" of a cancer cell refers to slowing, interrupting, arresting or stopping the growth of the cancer cell, and does not necessarily indicate a total elimination of the cancer cell growth. The terms "inhibit" and "inhibiting", or the like, denote quantitative differences between two states, refer to at least statistically significant differences between the two states. For example, "an amount effective to inhibit growth of cancer cells" means that the rate of growth of the cells will be at least statistically significantly different from the untreated cells. Such terms are applied herein to, for example, rates of cell proliferation.

The term "isolated" means separated from constituents, cellular and otherwise, in which the polynucleotide, peptide, polypeptide, protein, antibody or fragment(s) thereof, are normally associated with in nature. For example, an isolated polynucleotide is separated from the 3' and 5' contiguous nucleotides with which it is normally associated within its native or natural environment, e.g., on the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated," "separated" or "diluted" polynucleotide, peptide, polypeptide, protein, antibody or fragment(s) thereof, is distinguishable from its naturally occurring counterpart in that the concentration or number of molecules per volume is greater in a "concentrated" version or less than in a "separated" version than that of its naturally occurring counterpart.

The term "immunoconjugate" or "antibody drug conjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the immunoconjugate. Additionally, the immunoconjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "cytotoxin", or "cytotoxic agent" as used herein, refers to any agent that is detrimental to the growth and proliferation of cells and may act to reduce, inhibit, or destroy a cell or malignancy.

The term "drug moiety" or "payload" as used herein refers to a chemical moiety that is conjugated to an antibody or antigen binding fragment of the invention, and can include any therapeutic or diagnostic agent, for example, an anti-cancer, anti-inflammatory, anti-infective (e.g., anti-fungal, antibacterial, anti-parasitic, anti-viral), or an anesthetic agent. For example, the drug moiety can be an anti-cancer agent, such as a cytotoxin. In certain embodiments, a drug moiety is selected from a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Methods for attaching each of these to a linker compatible with the antibodies and method of the invention are known in the art. See, e.g., Singh et al., (2009) Therapeutic Antibodies: Methods and Protocols, vol. 525, 445-457. In addition, a payload can be a biophysical probe, a fluorophore, a spin label, an infrared probe, an affinity probe, a chelator, a spectroscopic probe, a radioactive probe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide.

As used herein, the terms "neoplastic cells," "neoplastic disease," "neoplasia," "tumor," "tumor cells," "cancer," and "cancer cells," (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign. A "metastatic cell or tissue" means that the cell can invade and destroy neighboring body structures.

A cancer that has "defective mismatch repair" (dMMR) or "dMMR character" includes cancer types associated with documented MLH1, PMS2, MSH2, MSH3, MSH6, MLH3, and PMS1 mutations, microsatellite fragile sites, or other gene inactivation mechanisms, including but not limited to cancers of the lung, breast, kidney, large intestine, ovary, prostate, upper aerodigestive tract, stomach, endometrium, liver, pancreas, haematopoietic and lymphoid tissue, skin, thyroid, pleura, autonomic ganglia, central nervous system, soft tissue, pediatric rhabdoid sarcomas, melanomas and other cancers. A cell or cancer with "defective" mismatch repair has a significantly reduced (e.g., at least about 25%, 30%, 40%, 50%, 60%, 70%, 80% or 90% decrease) in the amount of mismatch repair. In some cases, a cell or cancer which is defective in mismatch repair will perform no mismatch repair.

The term "PBMC" refers to peripheral blood mononuclear cells and includes "PBL"-peripheral blood lymphocytes.

The terms "nucleic acid" and "polynucleotide" are used interchangeably and refer to a polymeric form of nucleotides of any length, either deoxyribonucleotides or ribonucleotides or analogs thereof. Polynucleotides can have any three-dimensional structure and can perform any function. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, siRNAs, shRNAs, RNAi agents, and primers. A polynucleotide can be modified or substituted at one or more base, sugar and/or phosphate, with any of various modifications or substitutions described herein or known in the art. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

The term "polypeptide" is used interchangeably with the term "protein" and in its broadest sense refers to a compound of two or more subunit amino acids, amino acid analogs, or peptidomimetics. The subunits can be linked by peptide bonds. In another embodiment, the subunit may be linked by other bonds, e.g., ester, ether, etc.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is a short polynucleotide, generally with a free 3'—OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in PCR: A Practical Approach, M. MacPherson et al., IRL Press at Oxford University Press (1991). All processes of producing replicate copies of a polynucleotide, such as PCR or gene cloning, are collectively referred to herein as "replication." A primer can also be used as a probe in hybridization reactions, such as Southern or Northern blot analyses (Sambrook et al., Molecular Cloning: A Laboratory Manual, 2nd edition (1989)).

A polynucleotide or polynucleotide region (or a polypeptide or polypeptide region) has a certain percentage (for example, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Current Protocols in Molecular Biology, Ausubel et al., eds., (1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cut-off=60; expect=10; Matrix=BLOSUM62; Descriptions=50 sequences; sort by=HIGH SCORE; Databases=non-redundant.

A cell is "sensitive," displays "sensitivity" for inhibition, or is "amenable to treatment" with an inhibitor, e.g., an inhibitor to any of the targets disclosed in Tables 1 or 2, when the cell viability is reduced and/or the rate of cell proliferation is reduced upon treatment with an inhibitor, e.g., an inhibitor to any of the targets disclosed in Tables 1 or 2, when compared to an untreated control.

As used herein, "solid phase support" or "solid support," used interchangeably, is not limited to a specific type of support. Rather a large number of supports are available and are known to one of ordinary skill in the art. Solid phase supports include silica gels, resins, derivatized plastic films, glass beads, plastic beads, alumina gels, microarrays, and chips. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories), polyHIPE(R)™ resin (obtained from Aminotech, Canada), polyamide resin (obtained from Peninsula Laboratories), polystyrene resin grafted with polyethylene glycol (TentaGelR™, Rapp Polymere, Tubingen, Germany), or polydimethylacrylamide resin (obtained from Milligen/Biosearch, California).

A polynucleotide also can be attached to a solid support for use in high throughput screening assays. PCT WO 97/10365, for example, discloses the construction of high density oligonucleotide chips. See also, U.S. Pat. Nos. 5,405,783; 5,412,087 and 5,445,934. Using this method, the probes are synthesized on a derivatized glass surface to form chip arrays. Photoprotected nucleoside phosphoramidites are coupled to the glass surface, selectively deprotected by photolysis through a photolithographic mask and reacted with a second protected nucleoside phosphoramidite. The coupling/deprotection process is repeated until the desired probe is complete.

As an example, transcriptional activity can be assessed by measuring levels of messenger RNA using a gene chip such as the Affymetrix® HG-U133-Plus-2 GeneChips (Affymetrix, Santa Clara, Calif.). High-throughput, real-time quantitation of RNA of a large number of genes of interest thus becomes possible in a reproducible system.

The terms "stringent hybridization conditions" refers to conditions under which a nucleic acid probe will specifically hybridize to its target subsequence, and to no other sequences. The conditions determining the stringency of hybridization include: temperature, ionic strength, and the concentration of denaturing agents such as formamide. Varying one of these factors may influence another factor and one of skill in the art will appreciate changes in the conditions to maintain the desired level of stringency. An example of a highly stringent hybridization is: 0.015M sodium chloride, 0.0015M sodium citrate at 65-68° C. or 0.015M sodium chloride, 0.0015M sodium citrate, and 50% formamide at 42° C. An example of a "moderately stringent" hybridization is the conditions of: 0.015M sodium chloride, 0.0015M sodium citrate at 50-65° C. or 0.015M sodium chloride, 0.0015M sodium citrate, and 20% formamide at 37-50° C. The moderately stringent conditions are used when a moderate amount of nucleic acid mismatch is desired. One of skill in the art will appreciate that washing is part of the hybridization conditions. For example, washing conditions can include 02.x-0.1×SSC/0.1% SDS and temperatures from 42-68° C., wherein increasing temperature increases the stringency of the wash conditions.

When hybridization occurs in an antiparallel configuration between two single-stranded polynucleotides, the reaction is called "annealing" and those polynucleotides are described as "complementary." A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

"Suppressing" or "suppression" of tumor growth indicates a reduction in tumor cell growth when contacted with an inhibitor, e.g., an inhibitor of any of the targets disclosed in Tables 1 or 2, compared to tumor growth without contact with an inhibitor compound. Tumor cell growth can be assessed by any means known in the art, including, but not limited to, measuring tumor size, determining whether tumor cells are proliferating using a 3H-thymidine incorporation assay, measuring glucose uptake by FDG-PET (fluorodeoxyglucose positron emission tomography) imaging, or counting tumor cells. "Suppressing" tumor cell growth means any or all of the following states: slowing, delaying and stopping tumor growth, as well as tumor shrinkage. A "subject," "individual" or "patient" is used interchangeably herein, which refers to a vertebrate, preferably a mammal, more preferably a human. Mammals include, but are not limited to, mice, simians, humans, farm animals, sport animals, and pets.

The terms "synthetic lethality," and "synthetic lethal" are used to refer to a combination of mutations or approaches to cause loss of function (e.g., RNA interference) in two or more genes leads to reduced cell viability and/or a reduced rate of cell proliferation, whereas a mutation in only one of these genes does not.

As described further herein, a cancer cell, a cancer type, or a subject afflicted with a cancer, is "inhibitor sensitive," "sensitive to treatment with an inhibitor," "sensitive to therapeutic inhibition," or described in similar terms if it is amenable to treatment with an inhibitor for the target, e.g., due to a genetic alteration, or expression or activity level of the target or a target-associated molecule.

A "control cell," "normal cell" or "wild-type" refers to non-cancerous tissue or cells.

A "control tissue," "normal tissue" or "wild-type" refers to non-cancerous tissue or cells.

Other features, objects, and advantages of the invention will be apparent from the description and drawings, and from the claims.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

BRIEF DESCRIPTION OF THE DRAWINGS

FIGS. 1A-1D depicts project DRIVE informatics and outlier analysis. FIG. 1A shows project DRIVE screening and analytical workflow. 2-week pooled shRNA viability screens were followed by an NGS readout and shRNA gene-level aggregation by two complimentary methods, RSA and ATARiS. Feature correlation was performed using k-means clustering (k=3) to identify sensitive and insensitive populations with resulting display of top sensitivity correlations. KRAS example is shown. FIGS. 1B-1, 1B-2 and 1B-3 show DRIVE gene activity categorization into inert, active or essential profiles. Essential gene dependency correlations include self-CN/expr and AGO2 CN/expr correlations. RSA waterfall plot for PHF5A. RSA sensitivity cutoff shown at −3 indicates that this is an essential gene in most lines tested. PSMC5 RSA sensitivity plotted against AGO2 CN and by AGO2 expression. FIG. 1C shows normality LRT compares the fit of a skewed student-t distribution and a normal distribution. Profiles with better skewed Student-t distribution fit over normal have high NormLRT scores. FIG. 1D shows Top DRIVE Outliers by class colored by their presence in COSMIC. Non-COSMIC genes labeled and transcription factors shown as triangles.

FIG. 2A depicts ATARiS waterfall plots for top mutation driven dependencies, colored by their respective mutation status. FIG. 2B depicts self copy number/dependency Pearson correlation for each gene identifies amplified genetic drivers as well as CYCLOPS genes. Outliers shown in bold. Only CYCLOPS genes with a correlation >0.4 are listed. FIG. 2C depicts ATARiS profiles of CCNE1 (X axis) and CDK2 (Y axis) where each dot is a cell line colored by its CCNE1 copy number and sized by its CCNE1 expression. FIG. 2D depicts EGFR expression vs ligand AREG expression, colored by EGFR dependence as measured by ATARiS sensitivity score. P-value from Fisher exact test shown for upper right quadrant shows statistical significance for EGFR dependence with hi AREG and hi EGFR. FIG. 2E depicts E2F3 dependency (size) plotted with its copy number (X axis) and RB1 expression (Y axis). P-value from Fisher exact test shown for upper right and lower left quadrant shows statistical significance for E2F3 dependence with high E2F3 CN or low RB1 expression. FIG. 2F depicts KRAS dependency profile in Lung lineage colored by mutation status. On the right, KRAS mutant lung lines only are co-plotted with KRAS, NFE2L2 and SMARCA2 dependence, and by mutation/expression status of KEAP1 and SMARCA4.

FIG. 3 depicts URI1 DRIVE profile. URI1 Expression (X axis) is plotted compared to its Sensitivity Score (Y axis). Each dot represents a cell line colored by its AGO2 CN and sized by AGO2 expression.

FIG. 4A depicts self mRNA expression/dependency Pearson correlations for all genes in DRIVE are plotted. Outliers shown in bold. CYCLOPS shown in italics. FIG. 4B depicts ZEB1 expression vs CDH1 expression, colored by ZEB1 dependence. FIG. 4C depicts high level BCL2L1 expression (color) predicts its dependence (left waterfall). BCL2L1 dependence is also correlated with BCL2L15 expression (right waterfall). FIG. 4D depicts MPL dependence plotted versus expression, colored by hematopoietic subtypes or solid tumor cell line. FIG. 4E depicts dependence on individual D-type cyclins plotted versus expression.

FIG. 5A depicts ATARiS sensitivity score heatmap for each transcription factor outlier per lineage. Shading is representative of average TF activity across all cell lines of a given lineage. Whenever dendrograms are shown, a hierarchical clustering was used with Euclidean distance and average linkage. FIG. 5B depicts TF expression (X axis) plotted versus its dependency score (Y axis), colored by specific lineages or squamous histology. FIG. 5C depicts ATARiS sensitivity score heatmap for hematopoietic transcription factors. The hierarchical clustering results in subtype segregation (color side bar on top of dendrogram) based on functional activity of TFs.

FIG. 5D depicts breast lineage plotted at the cell line level with sensitivity scores for TFs and other outliers. Genes grouped by functional class and receptor expression for each models is shown at the bottom.

FIGS. 7A-7D depict synthetic lethal outlier class. FIG. 7A depicts vertical and parallel pathway lethality outliers with DRIVE outliers listed first and pathway predictors listed second. For vertical pathway examples, relationship is indicated by color. Example waterfall plots are colored by respective predictive feature. FIG. 7B depicts paralog outliers are either mutation driven or expression driven. Example waterfall plots are colored by respective predictive feature. FIG. 7C depicts collateral lethal outliers are listed with depiction of concept. Tumor suppressor (TS) deletion leads to collateral loss of nearby genes (B and Y) creating a dependency due to loss of B or Y. VPS4A ATARiS waterfall plot is shown, colored by VPS4B copy number. FIG. 7D depicts synthetic lethal outlier relationships identified in DRIVE associated with tumor suppressor alterations.

DETAILED DESCRIPTION

Figure 1A:
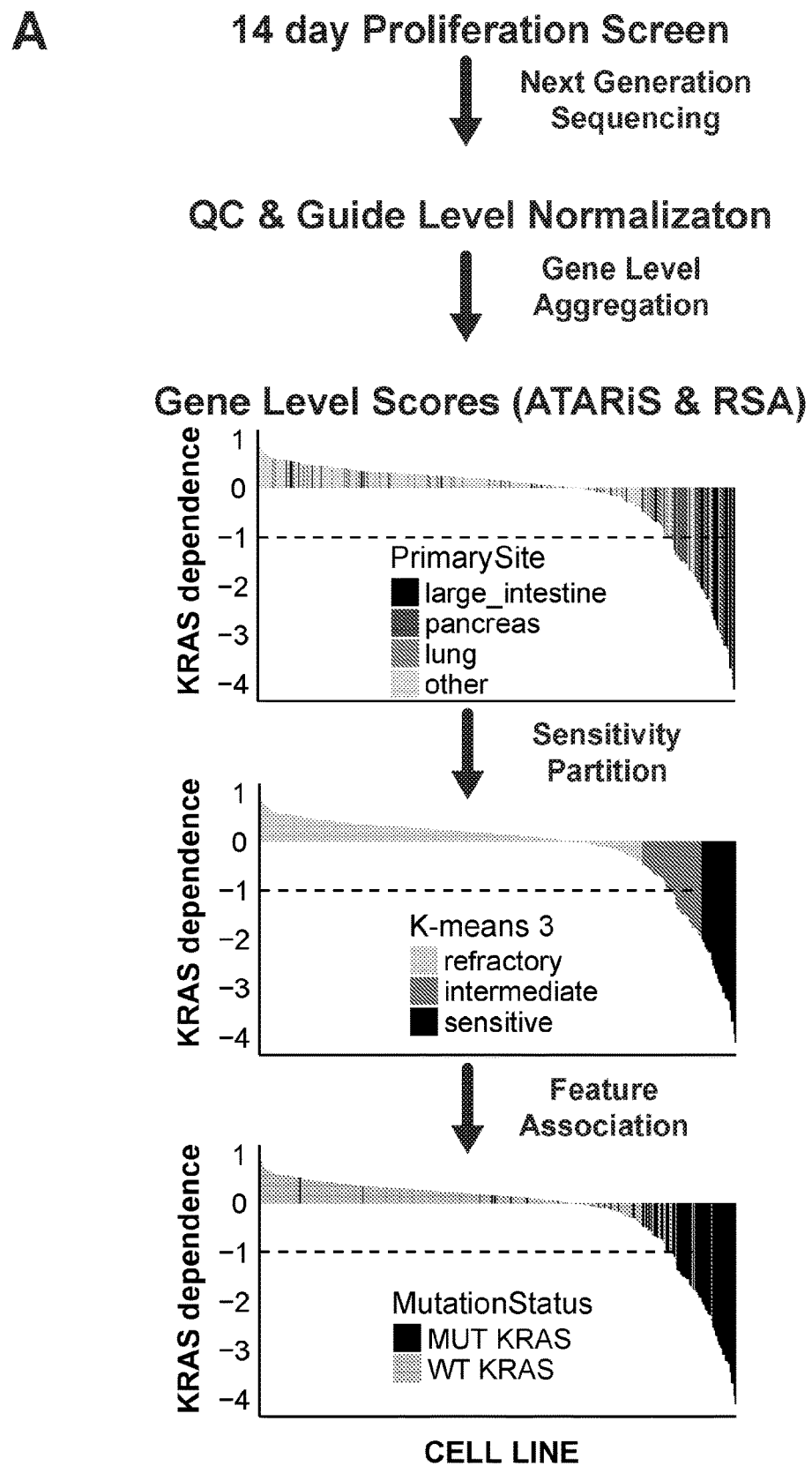

The present disclosure provides novel diagnostic methods and treatments for cancer patients by targeting gene expression or function of any of the targets disclosed in Tables 1 or 2. The present invention is based, in part, on the discovery that certain types of cancer cells are sensitive to inhibition of specific targets, e.g., cancers disclosed in Table 2 are sensitive to the inhibition of respective targets disclosed in Table 2.

TABLE 1

| | | | | | |
|---|---|---|---|---|---|
| List of 80 targets and associated cancer types | | | | | |
| No. | NCBI Gene ID | Gene Symbols | Norm LRT | Cosmic | Potential cancer types |
| 1 | 4893 | NRAS | 676.1693 | Cosmic | Across cancer types including skin, lung, and hematopoietic cancers |
| 2 | 1499 | CTNNB1 | 594.6094 | Cosmic | Across cancer types including colorectal cancer (CRC), stomach, and lung cancers |
| 3 | 6595 | SMARCA2 | 572.3442 | NA | Across cancer types including lung cancer |
| 4 | 673 | BRAF | 531.8816 | Cosmic | Across cancer types including skin, CRC, and thyroid cancers |
| 5 | 4286 | MITF | 448.6566 | Cosmic | Across cancer types including skin, and uveal cancers |
| 6 | 4602 | MYB | 428.5779 | Cosmic | Across cancer types including hematopoietic (ALL, AML), and CRC cancers |
| 7 | 3845 | KRAS | 422.8064 | Cosmic | Across cancer types including pancreatic, lung, and CRC cancers |
| 8 | 200916 | RPL22L1 | 402.6926 | NA | Across cancer types including CRC, endometrial, and stomach cancers |

TABLE 1-continued

List of 80 targets and associated cancer types

| No. | NCBI Gene ID | Gene Symbols | Norm LRT | Cosmic | Potential cancer types |
|---|---|---|---|---|---|
| 9 | 2313 | FLI1 | 374.0815 | Cosmic | Across cancer types including hematopoietic (ALL, AML, MM, DLBCL), and Ewing's sarcoma |
| 10 | 440 | ASNS | 364.8319 | NA | Across cancer types including breast, CRC, pancreatic, and skin cancers |
| 11 | 7486 | WRN | 355.5048 | Cosmic | Across cancer types including CRC, endometrial, and stomach cancers |
| 12 | 6663 | SOX10 | 332.1695 | NA | Across cancer types including melanoma (skin and uveal), and CNS cancers |
| 13 | 5832 | ALDH18A1 | 312.2923 | NA | Across cancer types including breast, lung, pancreatic, and skin cancers |
| 14 | 3169 | FOXA1 | 310.3314 | Cosmic | Across cancer types including breast, and prostate cancers |
| 15 | 6928 | HNF1B | 303.3582 | NA | Across cancer types including kidney, and lung cancers |
| 16 | 1019 | CDK4 | 299.0601 | Cosmic | Across cancer types including breast, lung, and skin cancers |
| 17 | 861 | RUNX1 | 250.8642 | Cosmic | Across cancer types including hematopoietic (ALL, AML) cancers |
| 18 | 7298 | TYMS | 242.6004 | NA | Across cancer types breast, CRC, lung, and pancreatic cancers |
| 19 | 6319 | SCD | 236.4781 | NA | Across cancer types including CRC, endometrium, and pancreatic cancers |
| 20 | 898 | CCNE1 | 222.976 | Cosmic | Across cancer types including breast, endometrial, lung, and ovarian cancers |
| 21 | 1956 | EGFR | 215.1623 | Cosmic | Across cancer types including bladder, CRC, lung, stomach, and upper aerodigestive cancers |
| 22 | 865 | CBFB | 214.1315 | Cosmic | Across cancer types including hematopoietic (ALL, AML) cancers |
| 23 | 5604 | MAP2K1 | 211.7167 | Cosmic | Across cancer types including CRC cancer |
| 24 | 8626 | TP63 | 208.5858 | NA | Across squamous cancer types bladder, esophageal and upper aerodigestive cancers |
| 25 | 2064 | ERBB2 | 202.7234 | Cosmic | Across cancer types including breast, CRC, stomach and esophageal cancers |
| 26 | 5291 | PIK3CB | 200.9034 | NA | Across cancer types including breast and CRC cancers |
| 27 | 4352 | MPL | 199.3918 | Cosmic | Across cancer types including AML |
| 28 | 4193 | MDM2 | 196.1677 | Cosmic | Across cancer types |
| 29 | 2263 | FGFR2 | 191.2429 | Cosmic | Across cancer types |
| 30 | 2322 | FLT3 | 181.9756 | Cosmic | Across cancer types including hematopoietic (ALL, AML) cancers |
| 31 | 5634 | PRPS2 | 180.3862 | NA | Across cancer types including breast, CRC, and lung cancers |

TABLE 1-continued

List of 80 targets and associated cancer types

| No. | NCBI Gene ID | Gene Symbols | Norm LRT | Cosmic | Potential cancer types |
|---|---|---|---|---|---|
| 32 | 5290 | PIK3CA | 174.7291 | Cosmic | Across cancer types breast, CRC and stomach cancers |
| 33 | 1017 | CDK2 | 174.3597 | NA | Across cancer types including breast, endometrial, lung and ovarian cancers |
| 34 | 27183 | VPS4A | 171.5517 | NA | Across cancer types including breast, CRC, lung, stomach, pancreatic and upper areodigestive cancers |
| 35 | 8682 | PEA15 | 171.2006 | NA | Across cancer types including skin cancer |
| 36 | 2099 | ESR1 | 169.9934 | Cosmic | Across cancer types including breast cancer |
| 37 | 10419 | PRMT5 | 167.0136 | NA | Across cancer types including but not restricted to bladder, CNS, AML, lung, pancreatic and skin |
| 38 | 1029 | CDKN2A | 165.5385 | Cosmic | N/A |
| 39 | 22937 | SCAP | 162.9848 | NA | Across cancer types including CRC, endometrial, esophageal, pancreatic and skin cancers |
| 40 | 896 | CCND3 | 162.8703 | Cosmic | Across cancer types including hematopoietic (ALL, DLBCL) and lung cancers |
| 41 | 6925 | TCF4 | 162.4801 | NA | Across cancer types including hematopoietic cancers and neuroblastoma |
| 42 | 7157 | TP53 | 162.0464 | Cosmic | N/A |
| 43 | 6390 | SDHB | 157.8968 | Cosmic | Across cancer types including breast, CRC, and lung cancers |
| 44 | 2879 | GPX4 | 156.6517 | NA | Across cancer types including CNS, kidney, AML, liver, lung, ovarian cancers and neuroblastoma |
| 45 | 1050 | CEBPA | 153.4186 | Cosmic | Across cancer types including liver cancer and AML |
| 46 | 468 | ATF4 | 151.9762 | NA | Across cancer types including breast, CRC, endometrial, pancreatic and skin cancers |
| 47 | 2625 | GATA3 | 150.1109 | Cosmic | Across cancer types including breast cancer and neuroblastoma |
| 48 | 10413 | YAP1 | 149.2448 | NA | Across cancer types including CRC, lung, stomach and ovarian cancers |
| 49 | 57492 | ARID1B | 144.0908 | Cosmic | Across cancer types |
| 50 | 55884 | WSB2 | 143.9142 | NA | Across cancer types |
| 51 | 8575 | PRKRA | 141.2148 | NA | Across cancer types including breast, CRC, lung, pancreatic, skin and upper aerodigestive cancers |
| 52 | 3480 | IGF1R | 140.2324 | NA | Across cancer types including CRC, lung cancer, multiple myeloma and neuroblastoma |
| 53 | 1854 | DUT | 139.924 | NA | Across cancer types including breast cancer |
| 54 | 3312 | HSPA8 | 137.9435 | NA | Across cancer types including CRC and skin cancer |

TABLE 1-continued

List of 80 targets and associated cancer types

| No. | NCBI Gene ID | Gene Symbols | Norm LRT | Cosmic | Potential cancer types |
|---|---|---|---|---|---|
| 55 | 4170 | MCL1 | 137.4848 | NA | Across cancer types including breast, CRC, hem, lung and skin cancers |
| 56 | 4194 | MDM4 | 137.1254 | Cosmic | Across cancer types including CRC, neuroblastoma and skin cancers |
| 57 | 7022 | TFAP2C | 135.1943 | NA | Across cancer types including breast, and skin cancers |
| 58 | 2771 | GNAI2 | 134.2611 | NA | Across cancer types including hematopoietic (AML, DLBCL) cancers |
| 59 | 378 | ARF4 | 131.6471 | NA | Across cancer types including breast, CRC, kidney, lung, pancreatic and skin cancers |
| 60 | 3662 | IRF4 | 130.6215 | Cosmic | Across cancer types including multiple myeloma |
| 61 | 6392 | SDHD | 129.2459 | Cosmic | Across cancer types including breast, and colon cancers |
| 62 | 1072 | CFL1 | 129.1845 | NA | Across cancer types including CRC, lung, esophageal, hematopoietic (AML, ALL, DLBCL) and ovarian cancers |
| 63 | 4976 | OPA1 | 127.2112 | NA | Across cancer types including breast, CRC, stomach and lung cancers |
| 64 | 6688 | SPI1 | 126.1878 | NA | Across cancer types including hematopoietic (ALL, AML) cancers |
| 65 | 4522 | MTHFD1 | 125.2011 | NA | Across cancer types including breast, CRC, lung, hematopoietic (AML, ALL) and pancreatic cancers |
| 66 | 6391 | SDHC | 123.664 | Cosmic | Across cancer types including breast cancer and CRC |
| 67 | 598 | BCL2L1 | 121.8786 | NA | Across cancer types |
| 68 | 8031 | NCOA4 | 121.4796 | Cosmic | Across cancer types including breast, CRC, endometrial and lung cancers |
| 69 | 6015 | RING1 | 121.3331 | NA | Across cancer types breast cancer and CRC |
| 70 | 3028 | HSD17B10 | 120.852 | NA | Across cancer types including CRC, stomach and Lung cancers |
| 71 | 103 | ADAR | 119.9291 | NA | Across cancer types including breast, lung, esophageal, upper aerodigestive, pancreatic and skin cancers |
| 72 | 22800 | RRAS2 | 116.2203 | NA | Across cancer types |
| 73 | 10972, 286102 | TMED10, TMED10P1 | 115.4564 | NA | Across cancer types including CNS, CRC, kidney, liver, ovarian and lung cancers |
| 74 | 156 | ADRBK1 | 115.115 | NA | Across cancer types including breast, CRC, lung, upper aerodigestive cancers |
| 75 | 498 | ATP5A1 | 114.2978 | NA | Across cancer types including CRC and lung cancers |
| 76 | 7013 | TERF1 | 114.0913 | NA | Across cancer types including uveal and skin melanoma |

TABLE 1-continued

List of 80 targets and associated cancer types

| No. | NCBI Gene ID | Gene Symbols | Norm LRT | Cosmic | Potential cancer types |
|---|---|---|---|---|---|
| 77 | 9361 | LONP1 | 114.0681 | NA | Across cancer types including breast, CRC, lung, esophageal, ovarian and upper aerodigestive cancers |
| 78 | 4780 | NFE2L2 | 113.9851 | Cosmic | Across cancer types including lung, esophageal and kidney cancers |
| 79 | 10979 | FERMT2 | 113.6685 | NA | Across cancer types including breast, CNS, kidney, liver, lung, esophageal, ovarian and skin cancers |
| 80 | 9948 | WDR1 | 112.5945 | NA | Across cancer types including CNS, CRC, lung, esophageal, neuroblastoma and ovarian cancers |

TABLE 2

List of 25 targets, molecular stratification and associated cancer types.

| No* | NCBI Gene ID | Gene Symbols | Norm LRT | COSMIC | Molecular Stratification based on DRIVE data | Potential Cancer types |
|---|---|---|---|---|---|---|
| 5 | 4286 | MITF | 448.6566 | COSMIC | Hi MITF expression | Across cancer types including skin, and uveal cancers |
| 6 | 4602 | MYB | 428.5779 | COSMIC | Hi MYB expression | Across cancer types including hematopoietic (ALL, AML), and CRC cancers |
| 9 | 2313 | FLI1 | 374.0815 | COSMIC | Hi FLI1 expression | Across cancer types including hematopoietic (ALL, AML, MM, DLBCL), and Ewing's sarcoma |
| 10 | 440 | ASNS | 364.8319 | NA | Unclear | Across cancer types including breast, CRC, pancreatic, and skin cancers |
| 11 | 7486 | WRN | 355.5048 | COSMIC | Microsatellite instable (MSI+) cancers | Across cancer types including CRC, endometrial, and stomach cancers |
| 12 | 6663 | SOX10 | 332.1695 | NA | Hi SOX10 expression | Across cancer types including melanoma (skin and uveal), and CNS cancers |
| 13 | 5832 | ALDH18A1 | 312.2923 | NA | Unclear | Across cancer types including breast, lung, pancreatic, and skin cancers |
| 14 | 3169 | FOXA1 | 310.3314 | COSMIC | Hi FOXA1 expression | Across cancer types including breast, and prostate cancers |
| 15 | 6928 | HNF1B | 303.3582 | NA | Hi HNF1B expression | Across cancer types including kidney and lung cancers |
| 17 | 861 | RUNX1 | 250.8642 | COSMIC | Hi RUNX1 expression | Across cancer types including hematopoietic (ALL, AML) cancers |

TABLE 2-continued

List of 25 targets, molecular stratification and associated cancer types.

| No* | NCBI Gene ID | Gene Symbols | Norm LRT | COSMIC | Molecular Stratification based on DRIVE data | Potential Cancer types |
|---|---|---|---|---|---|---|
| 22 | 865 | CBFB | 214.1315 | COSMIC | Hi RUNX1 expression or hi IKZF1 expression | Across cancer types including hematopoietic (ALL, AML) cancers |
| 24 | 8626 | TP63 | 208.5858 | NA | Hi TP63 expression | Across cancer types including squamous cancers, including bladder, esophageal and upper aerodigestive |
| 33 | 1017 | CDK2 | 174.3597 | NA | Hi CCNE1 expression or amplification | Across cancer types including breast, endometrial, lung, and ovarian cancers |
| 34 | 27183 | VPS4A | 171.5517 | NA | Copy number deletion of VPS4B | Across cancer types including breast, CRC, lung, stomach, pancreatic and upper areodigestive cancers |
| 41 | 6925 | TCF4 | 162.4801 | NA | Hi TCF4 expression | Across cancer types including hematopoietic cancers and neuroblastoma |
| 45 | 1050 | CEBPA | 153.4186 | COSMIC | Hi CEBPA expression | Across cancer types including liver cancer and AML |
| 47 | 2625 | GATA3 | 150.1109 | COSMIC | Hi GATA3 expression | Across cancer types including breast cancer and neuroblastoma |
| 49 | 57492 | ARID1B | 144.0908 | COSMIC | ARID1A Mutation | Across cancer types |
| 51 | 8575 | PRKRA | 141.2148 | NA | Hi EIF2AK2 expression | Across cancer types including breast, CRC, lung, pancreatic, skin and upper aerodigestive cancers |
| 54 | 3312 | HSPA8 | 137.9435 | NA | Low HSP1A1 expression | Across cancer types including CRC and skin cancer |
| 60 | 3662 | IRF4 | 130.6215 | COSMIC | Hi IRF4 Expression | Across cancer types including multiple myeloma |
| 64 | 6688 | SPI1 | 126.1878 | NA | Hi SPI1 expression | Across cancer types including hematopoietic (ALL, AML) cancers |
| 65 | 4522 | MTHFD1 | 125.2011 | NA | Unclear | Across cancer types including breast, CRC, lung, hematopoietic (AML, ALL), and pancreatic cancers |
| 71 | 103 | ADAR | 119.9291 | NA | Interferon stimulated gene (ISG) signature positive | Across cancer types including breast, lung, esophageal, upper aerodigestive, pancreatic and skin cancers |

TABLE 2-continued

List of 25 targets, molecular stratification and associated cancer types.

| No* | NCBI Gene ID | Gene Symbols | Norm LRT | COSMIC | Molecular Stratification based on DRIVE data | Potential Cancer types |
|---|---|---|---|---|---|---|
| 78 | 4780 | NFE2L2 | 113.9851 | COSMIC | KEAP1 mutation or NFE2L2 mutation; high SQSTM1 expression; NFE2L2 gene signature positive | Across cancer types including lung, esophageal and kidney cancers |

*Numbers corresponding to entry in Table 1
CRC = Colorectal Cancer;
ALL = Acute Lymphocytic Leukemia;
AML = Acute Myeloid Leukemia;
DLBCL = Diffuse Large B-Cell Lymphoma;
CNS = Central Nervous System;
MM = MultipleMyeloma In various aspects, the present disclosure provides a method for inhibiting proliferation of cancer cells in a subject, the method comprising the step of administering an inhibitor, e.g., an inhibitor of any of the targets disclosed in Tables 1 or 2, to a subject in need thereof, in an amount that is effective to inhibit proliferation of the cancer cells. In some embodiments, the cancer is a hematological cancer, solid tumor or any of the cancers disclosed in Tables 1 or 2. In some embodiments, the cancer is associated with microsatellite instability, gene amplifications, duplications, deletions or mutations. According to the present invention, an inhibitor is a therapeutic modality, including but not limited to, a low molecular weight compound, an RNA inhibitor (e.g., an RNAi agent), a CRISPR, a TALEN, a zinc finger nuclease, an mRNA, a miRNA, an antibody or derivative thereof, or a chimeric antigen receptor T cell (CART). Additionally, according to the present invention, an agonist is a therapeutic modality, including but not limited to, a low molecular weight compound, a small molecule, an mRNA, a miRNA, an antibody or derivative thereof, or a peptide mimetic or an analog.

The present disclosure further provides an inhibitor, e.g., an inhibitor of any of the targets disclosed in Tables 1 or 2, such as low molecular weight compound, an RNA inhibitor (e.g., an RNAi agent), a CRISPR, a TALEN, a zinc finger nuclease, an mRNA, a miRNA, an antibody or derivative thereof, or a chimeric antigen receptor T cell (CART), for use in the treatment of cancer, such as colon or endometrial cancer. Also provided is a use of an inhibitor, such as low molecular weight compound, an RNA inhibitor (e.g., an RNAi agent), a CRISPR, a TALEN, a zinc finger nuclease, an mRNA, a miRNA, an antibody or derivative thereof, or a chimeric antigen receptor T cell (CART), for the manufacture of a medicament for treating cancer, such as colon or endometrial cancer.

In one embodiment, the present invention provides a method of treating cancer associated with any of the targets disclosed in Tables 1 or 2, by administering to a subject in need thereof a therapeutically effective amount of a pharmaceutical composition comprising a molecule that reduces, e.g., inhibits the expression of a target, e.g., any of the targets disclosed in Tables 1 or 2, wherein said molecule is a low molecular weight compound.

The present disclosure further provides a low molecular weight compound for use in the treatment of cancer, e.g., any of the cancers disclosed in Tables 1 or 2. Also provided is a use of a low molecular weight compound for the manufacture of a medicament for treating cancer, e.g., any of the cancers disclosed in Tables 1 or 2.

In another embodiment, the present invention provides a method of treating cancer, e.g., any of the cancers disclosed in Tables 1 or 2, by administering to a subject in need thereof a therapeutically effective amount of a pharmaceutical composition comprising a molecule that inhibits the normal cellular function of the target protein, e.g., any of the inhibitors disclosed herein.

The present disclosure further provides a molecule that inhibits a normal cellular function of a target, e.g., a target protein for use in the treatment of cancer, such any of the cancers disclosed in Tables 1 or 2 Also provided is a use of a molecule that inhibits a normal cellular function of a target, e.g., a target protein for the manufacture of a medicament for treating cancer, such as any of the cancers disclosed in Tables 1 or 2.

In another embodiment, the present invention provides a method of treating cancer associated with microsatellite instability, gene amplifications, duplications, deletions or mutations, such any of the cancers disclosed in Tables 1 or 2, by administering to a subject in need thereof a therapeutically effective amount of a pharmaceutical composition comprising a molecule which inhibits the expression of a target, e.g., any of the targets disclosed in Tables 1 or 2, including, but not limited to, a low molecular weight compound, an RNA inhibitor (e.g., an RNAi agent), a CRISPR, a TALEN, a zinc finger nuclease, an mRNA, a miRNA, an antibody or derivative thereof, or a chimeric antigen receptor T cell (CART). Examples of such inhibitors are described herein.

In another embodiment, a molecule is disclosed which inhibits the expression of a target, e.g., any of the targets disclosed in Tables 1 or 2 for use in the treatment of cancer, such as any of the cancers disclosed in Tables 1 or 2. Such molecule includes, but is not limited to, a low molecular weight compound, an RNA inhibitor (e.g., an RNAi agent), a CRISPR, a TALEN, a zinc finger nuclease, an mRNA, a miRNA, an antibody or derivative thereof, or a chimeric antigen receptor T cell (CART). Examples of such inhibitors are described herein.

In another embodiment, the present invention provides a method of treating cancer associated with microsatellite instability, gene amplifications, duplications, deletions or mutations, such as any of the cancers disclosed in Tables 1 or 2, by administering to a subject in need thereof a therapeutically effective amount of a pharmaceutical composition comprising an inhibitor that inhibits the expression of a target, e.g., any of the target disclosed in Tables 1 or 2, wherein the inhibitor includes, but not limited to, a low molecular weight compound, an RNA inhibitor (e.g., an RNAi agent), a CRISPR, a TALEN, a zinc finger nuclease, an mRNA, a miRNA, an antibody or derivative thereof, or a chimeric antigen receptor T cell (CART). Examples of such antibodies or antibody derivatives are described herein.

The present disclosure further provides an RNA inhibitor (e.g., an RNAi agent), a CRISPR, a TALEN, a zinc finger nuclease, an mRNA, a miRNA, an antibody or derivative thereof, or a chimeric antigen receptor T cell (CART) for use in the treatment of cancer, such as any of the cancers disclosed in Tables 1 or 2. Also provided is a use of an RNA inhibitor (e.g., an RNAi agent), a CRISPR, a TALEN, a zinc finger nuclease, an mRNA, a miRNA, an antibody or derivative thereof, or a chimeric antigen receptor T cell (CART) for the manufacture of a medicament for treating cancer, such as any of the cancers disclosed in Tables 1 or 2.

Description of Targets and Exemplary Inhibitors

MITF

The term "MITF" as used herein refers to the gene or protein of "Microphthalmia-associated transcription factor". The term "MITF" includes mutants, fragments, variants, isoforms, and homologs of full-length wild-type MITF. In one embodiment, the protein is encoded by the MITF gene (Gene ID: 4286; Ensembl ID ENSG00000187098). Exemplary MITF sequences are available at the Uniprot database under the accession number O75030. MITF is a transcription factor involved in melanocyte cell development, and neoplasia (Cronin, *Julia* C. et al. Pigment cell & melanoma research 22.4 (2009): 435-444. PMC. Web. 30 Jun. 2017).

In some embodiments, the MITF inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In some embodiments, the MITF inhibitor is ML329, e.g., as disclosed in Faloon P W et al., 2012 Dec. 13, In: Probe Reports from the NIH Molecular Libraries Program [Internet]. ML329 is a MITF inhibitor with an IC50 of 1.2 µM. ML329 has the chemical name: 4-((1,4-dioxo-1,4-dihydronaphthalen-2-yl)amino)benzenesulfonamide, and has the following structure:

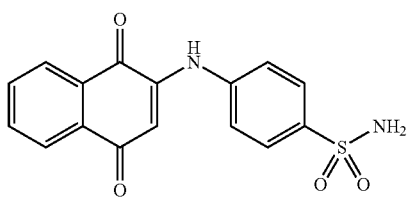

Chemical Structure
Molecular Weight: 328.342

In some embodiments, the MITF inhibitor is PIAS3 (protein inhibitor of activated STAT3) or an agonist for PIAS3 as disclosed in Levy C et al., Blood 2006 107:2839-2845. PIAS3 is an E3-type small ubiquitin-like modifier (SUMO) ligase.

MYB

The term "MYB" as used herein refers to the "Myeloblastosis" proto-oncogene gene or protein which is also known as "c-Myb". The term "MYB" includes mutants, fragments, variants, isoforms, and homologs of full-length wild-type MYB. In one embodiment, the protein is encoded by the MYB gene (Gene ID: 4602; Ensembl ID ENSG00000118513). Exemplary MYB sequences are available at the Uniprot database under the accession number P10242. MYB is a transcription factor involved in hematopoiesis and regulates the expression of genes involved in lineage determination, cell proliferation and differentiation. MYB has also been implicated in the development of leukemia (Uttarkar S. et al., 2016, Blood 3;127(9):1173-82).

In some embodiments, the MYB inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the MYB inhibitor is Celastrol, e.g., as disclosed in Uttarkar S. et al., 2016, Blood 3;127(9):1173-82. Celastrol is a triterpenoid and is also known as Tripterine. Celastrol has the chemical name 3-Hydroxy-9β,13a-dimethyl-2-oxo-24,25,26-trinoroleana-1(10),3,5,7-tetraen-29-oic acid, and the following chemical structure:

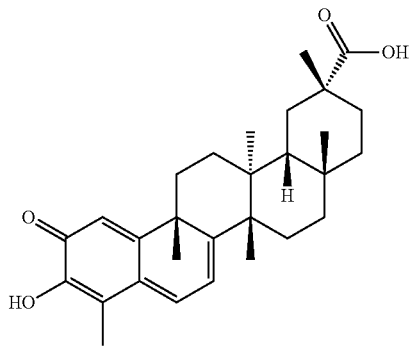

Chemical Structure
Molecular Weight: 450.62

In one embodiment, the MYB inhibitor is Mexicanin-I, e.g., as disclosed in Bujnicki T. et al., (2012) Leukemia 26, 615-622. Mexicanin-I is a sesquiterpene lactone. Mexicanin-I has the chemical name: (3as,4r,4ar,7ar,8r,9as)-4-hydroxy-4a,8-dimethyl-3-methylidene-3,3a,4,4a,7a,8,9,9a-octahydroazuleno[6,5-b]furan-2,5-dione, and the following chemical structure:

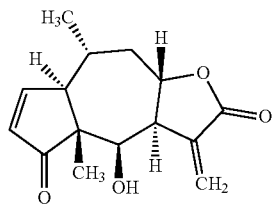

Chemical Structure
Molecular Weight: 262.305

FLI1

The term "FLI1" as used herein refers to the gene or protein of "Friend leukemia integration 1 transcription factor". FLI1 is also known as ERGB. The term "FLI1"

includes mutants, fragments, variants, isoforms, and homologs of full-length wild-type FLI1. In one embodiment, the protein is encoded by the FLI1 gene (Gene ID: 2313; Ensembl ID ENSG00000151702). Exemplary FLI1 sequences are available at the Uniprot database under the accession number Q01543. FLI1 is a transcription factor which is a member of the ETS transcription factor family (Truong A H L and Ben-David Y, (2000) Oncogene 19, 6482-6489).

In some embodiments, the FLI1 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment the FLI1 inhibitor is TK-216. TK-216 is a clinical derivative of YK-4-279 with an IC50 of 449 nM. TK-216 has the chemical name: 4,7-dichloro-1,3-dihydro-3-hydroxy-3-[2-(4-methoxyphenyl)-2-oxoethyl]-(3R)-2H-indol-2-one and has the following chemical structure:

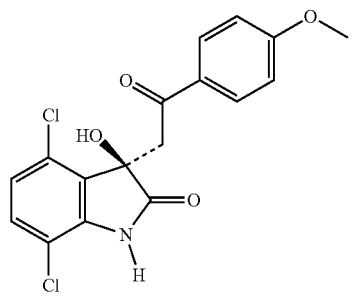

Chemical Structure
Molecular Weight: 366.2

In one embodiment, the FLI1 inhibitor is Mithramycin, e.g., as disclosed in Grohar P J et al., (2011) J. National Cancer Institute 102(12):962-78. Mithramycin is an RNA synthesis inhibitor and an anti-neoplastic antibiotic. Mithramycin has the chemical name: (1S)-5-deoxy-1-C-((2S,3S)-7-{[2,6-dideoxy-3-O-(2,6-dideoxy-β-D-arabino-hexopyranosyl)-β-D-arabino-hexopyranosyl]oxy}-3-{[2,6-dideoxy-3-C-methyl-β-D-ribo-hexopyranosyl-(1→3)-2,6-dideoxy-β-D-arabino-hexopyranosyl-(1→3)-2,6-dideoxy-β-D-arabino-hexopyranosyl]oxy}-5,10-dihydroxy-6-methyl-4-oxo-1,2,3,4-tetrahydroanthracen-2-yl)-1-O-methyl-D-xylulose, and the following chemical structure:

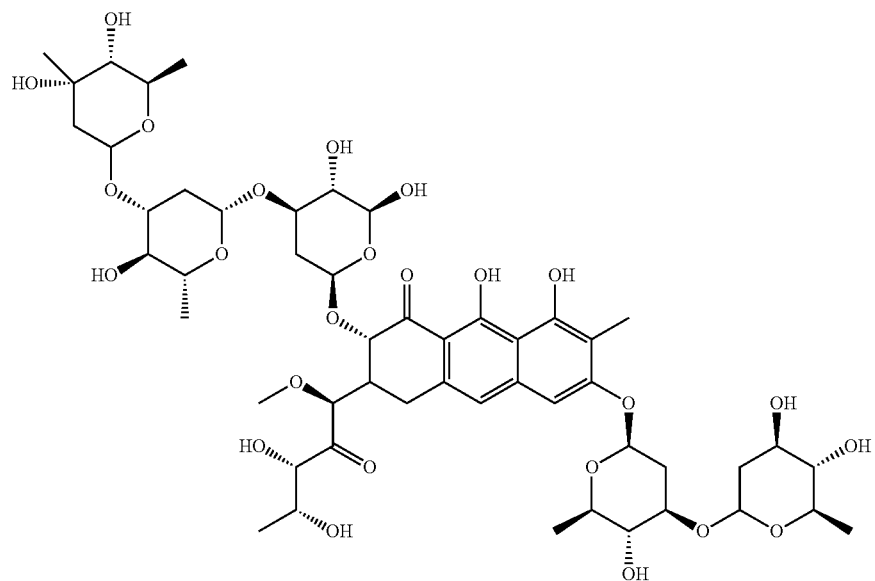

Chemical Structure
Molecular Weight: 1085.15

In one embodiment, the FL11 inhibitor is EC-8105, e.g., as disclosed in Osgood C L et al., (2016) Clinical Cancer Research 22(16) 4105-18. EC-8105 is a second-generation Mithramycin analogue. In one embodiment, the FL11 inhibitor is EC-8042, e.g., as disclosed in Osgood C L et al., (2016) Clinical Cancer Research 22(16) 4105-18. EC-8042 is a second-generation Mithramycin analogue.

ASNS

The term "ASNS" as used herein refers to the gene or protein of "Asparagine synthetase". The term "ASNS" includes mutants, fragments, variants, isoforms, and homologs of full-length wild-type ASNS. In one embodiment, the protein is encoded by the ASNS gene (Gene ID: 440; Ensembl ID ENSG00000070669). Exemplary ASNS sequences are available at the Uniprot database under the accession number P08243. ASNS is an enzyme involved in the synthesis of L-asparagine from L-aspartate (Zhang Y, (1989) Genomics 4:259-265).

In some embodiments, the ASNS inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the ASNS inhibitor is adenylated sulfoximine 1, e.g., as disclosed in Gutierrez J A et. al., (2006) 13(12): 1339-1347. Adenylated sulfoximine 1 is a mixture of diastereoisomers, e.g., diastereoisomers 1a and 1b shown below. Adenylated sulfoximine has the following chemical structures:

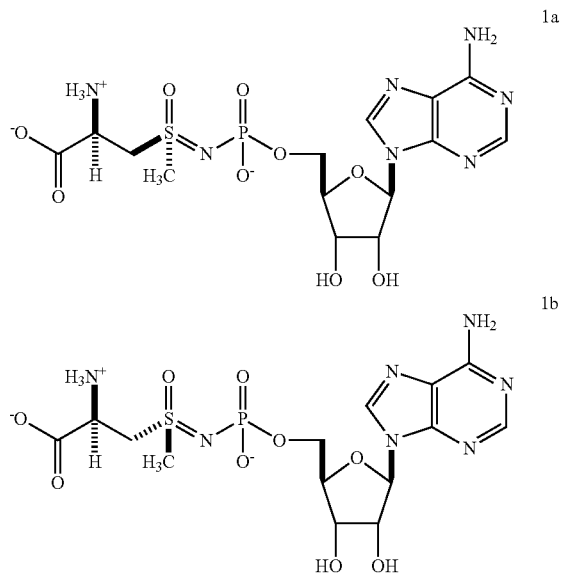

In some embodiments, the ASNS inhibitor adenylated sulfoximine 1 is L-methionine sulfoximine. L-methionine sulfoximine has the following chemical structure:

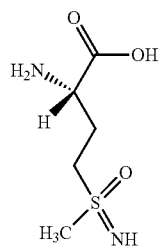

Chemical Structure
Molecular Weight: 180.23

In some embodiments, the ASNS agonist is chosen from a low molecular weight compound, a small molecule, an mRNA, a miRNA, an antibody or derivative thereof, a peptide mimetic or an analog of ASNS. Exemplary ASNS agonists are described in U.S. Pat. No. 6,040,163, which is hereby incorporated by reference in its entirety.

SOX10

The term "SOX10" as used herein refers to the gene or protein of "SRY Box 10". The term "SOX10" includes mutants, fragments, variants, isoforms, and homologs of full-length wild-type SOX10. In one embodiment, the protein is encoded by the SOX10 gene, e.g., as disclosed in Pusch C et al., (1998) Human Genetics 103:115-123. SOX10 gene can be identified by the following designations: Gene ID: 6663; Ensembl ID ENSG00000100146. Exemplary SOX10 sequences are available at the Uniprot database under the accession number P56693. SOX10 is a transcription factor which is a member of the SOX (SRY-related HMG-box) family of transcription factors involved in embryonic development and cell fate determination.

In some embodiments, the SOX10 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the SOX10 inhibitor is an RNAi agent, e.g., as disclosed in Graf S A et al., (2014) Journal of Investigative Dermatology 134(8):2212-20. In some embodiments, the RNAi agent is an siRNA with the sequence of: CCGUAUGCAGCACAAGAAA (SEQ ID NO:1). In some embodiments, the RNAi agent is an siRNA with the sequence of: GUAUGCAGCACAAGAAAGA (SEQ ID NO:2). In another embodiment, the SOX10 inhibitor is an RNAi agent, e.g., as disclosed in Tong X et al., (2014) Oncotarget 5(21):10571-10583.

ALDH18A1

The term "ALDH18A1" as used herein refers to the gene or protein of "aldehyde dehydrogenase 18 family member A1". ALDH18A1 is also known as P5CS. The term "ALDH18A1" includes mutants, fragments, variants, isoforms, and homologs of full-length wild-type ALDH18A1. In one embodiment, the protein is encoded by the ALDH18A1 gene (Gene ID: 5832; Ensembl ID ENSG00000059573). Exemplary ALDH18A1 sequences are available at the Uniprot database under the accession number P54886. ALDH18A1 is a bi-functional ATP- and NADPH-dependent mitochondrial enzyme (Panza E et al., (2016) Brain 139:e3).

In some embodiments, the ALDH18A1 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the ALDH18A1 inhibitor is an RNAi as disclosed in Kardos G R et al., 2015, Molecular Cancer Research (10)1408-20, hereby incorporated by reference in its entirety.

In some embodiments, the ALDH18A1 agonist is chosen from a low molecular weight compound, a small molecule, an mRNA, a miRNA, an antibody or derivative thereof, a peptide mimetic, or an analog of ALDH18A1.

FOXA1

The term "FOXA1" as used herein refers to the gene or protein of "Forkhead box A1". FOXA1 is also known as HNF3A. The term "FOXA1" includes mutants, fragments, variants, isoforms, and homologs of full-length wild-type FOXA1. In one embodiment, the protein is encoded by the FOXA1 gene, e.g., as disclosed in Bingle and Gowan (1996) Biochim. Biophys. Acta 1307: 17-20. FOXA1 gene can be identified by the following designations: Gene ID: 3169; Ensembl ID ENSG00000129514. Exemplary FOXA1 sequences are available at the Uniprot database under the accession number P55317. FOXA1 is a transcription factor which is a member of the forkhead class of DNA binding proteins.

In some embodiments, the FOXA1 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the FOXA1 inhibitor is a kinase inhibitor, e.g., as disclosed in Sunkel B et al., (2016) Nucleic Acids Research 44(9): 4105-4122. In one embodiment, the FOXA1 inhibitor is chosen from H89, MK-2206 or U0126, e.g., as disclosed in Sunkel B et al., (2016) Nucleic Acids Research 44(9): 4105-4122. In one embodiment, the FOXA1 inhibitor is H89. H89 is a Protein Kinase A inhibitor with the chemical name: N-[2-[[3-(4-Bromophenyl)-2-propenyl]amino]ethyl]-5-isoquinolinesulfonamide, and the following chemical structure:

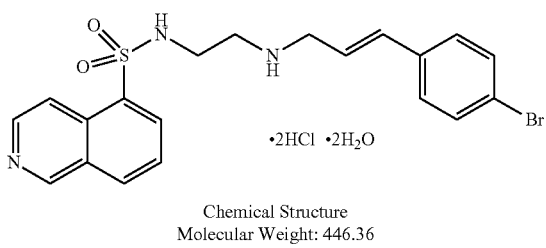 [SMILES: O=S(=O)(NCCNC/C=C/c1ccc(Br)cc1)c1cccc2cnccc12]

Chemical Structure
Molecular Weight: 446.36

In one embodiment, the FOXA1 inhibitor is MK-2206. MK-2206 is an orally active, allosteric Akt inhibitor that is equally potent toward purified human recombinant Akt1 and Akt2 (IC50s=5 and 12 nM, respectively) and approximately 5-fold less potent against human Akt3 (IC50=65 nM). MK-2206 has the chemical name: 8-[4-(1-aminocyclobutyl)phenyl]-9-phenyl-1,2,4-triazolo[3,4-f][1,6]naphthyridin-3(2H)-one, dihydrochloride, and has the following chemical structure:

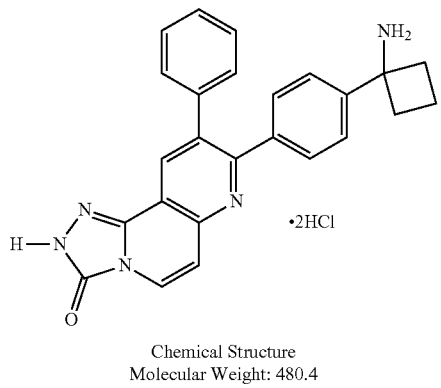 [SMILES: NC1(c2ccc(-c3nc4ccn5c(=O)[nH]nc5c4cc3-c3ccccc3)cc2)CCC1]

Chemical Structure
Molecular Weight: 480.4

In one embodiment, the FOXA1 inhibitor is U0126. U0126 is a selective non-competitive inhibitor of MAP kinase, e.g., MEK-1 and MEK-2. U0126 has the chemical name: 1,4-Diamino-2,3-dicyano-1,4-bis[2-aminophenylthio]butadiene, and the following chemical structure:

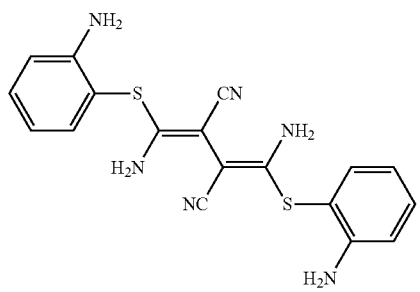

Chemical Structure
Molecular Weight: 380.48

In one embodiment, the FOXA1 inhibitor is a kinase inhibitor, e.g., as disclosed in Johnston S J et al., In: Proceedings of the 107th Annual Meeting of the AACR; Cancer Res 2016;76(14 Suppl): Abstract nr 2906.

HNF1B

The term "HNF1B" as used herein refers to the gene or protein of "Hepatocyte nuclear factor 1 Homeobox B".

HNF1B is also known as TCF2. The term "HNF1B" includes mutants, fragments, variants, isoforms, and homologs of full-length wild-type HNF1B. In one embodiment, the protein is encoded by the HNF1B gene, e.g., as disclosed in Bach I et al., (1991) Nucleic Acids Research 19:3553-3559. HNF1B gene can be identified by the following designations: Gene ID: 6928; Ensembl ID ENSG00000275410. Exemplary HNF1B sequences are available at the Uniprot database under the accession number P35680. HNF1 B is a transcription factor which is a member of the homeobox-containing superfamily of transcription factors.

In some embodiments, the HNF1B inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the HNF1B inhibitor is a Calcineurin inhibitor, e.g., as disclosed in Faguer S et al., (2016) Transplantation 100(9):1970-8. Calcineurin inhibitors include Tacrolimus and cyclosporine. In embodiments, the HNF1B inhibitor is Tacrolimus. Tacrolimus, also known as FK-506, has the chemical name:

3S[3R*[E(1S*,3S*,4S*)]4S*,5R*,8S*,9E,12R*,14R*,15S*,16R*,18S*,19S*,26aR*-5,6,8,11,12,13,14,15,16,17,18,19,24,25,26,26a-hexadecahydro-5, 19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4] oxaazacyclotricosine-1,7,20,21(4H,23H)-tetrone, monohydrate, and the following chemical structure:

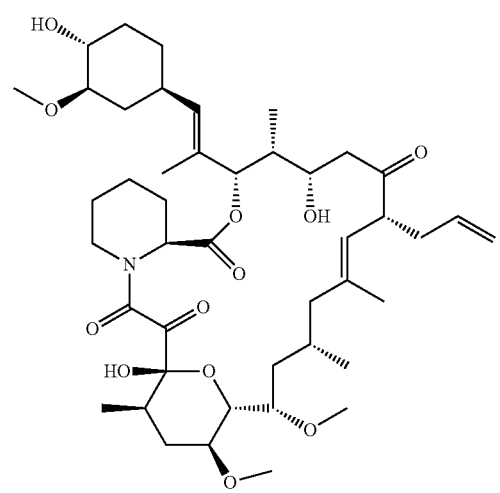

Chemical Structure
Molecular Weight: 804.018

In some embodiments, the HNF1B inhibitor is Cyclosporine. Cyclosporine has the chemical name: (3S,6S,9S,12R,15S,18S,21S,24S,30S,33S)-30-Ethyl-33-[(1R,2R,4E)-1-hydroxy-2-methyl-4-hexen-1-yl]-6,9,18,24-tetraisobutyl-3,21-diisopropyl-1,4,7,10,12,15,19,25,28-nonamethyl-1,4,7,10,13,16,19,22,25,28,31-undecaazacyclotritriacontane-2,5,8,11,14,17,20,23,26,29,32-undecone, and the following chemical structure:

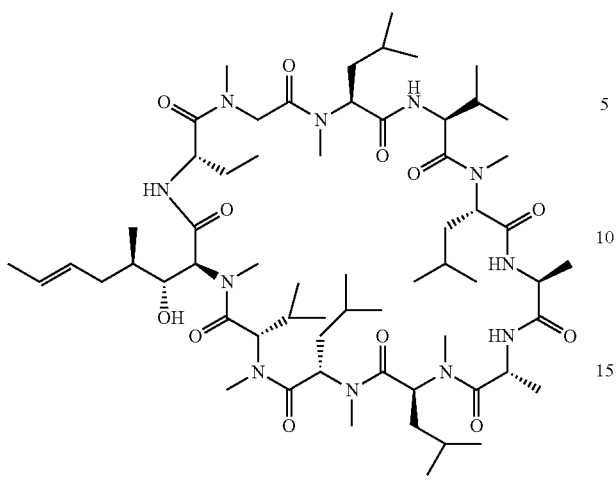

Chemical Structure
Molecular Weight: 1202.61

RUNX1

The term "RUNX1" as used herein refers to the gene or protein of "Runt related transcription factor 1". RUNX1 is also known as AML1, PEBP2 or CBFA2. The term "RUNX1" includes mutants, fragments, variants, isoforms, and homologs of full-length wild-type RUNX1. In one embodiment, the protein is encoded by the RUNX1 gene, e.g., as disclosed in Miyoshi H, et al., (1995) Nucleic Acids Research 23:2762-2769. RUNX1 gene can be identified by the following designations: Gene ID: 861; Ensembl ID ENSG00000159216. Exemplary RUNX1 sequences are available at the Uniprot database under the accession number Q01196. RUNX1 is a Runt-related transcription factor which is a member of the RUNX gene family. RUNX1 has a role in the development of hematopoietic cells. RUNX1 forms a heterodimeric complex with Core Binding Factor beta (CBFB).

In some embodiments, the RUNX1 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the RUNX1 inhibitor is a CBFB inhibitor. In some embodiments, CBFB inhibitor is a small molecule that binds to CBFbeta and prevents its association with Runx1 (IC50=3.2 µM). CBFB inhibitor has the chemical name: 5-ethyl-4-(4-methoxyphenyl)-2-thiazolamine, and the following chemical structure:

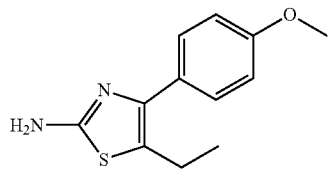

Chemical Structure
Molecular Weight: 234.3

In one embodiment, the RUNX1 inhibitor is Ro5-3335, e.g., as disclosed in Cunningham L et al., (2012) PNAS 109(36): 14592-14597. Ro5-3335 is a benzodiazepine and is a CBFB inhibitor. Ro5-3335 is a CBFB inhibitor with an IC50 of 1.1 uM. Ro5-3335 has the chemical name: 7-Chloro-1,3-dihydro-5-(1H-pyrrol-2-yl)-2H-1,4-benzodiazepin-2-one, and the following chemical structure:

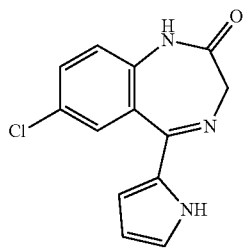

Chemical Structure
Molecular Weight: 259.63

In one embodiment, the RUNX1 inhibitor is a CBFB inhibitor as disclosed in Illendula, Anuradha et al., EBioMedicine 8 (2016): 117-131. PMC. Web. 5 Jul. 2017. In some embodiments, the CBFB inhibitor is AI-4-57 which has an IC50 of 34.4 um. AI-4-57 has the chemical name: 5-Methoxy-2-pyridin-2-yl-1H-benzoimidazole Hydrochloride, and has the following chemical structure.

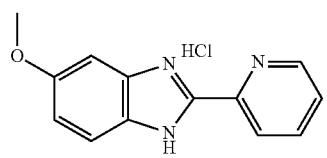

Chemical Structure
Molecular Weight: 261.71

In other embodiments, the CBFB inhibitor is AI-10-104 which has an IC50 of 1.25 um. AI-10-104 has the following chemical structure.

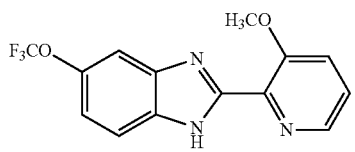

Chemical Structure

CBFB

The term "CBFB" as used herein refers to the gene or protein of "Core Binding Factor subunit Beta". CBFB is also known as PEBP2B. The term "CBFB" includes mutants, fragments, variants, isoforms, and homologs of full-length wild-type CBFB. In one embodiment, the protein is encoded by the CBFB gene, e.g., as disclosed in Liu P, et al., (1993) Science 261: 1041-1044. CBFB gene can be identified by the following designations: Gene ID: 865; Ensembl ID ENSG00000067955. Exemplary CBFB sequences are available at the Uniprot database under accession numbers Q13951. CBFB protein is the beta subunit of a heterodimeric core-binding transcription factor (CBF). The CBF complex comprises a beta subunit, and an alpha subunit, e.g., RUNX1, RUNX2 or RUNX3.

In some embodiments, the CBFB inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the CBFB inhibitor is a small molecule that binds to CBFB and prevents its association with Runx1 (IC50=3.2 µM). In some embodiments, the CBFB inhibitor has the chemical name: 5-ethyl-4-(4-methoxyphenyl)-2-thiazolamine, and the following chemical structure:

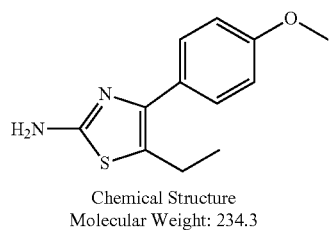 [SMILES: CCc1sc(N)nc1-c1ccc(OC)cc1]

Chemical Structure
Molecular Weight: 234.3

In one embodiment, the CBFB inhibitor is Ro5-3335, e.g., as disclosed in Cunningham L et al., (2012) PNAS 109(36): 14592-14597. Ro5-3335 is a benzodiazepine and is a CBFB inhibitor. Ro5-3335 is a CBFB inhibitor with an IC50 of 1.1 uM. Ro5-3335 has the chemical name: 7-Chloro-1,3-dihydro-5-(1H-pyrrol-2-yl)-2H-1,4-benzodiazepin-2-one, and the following chemical structure:

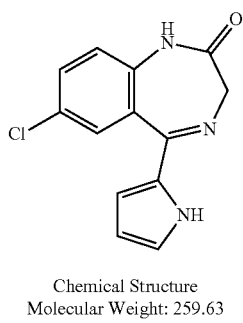 [SMILES: O=C1CN=C(c2ccc[nH]2)c2cc(Cl)ccc2N1]

Chemical Structure
Molecular Weight: 259.63

In one embodiment, the CBFB inhibitor is a CBFB inhibitor as disclosed in Illendula, Anuradha et al., EBioMedicine 8 (2016): 117-131. PMC. Web. 5 Jul. 2017. In some embodiments, the CBFB inhibitor is AI-4-57 which has an IC50 of 34.4 um. AI-4-57 has the chemical name: 5-Methoxy-2-pyridin-2-yl-1H-benzoimidazole Hydrochloride, and has the following chemical structure.

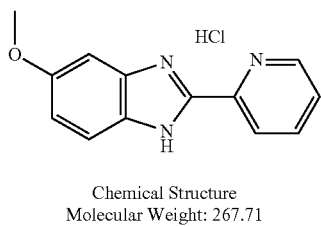 [SMILES: COc1ccc2[nH]c(-c3ccccn3)nc2c1 ; Cl]

Chemical Structure
Molecular Weight: 267.71

In other embodiments, the CBFB inhibitor is AI-10-104 which has an IC50 of 1.25 um. AI-10-104 has the following chemical structure.

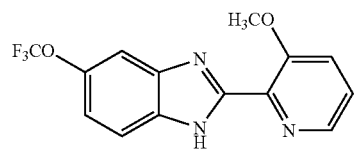

Chemical Structure

TP63

The term "TP63" as used herein refers to the gene or protein of "Tumor protein 63". TP63 is also known as NBP, and p63. The term "TP63" includes mutants, fragments, variants, isoforms, and homologs of full-length wild-type TP63. In one embodiment, the protein is encoded by the TP63 gene, e.g., as disclosed in Di Iorio, et al., (2005) PNAS 102: 9523-9528. TP63 gene can be identified by the following designations: Gene ID: 8626; Ensembl ID ENSG00000073282. Exemplary TP63 sequences are available at the Uniprot database under accession numbers Q9H3D4. TP63 is a transcription factor which is a member of the p53 gene family based on structural similarity.

In some embodiments, the TP63 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the TP63 inhibitor is an RNAi agent, e.g., a shRNA or siRNA oligonucleotide, which reduces the expression of TP63. Exemplary oligonucleotides are disclosed in U.S. Pat. No. 8,962,585, the entire contents of which are hereby incorporated by reference.

CDK2

The term "CDK2" as used herein refers to the gene or protein of "Cyclin dependent kinase 2". CDK2 is also known as cell division kinase 2. The term "CDK2" includes mutants, fragments, variants, isoforms, and homologs of full-length wild-type CDK2. The CDK2 protein is encoded by the CDK2 gene which can be identified by the following designations: Gene ID: 1017; Ensembl ID ENSG00000123374. Exemplary CDK2 sequences are available at the Uniprot database under accession numbers P24941. CDK2 is an enzyme and is a member of the cyclin-dependent kinase family of serine threonine kinases.

In some embodiments, the CDK2 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the CDK2 inhibitor is a CDK2 inhibitor disclosed in, e.g., Lapenna and Giordano (2009) Nature Reviews Drug Discovery 8, 547-566. In embodiments, the CDK2 inhibitor is chosen from AG-024322, AT7519, Flavopiridol, R547, SCH 727965, SNS-032 or ZK 304709.

In one embodiment, the CDK2 inhibitor is AG-024322. AG-024322 is a second generation CKD inhibitor and has Ki of 1-3 Nm. AG-024322 has the chemical name: N-((5-(3-(4,6-difluoro-1H-benzo[d]imidazol-2-yl)-1H-indazol-4-yl)-4-methylpyridin-3-yl)methyl)ethanamine and has the following chemical structure.

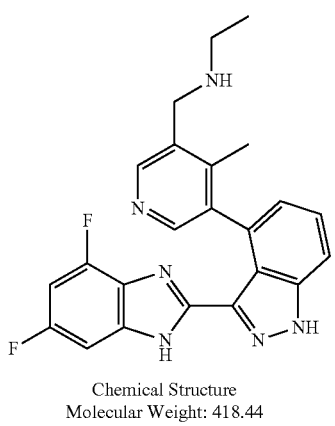 [SMILES: CCNCc1cncc(-c2cccc3[nH]nc(-c4nc5c(F)cc(F)cc5[nH]4)c23)c1C]

Chemical Structure
Molecular Weight: 418.44

In one embodiment, the CDK2 inhibitor is AT7519. AT7519 is a multi-CDK inhibitor with an IC50 of 10-210 nm. AT7519 has the chemical name: 4-[(2,6-Dichlorobenzoyl)amino]-N-(4-piperidinyl)-1H-pyrazole-3-carboxamide and has the following chemical structure.

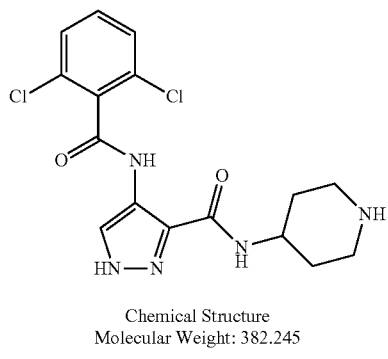 [SMILES: O=C(NC1CCNCC1)c1n[nH]cc1NC(=O)c1c(Cl)cccc1Cl]

Chemical Structure
Molecular Weight: 382.245

In one embodiment, the CDK2 inhibitor is Flavopiridol. Flavopiridol is a multi-CDK inhibitor with an IC50 of ~40 nM and is also known as HMR-1275 or Alvocidib. Flavopiridol has the chemical name: 2-(2-chlorophenyl)-5,7-dihydroxy-8-[(3S,4R)-3-hydroxy-1-methyl-4-piperidinyl]-4-chromenone and has the following chemical structure.

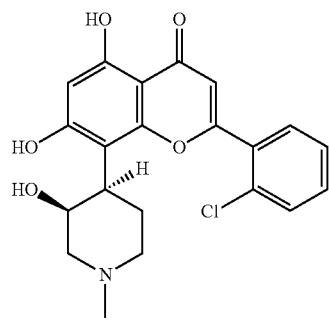

Chemical Structure
Molecular Weight: 401.84

VPS4A

The term "VPS4A" as used herein refers to the gene or protein of "vacuolar protein sorting 4 homolog A". VPS4A is also known as SKD1A, or VPS4. The term "VPS4A" includes mutants, fragments, variants, isoforms, and homologs of full-length wild-type VPS4A. The VPS4A protein is encoded by the VPS4A gene, e.g., as disclosed in Bishop N et al., (2003) Gene 305: 47-59. VPS4A can be identified by the following designations: Gene ID: 27183; Ensembl ID ENSG00000132612. Exemplary VPS4A sequences are available at the Uniprot database under accession numbers Q9UN37. VPS4A associates with endosomal compartments and is involved in intracellular protein trafficking.

In some embodiments, the VPS4A inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the VPS4A inhibitor is a dominant negative VPS4A, e.g., as disclosed in Watanabe and Lamb (2010) Virus Research 153(1): 58-63. In some embodiments, the dominant negative VPS4A comprises a mutation in amino acid residue E228 to Q.

TCF4

The term "TCF4" as used herein refers to the gene or protein of "transcription factor 4". TCF4 is also known as ITF2 or bHLHb19. The term "TCF4" includes mutants, fragments, variants, isoforms, and homologs of full-length wild-type TCF4. The TCF4 protein is encoded by the TCF4 gene, e.g., as disclosed in Henthorn P et al., (1990) Science 247: 467-470. TCF4 can be identified by the following designations: Gene ID: 6925; Ensembl ID ENSG00000196628. Exemplary TCF4 sequences are available at the Uniprot database under accession numbers P15884. TCF4 is a basic helix-loop-helix transcription factor which functions as a homodimer or heterodimer and binds to E-box motifs on DNA.

In some embodiments, the TCF4 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

CEBPA

The term "CEBPA" as used herein refers to the gene or protein of "CCAAT/enhancer binding protein alpha". CEBPA is also known as CEBP. The term "CEBPA" includes mutants, fragments, variants, isoforms, and homologs of full-length wild-type CEBPA. The CEBPA protein is encoded by the CEBPA gene, e.g., as disclosed in Swart G W M et al., (1997) Biol. Chemistry 378: 373-379. CEBPA can be identified by the following designations: Gene ID: 1050; Ensembl ID ENSG00000245848. Exemplary CEBPA sequences are available at the Uniprot database under accession numbers P49715. CEBPA is a bZIP transcription factor involved in the differentiation of hematopoietic cells.

In some embodiments, the CEBPA inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

GATA3

The term "GATA3" as used herein refers to the gene or protein of "GATA-3". The term "GATA3" includes mutants, fragments, variants, isoforms, and homologs of full-length wild-type GATA3. The GATA3 protein is encoded by the GATA3 gene, e.g., as disclosed in Labastie M et al., (1994) Genomics 21: 1-6. GATA3 can be identified by the following designations: Gene ID: 2625; Ensembl ID ENSG00000107485. Exemplary GATA3 sequences are available at the Uniprot database under accession numbers P23771. GATA3 is a transcription factor that belongs to the GATA family of transcription factors which bind to the DNA sequence "GATA".

In some embodiments, the GATA3 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the GATA3 inhibitor is a glucocorticoid, e.g., dexamethasone, e.g., as disclosed in Liberman A C (2009) FASEB Journal 23(5): 1558-71. In some embodiments, the GATA3 inhibitor is dexamethasone. Dexamethasone is a steroid with an IC50 OF 10 nm. Dexamethasone has the chemical name: (8S,9R,10S,11S,13S,14S,16R,17R)-9-Fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one and the following chemical structure:

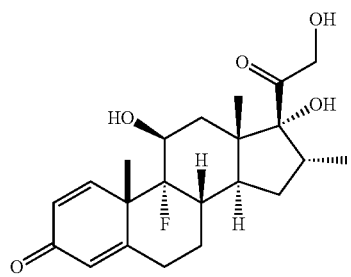

Chemical Structure
Molecular Weight: 392.461

In one embodiment, the GATA3 inhibitor is an RNAi agent, e.g., a short interfering nucleic acid (siNA). Exemplary siNAs are disclosed in WO 2010/107957, hereby incorporated by reference in its entirety.

ARID1B

The term "ARID1B" as used herein refers to the gene or protein of "AT rich interaction domain 1B". The term "ARID1B" includes mutants, fragments, variants, isoforms, and homologs of full-length wild-type ARID1 B. The ARID1B protein is encoded by the ARID1 B gene, and can be identified by the following designations: Gene ID: 57492; Ensembl ID ENSG00000049618. Exemplary ARID1B sequences are available at the Uniprot database under accession numbers Q8NFD5. ARID1B is a component of the SWI/SNF chromatin remodeling complex.

In some embodiments, the ARID1B inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

PRKRA

The term "PRKRA" as used herein refers to the gene or protein of "Protein kinase, interferon-inducible double stranded RNA dependent activator". PRKRA is also known as PACT or RAX. The term "PRKRA" includes mutants, fragments, variants, isoforms, and homologs of full-length wild-type PRKRA. The PRKRA protein is encoded by the PRKRA gene, e.g., as disclosed in Paten and Sen (1998) EMBO 17: 4379-4390. The PRKRA gene can be identified by the following designations: Gene ID: 8575; Ensembl ID ENSG00000180228. Exemplary PRKRA sequences are available at the Uniprot database under accession number O75569. EIF2AK2 or protein kinase R (PKR) is a protein kinase which is activated by double-stranded RNA. PRKRA heterodimerizes with protein kinase R and activates it.

In some embodiments, the PRKRA inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

HSPA8

The term "HSPA8" as used herein refers to the gene or protein of "heat-shock 70 kD protein 8". The term "HSPA8" includes mutants, fragments, variants, isoforms, and homologs of full-length wild-type HSPA8. The HSPA9 protein is encoded by the HSPA9 gene, e.g., as disclosed in Dworniczak B et al., (1987) Nucleic Acids Research 15:5181-5197. The HSPA8 gene can be identified by the following designations: Gene ID: 3312; Ensembl ID ENSG00000109971. Exemplary HSPA8 sequences are available at the Uniprot database under accession number P11142. HSPA8 is a heat shock protein which is a member of the heat shock protein 70 family and has a role as a chaperone protein.

In some embodiments, the HSPA8 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the HSPA8 inhibitor is VER 15508, e.g., as disclosed in Schlecht R et al., (2013) PlosOne 0078443. VER 15508 is an adenosine-derived inhibitor and has the chemical name: 5'-O-[(4-Cyanophenyl)methyl]-8-[[(3,4-dichlorophenyl)methyl]amino]-adenosine. VER 15508 has the following chemical structure:

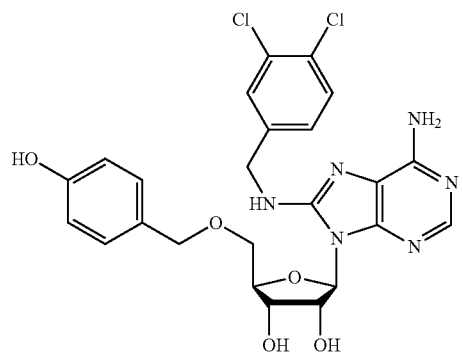

Chemical Structure
Molecular Weight: 556.4

In one embodiment, the HSPA8 inhibitor is Deoxyspergualin (DSG), e.g., as disclosed in Jose-Eneriz et al., (2008) British Journal of Hematology 142(4) 571-582. DSG is also known as Gusperimus and is an immunosuppressive agent. DSG has the chemical name: N-[2-[4-(3-Aminopropylamino)butylamino]-1-hydroxy-2-oxoethyl]-7-(diaminomethylideneamino)heptanamide and has the following chemical structure:

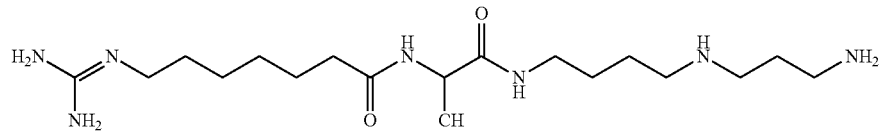

Chemical Structure
Molecular Weight: 387.53

IRF4

The term "IRF4" as used herein refers to the gene or protein of "Interferon regulatory factor 4". IRF4 is also known as MUM 1. The term "IRF4" includes mutants, fragments, variants, isoforms, and homologs of full-length wild-type IRF4. The IRF4 protein is encoded by the IRF4 gene, e.g., as disclosed in Grossman A et al., (1996) Genomics 37: 229-233. The IRF4 gene can be identified by the following designations: Gene ID: 3662; Ensembl ID ENSG00000137265. Exemplary IRF4 sequences are available at the Uniprot database under accession number q15306. IRF4 is a transcription factor that is associated with pigmentation.

In some embodiments, the IRF4 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the IRF4 inhibitor is 10-E-09, e.g., as disclosed in Vatolin S et al., (2012) Plos One 0044690.

SPI1

The term "SPI1" as used herein refers to the "SPI1" gene or protein of "transcription factor PU.1". The term "SPI1" includes mutants, fragments, variants, isoforms, and homologs of full-length wild-type SPI1. The PU.1 protein is encoded by the SPI1 gene, e.g., as disclosed in Ray D (1990) Oncogene 5: 663-667. The SPI1 gene can be identified by the following designations: Gene ID: 6688; Ensembl ID ENSG00000066336. Exemplary SPI1 amino acid sequences are available at the Uniprot database under accession number P17947. PU.1 is an ETS-domain transcription factor that binds to purine-rich sequences on DNA known as PU box.

In some embodiments, the SPI1 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In an embodiment, the SPI1 inhibitor is a furan-bisbenzimidazole-diamidine, e.g., as disclosed in Stephens D C et al., (2016) Nucleic Acids Research 44(9) 4005-4013. In some embodiments, the furan-bisbenzimidazole-diamidine SPI1 inhibitor is DB270. DB270 has the following chemical structure:

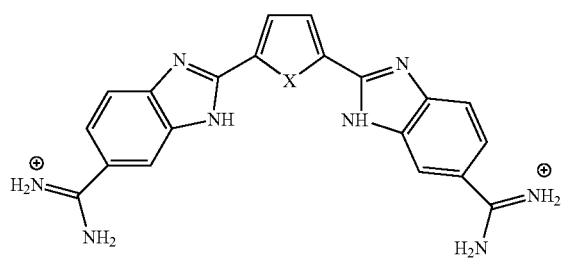

Chemical Structure (X=O)

In some embodiments, the furan-bisbenzimidazole-diamidine SPI1 inhibitor is DB1976. DB1976 has the following chemical structure:

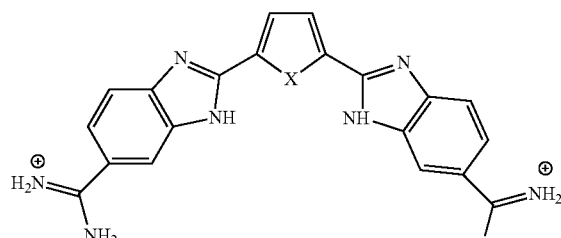

Chemical Structure (X=Se)

MTHFD1

The term "MTHFD1" as used herein refers to the gene MTHFD1 or protein of methylenetetrahydrofolate dehydrogenase 1. The term "MTHFD1" includes mutants, fragments, variants, isoforms, and homologs of full-length wild-type MTHFD1. The MTHFD1 encodes for the C-1-tetrahydrofolate synthase, cytoplasmic protein (C1-THF synthase). The C1-THF protein is encoded by the MTHFD1 gene, e.g., as disclosed in Hum et al., (1998) JBC 263: 15946-15950. The MTHFD1 gene can be identified by the following designations: Gene ID: 4522; Ensembl ID ENSG00000100714. Exemplary MTHFD1 sequences are available at the Uniprot database under accession number P11586. MTHFD1 encodes for the tri-functional C1-THF enzyme.

In some embodiments, the MTHFD1 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In some embodiments, the MTHFD1 agonist is chosen from a low molecular weight compound, a small molecule, an mRNA, a miRNA, an antibody or derivative thereof, a peptide mimetic, or an analog of MTHFD1.

ADAR

The term "ADAR" as used herein refers to the gene or protein of "double stranded RNA specific adenosine deaminase". ADAR is also known as ADAR1. The term "ADAR" includes mutants, fragments, variants, isoforms, and homologs of full-length wild-type ADAR. The ADAR protein is encoded by the ADAR gene, e.g., as disclosed in Kim U et al., (1994) PNAS 91: 11457-11461. The ADAR gene can be identified by the following designations: Gene ID: 103; Ensembl ID ENSG00000160710. Exemplary ADAR sequences are available at the Uniprot database under accession number P55265. ADAR is an adenosine deaminase specific for RNA which binds to dsRNA and converts adenosine to inosine by deamination.

In some embodiments, the ADAR inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the ADAR inhibitor is O-phenanthroline, e.g., as disclosed in Kim et al., (1994) JBC 13480-13489. O-phenanthroline has the chemical name 1,10-Phenanthroline, and has the following chemical structure:

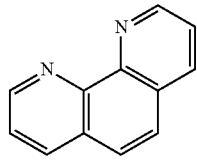

Chemical Structure
Molecular Weight: 180.21

In one embodiment, the ADAR inhibitor is ADAR3, e.g., as disclosed in Samuel C E (2011) Virology 411(2), 180-193.

NFE2L2

The term "NFE2L2" as used herein refers to the gene or protein of "nuclear factor, erythroid 2 like 2". NFE2L2 is also known as NRF2. The term "NFE2L2" includes mutants, fragments, variants, isoforms, and homologs of full-length wild-type NFE2L2. The NFE2L2 protein is encoded by the NFE2L2 gene, e.g., as disclosed in Moi et al., (1994) PNAS 91: 9926-9930. The NFE2L2 gene can be identified by the following designations: Gene ID: 4780; Ensembl ID ENSG00000116044. Exemplary NFE2L2 sequences are available at the Uniprot database under accession number Q16236. NFE2L2 is a basic leucine zipper (bZIP) transcription factor that is involved in the regulation of expression of antioxidant proteins that protect against oxidative damage.

In some embodiments, the NFE2L2 inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In one embodiment, the NFE2L2 inhibitor is a NRF2 inhibitor disclosed in Tong et al., (2015) Chronic Diseases and Translational Medicine 1(13): 175-186. In some embodiments, the NFE2L2 inhibitor is chosen from Brusatol, Luteolin or Trigonelline. Brusatol has the chemical name: (11β,12α,15β)-13,20-Epoxy-3,11,12-trihydroxy-15-[(3-methyl-1-oxo-2-buten-1-yl)oxy]-2,16-dioxo-picras-3-en-21-oic acid methyl ester and has the following chemical structure:

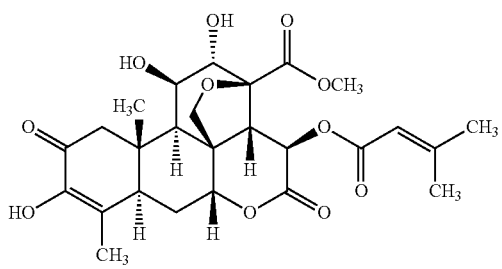

Chemical Structure
Molecular Weight: 502.53

In one embodiment, the NFE2L2 inhibitor is Luteolin. Luteolin is a flavone, has the chemical name: 2-(3,4-Dihydroxyphenyl)-5,7-dihydroxy-4-chromenone and has the following chemical structure:

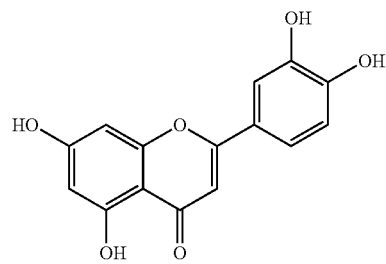

Chemical Structure
Molecular Weight: 286.24

In one embodiment, the NFE2L2 inhibitor is Trigenolline. Trigenolline has the chemical name: 1-Methylpyridinium-3-carboxylate and the following chemical structure:

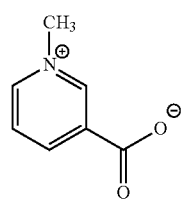

Chemical Structure
Molecular Weight: 137.14

WRN

The term "WRN" as used herein refers to the gene or protein of Werner Syndrome RecQ DNA helicase. The term "WRN" includes mutants, fragments, variants, isoforms, and homologs of full-length wild-type WRN. In one embodiment, the protein is encoded by the WRN gene (Entrez gene ID 7486; Ensembl ID ENSG00000165392). Exemplary WRN sequences are available at the Uniprot database under accession number Q14191.

In some embodiments, the WRN inhibitor is chosen from: an RNA inhibitor (e.g., an RNAi agent), a CRISPR, a TALEN, a zinc finger nuclease, a small molecule, an mRNA, a miRNA, an antibody or derivative thereof, or a chimeric antigen receptor T cell (CART).

In some embodiment, the WRN inhibitor is a Helicase Inhibitor, e.g. ML-216; Chemical Name, 1-[4-Fluoro-3-(trifluoromethyl)phenyl]-3-(5-pyridin-4-yl-1,3,4-thiadiazol-2-yl)urea; CAS 1430213-30-1.

RNAi Agents

As used herein, the term "RNAi agent," "RNAi agent to a target", "siRNA to a target", "target siRNA" and the like refer to an siRNA (short inhibitory RNA), shRNA (short or small hairpin RNA), iRNA (interference RNA) agent, RNAi (RNA interference) agent, dsRNA (double-stranded RNA), microRNA, and the like, which specifically binds to the target gene, e.g., a gene of any of the targets disclosed in Tables 1 or 2, and which mediates the targeted cleavage of another RNA transcript via an RNA-induced silencing complex (RISC) pathway. In one embodiment, the RNAi agent is an oligonucleotide composition that activates the RISC complex/pathway. In another embodiment, the RNAi agent comprises an antisense strand sequence (antisense oligonucleotide). In one embodiment, the RNAi comprises a single strand. This single-stranded RNAi agent oligonucleotide or polynucleotide can comprise the sense or antisense strand, as described by Sioud 2005 J. Mol. Bioi. 348:1079-1090, and references therein. Thus the disclosure encompasses RNAi agents with a single strand comprising either the sense or antisense strand of an RNAi agent described herein. The use of the RNAi agent to a target results in a decrease of target activity, level and/or expression, e.g., a "knock-down" or "knock-out" of the target gene or target sequence.

RNA interference is a post-transcriptional, targeted gene-silencing technique that, usually, uses double-stranded RNA (dsRNA) to degrade messenger RNA (mRNA) containing the same sequence as the dsRNA. The process of RNAi occurs naturally when ribonuclease III (Dicer) cleaves longer dsRNA into shorter fragments called siRNAs. Naturally-occurring siRNAs (small interfering RNAs) are typically about 21 to 23 nucleotides long and comprise about 19 base pair duplexes. The smaller RNA segments then mediate the degradation of the target mRNA. Dicer has also been implicated in the excision of 21- and 22-nucleotide small temporal RNAs (stRNAs) from precursor RNA of conserved structure that are implicated in translational control. Hutvagner et al. 2001, Science, 293, 834. The RNAi response also features an endonuclease complex, commonly referred to as an RNA-induced silencing complex (RISC), which mediates cleavage of single-stranded mRNA complementary to the antisense strand of the siRNA. Cleavage of the target RNA takes place in the middle of the region complementary to the antisense strand of the siRNA duplex.

"RNAi" (RNA interference) has been studied in a variety of systems. Early work in *Drosophila* embryonic lysates (Elbashir et al. 2001 EMBO J. 20: 6877 and Tuschl et al. International PCT Publication No. WO 01/75164) revealed certain parameters for siRNA length, structure, chemical composition, and sequence that are beneficial to mediate efficient RNAi activity. These studies have shown that 21-nucleotide siRNA duplexes are most active when containing 3'-terminal dinucleotide overhangs. Substitution of the 3'-terminal siRNA overhang nucleotides with 2'-deoxy nucleotides (2'-H) was tolerated. In addition, a 5'-phosphate on the target-complementary strand of an siRNA duplex is usually required for siRNA activity. Later work showed that a 3'-terminal dinucleotide overhang can be replaced by a 3' end cap, provided that the 3' end cap still allows the molecule to mediate RNA interference; the 3' end cap also reduces sensitivity of the molecule to nucleases. See, for example, U.S. Pat. Nos. 8,097,716; 8,084,600; 8,404,831; 8,404,832; and 8,344,128. Additional later work on artificial RNAi agents showed that the strand length could be shortened, or a single-stranded nick could be introduced into the sense strand. In addition, mismatches can be introduced between the sense and antisense strands and a variety of modifications can be used. Any of these and various other formats for RNAi agents known in the art can be used to produce RNAi agents to any of the targets disclosed in Tables 1 or 2. In some embodiments, the RNAi agent to any of the targets disclosed in Tables 1 or 2 is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

Kits for RNAi synthesis are commercially available, e.g., from New England Biolabs and Ambion.

A suitable RNAi agent can be selected by any process known in the art or conceivable by one of ordinary skill in the art. For example, the selection criteria can include one or more of the following steps: initial analysis of the target gene sequence and design of RNAi agents; this design can take into consideration sequence similarity across species (human, cynomolgus, mouse, etc.) and dissimilarity to other (non-target) genes; screening of RNAi agents in vitro (e.g., at 10 nM in cells); determination of EC50 in HeLa cells; determination of viability of various cells treated with RNAi agents, wherein it is desired that the RNAi agent to a target not inhibit the viability of these cells; testing with human PBMC (peripheral blood mononuclear cells), e.g., to test levels of TNF-alpha to estimate immunogenicity, wherein immunostimulatory sequences are less desired; testing in human whole blood assay, wherein fresh human blood is treated with an RNAi agent and cytokine/chemokine levels are determined [e.g., TNF-alpha (tumor necrosis factor-alpha) and/or MCPI (monocyte chemotactic protein 1)], wherein immunostimulatory sequences are less desired; determination of gene knockdown in vivo using subcutaneous tumors in test animals; target gene modulation analysis, e.g., using a pharmacodynamic (PD) marker, and optimization of specific modifications of the RNAi agents.

In some embodiments, the present invention provides an RNAi agent to a target, e.g., a target disclosed in Tables 1 or 2, and methods of using an RNAi agent to a target, e.g., a target disclosed in Tables 1 or 2. RNAi agents disclosed herein include those compositions capable of mediating RNA interference, including, interalia, shRNAs and siRNAs. In some embodiments, the RNAi agent comprises an antisense strand and a sense strand.

An embodiment of the invention provides a composition comprising an RNAi agent comprising a first (sense) or second (antisense) strand, wherein the sense and/or antisense strand comprises at least 15 contiguous nucleotides differing by 0, 1, 2, or 3 nucleotides from the antisense strand of an RNAi agent to a target, e.g., a target disclosed in Tables 1 or 2. In another embodiment, the present invention provides a composition comprising an RNAi agent comprising a sense strand and an antisense strand, wherein the antisense strand comprises at least 15 contiguous nucleotides differing by 0, 1, 2, or 3 nucleotides from the antisense strand of an RNAi agent.

In another embodiment, the present invention provides a composition comprising an RNAi agent comprising a sense strand and an antisense strand, wherein the sense strand comprises at least 15 contiguous nucleotides differing by 0, 1, 2, or 3 nucleotides from the sense strand and the antisense strand comprises at least 15 contiguous nucleotides differing by 0, 1, 2, or 3 nucleotides from the antisense strand of an RNAi agent to a target, e.g., a target disclosed in Tables 1 or 2.

In one embodiment, the present invention provides particular compositions comprising an RNAi agent comprising an antisense strand, wherein the antisense strand comprises at least 15 contiguous nucleotides from the antisense strand of an RNAi agent to a target, e.g., a target disclosed in Tables 1 or 2. In another embodiment, the present invention provides a composition comprising an RNAi agent comprising a sense strand and an antisense strand, wherein the sequence of the antisense strand is the sequence of the antisense strand of an RNAi agent to a target, e.g., a target disclosed in Tables 1 or 2. In another embodiment, the present invention provides a composition comprising an RNAi agent comprising a sense strand and an antisense strand, wherein the sequence of the antisense strand comprises the sequence of the antisense strand of an RNAi agent to a target, e.g., a target disclosed in Tables 1 or 2.

In some embodiments, the antisense and sense strand can be two physically separated strands, or can be components of a single strand or molecule, e.g., they are linked a loop of nucleotides or other linker. A non-limiting example of the former is a siRNA; a non-limiting example of the latter is a shRNA. The can also, optionally, exist single-stranded nicks in the sense strand, or one or more mismatches between the antisense and sense strands.

Additional modified sequences (e.g., sequences comprising one or more modified base) of each of the compositions above are also contemplated as part of the disclosure.

In one embodiment, the antisense strand is about 30 or fewer nucleotides in length. In one embodiment, the antisense strand forms a duplex region with a sense strand, wherein the duplex region is about 15 to 30 nucleotide pairs in length.

In one embodiment, the antisense strand is about 15 to about 30 nucleotides in length, including about 19 to about 23 nucleotides in length. In one embodiment, the antisense strand has at least the length selected from about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides and 30 nucleotides.

In one embodiment, the RNAi agent comprises a modification that causes the RNAi agent to have increased stability in a biological sample or environment.

In one embodiment, the RNAi agent comprises at least one sugar backbone modification (e.g., phosphorothioate linkage) or at least one 2'-modified nucleotide.

In one embodiment, the RNAi agent comprises: at least one 5'-uridine-adenine-3' (5'-ua-3') dinucleotide, wherein the uridine is a 2'-modified nucleotide; at least one 5'-uridine-5 guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5'-uu-3') dinucleotide, wherein the 5'-uridine is a 2'-modified nucleotide. These dinucleotide motifs are particularly prone to serum nuclease degradation (e.g. RNase A). Chemical modification at the 2'-position of the first pyrimidine nucleotide in the motif prevents or slows down such cleavage. This modification recipe is also known under the term 'endo light'.

In one embodiment, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one embodiment, all pyrimidines (uridine and cytidine) are 2'-O-methyl-modified nucleosides. In some embodiments, one or more nucleotides can be modified, or substituted with DNA, a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), unlocked nucleic acid (UNA).

In some embodiments, the sense and/or antisense strand can terminate at the 3' end with a phosphate or modified internucleoside linker, and further comprise, in 5' to 3' order: a spacer, a second phosphate or modified internucleoside linker, and a 3' end cap. In some embodiments, modified internucleoside linker is selected from phosphorothioate, phosphorodithioate, phosphoramidate, boranophosphonoate, an amide linker, and a compound of formula (I):

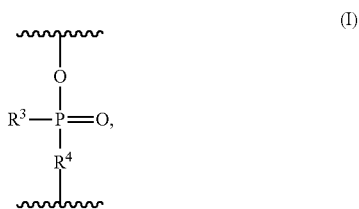

where R3 is selected from O—, S—, NH2, BH3, CH3, C1-6 alkyl, C6-10 aryl, C1-6 alkoxy and C6-10 aryl-oxy, wherein C1-6 alkyl and C6-10 aryl are unsubstituted or optionally independently substituted with 1 to 3 groups independently selected from halo, hydroxyl and NH2; and R4 is selected from O, S, NH, and CH2. In some embodiments, the spacer can be a sugar, alkyl, cycloakyl, ribitol or other type of abasic nucleotide, 2'-deoxy-ribitol, diribitol, 2'-methoxy-ethoxy-ribitol (ribitol with 2'-MOE), C3-6 alkyl, or 4-methoxybutane-1,3-diol (5300). In some embodiments, the 3' end cap can be selected from any of various 3' end caps described herein or known in the art. In some embodiments, one or more phosphates can be replaced by a modified internucleoside linker.

In one embodiment, the RNAi agent comprises at least one blunt end.

In one embodiment, the RNAi agent comprises an overhang having 1 nt to 4 nt.

In one embodiment, the RNAi agent comprises an overhang at the 3'-end of the antisense strand of the RNAi agent.

In one embodiment, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

In one embodiment, the composition further comprises a second RNAi agent to a target, e.g., a target disclosed in Tables 1 or 2. RNAi agents of the present invention can be delivered or introduced (e.g., to a cell in vitro or to a patient) by any means known in the art. "Introducing into a cell," when referring to an iRNA, means facilitating or effecting uptake or absorption into the cell, as is understood by those skilled in the art. Absorption or uptake of an iRNA can occur through unaided diffusive or active cellular processes, or by auxiliary agents or devices. The meaning of this term is not limited to cells in vitro; an iRNA may also be "introduced into a cell," wherein the cell is part of a living organism. In such an instance, introduction into the cell will include the delivery to the organism. For example, for in vivo delivery, iRNA can be injected into a tissue site or administered systemically. In vivo delivery can also be by a beta-glucan delivery system, such as those described in U.S. Pat. Nos. 5,032,401 and 5,607,677, and U.S. Publication No. 2005/0281781 which are hereby incorporated by reference in their entirety. In vitro introduction into a cell includes methods known in the art such as electroporation and lipofection. Further approaches are described below or known in the art.

Delivery of RNAi agent to tissue is a problem both because the material must reach the target organ and must also enter the cytoplasm of target cells. RNA cannot penetrate cellular membranes, so systemic delivery of naked RNAi agent is unlikely to be successful. RNA is quickly degraded by RNAse activity in serum. For these reasons, other mechanisms to deliver RNAi agent to target cells has been devised. Methods known in the art include but are not limited to: viral delivery (retrovirus, adenovirus, lentivirus, baculovirus, AAV); liposomes (Lipofectamine, cationic DOTAP, neutral DOPC) or nanoparticles (cationic polymer, PEI), bacterial delivery (tkRNAi), and also chemical modification (LNA) of siRNA to improve stability. Xia et al. 2002 Nat. Biotechnol. 20 and Devroe et al. 2002. BMC Biotechnol. 21: 15, disclose incorporation of siRNA into a viral vector. Other systems for delivery of RNAi agents are contemplated, and the RNAi agents of the present invention can be delivered by various methods yet to be found and/or approved by the FDA or other regulatory authorities. Liposomes have been used previously for drug delivery (e.g., delivery of a chemotherapeutic). Liposomes (e.g., cationic liposomes) are described in PCT publications WO02/100435A1, WO03/015757A1, and WO04029213A2; U.S. Pat. Nos. 5,962,016; 5,030,453; and 6,680,068; and U.S. Patent Application 2004/0208921. A process of making liposomes is also described in WO04/002453AI. Furthermore, neutral lipids have been incorporated into cationic liposomes (e.g., Farhood et al. 1995). Cationic liposomes have been used to deliver RNAi agent to various cell types (Sioud and Sorensen 2003; U.S. Patent Application 2004/0204377; Duxbury et al., 2004; Donze and Picard, 2002). Use of neutral liposomes disclosed in Miller et al. 1998, and U.S. Publ. 2003/0012812.

As used herein, the term "SNALP" refers to a stable nucleic acid-lipid particle. A SNALP represents a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817. These applications are incorporated herein by reference in their entirety.

Chemical transfection using lipid-based, amine-based and polymer-based techniques, is disclosed in products from Ambion Inc., Austin, Tex.; and Novagen, EMD Biosciences, Inc, an Affiliate of Merck KGaA, Darmstadt, Germany); Ovcharenko D (2003) "Efficient delivery of siRNAs to human primary cells." Ambion TechNotes 10 (5): 15-16). Additionally, Song et al. (Nat Med. published online (Fete 10, 2003) doi: 10.1038/nm828) and others [Caplen et al. 2001 Proc. Natl. Acad. Sci. (USA), 98: 9742-9747; and McCaffrey et al. Nature 414: 34-39] disclose that liver cells can be efficiently transfected by injection of the siRNA into a mammal's circulatory system.

A variety of molecules have been used for cell-specific RNAi agent delivery. For example, the nucleic acid-condensing property of protamine has been combined with specific antibodies to deliver siRNAs. Song et al. 2005 Nat Biotech. 23: 709-717. The self-assembly PEGylated polycation polyethylenimine has also been used to condense and protect siRNAs. Schiffelers et al. 2004 Nucl. Acids Res. 32: 49, 141-110.

The siRNA-containing nanoparticles were then successfully delivered to integrin overexpressing tumor neovasculature. Hu-Lieskovan et al. 2005 Cancer Res. 65: 8984-8992. The RNAi agents of the present invention can be delivered via, for example, Lipid nanoparticles (LNP); neutral liposomes (NL); polymer nanoparticles; double-stranded RNA binding motifs (dsRBMs); or via modification of the RNAi agent (e.g., covalent attachment to the dsRNA).

Lipid nanoparticles (LNP) are self-assembling cationic lipid based systems. These can comprise, for example, a neutral lipid (the liposome base); a cationic lipid (for siRNA loading); cholesterol (for stabilizing the liposomes); and PEG-lipid (for stabilizing the formulation, charge shielding and extended circulation in the bloodstream). The cationic lipid can comprise, for example, a headgroup, a linker, a tail and a cholesterol tail. The LNP can have, for example, good tumor delivery, extended circulation in the blood, small particles (e.g., less than 100 nm), and stability in the tumor microenvironment (which has low pH and is hypoxic).

Neutral liposomes (NL) are non-cationic lipid based particles. Polymer nanoparticles are self-assembling polymer-based particles. Double-stranded RNA binding motifs (dsRBMs) are self-assembling RNA binding proteins, which will need modifications.

The present disclosure further provides use of an RNAi agent for the treatment of cancer, such as colon or endometrial cancer. Also provided is a use of an RNAi agent protein for the manufacture of a medicament for treating cancer, such as a cancer disclosed in Tables 1 or 2.

In another embodiment, the present invention provides a method of treating cancer associated with microsatellite instability, gene amplifications, duplications, deletions or mutations, such as a cancer disclosed in Tables 1 or 2, by administering to a subject in need thereof a therapeutically effective amount of a pharmaceutical composition comprising an RNAi agent described herein.

In another embodiment, an RNAi agent which inhibits the expression of a target, e.g., any of the targets disclosed in Tables 1 or 2, for use in the treatment of cancer is provided. The cancer is chosen from any of the cancers disclosed in Tables 1 or 2.

Several other molecules may be suitable to inhibit a target disclosed herein, such as low molecular weight compounds, cyclic peptides, RNAi agents, Aptamers, CRISPRs, TALENs, ZFNs, and antibodies.

Low Molecular Weight Compounds and Therapies

In one embodiment, the disclosure comprises a low molecular weight compound inhibiting gene expression that inhibits the expression of a target, e.g., any of the targets disclosed in Tables 1 or 2.

In another embodiment, the present invention provides a molecule that inhibits the normal cellular function of the target protein. Exemplary small molecules that inhibit targets described herein are provided in this disclosure.

The present disclosure thus provides use of a low molecular weight inhibitor for a target, e.g., a target disclosed in Tables 1 or 2 for the treatment of cancer, such as a cancer disclosed herein. Also provided is a use of a low molecular weight inhibitor of a target, e.g., a target disclosed in Tables 1 or 2 for the manufacture of a medicament for treating cancer, such as a cancer disclosed in Tables 1 or 2.

In another embodiment, the present invention provides a method of treating cancer associated with microsatellite instability, gene amplifications, duplications, deletions or mutations, such as a cancer disclosed in Tables 1 or 2, by administering to a subject in need thereof a therapeutically effective amount of a pharmaceutical composition comprising an RNAi agent described herein.

In another embodiment, a low molecular weight inhibitor for use in the treatment of cancer is provided. The cancer may be a cancer disclosed in Tables 1 or 2.

The inhibitor of the present disclosure can also be, inter alia, derived from a CRISPR/Cas system, TALEN, or ZFN.

CRISPR

By "CRISPR" or "CRISPR to a target" or "CRISPR to inhibit a target" and the like is meant a set of clustered regularly interspaced short palindromic repeats, or a system comprising such a set of repeats. By "Cas" is meant a CRISPR-associated protein. By "CRISPR/Cas" system is meant a system derived from CRISPR and Cas which can be used to silence, enhance or mutate the target gene, e.g., a target gene of any of the targets disclosed in Tables 1 or 2.

Naturally-occurring CRISPR/Cas systems are found in approximately 40% of sequenced eubacteria genomes and 90% of sequenced archaea. Grissa et al. 2007. BMC Bioinformatics 8: 172. This system is a type of prokaryotic immune system that confers resistance to foreign genetic elements such as plasmids and phages and provides a form of acquired immunity. Barrangou et al. 2007. Science 315: 1709-1712; Marragini et al. 2008 Science 322: 1843-1845. The CRISPR/Cas system has been modified for use in gene editing (silencing, enhancing or changing specific genes) in eukaryotes such as mice or primates. Wiedenheft et al. 2012. Nature 482: 331-8. This is accomplished by introducing into the eukaryotic cell a plasmid containing a specifically designed CRISPR and one or more appropriate Cas.

The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the target CRISPR/Cas system, the spacers are derived from the target gene sequence. The repeats generally show some dyad symmetry, implying the formation of a secondary structure such as a hairpin, but they are not truly palindromic.

RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. 2010. Science 327: 167-170; Makarova et al. 2006 Biology Direct 1: 7. The spacers thus serve as templates for RNA molecules, analogously to siRNAs. Pennisi 2013. Science 341: 833-836.

As these naturally occur in many different types of bacteria, the exact arrangements of the CRISPR and structure, function and number of Cas genes and their product differ somewhat from species to species. Haft et al. 2005 PLoS Comput. Biol. 1: e60; Kunin et al. 2007. Genome Biol. 8: R61; Mojica et al. 2005. J. Mol. Evol. 60: 174-182; Bolotin et al. 2005. Microbiol. 151: 2551-2561; Pourcel et al. 2005. Microbiol. 151: 653-663; and Stern et al. 2010. Trends. Genet. 28: 335-340. For example, the Cse (Cas subtype, E. coli) proteins (e.g., CasA) form a functional complex, Cascade, that processes CRISPR RNA transcripts into spacer-repeat units that Cascade retains. Brouns et al. 2008. Science 321: 960-964. In other prokaryotes, Cas6 processes the CRISPR transcript. The CRISPR-based phage inactivation in E. coli requires Cascade and Cas3, but not Cas1 or Cas2. The Cmr (Cas RAMP module) proteins in Pyrococcus furiosus and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi 2013. Science 341: 833-836.

The CRISPR/Cas system can thus be used to edit a target gene, e.g., a target gene disclosed in Tables 1 or 2 (adding or deleting a basepair), e.g., repairing a damaged target gene, or introducing a premature stop which thus decreases expression of an over-expressed target. The CRISPR/Cas system can alternatively be used like RNA interference, turning off the target gene in a reversible fashion. In a mammalian cell, for example, the RNA can guide the Cas protein to the target promoter, sterically blocking RNA polymerases.

Artificial CRISPR/Cas systems can be generated which inhibit a target, e.g., a target disclosed in Tables 1 or 2, using technology known in the art, e.g., that described in U.S. patent application Ser. No. 13/842,859. The present disclosure thus provides a CRISPR/Cas system suitable for editing a target, e.g., any of the targets disclosed in Tables 1 or 2, for use in the treatment of cancer, such as a cancer disclosed in Tables 1 or 2. Also provided is a use of a CRISPR/Cas system suitable for editing a target gene, e.g., any of the target genes disclosed Tables 1 or 2 for the manufacture of a medicament for treating cancer, such as a cancer disclosed in Tables 1 or 2.

In another embodiment, the present invention provides a method of treating cancer associated with microsatellite instability, gene amplifications, duplications, deletions or mutations, such as a cancer disclosed in Tables 1 or 2, by administering to a subject in need thereof a therapeutically effective amount of a pharmaceutical composition comprising a CRISPR/Cas system suitable for editing a target, e.g., any of the targets disclosed in Tables 1 or 2.

In another embodiment, a CRISPR/Cas system suitable for editing a target, e.g., any of the targets disclosed in Tables 1 or 2, for use in the treatment of cancer is provided. The cancer may be a cancer disclosed in Tables 1 or 2.

An inhibitory CRISPR system can include a guide RNA (gRNA) comprising a targeting domain, i.e., a nucleotide sequence that is complementary to a target DNA strand, and a second domain that interacts with an RNA-directed nuclease, e.g., cpf1 or Cas molecule, e.g., Cas9 molecule.

In some embodiments, the ability of an RNA-directed nuclease, e.g., cpf1 or Cas molecule, e.g., Cas9 molecule, to interact with and cleave a target nucleic acid is Protospacer Adjacent Motif (PAM) sequence dependent. A PAM sequence is a sequence in the target nucleic acid. In some embodiments, cleavage of the target nucleic acid occurs upstream from the PAM sequence. RNA-directed nuclease molecules, e.g., cpf1 or Cas molecules, e.g., Cas9 molecules, from different bacterial species can recognize different sequence motifs (e.g., PAM sequences). In addition to recognizing different PAM sequences, RNA-directed nucleases, e.g., cpf1 or Cas molecules, e.g., Cas9 molecules, from different species may be directed to different target sequences (e.g., target sequences adjacent, e.g., immediately upstream, to the PAM sequence) by gRNA molecules comprising targeting domains capable of hybridizing to said target sequences and a tracr sequence that binds to said RNA-directed nuclease, e.g., cpf1 or Cas molecule, e.g., Cas9 molecule.

In some embodiments, the CRISPR system comprises a gRNA molecule and a Cas9 molecule from S. pyogenes. A Cas9 molecule of S. pyogenes recognizes the sequence motif NGG and directs cleavage of a target nucleic acid sequence 1 to 10, e.g., 3 to 5, base pairs upstream from that sequence.

In some embodiments, the CRISPR system comprises a gRNA molecule and a Cas9 molecule from S. thermophilus. A Cas9 molecule of S. thermophilus recognizes the sequence motif NGGNG and NNAGAAW (W=A or T) and directs cleavage of a core target nucleic acid sequence 1 to 10, e.g., 3 to 5, base pairs upstream from these sequences. A gRNA molecule useful with S. thermophilus-based CRISPR systems may include a tracr sequence known to interact with S. thermophilus. See, e.g., Horvath et al., SCIENCE 2010; 327(5962): 167-170, and Deveau et al., J BACTERIOL 2008; 190(4): 1390-1400.

In some embodiments, the CRISPR system comprises a gRNA molecule and a Cas9 molecule from S. aureus. A Cas9 molecule of S. aureus recognizes the sequence motif NNGRR (R=A or G) and directs cleavage of a target nucleic acid sequence 1 to 10, e.g., 3 to 5, base pairs upstream from that sequence.

In some embodiments, the CRISPR system comprises a gRNA molecule and an RNA-directed nuclease, e.g., cpf1 molecule, e.g., a cpf1 molecule from L. bacterium or a cpf1 molecule from A. sp. A cpf1 molecule, e.g., a cpf1 molecule from L. bacterium or a cpf1 molecule from A. sp., recognizes the sequence motive of TTN (where N=A, T, G or C) or preferably TTTN (where N=A, T, G or C), and directs cleavage of a target nucleic acid sequence 1-25 base pairs upstream of the PAM sequence, e.g., 18-19 base pairs upstream from the PAM sequence on the same strand as the PAM and 23 base pairs upstream of the PAM sequence on the opposite strand as the PAM, creating a sticky end break.

TALEN

By "TALEN" or "TALEN to target" or "TALEN to inhibit target" and the like is meant a transcription activator-like effector nuclease, an artificial nuclease which can be used to edit a target gene, e.g., any of the targets disclosed in Tables 1 or 2.

TALENs are produced artificially by fusing a TAL effector DNA binding domain to a DNA cleavage domain. Transcription activator-like effects (TALEs) can be engineered to bind any desired DNA sequence, including a portion of the target gene. By combining an engineered TALE with a DNA cleavage domain, a restriction enzyme can be produced which is specific to any desired DNA sequence, including a target sequence, e.g., a target disclosed in Tables 1 or 2. These can then be introduced into a cell, wherein they can be used for genome editing. Boch 2011 Nature Biotech. 29: 135-6; and Boch et al. 2009 Science 326: 1509-12; Moscou et al. 2009 Science 326: 3501.

TALEs are proteins secreted by Xanthomonas bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. 2011 Nucl. Acids Res. 39: e82; Miller et al. 2011 Nature Biotech. 29: 143-8; Hockemeyer et al. 2011 Nature Biotech. 29: 731-734; Wood et al. 2011 Science 333: 307; Doyon et al. 2010 Nature Methods 8: 74-79; Szczepek et al. 2007 Nature Biotech. 25: 786-793; and Guo et al. 2010 J. Mol. Biol. 200: 96.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. 2011 Nature Biotech. 29: 143-8.

A TALEN to a target can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the target gene or introduce such a defect into a wt target gene, thus decreasing expression of target gene.

TALENs specific to sequences in a target gene, e.g., a target gene disclosed in Tables 1 or 2, can be constructed using any method known in the art, including various schemes using modular components. Zhang et al. 2011 Nature Biotech. 29: 149-53; Geibler et al. 2011 PLoS ONE 6: e19509.

The present disclosure thus provides use of a TALEN for a target gene, e.g., a target gene disclosed in Tables 1 or 2, for the treatment of cancer, such as a cancer disclosed in Tables 1 or 2. Also provided is a use of a TALEN for the manufacture of a medicament for treating cancer, such as a cancer disclosed in Tables 1 or 2.

In another embodiment, the present invention provides a method of treating cancer associated with microsatellite instability gene amplifications, duplications, deletions or mutations, such as a cancer disclosed in Tables 1 or 2, by administering to a subject in need thereof a therapeutically effective amount of a pharmaceutical composition comprising a TALEN of a target described herein. In another embodiment, a TALEN of a target, e.g., a target gene disclosed in Tables 1 or 2 for use in the treatment of cancer is provided. The cancer may be a cancer disclosed in Tables 1 or 2.

Zinc Finger Nuclease to Inhibit Target Genes

By "ZFN", or "Zinc Finger Nuclease" or "ZFN to a target gene" or "ZFN to inhibit target gene" and the like is meant a zinc finger nuclease, an artificial nuclease which can be used to edit a target gene, e.g., a target disclosed in Tables 1 or 2.

Like a TALEN, a ZFN comprises a FokI nuclease domain (or derivative thereof) fused to a DNA-binding domain. In the case of a ZFN, the DNA-binding domain comprises one or more zinc fingers. Carroll et al. 2011. Genetics Society of America 188: 773-782; and Kim et al. Proc. Natl. Acad. Sci. USA 93: 1156-1160.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs is required to target non-palindromic DNA sites. The two individual ZFNs must bind opposite strands of the DNA with their nucleases properly spaced apart. Bitinaite et al. 1998 Proc. Natl. Acad. Sci. USA 95: 10570-5.

Also like a TALEN, a ZFN can create a double-stranded break in the DNA, which can create a frame-shift mutation if improperly repaired, leading to a decrease in the expression and amount of a target in a cell. ZFNs can also be used with homologous recombination to mutate, or repair defects, in the target gene.

ZFNs specific to sequences in a target gene, e.g., a target disclosed in Tables 1 or 2, can be constructed using any method known in the art. Cathomen et al. Mol. Ther. 16: 1200-7; and Guo et al. 2010. J. Mol. Biol. 400: 96.

The present disclosure thus provides use of a ZFN specific to sequences in a target gene, e.g., a target disclosed in Tables 1 or 2 for the treatment of cancer, such as colon or endometrial cancer. Also provided is a use of a ZFN specific to sequences in a target gene, e.g., a target disclosed in Tables 1 or 2 for the manufacture of a medicament for treating cancer, such a cancer disclosed in Tables 1 or 2.

In another embodiment, the present invention provides a method of treating cancer associated with microsatellite instability, gene amplifications, duplications, deletions or mutations, such as a cancer disclosed in Tables 1 or 2, by administering to a subject in need thereof a therapeutically effective amount of a pharmaceutical composition comprising a ZFN specific to sequences in a target gene, e.g., a target disclosed in Tables 1 or 2. In another embodiment, a ZFN specific to sequences in a target gene, e.g., a target disclosed in Tables 1 or 2 for use in the treatment of cancer is provided. The cancer may be a cancer disclosed in Tables 1 or 2.

Antibodies to Target Genes

In some embodiments, the present invention provides an inhibitor, e.g., an inhibitor to any of the targets disclosed in Tables 1 or 2, which is an antibody or epitope-binding fragment or derivative thereof, and methods of using the same. Various types of antibodies and epitope-binding fragments and derivatives thereof are known in the art, as are methods of producing these. Any of these, including but not limited to those described herein, can be used to produce an inhibitor, e.g., an inhibitor to any of the targets disclosed in Tables 1 or 2, which can be used in various methods of inhibiting a target and treating a target-related disease, such as cancer, e.g., a cancer disclosed in Tables 1 or 2.

In certain embodiments of the invention, the antibody to a target, e.g., a target disclosed in Tables 1 or 2 is an intrabody. Single chain antibodies expressed within the cell (e.g. cytoplasm or nucleus) are called intrabodies. Due to the reducing environment within the cell, disulfide bridges, believed to be critical for antibody stability, are not formed. Thus, it was initially believed that applications of intrabodies are not suitable. But several cases are described showing the feasibility of intrabodies (Beerli et al., 1994 J Biol Chem, 269, 23931-6; Biocca et al., 1994 Bio/Technology, 12, 396-9; Duan et al., 1994 Proceedings of the National Academy of Sciences of the United States of America, 91, 5075-9; Gargano and Cattaneo, 1997 FEBS Lett, 414, 537-40; Greenman et al., 1996 J Immunol Methods, 194, 169-80; Martineau et al., 1998 Journal of Molecular Biology, 280, 117-27; Mhashilkar et al., 1995 EMBO Journal, 14, 1542-51; Tavladoraki et al., 1993 Nature, 366, 469-72). In these cases, intrabodies work by, e.g., blocking the cytoplasmic antigen and therefore inhibiting its biological activity.

Such intracellular antibodies are also referred to as intrabodies and may comprise a Fab fragment, or preferably comprise a scFv fragment (see, e.g., Lecerf et al., Proc. Natl. Acad. Sci. USA 98:4764-49 (2001). The framework regions flanking the CDR regions can be modified to improve expression levels and solubility of an intrabody in an intracellular reducing environment (see, e.g., Worn et al., J. Biol. Chem. 275:2795-803 (2000). An intrabody may be directed to a particular cellular location or organelle, for example by constructing a vector that comprises a polynucleotide sequence encoding the variable regions of an intrabody that may be operatively fused to a polynucleotide sequence that encodes a particular target antigen within the cell (see, e.g., Graus-Porta et al., Mol. Cell Biol. 15:1182-91 (1995); Lener et al., Eur. J. Biochem. 267:1196-205 (2000)). An intrabody may be introduced into a cell by a variety of techniques available to the skilled artisan including via a gene therapy vector, or a lipid mixture (e.g., Provectin™ manufactured by Imgenex Corporation, San Diego, Calif.), or according to photochemical internalization methods.

Intrabodies can be derived from monoclonal antibodies which were first selected with classical techniques (e.g., phage display) and subsequently tested for their biological activity as intrabodies within the cell (Visintin et al., 1999 Proceedings of the National Academy of Sciences of the United States of America, 96, 11723-11728). For additional information, see: Cattaneo, 1998 Bratisl Lek Listy, 99, 413-8; Cattaneo and Biocca, 1999 Trends In Biotechnology, 17, 115-21. The solubility of an intrabody can be modified by either changes in the framework (Knappik and Plucktuhn, 1995 Protein Engineering, 8, 81-9) or the CDRs (Kipriyanov et al., 1997; Ulrich et al., 1995 Protein Engineering, 10, 445-53). Additional methods for producing intrabodies are described in the art, e.g., U.S. Pat. Nos. 7,258,985 and 7,258,986.

In one embodiment, antigen-binding proteins, such as antibodies, that are able to target cytosolic/intracellular proteins, for example, a target protein, e.g., a target disclosed in Tables 1 or 2. The disclosed antibodies target a peptide/MHC complex as it would typically appear on the surface of a cell following antigen processing of the target protein and presentation by the cell. HLA class I binds to peptides approximately 9 amino acids in length and presents them on the surface of the cell to cytotoxic T lymphocytes. The presentation of these peptides is the product of cytoplasmic cleavage by enzymes and active transport by transporter proteins. Further, the binding of particular peptides after processing and localization is heavily influenced by the amino acid sequence of the particular HLA protein. Most of these steps are amenable to in vitro characterization, allowing one to predict the likelihood that a particular amino acid sequence, derived from a larger peptide or protein of interest, will be successfully processed, transported, bound by MHC class I, and presented to cytotoxic T lymphocytes. In that regard, the antibodies mimic T-cell receptors in that the antibodies have the ability to specifically recognize and bind to a peptide in an MHC-restricted fashion, that is, when the peptide is bound to an MHC antigen. The peptide/MHC complex recapitulates the antigen as it would typically appear on the surface of a cell following antigen processing and presentation of the target protein to a T-cell. The accurate prediction for a particular step in this process is dependent upon models informed by experimental data. The cleavage specificity of the proteasome, producing peptides often <30 amino acids in length, can be determined by in vitro assays. The affinity for the transporter complex can similarly be determined by relatively straight-forward in vitro binding assays. The MHC class I protein's affinity is highly variable, depending on the MHC allele, and generally must be determined on an allele-by-allele basis. One approach is to elute the peptides presented by the MHC protein on the cell surface to generate a consensus motif. An alternative approach entails generating cells deficient in a peptide processing step such that most or all of the MHC proteins on the cell surface are not loaded with a peptide. Many different peptides can be washed over the cells in parallel and monitored for binding. The set of peptides that do and do not bind can be used to train a classifier (such as an artificial neural network or support vector machine) to discriminate between the two peptide sets. This trained classifier can then be applied to novel peptides to predict their binding to the MHC allele. Alternatively, the affinity for each peptide can be used to train a regression model, which can then be used to make quantitative predictions regarding the MHC protein's affinity for an untested peptide. The collection of such datasets is laborious, so methods exist to combine data collected for one HLA allele with the knowledge of the amino acid differences between that particular allele and another unstudied MHC allele to predict its peptide binding specificity.

Additional methods for constructing antibodies to cytosolic peptides such as a target gene disclosed in Tables 1 or 2 are described in, for example, WO 2012/135854, which is hereby incorporated by reference in its entirety. This document describes production of antibodies which recognize and bind to epitopes of a peptide/MHC complex, such as a peptide/HLA-A2 or peptide/HLA-A0201 complex. In some embodiments of the invention, the peptide is portion of a target gene disclosed in Tables 1 or 2.

HLA class I binds to peptides approximately 9 amino acids in length and presents them on the surface of the cell to cytotoxic T lymphocytes. The presentation of these peptides is the product of cytoplasmic cleavage by enzymes and active transport by transporter proteins. Further, the binding of particular peptides after processing and localization is heavily influenced by the amino acid sequence of the particular HLA protein. Most of these steps are amenable to in vitro characterization, allowing one to predict the likelihood that a particular amino acid sequence, derived from a larger peptide or protein of interest, will be successfully processed, transported, bound by MHC class I, and presented to cytotoxic T lymphocytes. The accurate prediction for a particular step in this process is dependent upon models informed by experimental data. The cleavage specificity of the proteasome, producing peptides often <30 amino acids in length, can be determined by in vitro assays. The affinity for the transporter complex can similarly be determined by relatively straight-forward in vitro binding assays. The MHC class I protein's affinity is highly variable, depending on the MHC allele, and generally must be determined on an allele-by-allele basis. One approach is to elute the peptides presented by the MHC protein on the cell surface to generate a consensus motif. An alternative approach entails generating cells deficient in a peptide processing step such that most or all of the MHC proteins on the cell surface are not loaded with a peptide. Many different peptides can be washed over the cells in parallel and monitored for binding. The set of peptides that do and do not bind can be used to train a classifier (such as an artificial neural network or support vector machine) to discriminate between the two peptide sets. This trained classifier can then be applied to novel peptides to predict their binding to the MHC allele. Alternatively, the affinity for each peptide can be used to train a regression model, which can then be used to make quantitative predictions regarding the MHC protein's affinity for an untested peptide. The collection of such datasets is laborious, so methods exist to combine data collected for one HLA allele with the knowledge of the amino acid differences between that particular allele and another unstudied MHC allele to predict its peptide binding specificity.

One such machine learning approach that combines prediction of likely proteasomal cleavage, transporter affinity, and MHC affinity is SMM (Stabilized Matrix Method, Tenzer S et al, 2005. PMID 15868101). This approach can be extended to mutations specific to an indication: a mutation leading to an amino acid change alters the peptide sequence and can lead to a peptide that produces a different score than the wildtype sequence. By focusing on such mutations and selecting those mutant peptide sequences that score highly, one can generate peptides that are presented solely in a diseased state because the sequence simply does not exist in a non-diseased individual. Cross-reactivity can be further minimized by also evaluating the wildtype sequence and selecting for downstream analyses only those peptides whose non-mutant sequence is not predicted to be processed and presented by MHC efficiently.

Once appropriate peptides have been identified, peptide synthesis may be done in accordance with protocols well known to those of skill in the art. Peptides may be directly synthesized in solution or on a solid support in accordance with conventional techniques (See for example, Solid Phase Peptide Synthesis by John Morrow Stewart and Martin et al. Application of Almez-mediated Amidation Reactions to Solution Phase Peptide Synthesis, Tetrahedron Letters Vol. 39, pages 1517-1520 1998). Peptides may then be purified by high-pressure liquid chromatography and the quality assessed by high-performance liquid chromatography analysis. Purified peptides may be dissolved in DMSO diluted in PBS (pH7.4) or saline and stored at −80 C. The expected molecular weight may be confirmed using matrix-assisted laser desorption mass spectrometry.

Subsequent to peptide selection, binding of the peptide to HLA-A may be tested. In one method, binding activity is tested using the antigen-processing deficient T2 cell line, which stabilizes expression of HLA-A on its cell surface when a peptide is loaded exogenously in the antigen-presenting groove by incubating the cells with peptide for a sufficient amount of time. This stabilized expression is read out as an increase in HLA-A expression by flow cytometry using HLA-A2 specific monoclonal antibodies (for example, BB7.2) compared to control treated cells. In another method, presence of the peptide in the HLA-A2 antigen-presenting groove of T2 cells may be detected using targeted mass spectrometry. The peptides are enriched using a MHC-specific monoclonal Ab (W6/32) and then specific MRM assays monitor the peptides predicted to be presented (See for example, Kasuga, Kie. (2013) Comprehensive Analysis of MHC Ligands in Clinical material by Immunoaffinity-Mass Spectrometry, Helena Backvall and Janne Lethio, The Low Molecular Weight Proteome: Methods and Protocols (203-218), New York, N.Y.: Springer Sciences+Business Media and Kowalewski D and Stevanovic S. (2013) Biochemical Large-Scale Identification of MHC Class I Ligands, Peter van Endert, Antigen Processing: Methods and Protocols, Methods in Molecular Biology, Vol 960 (145-158), New York, N.Y.: Springer Sciences+Business Media).

This strategy differs slightly than the normally applied tandem mass spectrometry based peptide sequencing. Heavy labeled internal standards are used for identification which results in a more sensitive and quantitative approach.

Once a suitable peptide has been identified the next step would be identification of specific antibodies to the peptide/HLA-A complex, the "target antigen", utilizing conventional antibody generation techniques such as phage display or hybridoma technology in accordance with protocols well known to those skilled in the art. The target antigen (for example, the peptide/HLA-A02-01 complex) is prepared by bringing the peptide and the HLA-A molecule together in solution to form the complex. Next, selection of Fab or scFv presenting phage that bind to the target antigen are selected by iterative binding of the phage to the target antigen, which is either in solution or bound to a solid support (for example, beads or mammalian cells), followed by removal of non-bound phage by washing and elution of specifically bound phage. The targeted antigen may be first biotinylated for immobilization, for example, to streptavidin-conjugated (for example, Dynabeads M-280).

Positive Fab or scFv clones may be then tested for binding to peptide/HLA-A2 complexes on peptide-pulsed T2 cells by flow cytometry. T2 cells pulsed with the specific peptide or a control irrelevant peptide may be incubated with phage clones. The cells are washed and bound phage are detected by binding an antibody specific for the coat protein (for example, M13 coat protein antibody) followed by a fluorescent labelled secondary antibody to detect the coat protein antibody (for example, anti-mouse Ig). Binding of the antibody clones to human tumor cells expressing both HLA-A2 and the target can also be assessed by incubating the tumor cells with phage as described or purified Fab or scFv flow cytometry and appropriate secondary antibody detection.

An alternative method to isolating antibodies specific to the peptide/HLA-A2 complex may be achieved through conventional hybridoma approaches in accordance with protocols well known to those of skill in the art. In this method, the target antigen is injected into mice or rabbits to elicit an immune response and monoclonal antibody producing clones are generated. In one embodiment, the host mouse may be one of the available human HLA-A2 transgenic animals which may serve to reduce the abundance of non-specific antibodies generated to HLA-A2 alone. Clones may then be screened for specific binding to the target antigen using standard ELISA methods (for example, incubating supernatant from the clonal antibody producing cells with biotinylated peptide/MHC complex captured on streptavidin coated ELISA plates and detected with anti-mouse antibodies). The positive clones can also be identified by incubating supernatant from the antibody producing clones with peptide pulsed T2 cells by flow cytometry and detection with specific secondary antibodies (for example, fluorescent labelled anti-mouse IgG antibodies). Binding of the antibody clones to human tumor cells expressing both HLA-A2 and the target can also be assessed by incubating the tumor cells with supernatant or purified antibody from the hybridoma clones by flow cytometry and appropriate secondary antibody detection.

Immunotherapy (CART)

Adoptive cell transfer has been shown to be a promising treatment for various types of cancer. Adoptive cell transfer in cancer therapy involves the transfer of autologous or allogeneic immune effector cells (such as T cells) to enhance immune response against the tumor in a patient having cancer. Recent methods of adoptive cell transfer that have shown promise in cancer therapy include the genetic modification of cells prior to delivery to the patient to express molecules that target antigens expressed on cancer cells and improve the anti-cancer immune response. Examples of such molecules include T cell receptors (TCRs) and chimeric antigen receptors (CARs), which are described in further detail below.

TCR is a disulfide-linked membrane-anchored heterodimer present on T cell lymphocytes, and normally consisting of an alpha chain and a beta chain. Each chain comprises a variable (V) and a constant (C) domain, wherein the variable domain recognizes an antigen, or an MHC-presented peptide. Signaling is mediated through interaction between the antigen-bound alpha beta heterodimer to CD3 chain molecules, e.g., CD3zeta. Upon binding of a TCR to its antigen, a signal transduction cascade is initiated that can result in T cell activation, T cell expansion, and antitumor effect, e.g., increased cytolytic activity against tumor cells.

In TCR gene therapy, naturally occurring or modified TCRalpha and TCR alpha beta chains with a known specificity and avidity for tumor antigens are introduced and expressed in a T cell. Briefly, a tumor antigen-specific T cell clone, e.g., with high affinity to the target antigen, is isolated from a donor or patient sample, e.g., a blood or PBMC sample. The tumor antigen-specific TCR alpha and beta chains are isolated using standard molecular cloning techniques known in the art, and a recombinant expression vector for delivery into a host PBMC or T cell population, or subpopulation thereof, is generated. The host cell population is transduced, and the TCR-engineered cells are expanded and/or activated ex vivo prior to administration to the patient. T cells redirected with TCRs that target tumor antigens, such as glycoprotein-100 (gp100) and MART-1, have shown success in recent studies. TCR-redirected T cells recognizing any antigens that are uniquely or preferentially expressed on tumor cells can be used in the present invention.

The TCR chains can be modified to improve various TCR characteristics for enhancing therapeutic efficacy. Modifications can be made to the TCR to improve TCR surface expression by any of the following: utilizing promoters that drive high level of gene expression in T cells, e.g., retroviral long terminal repeats (LTRs), CMV, MSCV, SV40 promoters (Cooper et al., J. Virol., 2004; Jones et al., Hum. Gene Ther., 2009); introducing other regulatory elements that can enhance transgene expression, e.g., woodchuck hepatitis virus posttranscriptional regulatory element which increases RNA stability (Zufferey et al., J. Virol.,1999); codon optimization (Gustafsson et al., Trends Biotechnol., 2004); or eliminating mRNA instability motifs or cryptic splice sites (Scholten et al., Clin. Immunol., 2006); or a combination thereof. To reduce TCR chain mispairing between the introduced and endogenous TCR chains, and promote the preferential pairings of the introduced TCR chains with each other, any one of the following: introducing foreign constant domains, e.g., from another organism, to the TCRalpha and TCRbeta chains, e.g., murine constant domains for human TCR chains; increasing interchain affinity by engineering a second disulfide bond in the introduced TCR, e.g., introducing additional cysteine residues in the constant domains (Kuball et al., Blood, 2007); or introducing mutations, e.g., point mutations, that increase the "knob in hole" interface between the TCRalpha and TCRbeta chain (Voss et al., J. Immunol., 2008); or fusing signaling domains, e.g., CD3z domains, directly to the variable domains of the TCRalpha and TCRbeta (Sebestyen et al., 2008); or any combination thereof. The different TCR modifications described above merely represent exemplary modifications, and do not represent an exhaustive or comprehensive list of modifications. Other modifications that increase specificity, avidity, or function of the TCRs or the engineered T cells expressing the TCRs can be readily envisioned by the ordinarily skilled artisan. Methods for introducing the TCRs into host cells and administration of the TCR-engineered cells are further described below.

Single-chain TCRs has been described in, e.g., Willemsen R A et al, Gene Therapy 2000; 7: 1369-1377; Zhang T et al, Cancer Gene Ther 2004; 11: 487-496; Aggen et al, Gene Ther. 2012 April; 19(4):365-74.

Chimeric antigen receptors (CARs) are based upon TCRs, and generally comprise 1) an extracellular antigen binding domain; 2) a transmembrane domain; and 3) an intracellular domain comprising one or more intracellular signaling domains. Similar to TCR gene therapy, CAR gene therapy generally comprises isolating a host cell population from a donor or patient, e.g., PBMCs, T cells, or a subpopulation thereof, and introducing the CAR molecule to the host cells such that the host cells express the CAR. The CAR-redirected T cells are then expanded and activated ex vivo using methods known in the art, such as stimulation by anti-CD3 and anti-CD28 antibodies prior to delivery to the patient.

The antigen binding domain of a CAR refers to a molecule that has affinity for an antigen that is expressed on a target cell, e.g., a cancer cell. The antigen binding domain can be a ligand, a counterligand, or an antibody or antigen-binding fragment thereof, e.g., an Fab, Fab', F(ab')2, or Fv fragment, an scFv antibody fragment, a linear antibody, single domain antibody such as an sdAb (either VL or VH), a camelid VHH domain, a nanobody, and multi-specific antibodies formed from antibody fragments. The antibody or fragment thereof can be humanized. Any antibodies or fragments thereof that recognize and bind to tumor antigens known in the art can be utilized in a CAR.

The transmembrane domain of a CAR refers to a polypeptide that spans the plasma membrane, linking the extracellular antigen binding domain to the intracellular domain. A transmembrane domain can include one or more additional amino acids adjacent to the transmembrane region, e.g., one or more amino acid associated with the extracellular or intracellular region of the protein from which the transmembrane was derived (e.g., 1, 2, 3, 4, 5, 6, 7, 8, 9, 10 up to 15 amino acids of the extracellular or intracellular region). Examples of transmembrane domains can be derived from any one or more of the following: the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp. Additional sequences, e.g., hinge or spacer sequence, can be disposed between a transmembrane domain and another sequence or domain to which it is fused.

The intracellular domain of a CAR includes at least one primary signaling domain and, optionally, one or more co-stimulatory signaling domains, which are responsible for activation of at least one of the normal effector functions of the immune cell in which the CAR has been introduced. Examples of primary signaling domains include TCR zeta, FcR gamma, FcR beta, CD3 gamma, CD3 delta, CD3 epsilon, CD5, CD22, CD32, CD79a, CD79b, CD66d, DAP10, and DAP12. Examples of costimulatory signaling domains include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, and PAG/Cbp. The intracellular signaling sequences may be linked to each other in random or specified order, and may be separated by a short oligo or polypeptide linker.

Introduction of the TCR and CAR molecules described above to a host cell can be accomplished using any methods known in the art. The host cells are isolated from a patient, or optionally, a donor, and can be immune effector cells, preferably T cells. In some embodiments, specific subpopulations of the immune effector cells may be preferred, for example, tumor infiltrating lymphocytes (TIL), CD4+ T cells, CD8+ T cells, helper T cells (Th cells), or NK cells. Subpopulations of immune effector cells can be identified or isolated from a patient or a donor by the expression of surface markers, e.g., CD4, CD8. The host cells can be modified by transduction or transfection of an expression vector, e.g., a lentiviral vector, a retroviral vector, or a gamma-retroviral vector, encoding the TCR or CAR molecule for sustained or stable expression of the TCR or CAR molecule. With regard to TCR, the alpha and beta chain may be in different expression vectors, or in a single expression vector. In other embodiments, the host cells are modified by in vitro transcribed RNA encoding the TCR or CAR molecule, to transiently express the TCR or CAR. The RNA encoding the TCR or CAR molecule can be introduced to the host cell by transfection, lipofection, or electroporation. The TCR or CAR-modified host cells are cultured under conditions sufficient for expression of the TCR or CAR molecules. In some aspects, the engineered cells are expanded and/or activated using methods known in the art, such as culturing in the presence of specific cytokines or factors that stimulate proliferation and activation known in the art. Examples include culturing in the presence of IL-2, and/or anti-CD3/CD28 antibodies.

The patient can receive one or more doses of a therapeutic amount of TCR or CAR-engineered cells. The therapeutic amount of TCR or CAR-engineered cells in each dosage can be determined by a physician with consideration of individual differences in age, weight, tumor size, extent of infection or metastasis, and condition of the patient. It can generally be stated that a pharmaceutical composition comprising the immune TCR or CAR-engineered cells described herein may be administered at a dosage of 104 to $10^9$ cells/kg body weight, in some instances 105 to $10^6$ cells/kg body weight, including all integer values within those ranges. The pharmaceutical compositions may also be administered multiple times at these dosages. The cells can be administered by using infusion techniques that are commonly known in immunotherapy (see, e.g., Rosenberg et al., New Eng. J. of Med. 319:1676, 1988), e.g., intravenous injection, or direct delivery to the site of the tumor.

Cancer vaccines generally involve inoculating a patient with a reagent designed to induce an antigen specific immune response. Preventative cancer vaccines are typically administered prior to diagnosis or development of a cancer to reduce the incidence of cancer. Preventative cancer vaccines are designed to target infectious agents, e.g., oncogenic viruses, by stimulating the immune system to recognize the infectious agents for protecting the body against future exposure. Therapeutic cancer vaccines aim to treat cancer after diagnosis by delaying or inhibiting cancer cell growth, causing tumor regression, preventing cancer relapse, or eliminating cancer cells that are not killed by other forms of treatment.

Cancer vaccines may comprise peptides or proteins, antibodies, glycoproteins, recombinant vectors or other recombinant microorganisms, killed tumor cells, protein- or peptide-activated dendritic cells. The composition of the cancer vaccine depends upon multiple factors, such as the particular tumor antigen that is targeted, the disease and disease stage, and whether the vaccine is administered in combination with another mode of cancer therapy. Adjuvants known in the art that modify or boost the immune response can be added to the cancer vaccine composition.

Antibody cancer vaccines have been developed, including anti-idiotype vaccines which comprise antibodies that recognize the antigenic determinants of tumor antigen-specific antibodies, called idiotopes. Thus, these anti-idiotype antibodies mimic distinct tumor antigens and act as surrogate antigens for triggering humoral and/or cellular immune response in the patient against the tumor cells. The anti-idiotype antibodies can also be fragments thereof that recognize idiotopes, e.g., single chain antibodies, scFv fragments, and sdAbs. Anti-idiotype cancer vaccines have had some success in clinical trials for treating melanoma, lung cancer, colorectal carcinoma, breast cancer, and ovarian carcinomas (Ladjemi et al., Front Oncol., 2012).

Other therapies that can be used in the context of the present invention include passive immunotherapy through delivery of antibodies that target a tumor antigen to a patient. The most common form of passive immunotherapy is monoclonal antibody therapy, in which monoclonal antibodies target the tumor cell resulting in tumor cell death through antibody-dependent cell-mediated cytotoxicity (ADCC) or complement-dependent cytotoxicity.

Antibody Drug Conjugate

The present invention further provides uses of antibodies or fragments thereof against a target, e.g., a target disclosed in Tables 1 or 2, linked to a therapeutic moiety. An antibody or fragment thereof can be conjugated to a label, such as a drug moiety, e.g., an anti-cancer agent, an autoimmune treatment agent, an anti-inflammatory agent, an antifungal agent, an antibacterial agent, an anti-parasitic agent, an anti-viral agent, or an anesthetic agent.

In certain embodiments, the drug moiety of the antibody drug conjugates of the present invention is selected from a V-ATPase inhibitor, a HSP90 inhibitor, an IAP inhibitor, an mTor inhibitor, a microtubule stabilizer, a microtubule destabilizers, an auristatin, a dolastatin, a maytansinoid, a MetAP (methionine aminopeptidase), an inhibitor of nuclear export of proteins CRM1, a DPPIV inhibitor, proteasome inhibitors, an inhibitors of phosphoryl transfer reactions in mitochondria, a protein synthesis inhibitor, a kinase inhibitor, a CDK2 inhibitor, a CDK9 inhibitor, an EG5 inhibitor, an HDAC inhibitor, a DNA damaging agent, a DNA alkylating agent, a DNA intercalator, a DNA minor groove binder and a DHFR inhibitor.

Further, an anti-target antibody or antibody fragment may be conjugated to a drug moiety that modifies a given biological response. Drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or, a biological response modifier such as, for example, a lymphokine.

In one embodiment, an anti-target antibody or antibody fragment is conjugated to a drug moiety, such as a cytotoxin, a drug (e.g., an immunosuppressant) or a radiotoxin. Examples of cytotoxin include but are not limited to, taxanes (see, e.g., International (PCT) Patent Application Nos. WO 01/38318 and PCT/USO3/02675), DNA-alkylating agents (e.g., CC-1065 analogs), anthracyclines, tubulysin analogs, duocarmycin analogs, auristatin E, auristatin F, maytansinoids, and cytotoxic agents comprising a reactive polyethylene glycol moiety (see, e.g., Sasse et al., J. Antibiot. (Tokyo), 53, 879-85 (2000), Suzawa et al., Bioorg. Med. Chem., 8, 2175-84 (2000), Ichimura et al., J. Antibiot. (Tokyo), 44, 1045-53 (1991), Francisco et al., Blood (2003) (electronic publication prior to print publication), U.S. Pat. Nos. 5,475,092, 6,340,701, 6,372,738, and 6,436,931, U.S. Patent Application Publication No. 2001/0036923 A1, Pending U.S. patent application Ser. Nos. 10/024,290 and 10/116, 053, and International (PCT) Patent Application No. WO 01/49698), taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, anti-metabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). (See e.g., Seattle Genetics US20090304721).

Other examples of therapeutic cytotoxins that can be conjugated to an anti-target antibody or antibody fragment include duocarmycins, calicheamicins, maytansines and auristatins, and derivatives thereof. An example of a calicheamicin antibody conjugate is commercially available (Mylotarg™; Wyeth-Ayerst).

For further discussion of types of cytotoxins, linkers and methods for conjugating therapeutic agents to antibodies, see also Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264. According to the present invention, an anti-target antibody or antibody fragment can also be conjugated to a radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine131, indium111, yttrium90, and lutetium177. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention. In certain embodiments, the macrocyclic chelator is 1,4,7,10-tetraazacyclododecane-N, N',N",N'''-tetraacetic acid (DOTA) which can be attached to the antibody via a linker molecule. Such linker molecules are commonly known in the art and described in Denardo et al., (1998) Clin Cancer Res. 4(10):2483-90; Peterson et al., (1999) Bioconjug. Chem. 10(4):553-7; and Zimmerman et al., (1999) Nucl. Med. Biol. 26(8):943-50, each incorporated by reference in their entireties.

The present invention further encompasses an anti-target antibody or antibody fragment conjugated to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antibody fragment described herein (e.g., a Fab fragment, Fd fragment, Fv fragment, F(ab)2 fragment, a VH domain, a VH CDR, a VL domain or a VL CDR) and a heterologous protein, polypeptide, or peptide.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2):76-82; Hansson et al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen may be recombined with one or more components, motifs, sections, parts, domains, fragments, etc. of one or more heterologous molecules.

Moreover, an anti-target antibody or antibody fragment can be conjugated to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., (1989) Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "FLAG" tag (A. Einhauer et al., J. Biochem. Biophys. Methods 49: 455-465, 2001). According to the present invention, antibodies or antigen binding fragments can also be conjugated to tumor-penetrating peptides in order to enhance their efficacy.

In other embodiments, an anti-target antibody or antibody fragment is conjugated to a diagnostic or detectable agent. Such immunoconjugates can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, umbelliferone, fluorescein, fluorescein isothiocyanate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 64Cu, 113Sn, and 117Sn; and positron emitting metals using various positron emission tomographies, and non-radioactive paramagnetic metal ions.

An anti-target antibody or antibody fragment may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Combination Therapies

Many potential combination partners exist for treatment with inhibition of a target, e.g., inhibition of targets disclosed in Tables 1 or 2. The treatment could be partnered with current standards of care in the cancer types to be treated, as well as potential future drugs that might be approved.

The term "combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent.

By "combination", there is meant either a fixed combination in one dosage unit form, or a combined administration where a compound of the present invention and a combination partner may be administered independently at the same time or separately within time intervals that especially allow that the combination partners show a cooperative, e.g. synergistic effect. The single components may be packaged together in a kit or separately. One or both of the components (e.g., powders or liquids) may be reconstituted or diluted to a desired dose prior to administration.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

In certain instances, compounds of the present invention are combined with other therapeutic agents, such as other anti-cancer agents, anti-allergic agents, anti-nausea agents (or anti-emetics), pain relievers, cytoprotective agents, and combinations thereof.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with the compounds of the present invention include fluorouracil (5-FU) and irinotecan.

Further compounds of particular interest for combinations with the compounds of the present invention include: EGFR-inhibitors, such as cetuximab, panitumimab, erlotinib, gefitinib and EGFRi NOS; MAPK-pathway inhibitors, such as BRAFi, panRAFi, MEKi, ERKi; PI3K-mTOR pathway inhibitors, such as alpha-specific PI3Ki, pan-class I PI3Ki, mTOR/PI3Ki, and particularly also evirolimus and analogues thereof.

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids, such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®). dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g. Patents International (e.g. IMS World Publications).

The above-mentioned compounds, which can be used in combination with a compound of the present invention, can be prepared and administered as described in the art, such as in the documents cited above.

In one embodiment, the present invention provides pharmaceutical compositions comprising at least one compound of the present invention (e.g., a compound of the present invention) or a pharmaceutically acceptable salt thereof together with a pharmaceutically acceptable carrier suitable for administration to a human or animal subject, either alone or together with other anti-cancer agents.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of a compound of the present invention (e.g., a compound of the present invention) or a pharmaceutically acceptable salt thereof, either alone or in combination with other anti-cancer agents.

In particular, compositions will either be formulated together as a combination therapeutic or administered separately.

In combination therapy, the compound of the present invention and other anti-cancer agent(s) may be administered either simultaneously, concurrently or sequentially with no specific time limits, wherein such administration provides therapeutically effective levels of the two compounds in the body of the patient.

In a preferred embodiment, the compound of the present invention and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

A compound of the present invention may also be used to advantage in combination with known therapeutic processes, for example, the administration of hormones or especially radiation. A compound of the present invention may in particular be used as a radiosensitizer, especially for the treatment of tumors which exhibit poor sensitivity to radiotherapy.

Assaying for Biomarkers and Inhibitor Treatment

The invention provides, among other things, an assay for the detection of the identity of the nucleic acid sequence and amino acid sequence for a target, e.g., any of the targets disclosed in Tables 1 or 2. The method can include detecting the mutation in a body fluid such as blood (e.g., serum or plasma) bone marrow, cerebral spinal fluid, peritoneal/pleural fluid, lymph fluid, ascite, serous fluid, sputum, lacrimal fluid, stool, and urine, or in a tissue such as a tumor tissue. The tumor tissue can be fresh tissue or paraffin-embedded tissue.

A number of patient stratification strategies could be employed to find patients likely to be sensitive to a target, e.g., any of the targets disclosed in Tables 1 or 2, depletion, including but not limited to: testing for microsatellite instability, screening for mutations, amplifications, duplications or deletions of target genes, and testing for target or target-associated molecule expression (e.g., mRNA or protein) or activity (e.g., enzyme activity).

Once a patient has been assayed for target status and predicted to be sensitive to treatment with a target specific inhibitor, administration of an inhibitor to the target, e.g., an inhibitor disclosed herein, to a patient can be affected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents may be empirically adjusted.

Different inhibitors can be administered and followed by determining the status of the target. In this embodiment, more than one inhibitor of a target, e.g., any of the targets disclosed in Tables 1 or 2, is chosen and administered to the patient. Target expression, e.g., RNA or protein, or activity can then be assayed for after administration of each different inhibitor. This assay can also be done at multiple timepoints after administration of the different inhibitor. For example, a first inhibitor could be administered to the patient and target expression, e.g., RNA or protein, or activity assayed for at 1 hour, 2 hours, 3 hours, 4 hours, 8 hours, 16 hours, 24 hours, 48 hours, 3 days, 1 week or 1 month or several months after administration. A second inhibitor could then be administered and target expression, e.g., RNA or protein, or activity can be assayed for again at 1 hour, 2 hours, 3 hours, 4 hours, 8 hours, 16 hours, 24 hours, 48 hours, 3 days, 1 week or 1 month or several months after administration of the second inhibitor.

It is well known in the art that cancers can become resistant to chemotherapeutic treatment, especially when that treatment is prolonged. Determining the presence of target expression, e.g., RNA or protein, or activity can be done after prolonged treatment with any chemotherapeutic to determine if the cancer would be sensitive to the inhibitor. If the patient has been previously treated with another chemotherapeutic or another inhibitor, it is useful to assay for a target expression, e.g., RNA or protein, or activity to determine if the tumor is sensitive to the inhibitor of the target. This assay can be especially beneficial to the patient if the cancer goes into remission and then re-grows or has metastasized to a different site.

Sample Preparation

Body fluid samples can be obtained from a subject using any of the methods known in the art. Methods for extracting cellular DNA from body fluid samples are well known in the art. Typically, cells are lysed with detergents. After cell lysis, proteins are removed from DNA using various proteases. DNA is then extracted with phenol, precipitated in alcohol, and dissolved in an aqueous solution. Methods for extracting acellular DNA from body fluid samples are also known in the art. Commonly, a cellular DNA in a body fluid sample is separated from cells, precipitated in alcohol, and dissolved in an aqueous solution.

Generally, a solid tumor sample can be a test sample of cells or tissue that are obtained from a subject with cancer by biopsy or surgical resection. A sample of cells or tissue can be removed by needle aspiration biopsy. For this, a fine needle attached to a syringe is inserted through the skin and into the tissue of interest. The needle is typically guided to the region of interest using ultrasound or computed tomography (CT) imaging. Once the needle is inserted into the tissue, a vacuum is created with the syringe such that cells or fluid may be sucked through the needle and collected in the syringe. A sample of cells or tissue can also be removed by incisional or core biopsy. For this, a cone, a cylinder, or a tiny bit of tissue is removed from the region of interest. CT imaging, ultrasound, or an endoscope is generally used to guide this type of biopsy. More particularly, the entire cancerous lesion may be removed by excisional biopsy or surgical resection. In the present invention, the test sample is typically a sample of cells removed as part of surgical resection.

The test sample of, for example tissue, may also be stored in, e.g., RNAlater (Ambion; Austin Tex.) or flash frozen and stored at −80° C. for later use. The biopsied tissue sample may also be fixed with a fixative, such as formaldehyde, paraformaldehyde, or acetic acid/ethanol. The fixed tissue sample may be embedded in wax (paraffin) or a plastic resin. The embedded tissue sample (or frozen tissue sample) may be cut into thin sections. RNA or protein may also be extracted from a fixed or wax-embedded tissue sample.

Cancers amenable for treatment according to the present invention include any of the cancers disclosed in Tables 1 or 2, as well as other possible cancer types with microsatellite instability, gene amplifications, duplications, deletions or mutations.

Measurement of Gene Expression

Detection of gene expression can be by any appropriate method, including for example, detecting the quantity of mRNA transcribed from the gene or the quantity of cDNA produced from the reverse transcription of the mRNA transcribed from the gene or the quantity of the polypeptide or protein encoded by the gene. These methods can be performed on a sample by sample basis or modified for high throughput analysis. For example, using Affymetrix™ U133 microarray chips.

In one aspect, gene expression is detected and quantitated by hybridization to a probe that specifically hybridizes to the appropriate probe for that biomarker. The probes also can be attached to a solid support for use in high throughput screening assays using methods known in the art. WO 97/10365 and U.S. Pat. Nos. 5,405,783; 5,412,087 and 5,445,934, for example, disclose the construction of high density oligonucleotide chips which can contain one or more of the sequences disclosed herein. Using the methods disclosed in U.S. Pat. Nos. 5,405,783; 5,412,087 and 5,445, 934, the probes of this invention are synthesized on a derivatized glass surface. Photoprotected nucleoside phosphoramidites are coupled to the glass surface, selectively deprotected by photolysis through a photolithographic mask, and reacted with a second protected nucleoside phosphoramidite. The coupling/deprotection process is repeated until the desired probe is complete.

In one aspect, the expression level of a gene is determined through exposure of a nucleic acid sample to the probe-modified chip. Extracted nucleic acid is labeled, for example, with a fluorescent tag, preferably during an amplification step. Hybridization of the labeled sample is performed at an appropriate stringency level. The degree of probe-nucleic acid hybridization is quantitatively measured using a detection device. See U.S. Pat. Nos. 5,578,832 and 5,631,734.

Alternatively any one of gene copy number, transcription, or translation can be determined using known techniques. For example, an amplification method such as PCR may be useful. General procedures for PCR are taught in MacPherson et al., PCR: A Practical Approach, (IRL Press at Oxford University Press (1991)). However, PCR conditions used for each application reaction are empirically determined. A number of parameters influence the success of a reaction. Among them are annealing temperature and time, extension time, $Mg^{2+}$ and/or ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination.

In one embodiment, the hybridized nucleic acids are detected by detecting one or more labels attached to the sample nucleic acids. The labels can be incorporated by any of a number of means well known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g. fluorescein-labeled UTP and/or CTP) incorporates a label in to the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., 3H, 125I, 35S, 14C, or 32P) enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Detection of labels is well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the coloured label.

The detectable label may be added to the target (sample) nucleic acid(s) prior to, or after the hybridization, such as described in WO 97/10365. These detectable labels are directly attached to or incorporated into the target (sample) nucleic acid prior to hybridization. In contrast, "indirect labels" are joined to the hybrid duplex after hybridization. Generally, the indirect label is attached to a binding moiety that has been attached to the target nucleic acid prior to the hybridization. For example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization with Nucleic Acid Probes, P. Tijssen, ed. Elsevier, N.Y. (1993).

Detection of Polypeptides

Expression level of a target, e.g., any of the targets disclosed in Tables 1 or 2, can be determined by examining protein expression or the protein product. Determining the protein level involves measuring the amount of any immunospecific binding that occurs between an antibody that selectively recognizes and binds to the polypeptide of the biomarker in a sample obtained from a patient and comparing this to the amount of immunospecific binding of at least one biomarker in a control sample. The amount of protein expression of the target can be increased or reduced when compared with control expression.

A variety of techniques are available in the art for protein analysis. They include but are not limited to radioimmunoassays, ELISA (enzyme linked immunosorbent assays), "sandwich" immunoassays, immunoradiometric assays, in situ immunoassays (using e.g., colloidal gold, enzyme or radioisotope labels), Western blot analysis, immunoprecipitation assays, immunofluorescent assays, flow cytometry, immunohistochemistry, HPLC, mass spectrometry, confocal microscopy, enzymatic assays, surface plasmon resonance and PAGE-SDS. In one embodiment, a method of determining if a subject afflicted with a cancer will respond to therapeutic treatment with an inhibitor, e.g., an inhibitor of any of the targets disclosed in Tables 1 or 2, is provided.

The inhibitor may be selected from the group consisting of an RNA inhibitor (e.g., an RNAi agent), a CRISPR, a TALEN, a zinc finger nuclease, an mRNA, a miRNA, an antibody or derivative thereof, a chimeric antigen receptor T cell (CART) or a low molecular weight compound.

The inhibitor is a short hairpin RNA (shRNA) or a short inhibitory RNA (siRNAs).

In one embodiment, a method of determining the sensitivity of a cancer cell associated with the loss of target function through an inhibitor is provided.

In one embodiment, a method of screening for inhibitors of target is provided. The method comprises contacting a sample containing one or more cells harboring one or more mutations, amplification, deletions or microsatellite instability with an inhibitor of the target; measuring the reduction in viability of said cells in said sample; contacting a similar sample containing one or more cells harboring one or more mutations, amplifications, deletions or microsatellite instability with a known inhibitor of the target; measuring the reduction in viability of said cells in said similar sample; comparing the reduction in viability of said cells harboring one or more mutations, amplifications, deletions, or microsatellite instability from said sample with viability of said similar sample, wherein a similar reduction in viability indicates said candidate sample is an inhibitor of the target.

In one embodiment, a therapeutic method of treating a subject afflicted with a cancer associated with a genetic alteration disclosed in Table 2 is provided, comprising the steps of: contacting a sample obtained from said subject with a reagent capable of detecting human cancer cells harboring one or more mutations, amplifications, deletions, or microsatellite instabilities; comparing the sample obtained from said afflicted subject with a similar sample taken from a non-cancerous or normal control subject, wherein the presence of one or mutations, amplifications, deletions or microsatellite instability in said sample obtained from said afflicted subject indicates said afflicted subject will respond to therapeutic treatment with an inhibitor of the target, e.g., an inhibitor disclosed herein; and administering a therapeutically effective amount of the inhibitor to those subjects.

In one embodiment, a therapeutic method of treating a subject afflicted with a cancer associated with a genetic alteration disclosed in Table 2 comprising the steps of: contacting a sample obtained from said subject with a reagent capable of detecting human cancer cells harboring one or more mutations, amplifications, deletions or microsatellite instability; comparing the sample obtained from said afflicted subject with a similar sample taken from a non-cancerous or normal control subject, wherein the presence of one or more mutations, amplifications, deletions or microsatellite instability in said sample obtained from said afflicted subject indicates said afflicted subject will respond to therapeutic treatment with an inhibitor of the target, e.g., an inhibitor disclosed herein; and administering a therapeutically effective amount of the composition according to an aspect of the invention.

In one embodiment, a method of determining if a subject afflicted with a cancer associated with a genetic alteration disclosed in Table 2 will respond to therapeutic treatment with an inhibitor, e.g., an inhibitor of any of the target disclosed in Tables 1 or 2 is provided, comprising: contacting a sample obtained from said subject with a reagent capable of detecting human cancer cells exhibiting target protein loss of function; and comparing the sample obtained from said afflicted subject with a similar sample taken from a non-cancerous or normal control subject, wherein the detection of target protein loss of function in said sample obtained from said afflicted subject indicates said afflicted subject will respond to therapeutic treatment with an inhibitor of the target.

In one embodiment, a method of determining if a subject afflicted with a cancer associated with a genetic alteration disclosed in Table 2 will respond to therapeutic treatment with an inhibitor of the target, e.g., a target associated with the genetic alteration disclosed in Table 2 is provided, comprising: contacting a sample obtained from said subject with a reagent capable of detecting human cancer cells exhibiting lack of expression of the target; and comparing the sample obtained from said afflicted subject with a similar sample taken from a non-cancerous or normal control subject, wherein the detection of lack of expression of target in said sample obtained from said afflicted subject indicates said afflicted subject will not respond to therapeutic treatment with an inhibitor of the target.

In one embodiment, a method of determining if a subject afflicted with a cancer associated with a genetic alteration disclosed in Table 2 will respond to therapeutic treatment with an inhibitor of the target, e.g., a target associated with the genetic alteration disclosed in Table 2 is provided, comprising: contacting a sample obtained from said subject with a reagent capable of detecting human cancer cells exhibiting expression of the target; and comparing the sample obtained from said afflicted subject with a similar sample taken from a non-cancerous or normal control subject, wherein the detection of expression of target in said sample obtained from said afflicted subject indicates said afflicted subject will respond to therapeutic treatment with an inhibitor of the target.

Kits

Kits for assessing the activity of any inhibitor, e.g., an inhibitor to any of the targets disclosed in Tables 1 or 2, can be made. For example, a kit comprising nucleic acid primers for PCR or for microarray hybridization for a mutation, amplification, deletion, duplication or microsatellite instability can be used for assessing target inhibitor sensitivity.

In some embodiments kits related to methods of the invention are provided. In one embodiment, the kit comprises a solid support, and a DNA comprising a nucleotide sequence capable of detecting mutations, amplifications, deletions, duplications or instability, wherein the DNA is coupled to the support.

In one embodiment, a kit for predicting the sensitivity of a subject afflicted with a cancer associated with microsatellite instability, mutations, amplifications, deletions, target or target-associated molecule expression (e.g., high or low mRNA or protein expression) or activity, such as a cancer associated with mutations, amplifications, deletions, duplications, microsatellite instability, or target or target-associated molecule expression for treatment with an inhibitor is provided. The kit comprises: i) reagents capable of: a) detecting human cancer cells harboring one or more mutations, amplifications, deletions, duplications or microsatellite instability; or b) detecting expression level (e.g., mRNA or protein), or activity (e.g., enzyme activity), of a target (e.g., a target of the inhibitor administered) or a target-associated molecule (e.g., a downstream effector disclosed in Table 2) in human cancer cells from a subject; and ii) instructions for how to use said kit.

EXAMPLES

Example 1: DRIVE (Deep RNAi Interrogation of Viability Effects in Cancer) Screen to Map Cancer Dependencies and Identify Genes Important for Cell Viability To map cancer dependencies and identify genes important for cell viability in specific genetic and lineage subtypes of cancer, a large-scale RNAi screen was conducted. This screen is referred to as project DRIVE (Deep RNAi Interrogation of Viability Effects in cancer). In DRIVE, a lentiviral library was produced targeting 7837 human genes with a median of 20 shRNAs per gene and used to screen 398 cancer cell lines in a pooled format to ascertain the effect on cell viability.

Library Construction and Virus Production

The DRIVE library was synthesized by Cellecta as independent pools and were ordered from Cellecta using the following library ID numbers: 55K_PoolA-MS-NOVA; 55K_PoolB-MS-NOVA; 27KBGP2-MS-NOVA; 13K-hTF-GH-NOVA; 13K-hYAP-GH-NOVA; 13K-hEP12-GHNOVA. Pool A, Pool B and a combination of the other libraries (BGP2, TF, YAP, EPI2 combination is referred to as BGPD pool) were cloned in the pRSl16cb-U6-sh-13kCB18-HTS6-UbiC-TagRFP-2A-Puro vector. The DRIVE viral packaging was scaled up to 5-layer Cellstack (Corning, Cat No, 22250-152). $2.1 \times 10^8$ 293T cells were plated on one 5-layer Cellstack 24 hours prior to transfection. Cells were transfected according to the manufacturer's recommended protocol (Cellecta). For each 5-layer Cellstack, cells were transfected using 510.3 µL of TranslT reagent diluted into 18.4 ml of OPTI-MEM that was combined with 75.6 µg of the plasmid pool and 94.5 µg of the Cellecta packaging mix (containing the psPAX2 and pMD2 plasmids that encode Gag/Pol and VSV-G respectively). Virus was harvested at 72 hours post transfection, aliquoted, and frozen at −80 C for later use. Viral titers were measured and benchmarked against a reference virus that was used to assess infectability of each screened cell line.

Screening Approach 383 of the cell lines are part of the original Cancer Cell Line Encyclopedia (CCLE) and were handled accordingly while the remaining 15 lines were kindly provided by investigators. All models are regularly tested for being free of *mycoplasma* and their identity verified, both for the banked stocks (e.g., starting material for screen) as well as upon completion of screen (extracted gDNA for NGS). A 79 SNP identification panel has been uploaded to the CCLE website by the CCLE team to allow investigators to readily identify CCLE cell lines. For each cell line the optimal puromycin dose required to achieve >95% cell killing in 72 hours was determined by measuring cell viability with a Cell Titer Glo or a Methylene blue staining assay for a 6-point dose response ranging from 0 to 8 µg of puromycin. The volume of virus required to give an MOI of 0.5 (for delivery of only one shRNA per cell) was determined using a 10 point dose response ranging from 0 to 400 µL of viral supernatant in the presence of 8 µg/ml polybrene. Infectivity was determined using titered virus from the library backbone vector expressing RFP and measuring the % RFP-positive cells by FACS 4 days post-infection after three days of puromycin selection. Cell lines that could not pass these screening characterization criteria (puromycin sensitivity, reasonable infectivity and RFP positivity) did not enter the final screening queue.

The three DRIVE libraries were screened as independent pools across 398 cell lines. The cells were infected to maintain 1000× library representation during the duration of the 2 week viability screen. For large-scale infections, 90 million cells (per library) were plated 24 hrs prior to infection in 5-layer CellSTACK culture chambers (Corning) in 500 ml of medium (one CellSTACK per library). On the day of infection, the culture media was replaced with 500 ml of fresh media containing 8 □g/ml polybrene and required volume of virus for MOI of 0.5 was added. 24 hrs after infection the culture media was replaced with 500 ml fresh media containing puromycin at the cell line-specific concentration. 72 hrs following puromycin addition, cells were trypsinized, and 70-90 million cells were re-plated in 5-layer CellSTACK culture chambers. An aliquot of cells was used to measure transduction efficiency determined by measuring the % RFP positive cells and was typically >90-95%. Cells were maintained in culture and passaged as needed to ensure they did not exceed 90% confluence during the course of the screen. At each split, 70-90 million cells were passaged into new flasks, ensuring a representation of >1000 cells/shRNA in the library and the % RFP positive cells was measured to ensure stability of the transduced population over time. 14 days after infection, cells were trypsinized and samples of 70-90 million cells were harvested by centrifugation and stored at −80° C. prior to gDNA extraction.

Purification of Genomic DNA & PCR for Library Production and Next Generation Sequencing Cell pellets were processed according to the QIAamp® DNA Blood Maxi Spin Protocol (Cat #51192), and the resulting genomic DNA resuspended in 2 mls Qiagen buffer AE. Genomic DNA concentrations were measured using a Picogreen dye-binding assay giving a typical yield of 1 µg gDNA per million cells. For Next Generation Sequencing (NGS) library generation, the barcodes are PCR amplified in 24 independent 100 µL PCR reactions using 4 µg of input gDNA per reaction with Titanium Taq, a single forward primer and one of 24 indexing oligos (as listed below) for 30 cycles. Library input DNA was also sequenced and referred to as plasmid counts in the provided raw data. 24 independent PCR reactions were pooled and purified using the Agencourt AMPure XP PCR cleanup kit (Beckman Coulter). The resulting products were analyzed by agarose e-gel to confirm the expected ~190 bp product and the amount of purified product quantified using the Advanced Analytical Fragment Analyzer. Barcode representation was measured on the Illumina 2500 platform. For good representation of each shRNA in the NGS data, 40-60 million raw Illumina sequence reads were required per sample averaging approximately 1000 reads per shRNA. Note that the individual plasmid pools for each shRNA library were spiked into each NGS flowcell at 15% of the total loading volume as normalization controls.

From Raw Counts to shRNA Level Scores to Gene Level Scores

The drop-out value for each shRNA was calculated using the Bioconductor R package EdgeR (Robinson et al., 2010). The plasmid and sample raw counts per shRNAs were normalized in pairs using the Timed Mean of M-values (TMM) normalization. In the rare event that the plasmid spike-in failed to generate sufficient counts (<20 million total reads per plasmid) to be used as a normalization control then a virtual library was used in place of plasmid counts. This virtual library is obtained by equalizing the library size of the available plasmid libraries counts using the equalizeLibSizes function in edgeR and rounding the mean pseudo count of the resulting output to the nearest integer. The edgeR negative binomial model is fitted to obtain the log fold change (logFC) of counts between the sample and plasmid (the parameters used are common dispersion=0.2 and prior count=12). This is performed for each sample-plasmid pair to obtain a logFC per shRNA per cell line. Additionally this procedure is performed on each pool individually. The logFC are then normalized per sample using a quantile normalization to obtain a shRNA level sensitivity score. The shRNA level scores are further aggregated to gene level sensitivity scores using either the ATARiS algorithm (Shao et al., 2013) or the RSA algorithm (Konig et al., 2007). RSA uses all the shRNAs per gene to give a measure of the statistical significance of the drop-out of those 20 shRNAs compared to the background of the rest of the shNRAs logFC. The method is directional and only captures shRNA drop-out, not growth enhancing shRNAs. Additionally every gene incorporated in the screen is aggregated into a RSA score. ATARiS only uses the shRNAs which display consistent profiles across the 398 samples, thus mitigating the potential issue of off-targets. Additionally, inert genes will not generate ATARiS scores since the shRNAs are unlikely to correlate. The ATARiS algorithm can serially produce multiple solutions depending on the number of clusters of shRNA showing consistent phenotype across the cell lines. In those cases only the first solution is reported which generally represents the solution with the most shRNA (i.e. ~84% of cases). Finally, the procedure from raw counts to gene level scores is performed on each pool independently from each other.

Quality Control

Several QC metrics were considered when running the analysis pipeline. Those metrics were recorded and analysed in aggregate to identify potential outlier samples. In particular at the read count level the total number of read counts in each sample, the frequency of the most abundant shRNA, and the third quartile of the read counts after library size scaling were considered and recorded. After logFC estimation of the individual shRNA the proportion of pan-lethal genes represented in the lowest quartile within each sample was also considered. The proportion of shRNAs with logFC below the quantile with p=0.05 across samples was kept in order to identify potential hyper-sensitive lines. Finally some shRNAs are present in all three pools and the correlation of those shRNA logFC levels across the pools was assessed. Those metrics were then considered in aggregate to identify outliers which were removed.

Identifying Outlier Sensitivity Profiles

The distribution of the sensitivity scores can be used to identify potential genes of interest. In particular one hopes to prioritize genes which are neither inert nor essential, but display differential sensitivity across samples, i.e. a subset of samples is strongly sensitive to the knock down, while the rest is unaffected. To identify these profiles a "Likelihood Ratio Test"-based method was used (i.e. Normality LRT) which identifies profiles whose distribution diverge the most from the normal distribution. For each gene both a normal distribution and a skew Student t distribution are fitted to the distribution of sensitivity scores across all cell lines. The Normality LRT score is twice the log of the likelihood ratio of the fitted skewed distribution over the likelihood of the fitted normal distribution, i.e. the difference between the deviance of the two models.

TABLE 3

Primers used for sequencing

| SEQ ID NO | Index | Name | Sequence in the 5' to 3' direction |
|---|---|---|---|
| 3 | 1 | DRIVE PCR Rev Primer | CAAGCAGAAGACGGCATACGAGATCACTGTGTGACTGGAG TTCAGACGTGTGCTCTTCCGATCTgaggttcagagttcta cagtccGAA |
| 4 | 2 | DRIVE PCR Rev Primer | CAAGCAGAAGACGGCATACGAGATATTGGCGTGACTGGAG TTCAGACGTGTGCTCTTCCGATCTgaggttcagagttcta cagtccGAA |
| 5 | 3 | DRIVE PCR Rev Primer | CAAGCAGAAGACGGCATACGAGATGATCTGGTGACTGGAG TTCAGACGTGTGCTCTTCCGATCTgaggttcagagttcta cagtccGAA |
| 6 | 4 | DRIVE PCR Rev Primer | CAAGCAGAAGACGGCATACGAGATTCAAGTGTGACTGGAG TTCAGACGTGTGCTCTTCCGATCTgaggttcagagttcta cagtccGAA |
| 7 | 5 | DRIVE PCR Rev Primer | CAAGCAGAAGACGGCATACGAGATCTGATCGTGACTGGAG TTCAGACGTGTGCTCTTCCGATCTgaggttcagagttcta cagtccGAA |
| 8 | 6 | DRIVE PCR Rev Primer | CAAGCAGAAGACGGCATACGAGATAAGCTAGTGACTGGAG TTCAGACGTGTGCTCTTCCGATCTgaggttcagagttcta cagtccGAA |
| 9 | 7 | DRIVE PCR Rev Primer | CAAGCAGAAGACGGCATACGAGATGTAGCCGTGACTGGA GTTCAGACGTGTGCTCTTCCGATCTgaggttcagagttct acagtccGAA |
| 10 | 8 | DRIVE PCR Rev Primer | CAAGCAGAAGACGGCATACGAGATTACAAGGTGACTGGAG TTCAGACGTGTGCTCTTCCGATCTgaggttcagagttcta cagtccGAA |
| 11 | 9 | DRIVE PCR Rev Primer | CAAGCAGAAGACGGCATACGAGATTTGACTGTGACTGGAG TTCAGACGTGTGCTCTTCCGATCTgaggttcagagttcta cagtccGAA |
| 12 | 10 | DRIVE PCR Rev Primer | CAAGCAGAAGACGGCATACGAGATGGAACTGTGACTGGA GTTCAGACGTGTGCTCTTCCGATCTgaggttcagagttct acagtccGAA |
| 13 | 11 | DRIVE PCR Rev Primer | CAAGCAGAAGACGGCATACGAGATTGACATGTGACTGGAG TTCAGACGTGTGCTCTTCCGATCTgaggttcagagttcta cagtccGAA |
| 14 | 12 | DRIVE PCR Rev Primer | CAAGCAGAAGACGGCATACGAGATGGACGGGTGACTGGA GTTCAGACGTGTGCTCTTCCGATCTgaggttcagagttct acagtccGAA |
| 15 | 13 | DRIVE PCR Rev Primer | CAAGCAGAAGACGGCATACGAGATCTCTACGTGACTGGAG TTCAGACGTGTGCTCTTCCGATCTgaggttcagagttcta cagtccGAA |
| 16 | 14 | DRIVE PCR Rev Primer | CAAGCAGAAGACGGCATACGAGATGCGGACGTGACTGGA GTTCAGACGTGTGCTCTTCCGATCTgaggttcagagttct acagtccGAA |
| 17 | 15 | DRIVE PCR Rev Primer | CAAGCAGAAGACGGCATACGAGATTTTCACGTGACTGGAG TTCAGACGTGTGCTCTTCCGATCTgaggttcagagttcta cagtccGAA |
| 18 | 16 | DRIVE PCR Rev Primer | CAAGCAGAAGACGGCATACGAGATGGCCACGTGACTGGA GTTCAGACGTGTGCTCTTCCGATCTgaggttcagagttct acagtccGAA |
| 19 | 17 | DRIVE PCR Rev Primer | CAAGCAGAAGACGGCATACGAGATCGAAACGTGACTGGA GTTCAGACGTGTGCTCTTCCGATCTgaggttcagagttct acagtccGAA |
| 20 | 18 | DRIVE PCR Rev Primer | CAAGCAGAAGACGGCATACGAGATCGTACGGTGACTGGA GTTCAGACGTGTGCTCTTCCGATCTgaggttcagagttct acagtccGAA |
| 21 | 19 | DRIVE PCR Rev Primer | CAAGCAGAAGACGGCATACGAGATCCACTCGTGACTGGAG TTCAGACGTGTGCTCTTCCGATCTgaggttcagagttcta cagtccGAA |

TABLE 3-continued

Primers used for sequencing

| SEQ ID NO | Index | Name | Sequence in the 5' to 3' direction |
|---|---|---|---|
| 22 | 20 | DRIVE PCR Rev Primer | CAAGCAGAAGACGGCATACGAGATATCAGTGTGACTGGAG TTCAGACGTGTGCTCTTCCGATCTgaggttcagagttcta cagtccGAA |
| 23 | 21 | DRIVE PCR Rev Primer | CAAGCAGAAGACGGCATACGAGATAGGAATGTGACTGGAG TTCAGACGTGTGCTCTTCCGATCTgaggttcagagttcta cagtccGAA |
| 24 | 22 | DRIVE PCR Rev Primer | CAAGCAGAAGACGGCATACGAGATCTTTTGGTGACTGGAG TTCAGACGTGTGCTCTTCCGATCTgaggttcagagttcta cagtccGAA |
| 25 | 23 | DRIVE PCR Rev Primer | CAAGCAGAAGACGGCATACGAGATTAGTTGGTGACTGGAG TTCAGACGTGTGCTCTTCCGATCTgaggttcagagttcta cagtccGAA |
| 26 | 24 | DRIVE PCR Rev Primer | CAAGCAGAAGACGGCATACGAGATCCGGTGGTGACTGGA GTTCAGACGTGTGCTCTTCCGATCTgaggttcagagttct acagtccGAA |
| 27 | 25 | DRIVE PCR FWD Universal Primer | AATGATACGGCGACCACCGAGATCTACACATTCGCACCAG CACGCTACGCA |

Feature Association

To find potential hypotheses explaining the observed sensitivity profiles an automated separation of the samples population into sensitive and insensitive lines was performed for each gene using a k-means clustering method with k=3. The two extreme populations were designated as sensitive and insensitive, while the intermediate cluster was not used further. A differential representation of the known CCLE features across the two remaining populations was systematically undertaken to identify potential explanatory features (mutation, CNA, gene expression). The type of test performed was dependent on the feature type: Fisher Exact test for mutation, Wilcoxon test for CNA and Bioconductor Limma (Ritchie et al., 2015) for expression. The resulting p-values were adjusted for multiple testing within each feature type using the Benjamini Hochberg correction.

GO Term Enrichment

The enrichment of GO terms within the essential genes of the screen compared to the remaining genes of the screen was calculated. For this purpose "essential" genes were defined as genes with 50% or more cell lines displaying an RSA score below −3 upon knock down. For this analysis only the GO terms with 50 or more genes were considered (not restricted to the genes in the screen). For each remaining biological process GO term a contingency table was built using the number of essential genes within the term, the number of essential genes outside the term, the number of non-essential genes within the term and the number of non-essential genes outside the term in each of the entry of the 2×2 matrix. A Chi-square test was then performed on the resulting contingency table and the top 5 most enriched Biological Process GO terms among the essential genes were reported. The Benjamini Hochberg procedure was used to correct for multiple testing.

DRIVE Sensitivity Network

The DRIVE data was also used to build a co-sensitivity network (similarly to co-expression networks in expression datasets). In this case genes were used as vertices and the correlation between the sensitivity profiles of two genes defined the weight of the edge linking them (the correlation is performed across all samples using the Pearson correlation). To visualize the topology of the whole network in two dimensions a t-distributed Stochastic Neighbour Embedding (tSNE) (van der Maaten and Hinton, 2008) is used whereby the distance between two genes is defined as the square of one minus the absolute value of the correlation (1-abs(cor))^2. t-SNE is a non-linear dimension reduction technique which models similar points in high dimension by nearby points in the lower dimensional space although this is not always possible. The original network is high dimensional and reducing it to only two-dimensions does necessarily result in information loss. This can be seen in FIG. 6 whereby genes which are in each other's direct neighborhood in the high dimensional network are not represented close by in the 2D tSNE representation (e.g. TP53, USP7 and MDM4). However some global aspects of the topology of the network are still conserved in particular the distribution of essential genes in the network.

Coloring Scheme

Throughout the various figures a consistent coloring scheme was used whenever we represented CN or expression values. Namely the color is saturated to blue or red among the lowest and highest 10% of samples respectively. The median value is colored light grey and a linear scale is used between the 10th and 50th percentile (blue to grey) and 50th to 90th percentile (grey to red).

shRNA Power Analysis

To perform the shRNA power analysis we used a subset of the BGPD pool, focusing on 1381 genes with 20 and only 20 shRNAs per gene. The ATARiS solutions were built for each of the 1381 genes and the outlierness by Normality LRT was calculated. The top 100 outlier genes were recorded and used for further analysis. The ATARiS calculation was then performed on those 100 genes with 5, 10 and 15 shRNAs selected at random. This process was repeated 10 times with random resampling of the selected shRNAs. In each iteration, we recorded the number of top outlier genes for which an ATARiS solution was found.

Compound Sensitivity Calls and Comparison to DRIVE Profiles

The compound sensitivity calls are based on the results available in the CCLE (Barretina et al., 2012) and in the BYL719 report (Fritsch et al., 2014) whereby the Amax (maximum observed response) and EC50 (inflection point) using an 8-point dose-response matrix are combined to assess cell line sensitivity to compound treatment. Starting from the vector of responses Amax or EC50, we considered the distribution of response values (for Amax, log-transformed EC50) in order to assign cell lines into sensitive, and non-sensitive classes using a combination of EC50 and Amax cutoffs in a compound specific manner. In particular the cell lines below both of the following cutoffs were deemed sensitive: Amax=−40% and EC50=1.95 µM for Erlotinib, Amax=−40% and EC50=1.95 µM for PLX4720, Amax=−40% and EC50=1.28 µM for Lapatinib and Amax=−30% and EC50=3.04 µM for BYL719. For DRIVE the cell lines with phenotypic values below −1 were deemed sensitive. The consistency of compound vs shRNA response was assessed using fisher exact tests on the contingency of their respective sensitivity call (i.e. sensitive vs non-sensitive).

Results

Functional Genomic Screening Reveals 4 Categories of Dependency Outliers

In project DRIVE, deep coverage shRNA lentiviral libraries were constructed (median of 20 shRNAs/gene) targeting 7837 genes. Gene content included known mutated/amplified cancer drivers, epigenetic genes, transcription factors, cell surface proteins, and druggable enzymes, as well as known pan-essential complexes. This library was screened across 398 cell lines to identify gene dependencies (Table 4). $2.7\times10^8$ cells were infected (>1000× representation of the 151,504 member library) and passaged for 14 days post infection. Quantile normalized log fold change data was generated from next generation sequencing (NGS) counts of individual shRNAs post screen versus the shRNA abundance in the library input. The raw DRIVE data is available (dx.doi.org/10.17632/y3ds55n88r.1) and contains read counts across all interrogated shRNAs/genes and cell lines.

TABLE 4

Cell lines used in DRIVE

| CELLLINE | PRIMARY_SITE | PATHOLOGIST_ANNOTATION |
|---|---|---|
| 697 | haematopoietic_and_lymphoid_tissue | Leukemia: ALL |
| 921 | eye | Eye: Melanoma |
| 127399 | soft_tissue | Soft_Tissue: Sarcoma_Synovial |
| 2313287 | stomach | Gastric: Carcinoma |
| 1321n1 | central_nervous_system | CNS: Glioma |
| 769p | kidney | Kidney: Carcinoma |
| 786o | kidney | Kidney: Carcinoma |
| 8305c | thyroid | Thyroid: Carcinoma |
| 8505c | thyroid | Thyroid: Carcinoma |
| a101d | skin | Skin: Melanoma |
| a172 | central_nervous_system | CNS: Glioma_HighGrade |
| a204 | soft_tissue | Soft_Tissue: Sarcoma_Rhabdoid |
| a2058 | skin | Skin: Melanoma |
| a253 | salivary_gland | Salivary_Gland: Carcinoma |
| a2780 | ovary | Ovary: Carcinoma |
| a375 | skin | Skin: Melanoma |
| a498 | kidney | Kidney: Carcinoma |
| a549 | lung | Lung: NSCLC_Adeno |
| a673 | bone | Bone: Sarcoma_Ewing |
| a704 | kidney | Kidney: Carcinoma |
| abc1 | lung | Lung: NSCLC_Others |
| accmeso1 | pleura | Lung: Mesothelioma |
| achn | kidney | Kidney: Carcinoma |
| ags | stomach | Gastric: Carcinoma |
| an3ca | endometrium | Endometrium: Carcinoma |
| az521 | stomach | Gastric: Carcinoma |
| bc3c | urinary_tract | Bladder: Carcinoma |
| bcpap | thyroid | Thyroid: Carcinoma |
| bftc909 | kidney | Kidney: Carcinoma |
| bht101 | thyroid | Thyroid: Carcinoma |
| bicr6 | upper_aerodigestive_tract | Upper_Aerodigestive_Tract: Carcinoma |
| bt16 | central_nervous_system | PNET: Rhabdoid |
| bt20 | breast | Breast: Carcinoma |
| bt549 | breast | Breast: Carcinoma |
| bxpc3 | pancreas | Pancreas: Carcinoma |
| c32 | skin | Skin: Melanoma |
| caki1 | kidney | Kidney: Carcinoma |
| caki2 | kidney | Kidney: Carcinoma |
| cal120 | breast | Breast: Carcinoma |
| cal27 | upper_aerodigestive_tract | Upper_Aerodigestive_Tract: Carcinoma |
| cal29 | urinary_tract | Bladder: Carcinoma |
| cal33 | upper_aerodigestive_tract | Upper_Aerodigestive_Tract: Carcinoma |
| cal51 | breast | Breast: Carcinoma |
| cal54 | kidney | Kidney: Carcinoma |
| cal851 | breast | Breast: Carcinoma |
| calu6 | lung | Lung: NSCLC_Others |
| cama1 | breast | Breast: Carcinoma |
| caov3 | ovary | Ovary: Carcinoma |
| cas1 | central_nervous_system | CNS: Glioma_HighGrade |
| cck81 | large_intestine | Colorectal: Carcinoma |
| cfpac1 | pancreas | Pancreas: Carcinoma |
| chagok1 | lung | Lung: Others |
| cl11 | large_intestine | Colorectal: Carcinoma |
| cl34 | large_intestine | Colorectal: Carcinoma |
| cmk | haematopoietic_and_lymphoid_tissue | Leukemia: AML |
| cmk115 | haematopoietic_and_lymphoid_tissue | Leukemia: AML |
| colo201 | large_intestine | Colorectal: Carcinoma |
| colo205 | large_intestine | Colorectal: Carcinoma |
| colo320 | large_intestine | Colorectal: Carcinoma |
| colo678 | large_intestine | Colorectal: Carcinoma |
| colo679 | skin | Skin: Melanoma |
| colo741 | skin | Skin: Melanoma |
| colo829 | skin | Skin: Melanoma |
| corl105 | lung | Lung: NSCLC_Adeno |
| corl23 | lung | Lung: NSCLC_Large_Cell |
| cov318 | ovary | Ovary: Carcinoma |
| cov362 | ovary | Ovary: Carcinoma |
| cw2 | large_intestine | Colorectal: Carcinoma |
| dang | pancreas | Pancreas: Carcinoma |
| daoy | central_nervous_system | CNS: Medulloblastoma |
| detroit562 | upper_aerodigestive_tract | Upper_Aerodigestive_Tract: Carcinoma |
| dld1 | large_intestine | Colorectal: Carcinoma |
| dms114 | lung | Lung: SCLC |
| dms273 | lung | Lung: SCLC |
| du145 | prostate | Prostate: Carcinoma |
| ebc1 | lung | Lung: NSCLC_Squamous |
| efm192a | breast | Breast: Carcinoma |
| f36p | haematopoietic_and_lymphoid_tissue | Leukemia: AML |
| fadu | upper_aerodigestive_tract | Upper_Aerodigestive_Tract: Carcinoma |

TABLE 4-continued

Cell lines used in DRIVE

| CELLLINE | PRIMARY_SITE | PATHOLOGIST_ANNOTATION |
|---|---|---|
| fuji | soft_tissue | Soft_Tissue: Sarcoma_Synovial |
| fuov1 | ovary | Ovary: Carcinoma |
| g401 | soft_tissue | Soft_Tissue: Sarcoma_Rhabdoid |
| g402 | soft_tissue | Soft_Tissue: Sarcoma_Rhabdoid |
| gamg | central_nervous_system | CNS: Glioma |
| gb1 | central_nervous_system | CNS: Glioma_HighGrade |
| gi1 | central_nervous_system | CNS: Glioma |
| gistt1 | gastrointestinal_tract_(site_indeterminate) | Undefined: GIST |
| gp2d | large_intestine | Colorectal: Carcinoma |
| hcc1359 | lung | Lung: NSCLC_Large_Cell |
| hcc15 | lung | Lung: NSCLC_Squamous |
| hcc1500 | breast | Breast: Carcinoma |
| hcc1806 | breast | Breast: Carcinoma |
| hcc1833 | lung | Lung: NSCLC_Adeno |
| hcc1954 | breast | Breast: Carcinoma |
| hcc38 | breast | Breast: Carcinoma |
| hcc4006 | lung | Lung: NSCLC_Adeno |
| hcc44 | lung | Lung: NSCLC_Adeno |
| hcc827 | lung | Lung: NSCLC_Adeno |
| hcc827gr | lung | Lung: NSCLC_Adeno |
| hcc95 | lung | Lung: NSCLC_Squamous |
| hct116 | large_intestine | Colorectal: Carcinoma |
| hct15 | large_intestine | Colorectal: Carcinoma |
| hec1a | endometrium | Endometrium: Carcinoma |
| hec265 | endometrium | Endometrium: Carcinoma |
| hec50b | endometrium | Endometrium: Carcinoma |
| hec6 | endometrium | Endometrium: Carcinoma |
| hel | haematopoietic_and_lymphoid_tissue | Leukemia: AML |
| he19217 | haematopoietic_and_lymphoid_tissue | Leukemia: AML |
| hep3b217 | liver | Liver: HCC |
| hepg2 | liver | Liver: HCC |
| heya8 | ovary | Ovary: Carcinoma |
| hgc27 | stomach | Gastric: Carcinoma |
| hle | liver | Liver: HCC |
| hlf | liver | Liver: HCC |
| hmc18 | breast | Breast: Carcinoma |
| hrt18 | large_intestine | Colorectal: Carcinoma |
| h5294t | skin | Skin: Melanoma |
| h5578t | breast | Breast: Carcinoma |
| h5695t | skin | Skin: Melanoma |
| h5729 | soft_tissue | Soft_Tissue: Sarcoma_Rhabdoid |
| h5852t | skin | Skin: Melanoma |
| h5939t | skin | Skin: Melanoma |
| h5944t | skin | Skin: Melanoma |
| h5c3 | upper_aerodigestive_tract | Upper_Aerodigestive_Tract: Carcinoma |
| hssyii | soft_tissue | Soft_Tissue: Sarcoma_Synovial |
| ht1080 | soft_tissue | Soft_Tissue: Sarcoma_Fibro |
| ht115 | large_intestine | Colorectal: Carcinoma |
| ht1197 | urinary_tract | Bladder: Carcinoma |
| ht1376 | urinary_tract | Bladder: Carcinoma |
| ht29 | large_intestine | Colorectal: Carcinoma |
| ht55 | large_intestine | Colorectal: Carcinoma |
| hug1n | stomach | Gastric: Carcinoma |
| huh1 | liver | Liver: HCC |
| huh6 | liver | Liver: Hepatoblastoma |
| huh7 | liver | Liver: HCC |
| hupt3 | pancreas | Pancreas: Carcinoma |
| hupt4 | pancreas | Pancreas: Carcinoma |
| igr1 | skin | Skin: Melanoma |
| igr37 | skin | Skin: Melanoma |
| igr39 | skin | Skin: Melanoma |
| igrov1 | ovary | Ovary: Carcinoma |
| im95 | stomach | Gastric: Carcinoma |
| ipc298 | skin | Skin: Melanoma |
| ishikawaheraklio2er | endometrium | Endometrium: Carcinoma |
| jhh6 | liver | Liver: HCC |
| jhh7 | liver | Liver: HCC |
| jhos2 | ovary | Ovary: Carcinoma |
| jhuem2 | endometrium | Endometrium: Carcinoma |
| jimt1 | breast | Breast: Carcinoma |
| jl1 | pleura | Lung: Mesothelioma |
| jmsu1 | urinary_tract | Bladder: Carcinoma |
| k029ax | skin | Skin: Melanoma |
| kasumi1 | haematopoietic_and_lymphoid_tissue | Leukemia: AML |
| kasumi2 | haematopoietic_and_lymphoid_tissue | Leukemia: ALL |
| kelly | autonomic_ganglia | PNET: Neuroblastoma |
| km12 | large_intestine | Colorectal: Carcinoma |
| kmrc1 | kidney | Kidney: Carcinoma |
| kmrc20 | kidney | Kidney: Carcinoma |
| kms27 | haematopoietic_and_lymphoid_tissue | Lymphoma: Multiple_Myeloma |
| kms28bm | haematopoietic_and_lymphoid_tissue | Lymphoma: Multiple_Myeloma |
| kms34 | haematopoietic_and_lymphoid_tissue | Lymphoma: Multiple_Myeloma |
| kns42 | central_nervous_system | CNS: Glioma |
| kns62 | lung | Lung: NSCLC_Squamous |
| kns81 | central_nervous_system | CNS: Glioma_HighGrade |
| kp1n | pancreas | Pancreas: Carcinoma |
| kp3 | pancreas | Pancreas: Carcinoma |
| kp4 | pancreas | Pancreas: Carcinoma |
| kpl1 | breast | Breast: Carcinoma |
| kpnsi9s | autonomic_ganglia | PNET: Neuroblastoma |
| kpnyn | autonomic_ganglia | PNET: Neuroblastoma |
| ks1 | central_nervous_system | CNS: Glioma_HighGrade |
| ku1919 | urinary_tract | Bladder: Carcinoma |
| kym1 | soft_tissue | Soft_Tissue: Sarcoma_Rhabdoid |
| kyse150 | oesophagus | Oesophagus: Carcinoma |
| kyse180 | oesophagus | Oesophagus: Carcinoma |
| kyse30 | oesophagus | Oesophagus: Carcinoma |
| kyse410 | oesophagus | Oesophagus: Carcinoma |
| kyse450 | oesophagus | Oesophagus: Carcinoma |
| kyse510 | oesophagus | Oesophagus: Carcinoma |
| kyse70 | oesophagus | Oesophagus: Carcinoma |
| l33 | pancreas | Pancreas: Carcinoma |
| lclc103h | lung | Lung: NSCLC_Large_Cell |
| li7 | liver | Liver: HCC |
| lk2 | lung | Lung: NSCLC_Squamous |
| lmsu | stomach | Gastric: Carcinoma |
| ln18 | central_nervous_system | CNS: Glioma_HighGrade |
| ln229 | central_nervous_system | CNS: Glioma_HighGrade |
| lncapclonefgc | prostate | Prostate: Carcinoma |
| lovo | large_intestine | Colorectal: Carcinoma |
| loximvi | skin | Skin: Melanoma |
| ls180 | large_intestine | Colorectal: Carcinoma |
| ls411n | large_intestine | Colorectal: Carcinoma |
| ls513 | large_intestine | Colorectal: Carcinoma |
| ludlu1 | lung | Lung: NSCLC_Squamous |
| mcf7 | breast | Breast: Carcinoma |
| mdamb157 | breast | Breast: Carcinoma |
| mdamb231 | breast | Breast: Carcinoma |
| mdamb415 | breast | Breast: Carcinoma |
| mdamb436 | breast | Breast: Carcinoma |
| mdamb453 | breast | Breast: Carcinoma |
| mdamb468 | breast | Breast: Carcinoma |
| mdst8 | large_intestine | Colorectal: Carcinoma |
| me180 | cervix | Cervix: Carcinoma |
| mel285 | eye | Eye: Melanoma |
| melho | skin | Skin: Melanoma |
| meljuso | skin | Skin: Melanoma |

TABLE 4-continued

Cell lines used in DRIVE

| CELLLINE | PRIMARY_SITE | PATHOLOGIST_ANNOTATION |
|---|---|---|
| mewo | skin | Skin: Melanoma |
| mfe280 | endometrium | Endometrium: Carcinoma |
| mfe296 | endometrium | Endometrium: Carcinoma |
| mfe319 | endometrium | Endometrium: Carcinoma |
| miapaca2 | pancreas | Pancreas: Carcinoma |
| mkn1 | stomach | Gastric: Carcinoma |
| mkn45 | stomach | Gastric: Carcinoma |
| mkn7 | stomach | Gastric: Carcinoma |
| molm13 | haematopoietic_and_lymphoid_tissue | Leukemia: AML |
| molm16 | haematopoietic_and_lymphoid_tissue | Leukemia: AML |
| monomac1 | haematopoietic_and_lymphoid_tissue | Leukemia: AML |
| monomac6 | haematopoietic_and_lymphoid_tissue | Leukemia: AML |
| mpp89 | pleura | Lung: Mesothelioma |
| nb1 | autonomic_ganglia | PNET: Neuroblastoma |
| ncih1048 | lung | Lung: SCLC |
| ncih1299 | lung | Lung: NSCLC_Others |
| ncih1355 | lung | Lung: NSCLC_Adeno |
| ncih1373 | lung | Lung: NSCLC_Adeno |
| ncih1435 | lung | Lung: NSCLC_Adeno |
| ncih1437 | lung | Lung: NSCLC_Adeno |
| ncih1568 | lung | Lung: NSCLC_Adeno |
| ncih1573 | lung | Lung: NSCLC_Adeno |
| ncih1581 | lung | Lung: NSCLC_Large_Cell |
| ncih1693 | lung | Lung: NSCLC_Adeno |
| ncih1703 | lung | Lung: NSCLC_Squamous |
| ncih1792 | lung | Lung: NSCLC_Adeno |
| ncih1793 | lung | Lung: NSCLC_Adeno |
| ncih1838 | lung | Lung: NSCLC_Adeno |
| ncih1944 | lung | Lung: NSCLC_Adeno |
| ncih196 | lung | Lung: SCLC |
| ncih1975 | lung | Lung: NSCLC_Adeno |
| ncih2009 | lung | Lung: NSCLC_Adeno |
| ncih2030 | lung | Lung: NSCLC_Adeno |
| ncih2052 | pleura | Lung: Mesothelioma |
| ncih2066 | lung | Lung: SCLC |
| ncih2110 | lung | Lung: NSCLC_Others |
| ncih2122 | lung | Lung: NSCLC_Adeno |
| ncih2126 | lung | Lung: NSCLC_Adeno |
| ncih2170 | lung | Lung: NSCLC_Squamous |
| ncih2172 | lung | Lung: NSCLC_Others |
| ncih2228 | lung | Lung: NSCLC_Adeno |
| ncih2286 | lung | Lung: SCLC |
| ncih2291 | lung | Lung: NSCLC_Adeno |
| ncih23 | lung | Lung: NSCLC_Adeno |
| ncih28 | pleura | Lung: Mesothelioma |
| ncih358 | lung | Lung: NSCLC_Adeno |
| ncih441 | lung | Lung: NSCLC_Adeno |
| ncih446 | lung | Lung: SCLC |
| ncih460 | lung | Lung: NSCLC_Large_Cell |
| ncih508 | large_intestine | Colorectal: Carcinoma |
| ncih522 | lung | Lung: NSCLC_Adeno |
| ncih661 | lung | Lung: NSCLC_Large_Cell |
| ncih716 | large_intestine | Colorectal: Carcinoma |
| ncih747 | large_intestine | Colorectal: Carcinoma |
| ncih838 | lung | Lung: NSCLC_Adeno |
| ncin87 | stomach | Gastric: Carcinoma |
| nihovcar3 | ovary | Ovary: Carcinoma |
| nugc3 | stomach | Gastric: Carcinoma |
| ocum1 | stomach | Gastric: Carcinoma |
| oe21 | oesophagus | Oesophagus: Carcinoma |
| omm1 | eye | Eye: Melanoma |
| osrc2 | kidney | Kidney: Carcinoma |
| oum523 | large_intestine | Colorectal: Carcinoma |
| ov90 | ovary | Ovary: Carcinoma |
| ovcar4 | ovary | Ovary: Carcinoma |
| ovcar8 | ovary | Ovary: Carcinoma |
| ovsaho | ovary | Ovary: Carcinoma |
| panc0203 | pancreas | Pancreas: Carcinoma |
| panc0403 | pancreas | Pancreas: Carcinoma |
| panc0504 | pancreas | Pancreas: Carcinoma |
| panc1 | pancreas | Pancreas: Carcinoma |
| panc1005 | pancreas | Pancreas: Carcinoma |
| patu8902 | pancreas | Pancreas: Carcinoma |
| patu8988t | pancreas | Pancreas: Carcinoma |
| pecapj34clonec12 | upper_aerodigestive_tract | Upper_Aerodigestive_Tract: Carcinoma |
| pecapj41cloned2 | upper_aerodigestive_tract | Upper_Aerodigestive_Tract: Carcinoma |
| pfeiffer | haematopoietic_and_lymphoid_tissue | Lymphoma: NH_B_cell |
| pk1 | pancreas | Pancreas: Carcinoma |
| rcc4 | kidney | Kidney: Carcinoma |
| rchacv | haematopoietic_and_lymphoid_tissue | Leukemia: ALL |
| rd | soft_tissue | Soft_Tissue: Sarcoma_Rhabdoid |
| reh | haematopoietic_and_lymphoid_tissue | Leukemia: ALL |
| rerfcms | lung | Lung: NSCLC_Others |
| rh30 | soft_tissue | Soft_Tissue: Sarcoma_Rhabdoid |
| rh41 | soft_tissue | Soft_Tissue: Sarcoma_Rhabdoid |
| rko | large_intestine | Colorectal: Carcinoma |
| rl | haematopoietic_and_lymphoid_tissue | Lymphoma: NH_B_cell |
| rmgi | ovary | Ovary: Carcinoma |
| rmugs | ovary | Ovary: Carcinoma |
| rpmi7951 | skin | Skin: Melanoma |
| rpmi8226 | haematopoietic_and_lymphoid_tissue | Lymphoma: Multiple_Myeloma |
| rt112 | urinary_tract | Bladder: Carcinoma |
| rvh421 | skin | Skin: Melanoma |
| saos2 | bone | Bone: Sarcoma_Osteo |
| sbc5 | lung | Lung: SCLC |
| scc25 | upper_aerodigestive_tract | Upper_Aerodigestive_Tract: Carcinoma |
| sem | haematopoietic_and_lymphoid_tissue | Leukemia: ALL |
| sf268 | central_nervous_system | CNS: Glioma_HighGrade |
| sf295 | central_nervous_system | CNS: Glioma_HighGrade |
| sh4 | skin | Skin: Melanoma |
| shp77 | lung | Lung: SCLC |
| sjrh30 | soft_tissue | Soft_Tissue: Sarcoma_Rhabdoid |
| sjsa1 | bone | Bone: Sarcoma_Osteo |
| skco1 | large_intestine | Colorectal: Carcinoma |
| skes1 | bone | Bone: Sarcoma_Ewing |
| skhep1 | liver | Liver: Carcinoma _Adeno |
| skmel2 | skin | Skin: Melanoma |
| skmel28 | skin | Skin: Melanoma |
| skmel3 | skin | Skin: Melanoma |
| skmel30 | skin | Skin: Melanoma |
| skmel5 | skin | Skin: Melanoma |
| sknas | autonomic_ganglia | PNET: Neuroblastoma |
| sknbe2 | autonomic_ganglia | PNET: Neuroblastoma |
| skndz | autonomic_ganglia | PNET: Neuroblastoma |
| sknfi | autonomic_ganglia | PNET: Neuroblastoma |
| sknmc | bone | Bone: Sarcoma_Ewing |
| sknsh | autonomic_ganglia | PNET: Neuroblastoma |
| snb19 | central_nervous_system | CNS: Glioma_HighGrade |
| sngm | endometrium | Endometrium: Carcinoma |
| snu1 | stomach | Gastric: Carcinoma |
| snu1079 | biliary_tract | Biliary_Tract: Carcinoma |
| snu1105 | central_nervous_system | CNS: Glioma_HighGrade |
| snu349 | kidney | Kidney: Carcinoma |
| snu407 | large_intestine | Colorectal: Carcinoma |
| snu410 | pancreas | Pancreas: Carcinoma |
| snu423 | liver | Liver: HCC |
| snu449 | liver | Liver: HCC |

TABLE 4-continued

Cell lines used in DRIVE

| CELLLINE | PRIMARY_SITE | PATHOLOGIST_ANNOTATION |
|---|---|---|
| snu61 | large_intestine | Colorectal: Carcinoma |
| snu685 | endometrium | Endometrium: Others |
| snu719 | stomach | Gastric: Carcinoma |
| snu738 | central_nervous_system | CNS: Glioma |
| snu761 | liver | Liver: HCC |
| snu81 | large_intestine | Colorectal: Carcinoma |
| snu886 | liver | Liver: HCC |
| snuc2a | large_intestine | Colorectal: Carcinoma |
| snuc4 | large_intestine | Colorectal: Carcinoma |
| sq1 | lung | Lung: NSCLC_Squamous |
| ss1a | soft_tissue | Soft_Tissue: Sarcoma_Synovial |
| su8686 | pancreas | Pancreas: Carcinoma |
| sudhl4 | haematopoietic_and_lymphoid_tissue | Lymphoma: NH_B_cell |
| sudhl6 | haematopoietic_and_lymphoid_tissue | Lymphoma: NH_B_cell |
| suit2 | pancreas | Pancreas: Carcinoma |
| sum52pe | breast | Breast: Carcinoma |
| sw1088 | central_nervous_system | CNS: Glioma |
| sw1271 | lung | Lung: SCLC |
| sw1353 | bone | Bone: Sarcoma_Chondro |
| sw1417 | large_intestine | Colorectal: Carcinoma |
| sw1463 | large_intestine | Colorectal: Carcinoma |
| sw1573 | lung | Lung: NSCLC_Squamous |
| sw1783 | central_nervous_system | CNS: Glioma_HighGrade |
| sw1990 | pancreas | Pancreas: Carcinoma |
| sw403 | large_intestine | Colorectal: Carcinoma |
| sw48 | large_intestine | Colorectal: Carcinoma |
| sw480 | large_intestine | Colorectal: Carcinoma |
| sw579 | thyroid | Thyroid: Carcinoma |
| sw620 | large_intestine | Colorectal: Carcinoma |
| sw780 | urinary_tract | Bladder: Carcinoma |
| sw948 | large_intestine | Colorectal: Carcinoma |
| syo1 | soft_tissue | Soft_Tissue: Sarcoma_Synovial |
| t24 | urinary_tract | Bladder: Carcinoma |
| t47d | breast | Breast: Carcinoma |
| tc71 | bone | Bone: Sarcoma_Ewing |
| tccpan2 | pancreas | Pancreas: Carcinoma |
| tccsup | urinary_tract | Bladder: Carcinoma |
| te1 | oesophagus | Oesophagus: Carcinoma |
| te10 | oesophagus | Oesophagus: Carcinoma |
| te11 | oesophagus | Oesophagus: Carcinoma |
| te14 | oesophagus | Oesophagus: Carcinoma |
| te4 | oesophagus | Oesophagus: Carcinoma |
| te6 | oesophagus | Oesophagus: Carcinoma |
| te9 | oesophagus | Oesophagus: Carcinoma |
| ten | endometrium | Endometrium: Carcinoma |
| thp1 | haematopoietic_and_lymphoid_tissue | Leukemia: AML |
| tuhr4tkb | kidney | Kidney: Carcinoma |
| tyknu | ovary | Ovary: Carcinoma |
| u118mg | central_nervous_system | CNS: Glioma |
| u251mg | central_nervous_system | CNS: Glioma |
| u2os | bone | Bone: Sarcoma_Osteo |
| u87mg | central_nervous_system | CNS: Glioma |
| uacc257 | skin | Skin: Melanoma |
| uacc62 | skin | Skin: Melanoma |
| ublc1 | urinary_tract | Bladder: Carcinoma |
| umuc3 | urinary_tract | Bladder: Carcinoma |
| vmrcrcw | kidney | Kidney: Carcinoma |
| wm115 | skin | Skin: Melanoma |
| wm1799 | skin | Skin: Melanoma |
| wm2664 | skin | Skin: Melanoma |
| wm793 | skin | Skin: Melanoma |
| wm88 | skin | Skin: Melanoma |
| wsudlc12 | haematopoietic_and_lymphoid_tissue | Lymphoma: NH_B_cell |
| yd38 | upper_aerodigestive_tract | Upper_Aerodigestive_Tract: Carcinoma |
| ymb1 | breast | Breast: Carcinoma | shRNA activity was aggregated to gene level activity by two complimentary methods, ATARiS and Redundant siRNA Activity (RSA)(FIG. 1A). RSA uses all shRNA reagents against a given gene to calculate a statistical significance that knockdown of gene X leads to loss of viability (Konig et al., 2007). ATARiS gene level scores only incorporate shRNAs that have consistent activity across the entire dataset (Shao et al., 2013) and attempts to eliminate inert or potential off-target shRNAs. The ATARiS algorithm median centers shRNA level scores across all screened cell lines resulting in a metric of relative effects therefore essential and inert gene profiles appear no different. For this reason, RSA was used to determine whether a gene was essential, active or inert and all other analyses used ATARiS to focus on only shRNA reagents with consistent, on-target activity. As part of the Project DRIVE resource, a public portal was created using the Shiny framework (Chang et al., 2017) to allow visualization of gene profiles (Sensitivity Profile Viz tab @ oncologynibr.shinyapps.io/drivel).

Using RSA to categorize each gene as inert, active or essential (FIG. 1B-1), >4450 of the genes showed no significant growth effects. Genes with an RSA value of 5-3 for >50% of cell lines were deemed essential. Assignment of GO terms for this class demonstrated enrichment of critical cellular processes such as translation, gene expression and splicing. In addition, correlation analyses for the essential genes uncovered two principle features. First, gene dependence correlated with the expression and/or copy number of the target gene itself (FIG. 1B-2). For example, cell lines with low expression or a copy number deletion of an essential gene were sensitive to knockdown. This phenomenon is termed CYCLOPS for genes with heterozygous copy number deletion (Nijhawan et al., 2012). Notably, PHF5A had the highest CN-dependence correlation and while previously reported to be required for GBM stem cells survival (Hubert et al., 2013), our data suggest that PHF5A is instead a broadly essential gene. The second principle feature of essential genes was that gene dependence correlated with high expression and/or copy number gain of AGO2, a component of the RNA-induced silencing complex (RISC) (FIG. 1B-2). This strongly suggests that lines with increased AGO2 have improved knockdown efficiency leading to enhanced shRNA activity against essential genes. For example, the profile of the proteasome component PSMC5 is shown in relation to AGO2 CN and expression (FIG. 1B-3). These two confounders must be considered when genetic screens are conducted in small cell line sets. Here, essential genes will have varied anti-proliferative activity that may be falsely associated with a distinct marker. The evaluation of the therapeutic index of CYCLOPS genes might need to consider AGO2 expression as a confounder in trying to equate RNAi effects with compound inhibition. A complete list of putative CYCLOPS and pan-essential genes is provided (Table 5 and Table 6).

TABLE 5

List of essential genes

GENESYMBOLS

ABCB7
ABCE1
AFG3L2
ALYREF
ANAPC1
ANAPC4
AP2M1
ATP6V0C
AURKB
BCL2L1
BOP1
BRD4
BUB1B
CAPZB
CCND1
CCT2
CCT3
CCT7
CHAF1A
CHD4
CKAP5
CLTC
COPA
COPB2
COPS2
COPS4
COPS5
COPS6
COPZ1
CWC22
DDB1
DDX18
DDX21
DDX23
DHX8
DHX9
DYNC1I2
E2F5
EIF2B3
EIF2S2
EIF3A
EIF3B
EIF3G
EIF4A3
EIF4E
EIF4G1
EWSR1
FAU
GNB2L1
GPS1
HCFC1
HNRNPC
HNRNPM
HNRNPU
HSPD1
HSPE1
IK
INCENP
INO80
KIF11
KPNB1
LOC440563
MAD2L1
MED11
MED14
MED28
METAP2
MPRIP
MYBL2
NAA10
NACA
NCBP1
NCL
NEDD1
NEDD8
NUP214

TABLE 5-continued

List of essential genes

GENESYMBOLS

NUP98
NUTF2
NXF1
PCNA
PHF5A
POLA1
POLR2A
POLR2B
POLR2D
PPIE
PPP2R1A
PPWD1
PRPF19
PSMA3
PSMA4
PSMA6
PSMB5
PSMC1
PSMC2
PSMC3
PSMC5
PSMC6
PSMD12
PSMD2
RAD21
RAD51
RAN
RBM22
RBM42
RBX1
RNPS1
RPA1
RPA2
RPL14
RPL35
RPL7
RPS15A
RPS16
RPS18
RPS21
RPS27A
RRM1
RTF1
RUVBL1
RUVBL2
SEC13
SF3A1
SF3B1
SF3B14
SF3B2
SFPQ
SHFM1
SIN3A
SKP1
SMC2
SMC4
SMG1
SMU1
SNRNP200
SNRNP70
SNRPB
SRSF1
SRSF3
SRSF9
SUPT5H
SUPT6H
SYMPK
TACC3
TCERG1
TFDP1
TONSL
TPR
TRRAP
TSC22D4
TUBB
U2AF1

TABLE 5-continued

List of essential genes

GENESYMBOLS

U2AF2
U2SURP
UBA1
UBA52
UBC
USP39
VARS
VCP
WDR43
WDR5
XAB2
XPO1
YBX1
YY1
ZNF207

TABLE 6

CYCLOP genes

GENESYMBOLS

ABCE1
ALYREF
ANAPC4
ATP6V1B2
AURKB
BIRC5
BRIX1
BUD31
CARS
CASP8AP2
CCNK
CCT2
CCT3
CDC27
CDC45
CDC73
CHAF1A
CHAF1B
COPA
COPB2
COPS6
COPZ1
CTDP1
CTR9
CWC22
DDX10
DDX23
DDX46
DDX47
DDX56
DHX15
DHX16
EEF2
EIF2S2
EIF3A
EIF3B
EIF3G
EIF3I
EIF4A3
FAU
IK
KAT8
MAD2L1
MCM5
MCM7
MCRS1
MED11
MED28
MED7
NOL11
NRF1

TABLE 6-continued

CYCLOP genes

GENESYMBOLS

NUP98
NUTF2
NXT1
PCNA
PHF5A
PLK1
PLRG1
POLD2
POLR2A
POLR2B
POLR2D
PPIL2
PPWD1
PRPF4
PRPF4B
PSMA3
PSMA4
PSMA6
PSMC1
PSMC2
PSMC3
PSMC4
PSMC5
PSMC6
PSMD12
PSMD2
PWP2
RAE1
RAN
RBM22
RBM28
RBM39
RBM42
RBX1
RFC2
RIOK1
RNPS1
RPA1
RPA2
RPA3
RPL35
RPL7
RPP14
RPP40
RPS15A
RPS16
RPS18
RPS21
RRM1
RRP9
SEC13
SEH1L
SF3A1
SF3B4
SHFM1
SKIV2L2
SMNDC1
SMU1
SNRPB
SNRPF
SRSF1
SRSF3
SUPT16H
SUPT5H
SUPT6H
TRIP13
TXN
U2AF1
U2AF2
UBA52
UBL5
URI1
USP39
USPL1
VARS
VCP

TABLE 6-continued

CYCLOP genes

GENESYMBOLS

WDR3
WDR46
WDR61
WDR82
XAB2
XRCC6

Figure 1C:
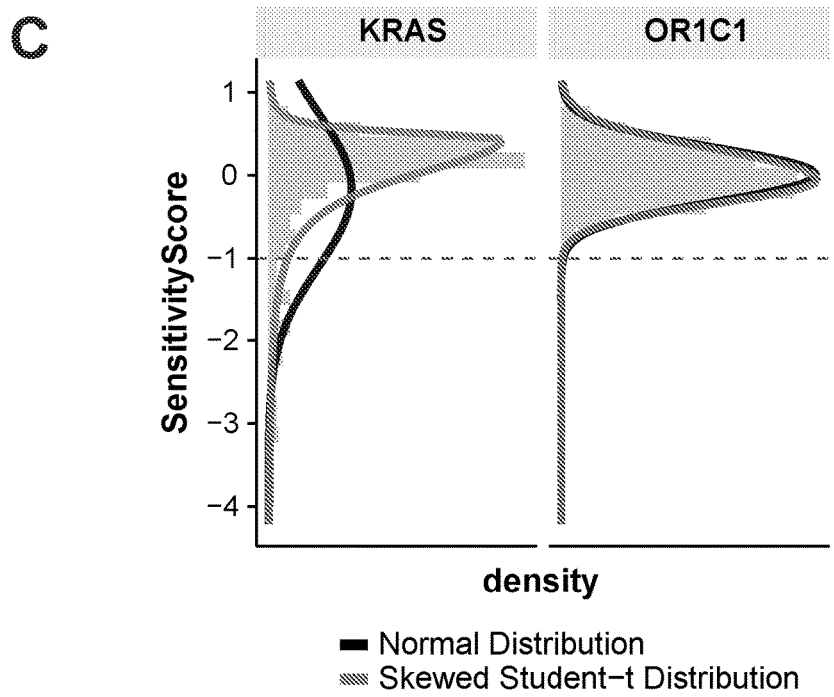
Figure 1D:
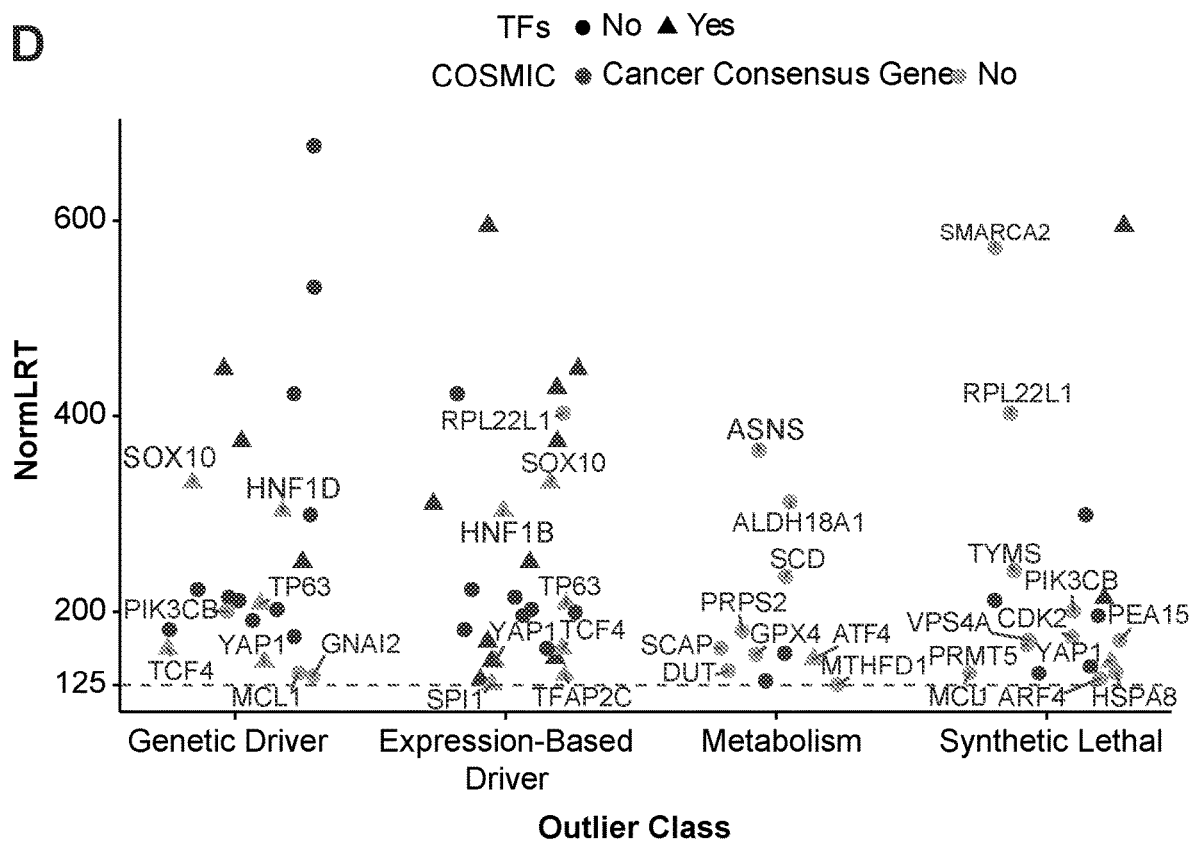

To enable the discovery of features predictive of sensitivity we developed a bioinformatics pipeline. K-means (k=3) clustering of gene profiles was used to delineate sensitive and insensitive populations and these classifications were used to interrogate the feature sets of the CCLE (Barretina et al., 2012) (FIG. 1A). The CCLE feature sets used in these analyses can be accessed via portals.broadinstitute.org/ccle/home. This workflow enabled the systematic identification of sensitivity predictors across the genes queried in Project DRIVE. We next identified selective cancer cell dependencies in an unbiased manner. To this end, an outlier analysis was performed to identify profiles that demonstrated dropout behavior in a subset of cancer cell lines (FIG. 1C). A normality likelihood ratio test (NormLRT) was applied to the gene level ATARiS scores to determine whether each gene profile had a distribution divergent from normal and to assign an outlier score based on the deviance between the normal distribution and the t-distributed skewed distribution. This approach is agnostic to the direction of the skew and therefore growth suppressors and enhancers are both detected. Importantly, it is also sensitive to a single cell line outlier, so profiles exhibiting a robust phenotype in only one model can also be detected. Lastly, Normality LRT incorporates the magnitude of the phenotypic effect in order to focus on genes with robust dependency. The top outliers (NormLRT>125) fall into distinct groups of dependence (Table 7). The majority (88%) can be categorized into 4 classes: genetic dependence, expression-based dependence, metabolic genes/enzymes and synthetic lethals (FIG. 1D) with some genes belonging to multiple classes. The first two classes encompass genes in which the feature correlations predictive of dependence are mutation, copy number amplification or high-level mRNA expression of the gene itself. Many of these genes are found on the COSMIC gene consensus list (Forbes et al., 2017). In the synthetic lethality and metabolism classes, the features correlated with cancer cell line dependence appear to relate more closely to an altered cell state or genetic alterations in other genes. Genes in these two classes have largely not been identified in cancer genomics efforts and are not contained on the cancer consensus list.

TABLE 7

Outlier Genes

| GENE-SYMBOLS | NormLRT | COSMIC | Outlier Categories | TFs | SL Category |
|---|---|---|---|---|---|
| CCND3 | 162.870303 | COSMIC | Expression based driver | No | |
| CEBPA | 153.418645 | COSMIC | Expression based driver | Yes | |
| ESR1 | 169.993436 | COSMIC | Expression based driver | Yes | |
| FOXA1 | 310.331357 | COSMIC | Expression based driver | Yes | |
| GATA3 | 150.110946 | COSMIC | Expression based driver | Yes | |
| IRF4 | 130.621536 | COSMIC | Expression based driver | Yes | |
| MPL | 199.391783 | COSMIC | Expression based driver | No | |
| MYB | 428.577929 | COSMIC | Expression based driver | Yes | |
| SPI1 | 126.187818 | NA | Expression based driver | Yes | |
| TFAP2C | 135.194288 | NA | Expression based driver | Yes | |
| CCNE1 | 222.975977 | COSMIC | Expression based driver, Genetic driver | No | |
| EGFR | 215.162316 | COSMIC | Expression based driver, Genetic driver | No | |
| ERBB2 | 202.7234 | COSMIC | Expression based driver, Genetic driver | No | |
| FLI1 | 374.081522 | COSMIC | Expression based driver, Genetic driver | Yes | |
| FLT3 | 181.975578 | COSMIC | Expression based driver, Genetic driver | No | |
| HNF1B | 303.35821 | NA | Expression based driver, Genetic driver | Yes | |
| KRAS | 422.806377 | COSMIC | Expression based driver, Genetic driver | No | |
| MITF | 448.656615 | COSMIC | Expression based driver, Genetic driver | Yes | |
| RUNX1 | 250.864185 | COSMIC | Expression based driver, Genetic driver | Yes | |
| SOX10 | 332.169486 | NA | Expression based driver, Genetic driver | Yes | |
| TCF4 | 162.480095 | NA | Expression based driver, Genetic driver | Yes | |
| TP63 | 208.585807 | NA | Expression based driver, Genetic driver | Yes | |
| YAP1 | 149.244774 | NA | Expression based driver, Genetic driver, Synthetic Lethal | Yes | Paralog Lethality |
| CTNNB1 | 594.609381 | COSMIC | Expression based driver, Synthetic Lethal | Yes | Vertical Pathway |
| MDM2 | 196.167736 | COSMIC | Expression based driver, Synthetic Lethal | No | Vertical Pathway |

TABLE 7-continued

Outlier Genes

| GENE-SYMBOLS | NormLRT | COSMIC | Outlier Categories | TFs | SL Category |
|---|---|---|---|---|---|
| RPL22L1 | 402.692583 | NA | Expression based driver, Synthetic Lethal | No | Paralog Lethality |
| BRAF | 531.881638 | COSMIC | Genetic driver | No | |
| FGFR2 | 191.242888 | COSMIC | Genetic driver | No | |
| GNAI2 | 134.261063 | NA | Genetic driver | No | |
| NRAS | 676.169317 | COSMIC | Genetic driver | No | |
| PIK3CA | 174.729074 | COSMIC | Genetic driver | No | |
| CDK4 | 299.060123 | COSMIC | Genetic driver, Synthetic Lethal | No | Paralog Lethality |
| MAP2K1 | 211.716658 | COSMIC | Genetic driver, Synthetic Lethal | No | Vertical Pathway |
| MCL1 | 137.484834 | NA | Genetic driver, Synthetic Lethal | No | Parallel Pathway |
| PIK3CB | 200.9034 | NA | Genetic driver, Synthetic Lethal | No | Vertical Pathway |
| ALDH18A1 | 312.292299 | NA | Metabolism | No | |
| ASNS | 364.831874 | NA | Metabolism | No | |
| ATF4 | 151.976198 | NA | Metabolism | Yes | |
| DUT | 139.923982 | NA | Metabolism | No | |
| GPX4 | 156.651727 | NA | Metabolism | No | |
| MTHFD1 | 125.201059 | NA | Metabolism | No | |
| PRPS2 | 180.386172 | NA | Metabolism | No | |
| SCAP | 162.984828 | NA | Metabolism | No | |
| SCD | 236.478109 | NA | Metabolism | No | |
| SDHB | 157.896827 | COSMIC | Metabolism | No | |
| SDHD | 129.245894 | COSMIC | Metabolism | No | |
| CFL1 | 129.184533 | NA | NA | No | |
| IGF1R | 140.232414 | NA | NA | No | |
| OPA1 | 127.211196 | NA | NA | No | |
| PRKRA | 141.21485 | NA | NA | No | |
| WRN | 355.504847 | COSMIC | NA | No | |
| WSB2 | 143.914228 | NA | NA | No | |
| ARF4 | 131.64709 | NA | Synthetic Lethal | No | Paralog Lethality |
| ARID1B | 144.090824 | COSMIC | Synthetic Lethal | No | Paralog Lethality |
| CBFB | 214.131504 | COSMIC | Synthetic Lethal | Yes | Vertical Pathway |
| CDK2 | 174.359727 | NA | Synthetic Lethal | No | Vertical Pathway |
| HSPA8 | 137.94353 | NA | Synthetic Lethal | No | Parallel Pathway |
| MDM4 | 137.125361 | COSMIC | Synthetic Lethal | No | Vertical Pathway |
| PEA15 | 171.200618 | NA | Synthetic Lethal | No | Vertical Pathway |
| PRMT5 | 167.013646 | NA | Synthetic Lethal | No | Collateral Lethality |
| SMARCA2 | 572.344152 | NA | Synthetic Lethal | No | Paralog Lethality |
| TYMS | 242.600363 | NA | Synthetic Lethal | No | Parallel Pathway |
| VPS4A | 171.551709 | NA | Synthetic Lethal | No | Collateral Lethality |
| CDKN2A | 165.538544 | COSMIC | Tumor Suppressor | No | |
| TP53 | 162.046367 | COSMIC | Tumor Suppressor | Yes | |

Figure 2A:
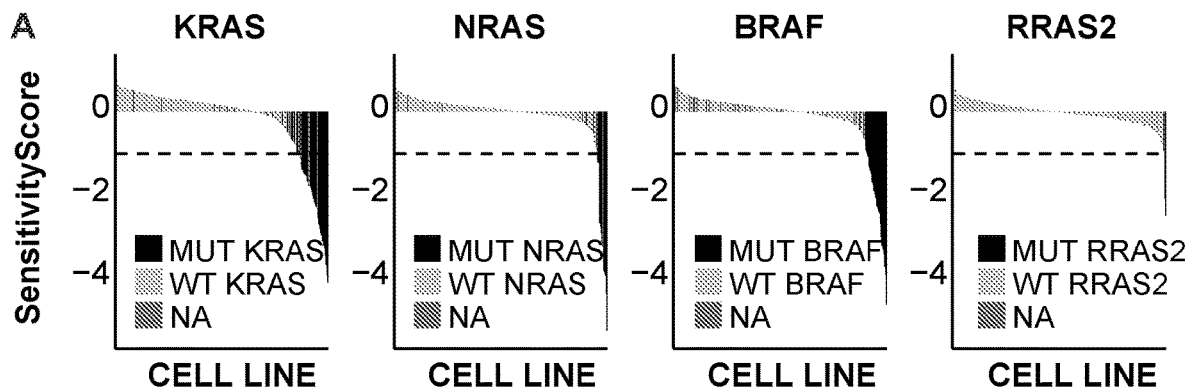
FIGS. 2A-2F depict genetic drivers and modifiers of oncogene dependence.

Genetic drivers of cancer dependency and modifiers of oncogene addiction Mutated oncogenes (e.g. NRAS, BRAF and KRAS) are among the most robust dependencies observed in DRIVE (FIG. 2A). As expected BRAF mutation and dependence are mainly observed in colon, thyroid and melanoma lines, while NRAS mutation and dependence is most prevalent in melanoma. KRAS mutation and dependence occurs in colon, pancreatic and lung lineages. Consistent with TCGA (Cancer Genome Atlas, 2012) and emerging clinical data (Mayer et al., 2017), PIK3CA shRNAs show activity across lineages with enrichment in PIK3CAmut ER+ breast lines. In the DRIVE data we observe a novel genetic dependence involving RRAS2 (TC21) (FIG. 2A). Both CAL51 and A2780 lines harbor RRAS2Q72L mutations that are analogous to the KRASQ61 position. Interestingly, NCI-H1048 harbors a G23S mutation that may mimic position G12 or G13 of other RAS proteins. While RRAS2 mutation appears to be a relatively rare event in the primary tumors sequenced as part of TCGA, position Q72 is the most recurrent and our data suggests that this creates an oncogenic dependence.

Figure 2B:
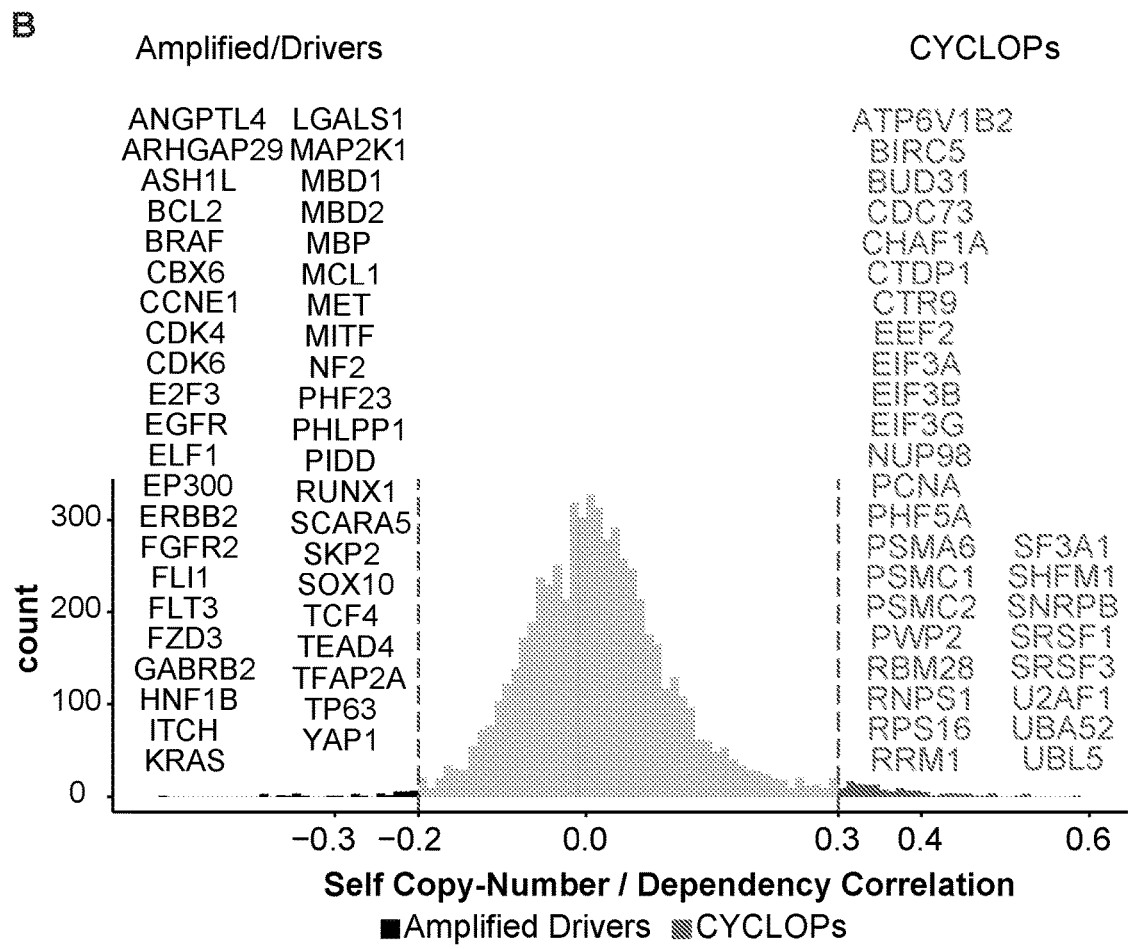
Figure 2C:
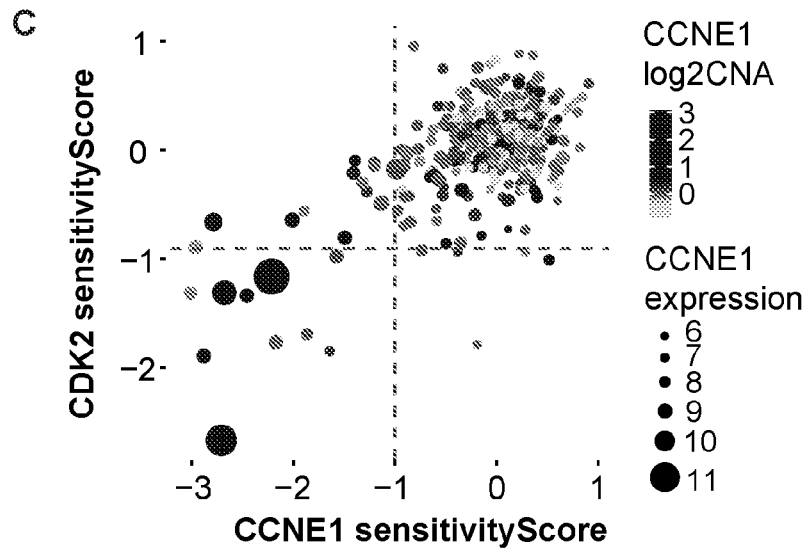
Figure 3:
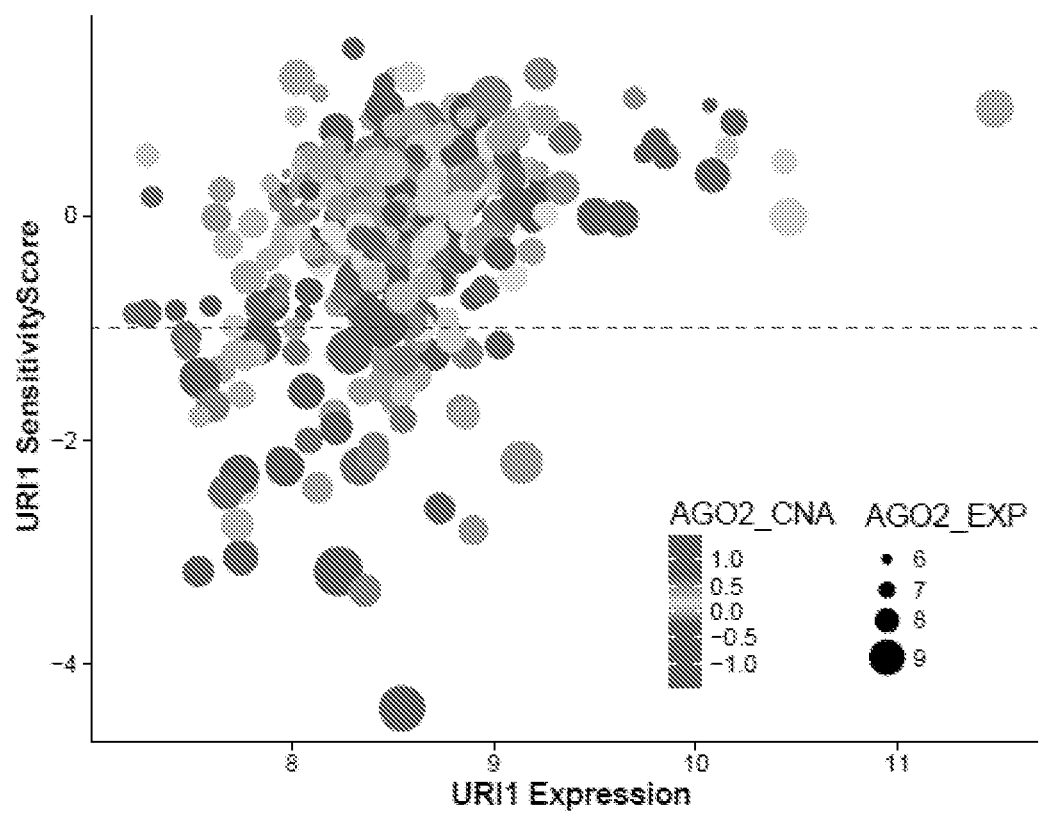

Recurrent gene amplification of either mutated alleles or wild-type alleles are a common mechanism for oncogene activation. Forty genes demonstrate a strong correlation between dependence and gene amplification (FIG. 2B). For KRAS and BRAF, amplification of the mutant allele likely contributes to dependence. On the other hand, wild-type ERBB2, MET and FGFR2 undergo extreme CN gain (>20 copies) associated with cancer dependence. High-level amplification of ITCH in a single thyroid cell line supports a role for ITCH in anaplastic thyroid cancer (Ishihara et al., 2008). The 19q12 amplicon, seen in primary breast, ovarian and endometrial cancers, harbors C19orf12, PLEKHF1, URI1, POP4 and CCNE1 (Cyclin E). Multiple genes in the amplicon exhibit elevated expression leading to controversy as to whether a single gene is the driver. We found that 19q12 amplified lines are dependent on CCNE1 and CDK2 (FIG. 2C) while the remaining genes showed no correlation between CN and dependence. In contrast to prior data (Theurillat et al., 2011), URI1 appears to be an essential gene rather than a 19q12 driver gene based on its dependency correlations with its own low expression and high AGO2 (FIG. 3). We also observed a set of genes in which knockdown was strongly correlated with copy number, yet the effect on cancer growth appeared to be modest. These correlations arise from the dual contribution of slight copy number gain in dependent lines and gene-deletion in the least dependent lines. This pattern seems unlikely to be indicative of key cancer dependent genes. Genes in this category include ASH1L, ELF1, MBD1, MBD2, PHLPP1, PLXNA4 and VAPB.

Figure 2D:
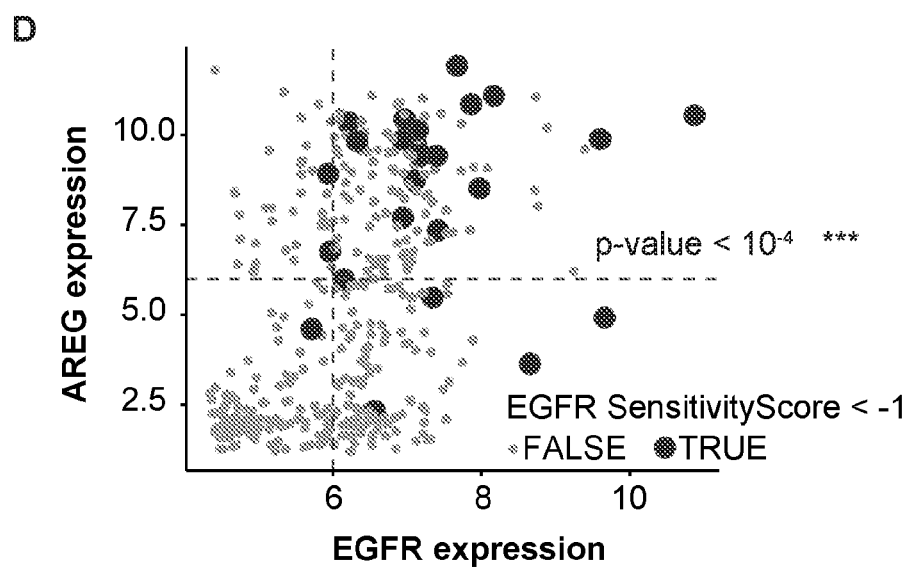
Figure 2E:
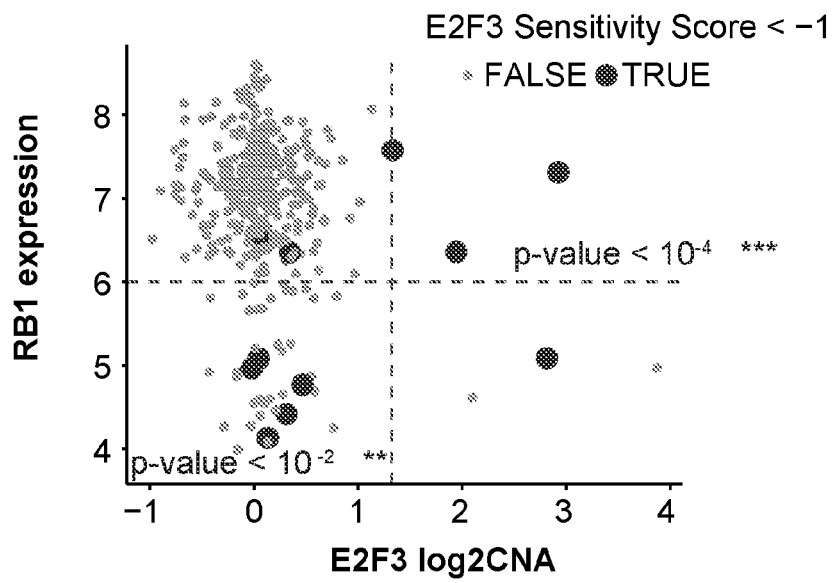

In using deep shRNA libraries we discovered not only the direct dependence on key drivers, but also genes that can act as modifiers. Indeed, modifiers of oncogene dependence can be observed in DRIVE. For example, EGFR dependence in lung and other solid tumors is not only associated with amplification and expression of EGFR but also with high levels of Amphiregulin (AREG) (FIG. 2D). These data may also speak to the therapeutic role of EGFR antibodies in this setting. Dependence on the transcription factor E2F3 is most correlated with E2F3 gene amplification and/or with loss of expression of RB (FIG. 2E). In lung cancer, we observed a substantial number of KRAS mutant cell lines in which KRAS is dispensable for growth. Instead, these KRAS mutant lung lines are susceptible to NFE2L2 (NRF2) and SMARCA2 (BRM) knockdown correlated with loss of function mutations in KEAP1 and/or low SMARCA4

Figure 2F:
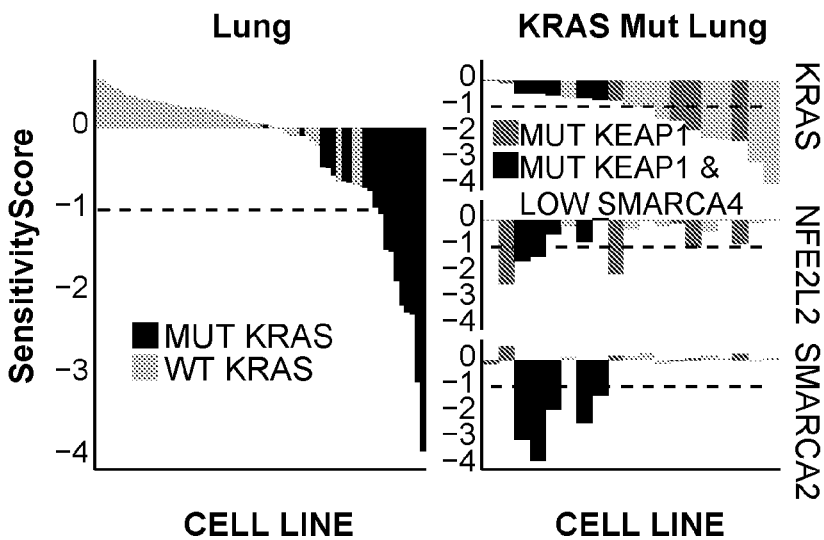

(BRG1), respectively (FIG. 2F). This has implications for treating KRAS mutant cancers with MAPK pathway inhibitors as co-occurring mutation is predicted to lead to de novo resistance.

Figure 4A:
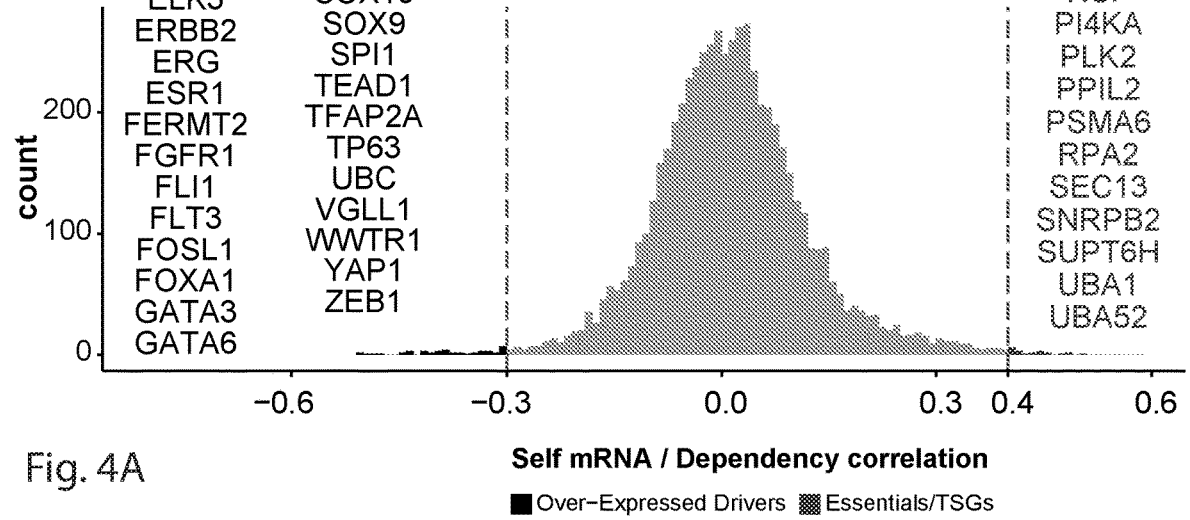
FIGS. 4A-4E depict expression based driver dependency outlier class.

Expression Correlation Analysis Identifies Oncogenes and Lineage Specific Transcription Factors The second class of cancer dependent genes was comprised of those in which high-level expression of the target gene was a top correlated feature. To further explore this class we directly correlated gene expression and gene dependence. 57 genes had a negative correlation (−0.3 or better) where high levels of target gene expression were associated with significant growth effects upon shRNA-induced target knockdown (FIG. 4A). Hits shown in bold were originally identified in the unbiased outlier analysis. Genes in this class include many previously described genetic drivers as amplification and mutation often leads to increased expression. Additionally, a number of genes are unique to this class and show either a pattern of broad expression correlations across different lineages (e.g. ZEB1, BCL2L1) or show a more lineage-restricted pattern (e.g. MPL and CCND3). Notably, many of the expression outliers are lineage restricted transcription factors (FIG. 1D) (see below).

Figure 4B:
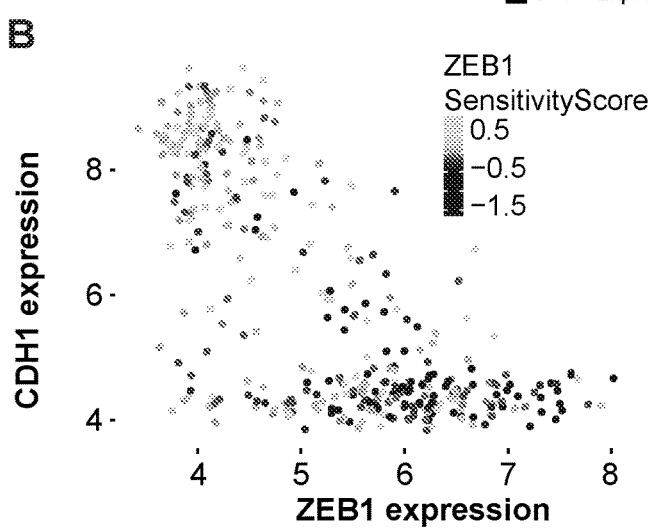
Figure 4C:
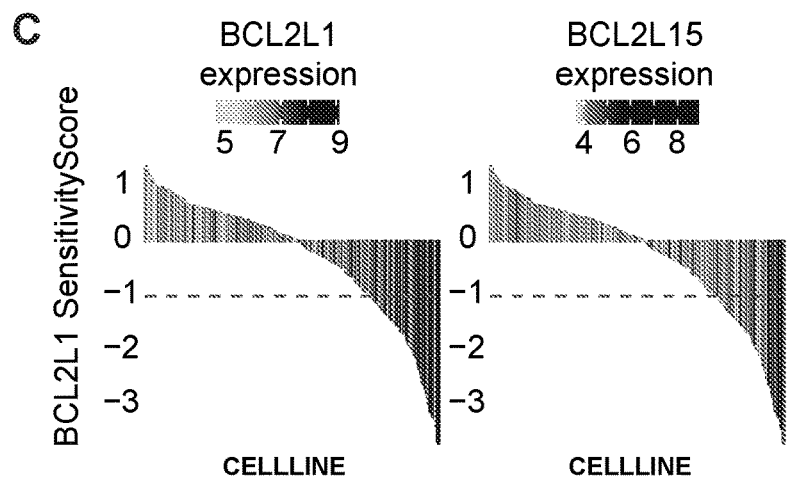
Figure 4D:
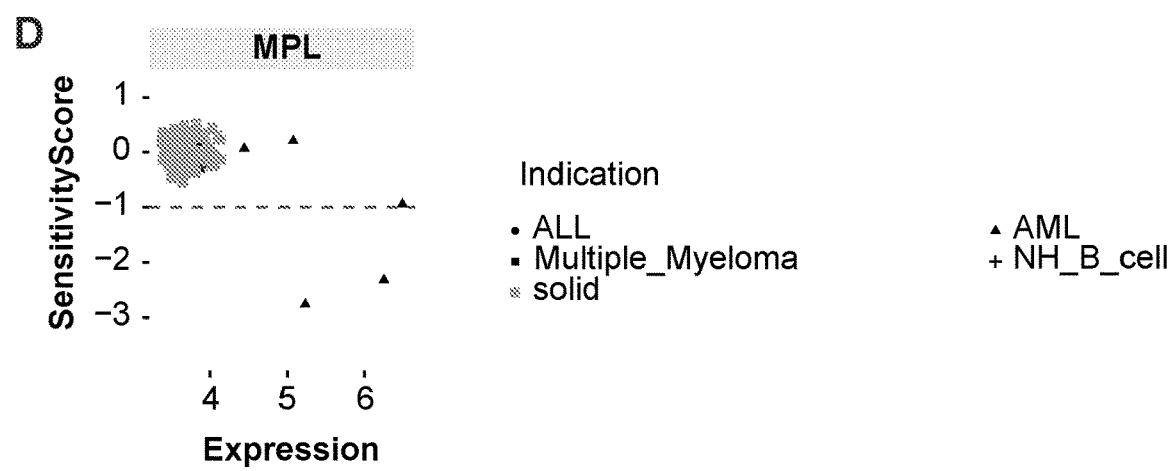
Figure 4E:
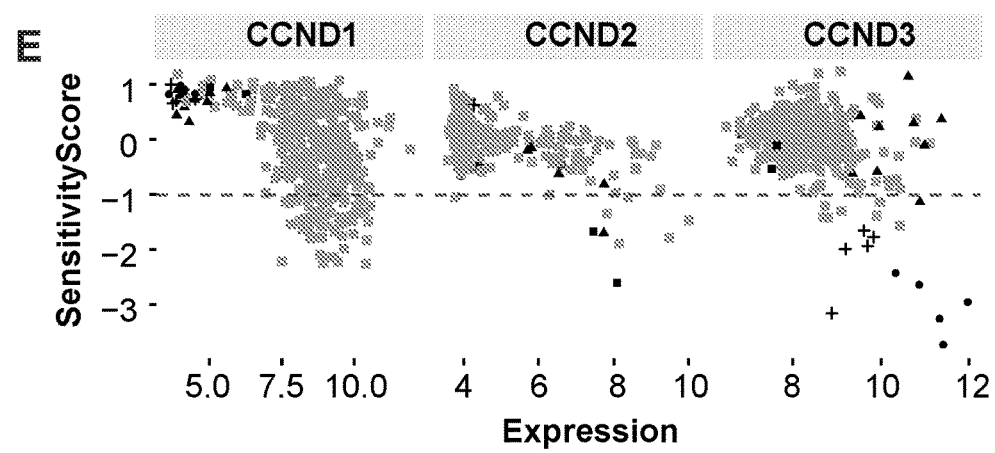

The transcriptional repressor ZEB1 shows a correlation between gene expression and gene dependence observed across multiple lineages. ZEB1 dependence is linked to both self-expression and lack of expression of CDH1, a transcriptional repression target of ZEB1 (Grooteclaes and Frisch, 2000)(FIG. 4B). BCL2L1 (BCLXL) is another example where high expression is predictive of dependence across lineages (FIG. 4C). Interestingly, the lines most sensitive to BCLXL depletion also express high levels of BCL2L15, a poorly studied BH2/BH3 containing family member with weak pro-apoptotic activity (Coultas et al., 2003). MPL is the receptor for thrombopoietin and sustains gain-of-function mutations in myeloproliferative neoplasms including essential thrombocythemia and primary myelofibrosis (Pardanani et al., 2006). In DRIVE, only 4 hematopoietic cell lines have appreciable MPL expression and three demonstrate MPL dependence (FIG. 40). The D-type cyclins interact with either CDK4 or CDK6 to govern control of the GUS transition (Otto and Sicinski, 2017). Each cyclin shows a strong expression-dependence correlation (FIG. 4E). CCND3 shows hematopoietic-specific expression and dependence in collaboration with CDK6 in ALL and DLBCL while CCND1 is active in solid tumor cell lines in collaboration with CDK4. CCND2 shows activity in a smaller subset of lines in both hematopoietic and solid tumor lineages but maintains a strong expression correlation. These data suggest that within a given cell line, a single D type cyclin in combination with CDK4 or 6 is required to mediate passage through the restriction point. Hence, greater therapeutic specificity might be achieved through the disruption of specific D-type cyclin-CDK4/6 interactions.

Figure 5A:
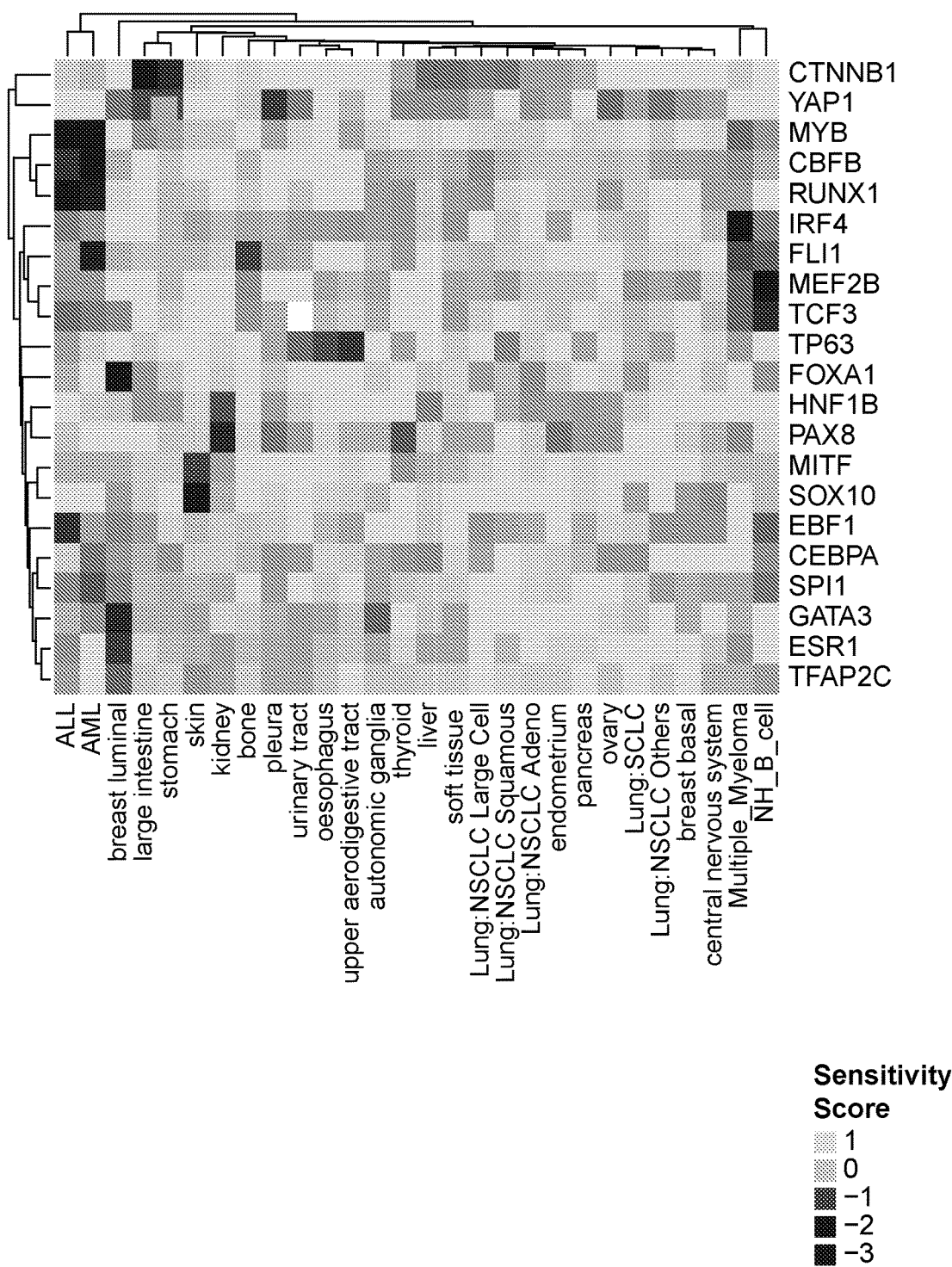
FIGS. 5A-5D depict lineage specific transcription factors.
Figure 5B:
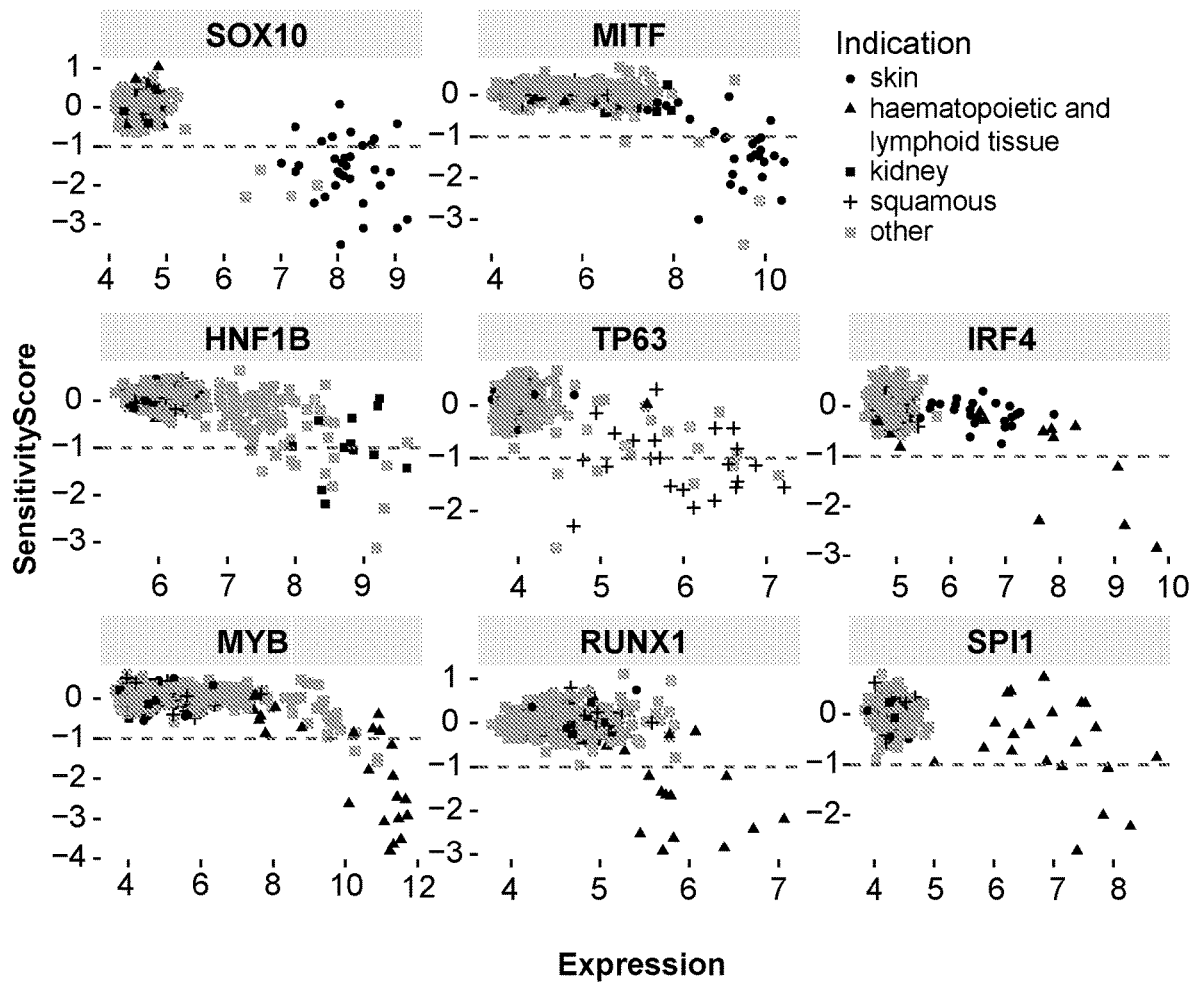

Within the expression outlier class is a large collection of lineage transcription factors (FIG. 5A). Certain lineages demonstrate master TF regulators where tissue restricted expression is highly correlated with sensitivity to gene depletion (MYB, PAX8, CTNNB1, SOX10 and MITF). SOX10 is expressed in neural crest progenitors during development (Bondurand and Sham, 2013) and is expressed in neural crest derived tumors including melanoma and glioma. The SOX10 relationship is binary where any detectable expression equates to dependence (FIG. 5B).

HNF1B functions developmentally to control distinct aspects of kidney, pancreatic and liver tissue specification with adult tissue expression also seen in the gonads and lung. In DRIVE, cancer dependence for HNF1B is observed in kidney, pancreatic, liver, lung and ovarian cell lines and shows a correlation between expression and dependence (FIG. 5B). In normal development HNF1 B functions with HNF1A. However, in the cancer cell line datasets we failed to observe HNF1A and B co-dependence suggesting that dependence might be driven by HNF1B homodimers.

Figure 5C:
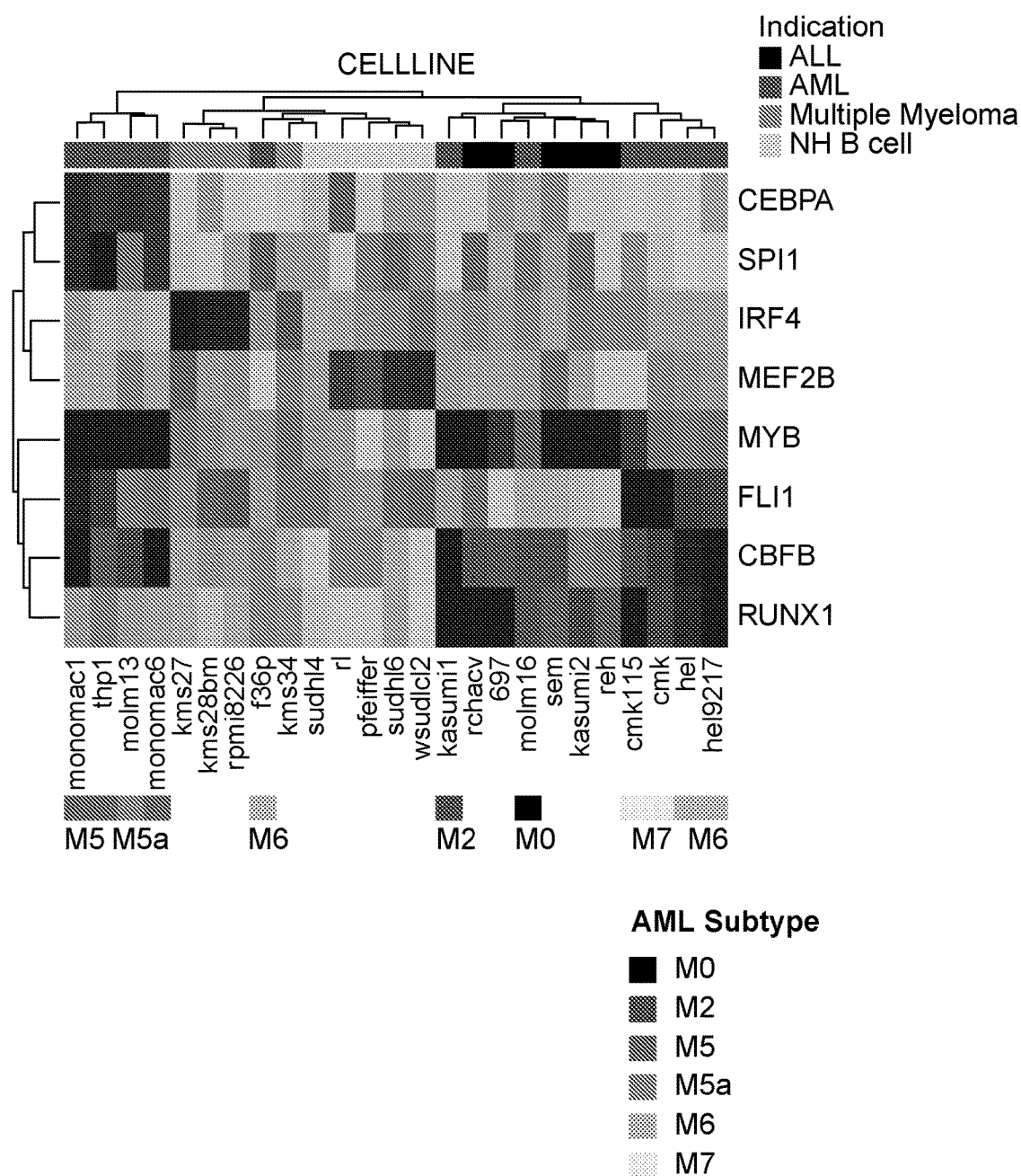

Within the hematopoietic lineage, specific subtypes have unique transcription factor dependencies (FIG. 5C). Indeed, hierarchical clustering based on TF dependence largely segregates these models by disease subtype. For example, models of DLBCL are uniquely dependent on MEF2B where mutations have been previously described (Lohr et al., 2012; Morin et al., 2011; Zhang et al., 2013). Both MYB and RUNX1 are required for proliferation across multiple leukemia subtypes (ALL and AML). RUNX1 forms the core binding transcription factor (CBF) in collaboration with CBFB to drive hematopoiesis (Tracey and Speck, 2000). RUNX1 knockdown was most closely phenocopied by knockdown of its binding partner CBFB and, to a lesser degree, MYB. shRNAs against FLI1 and SPI1 demonstrated robust activity across many AML lines whereas knockdown of CEBPA showed specific activity in the M5 subtype of AMLs. These observations are consistent with the model that myeloid leukemias suffer from a block in terminal differentiation arising as a result of aberrant TF activity (Orkin and Zon, 2008; Rosenbauer and Tenen, 2007). Finally, IRF4 expression is detectable across multiple lymphoma subtypes whereas IRF4 dependency is uniquely detected in multiple myeloma as previously described (Shaffer et al., 2008).

Figure 5D:
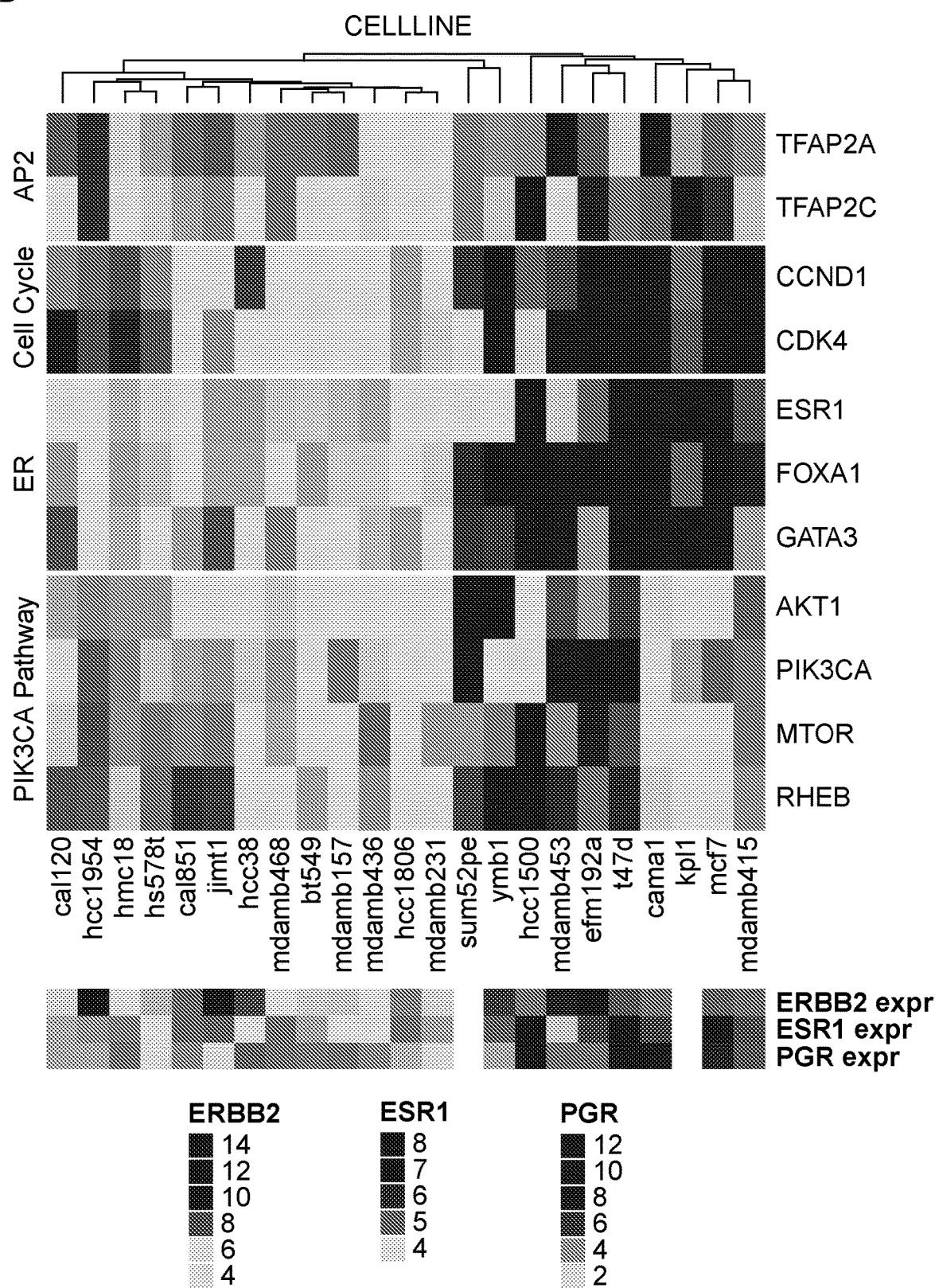

While no specific transcription factor requirements were identified for the maintenance of basal breast cancers, analysis of luminal breast cancer confirmed the network of transcription factors that coordinate the regulation of hormonal signaling including ESR1, FOXA1, GATA3 and TFAP2C (FIG. 5D) (Cyr et al., 2015; Lupien and Brown, 2009). In addition, we also observed models that are dependent on TFAP2A. Consistent with emerging clinical data, the luminal subtype also showed dependence on components of the PIK3CA/mTOR and CDK4 pathways (Baselga et al., 2012; Hortobagyi et al., 2016). The difference between the TF network observed in the luminal subtype compared to the absence of specific TF requirements in the basal subtype raises the possibility that basal phenotypes are a default differentiation state resulting from the absence of superimposed specification (Bernardo et al., 2013).

Synthetic Lethal Classes

Figure 6:
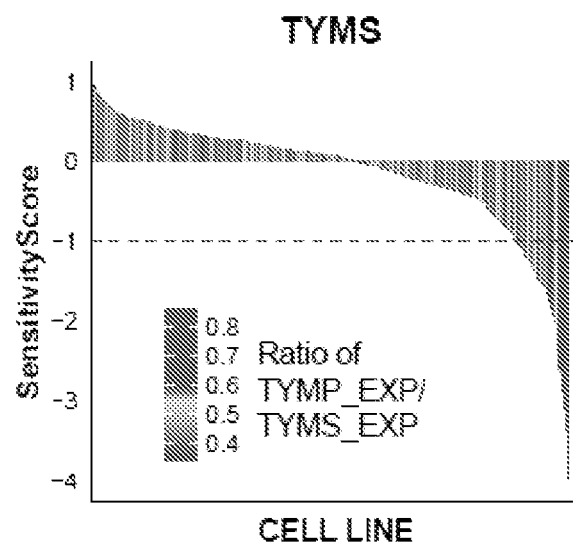
FIG. 6 depicts TYMS DRIVE profile. TYMS sensitivity score waterfall plot is colored by the ratio of TYMP/TYMS expression (high TYMP expression coupled with low TYMS expression indicative of sensitivity).
Figure 7A:
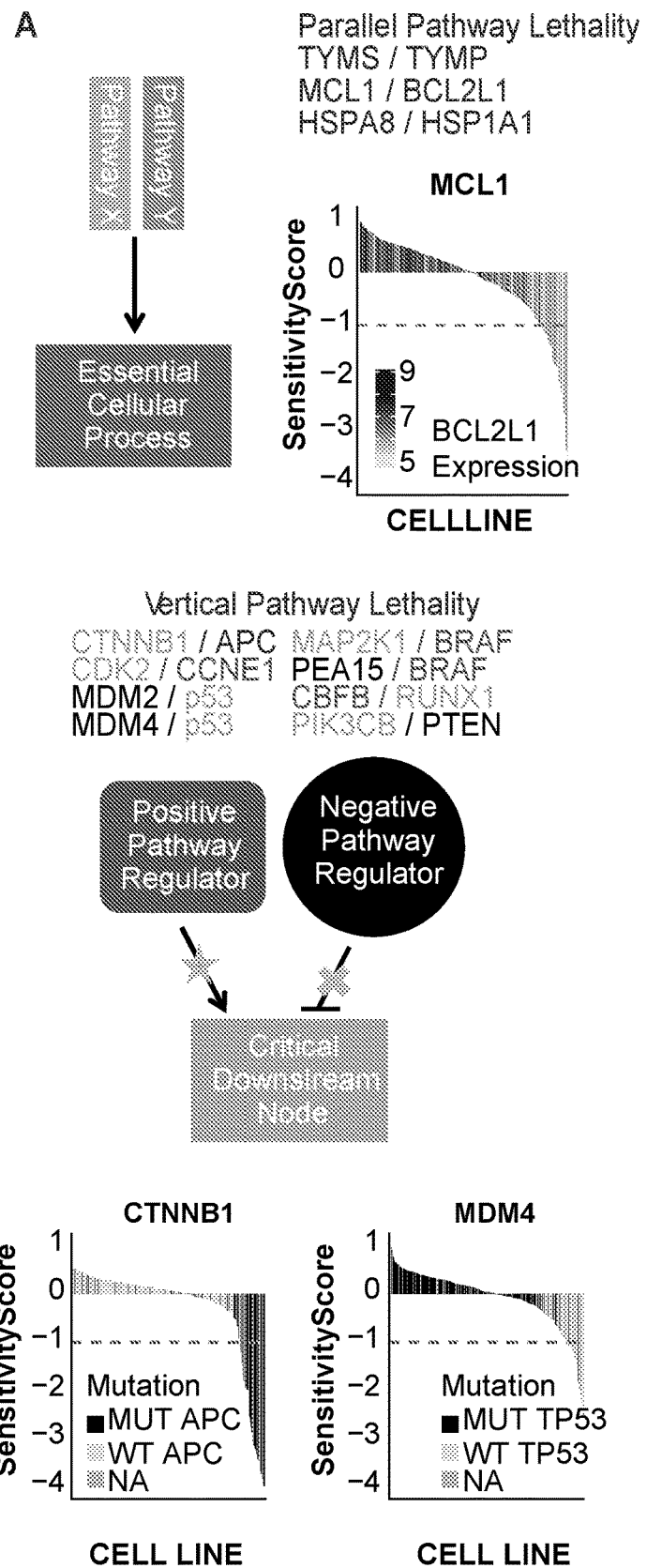

As used herein, synthetic lethality (SL) included any altered cell state (genetic, metabolic or otherwise) that was linked to a definable non-self genetic dependence. Within this class we observed distinct subsets including those where synthetic lethality was linked to a pathway, to loss of a paralog or to collateral lethality. In the parallel pathways of de novo synthesis and salvage of thymidine, TYMP (thymidine phosphorylase) mediates the reduction of thymidine to thymine. This activity reduces cellular thymidine which is normally produced by the activity of TYMS (thymidylate synthase) as part of the de novo pathway. A subset of cancer cell lines display an altered ratio of TYMP (high) to TYMS (low) expression leading to the apparent cellular dependence on residual TYMS (FIG. 6). Depletion of the anti-apoptotic protein MCL1 showed a robust dependent phenotype and a complex set of correlations with multiple BCL2 proteins from parallel pathways. Here, reduced expression of BCL2L1 (BCLXL) accompanied by increased expression of the pro-apoptotic BH3-only member BIM was most predictive of sensitivity to MCL1 downregulation. In contrast, cell lines with high BCLXL expression were refractory to MCL1 knockdown (FIG. 7A).

In addition to parallel pathway SL, we observed 8 distinct vertical pathway SL outlier dependences. These included dependence on β-catenin (CTNNB1) in the context of genetic loss of APC (FIG. 7A). Amplification and overexpression of Cyclin E was correlated with sensitivity to knockdown of CDK2 (FIG. 2C). Similarly, CBFB dependence was strongly associated with high expression of its binding partner RUNX1 in hematopoietic lines. Cancer cell lines that retained wild-type p53 were sensitive to depletion of either MDM2 or MDM4 (FIG. 7A) likely resulting from the inappropriate activation of p53 following MDM2/MDM4 depletion. We also observed the previously described SL pathway relationship between PTEN loss and PIK3CB (Wee et al., 2008).

Figure 8:
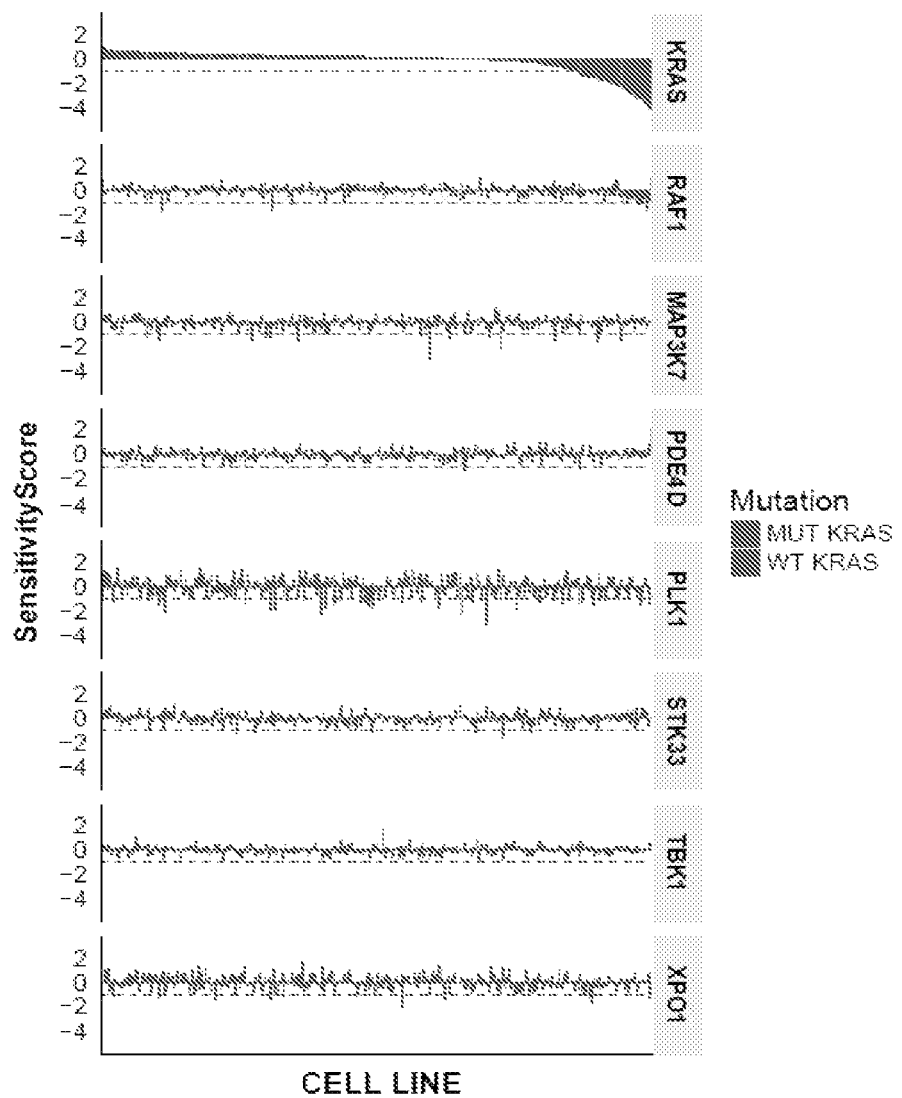
FIG. 8 depicts KRAS DRIVE profile with other reported synthetic lethal gene profiles. Cell lines are ordered by KRAS Sensitivity Score and colored by KRAS mutation status. Knockdown of a known MAPK pathway component, RAF1 (cRAF), is shown as a comparator for a gene that partially phenocopies KRAS knockdown.
Figure 9:
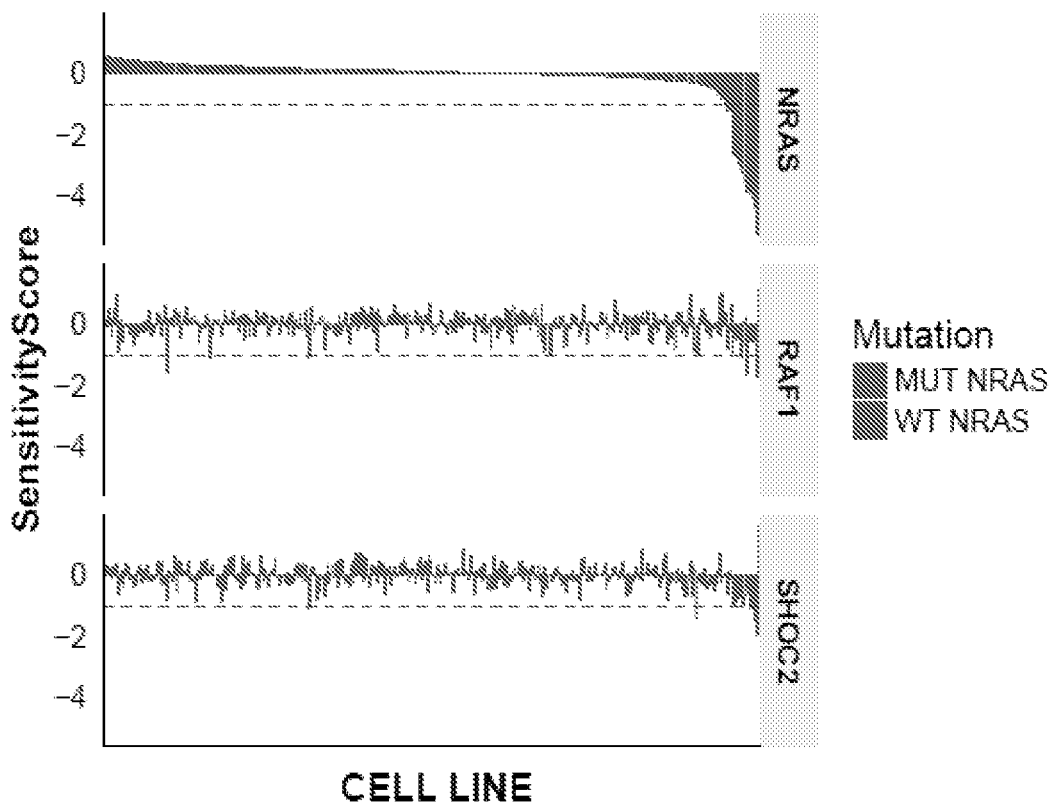
FIG. 9 depicts NRAS, RAF1 and SHOC2 DRIVE profiles. Cell lines are ordered by NRAS Sensitivity Score and colored by NRAS mutation status. The highest correlating DRIVE profiles to the SHOC2 profile are RAF1 and NRAS.

There has been significant interest in identifying synthetic lethal interactions pertaining to the RAS pathway. In DRIVE, we do not detect robust synthetic lethal interactions for mutant KRAS and previously published synthetic lethal interactions are not confirmed in this dataset (Barbie et al., 2009; Kim et al., 2016; Luo et al., 2009; Scholl et al., 2009; Singh et al., 2012; Zimmermann et al., 2013)(FIG. 8). Data supporting the notion that RAF1 (CRAF) is required for Ras-dependent transformation (Blasco et al., 2011; Karreth et al., 2011) can be observed but CRAF depletion does not phenocopy KRAS depletion (FIG. 8). This partial effect of CRAF depletion is also seen in the NRAS mutant setting. The partial effect is unlikely to be the result of insufficient CRAF knockdown as depletion of a known positive regulator of CRAF activation, SHOC2, phenocopies CRAF depletion (FIG. 9). Mutant RAS family members may require suppression of multiple RAF family members or suppression of additional effector arms beyond the MAPK pathway to achieve efficacy. On the other hand, we do observe synthetic lethal interactions for BRAF in the melanoma setting. Targeting of a node downstream of mutant BRAF (MEK1 or ERK2) was sufficient to induce vertical pathway lethality and in the case of MEK inhibition, this has been reduced to practice clinically (Flaherty et al., 2012). In addition to positive regulators of MAPK signaling, we also found the surprising observation that loss of negative regulators downstream of activated BRAF in melanoma, such as PEA15 and DUSP4, resulted in lethality suggesting that either too little or too much flux through the MAPK pathway is detrimental in this setting.

Figure 7B:
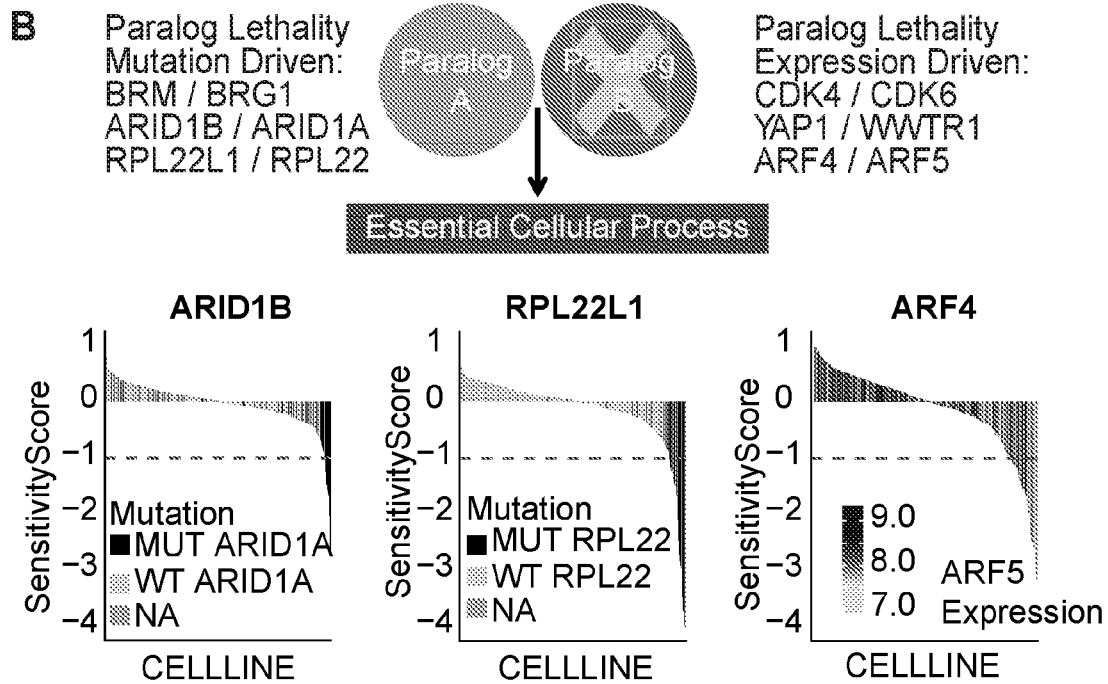

We, and others, have described synthetic lethal interactions among paralogous genes where one paralog is genetically inactivated through mutation and/or deletion. Specifically, we found that the loss of the SWI/SNF complex member BRG1 explains the sensitivity observed upon BRM depletion in NSCLC cell lines (Hoffman et al., 2014). Here, we observed a similar relationship for ARID1A and ARID1B (Helming et al., 2014) in which mutation of ARID1A renders cells dependent on ARID1B (FIG. 7B) and for RPL22 and RPL22L1. In this latter instance, microsatellite instable (MSI+) cell lines have frequent single nucleotide deletions in a mononucleotide repeat in RPL22, a ribosome subunit (Novetsky et al., 2013). RPL22 mutant lines were selectively dependent on the paralog RPL22L1 (FIG. 7B). In all three cases, inactivating somatic mutations result in a dependence on the remaining paralog.

We also observed paralog SL relationships where low or absent expression (rather than mutation) of a paralog is associated with dependence on the other. As previously discussed, CDK4 and CDK6 show largely non-overlapping dependence in the CCLE. In fact, the best predictor of CDK4 dependence in DRIVE is low expression of CDK6. Similarly, the best predictor of YAP1 sensitivity is low expression of the paralog WWTR1 (TAZ). ARF4 and 5 are the only two class II members of the ADP-ribosylation factor family (Jackson and Bouvet, 2014). We observed a novel synthetic lethal relationship where low expression of ARF5 predicts for ARF4 dependency (FIG. 7B). Finally, VPS4A and B are homologs of the essential yeast VPS4 gene (McCullough et al., 2013). VPS4B is located at 18q21.33 and is frequently lost in concert with homozygous deletions of SMAD4 (18q21.1) and this co-deletion event is associated with dependence on the paralog VPS4A.

Figure 7C:
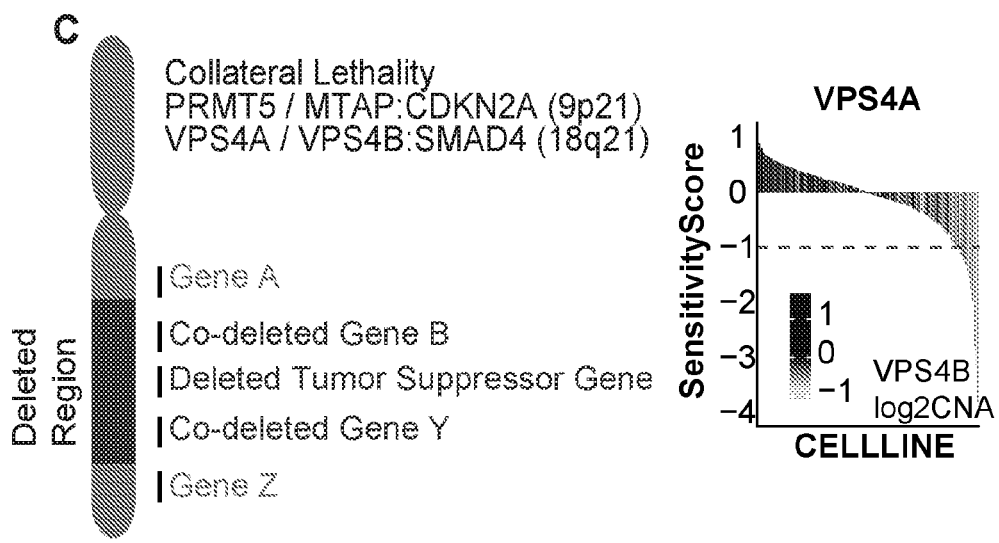
Figure 7D:
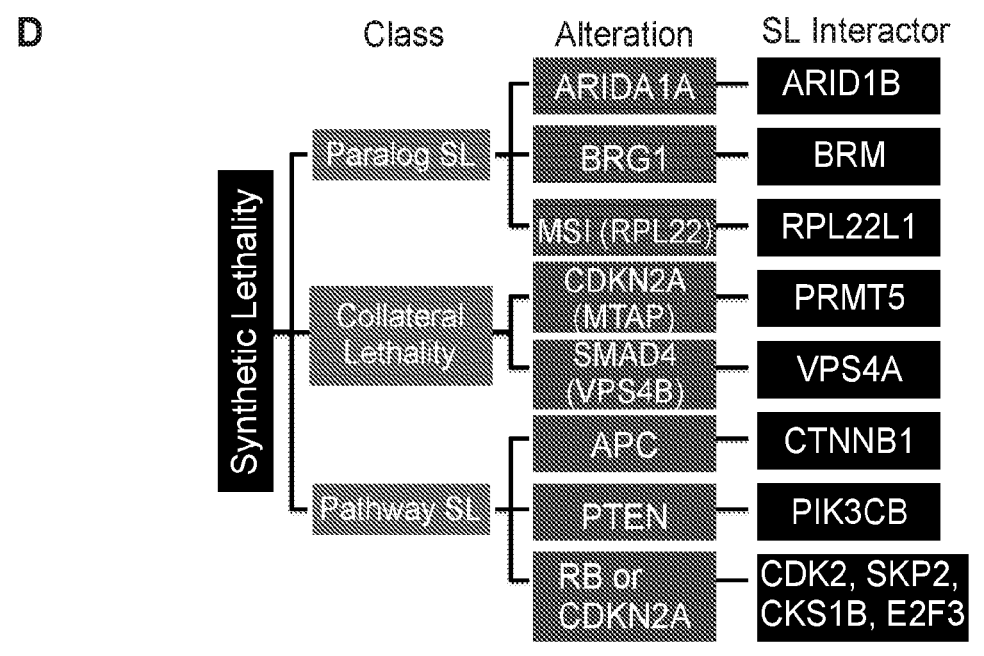
Figure 10:
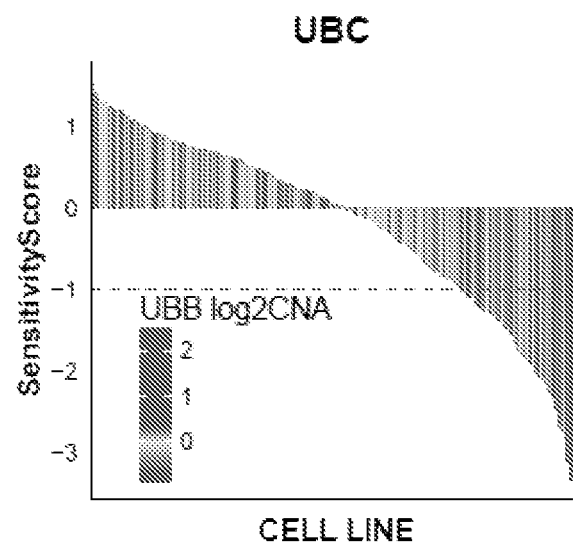
FIG. 10 depicts UBC DRIVE profile. UBC sensitivity is colored by the CN value of its paralog, UBB.
Figure 11:
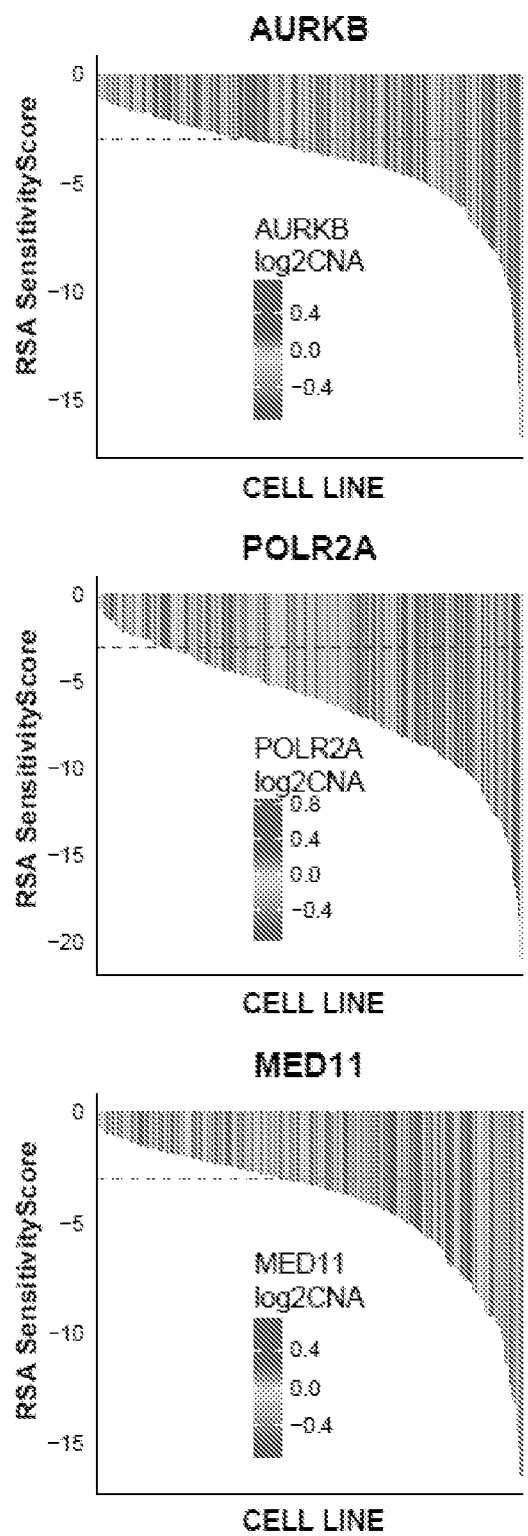
FIG. 11 depicts RSA sensitivity plots for POLR2A, MED11 and AURKB. Cell lines are colored by their CN value for each respective gene.

The VPS4A paralog dependence is also an example of collateral synthetic lethality where bystander deletion of a neighboring gene leads to cancer dependence (FIG. 7C). This was first described for the ENO1 locus on 1p36 resulting in dependence on the paralog ENO2 (Muller et al., 2012). We were unable to verify this finding due to the absence of relevant models in the CCLE. We and others previously reported a second example, namely the dependence on PRMT5 linked to the co-deletion of MTAP and the tumor suppressor CDKN2A (Kryukov et al., 2016; Marjon et al., 2016; Mavrakis et al., 2016). More recently, a collateral lethal relationship was described for SMAD4 and the nearby gene, ME2, leading to dependence on the paralog, ME3 (Dey et al., 2017). shRNAs for ME3 were not included in the DRIVE library and hence we cannot detect this event. While not a top outlier, we found that ubiquitin B (UBB) undergoes CN loss with p53 and is correlated with dependence on the paralog ubiquitin C (UBC) (FIG. 10). Finally, we observed that frequent heterozygous deletion of p53 results in heterozygous loss of three essential genes POLR2A, MED11 and AURKB and is associated with increased sensitivity to knockdown of these genes compared to cell lines with normal CN (FIG. 11). In aggregate, we have detected synthetic lethal interactions for some of the most prevalent tumor suppressors found in cancer (FIG. 7D).

Figure 12:
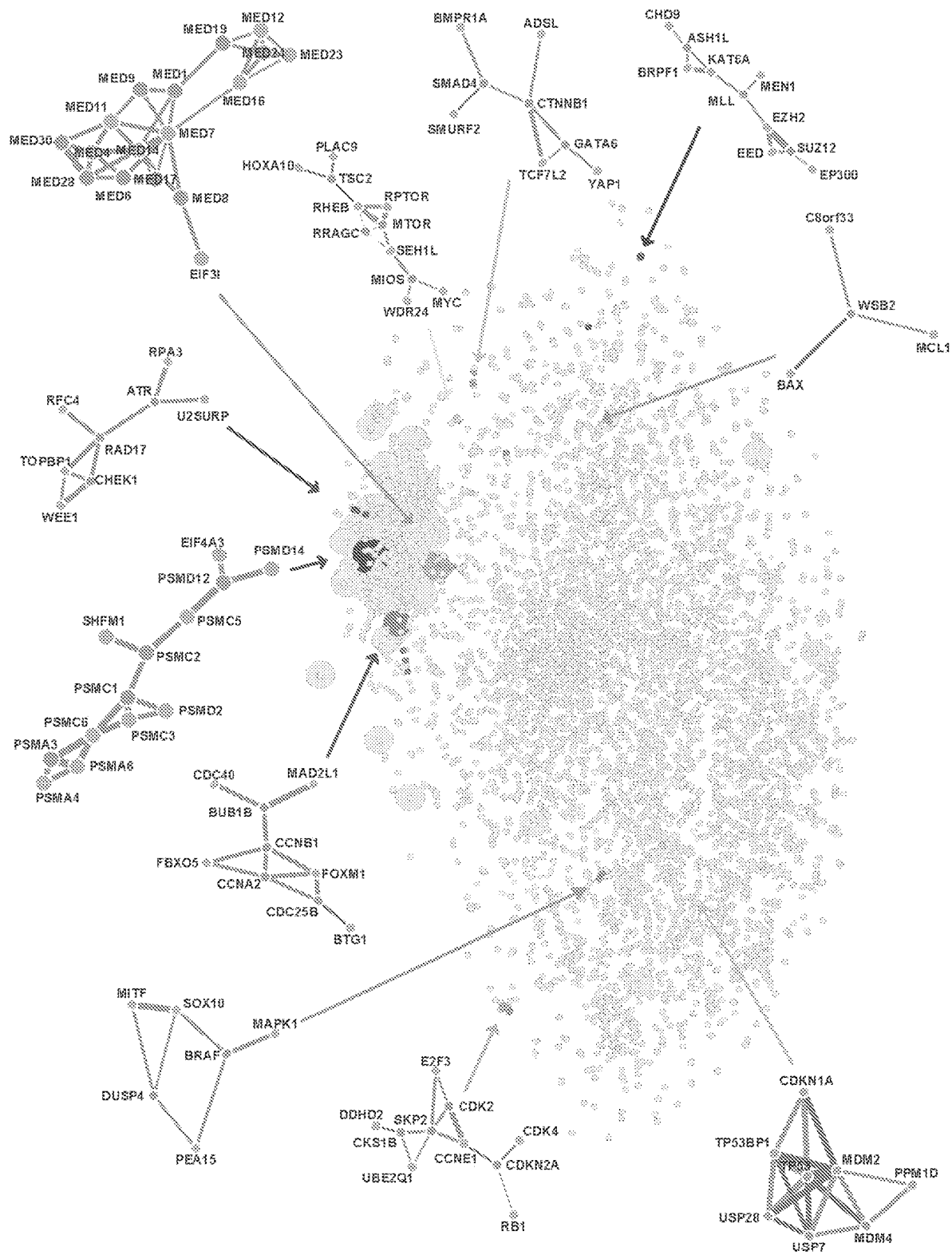
FIG. 12 depicts DRIVE Sensitivity Network DRIVE-DRIVE correlations are plotted in two dimensional space using tSNE algorithm. Enlarged circles represent essential genes highlighting an essential gene subnetwork. Specific DSN examples include complexes (proteasome, mediator, epigenetic neighborhood), pathways (ATR, p53, G1/S, G2/M, mTOR, WSB2) and lineages (skin, colon). Each subnetwork is displayed around the global tSNE plot with genes used to seed the subnetwork shown in orange. Top three neighborhood correlations for each seed gene are shown with positive correlations negative correlations (the top four correlations are used when building the p53 network). The thickness of the lines between two genes represents the strength of the correlation. Subnetwork seed genes are mapped back onto the global tSNE and colored by pathway to illustrate correlations in 2D space.

DRIVE Sensitivity Network Uncovers Signaling Pathways, Protein Complexes and Lineage Biology The density of shRNAs used per gene, the extensive set of cell lines tested and the robustness of the observed dependency correlations led us to test whether the viability effects of each gene knockdown would be varied and robust enough to find correlated gene-gene interactions based only on the gene knockdown data. To test this, a correlation matrix was calculated in which each gene profile was correlated with every other gene profile creating a matrix of 21,493,846 pairwise comparisons. This can be represented as a network where each gene represents a node and each edge represents the pairwise similarity between genes. We defined the distance between two genes as the squared absolute value of the Pearson correlation. The DRIVE Sensitivity Network (DSN) interactive tool (Network Viz tab @ oncologynibr.shinyapps.io/drive/) allows for a single or multi-gene entry point to explore their local correlation neighborhoods. In FIG. 12, a global genetic interaction map is represented in 2-dimensional space using the non-linear tSNE method which despite the limitations of 2-D enables a global view of the network and conserves many of its original features. Each point represents a gene dependence profile and the local "neighborhood" proximity between two points represents the similarity in the original high dimensional network between two gene profiles. Individual subnetwork examples created using the DSN tool are also shown (FIG. 12).

Within the global network, we observed a dense and large neighborhood comprised of essential genes (large circles) as defined in FIG. 1B. Despite the essential nature of this neighborhood, there still exists sufficient differential variation in growth effects across the cell lines to allow for the identification of large protein complexes including the proteasome, ribosome, RNA polymerase complex and the mediator complex. The co-localization of a large number of non-essential genes within this cluster suggests that full inactivation of these genes (by CRISPR) may result in lethality. One pathway example in the essential neighborhood is the DNA replication checkpoint. This includes ATR as well as pathway components RPA3 that senses ssDNA and RAD17 and TOPBP1 that help ATR transduce the signal to the downstream kinase CHEK1. In contrast to the essential gene neighborhood, the mTORC1 arm of the mTOR signaling complex shows less activity across the dataset but still shows robust correlations. Starting with the negative regulator TSC2, its direct downstream target, RHEB, as well as mTOR and RAPTOR can be seen as anti-correlations. Additional Ragulator complex components are also seen in this mTOR amino acid sensing neighborhood including SEH1L, RRAGC, WDR24 and MIOS.

Figure 13:
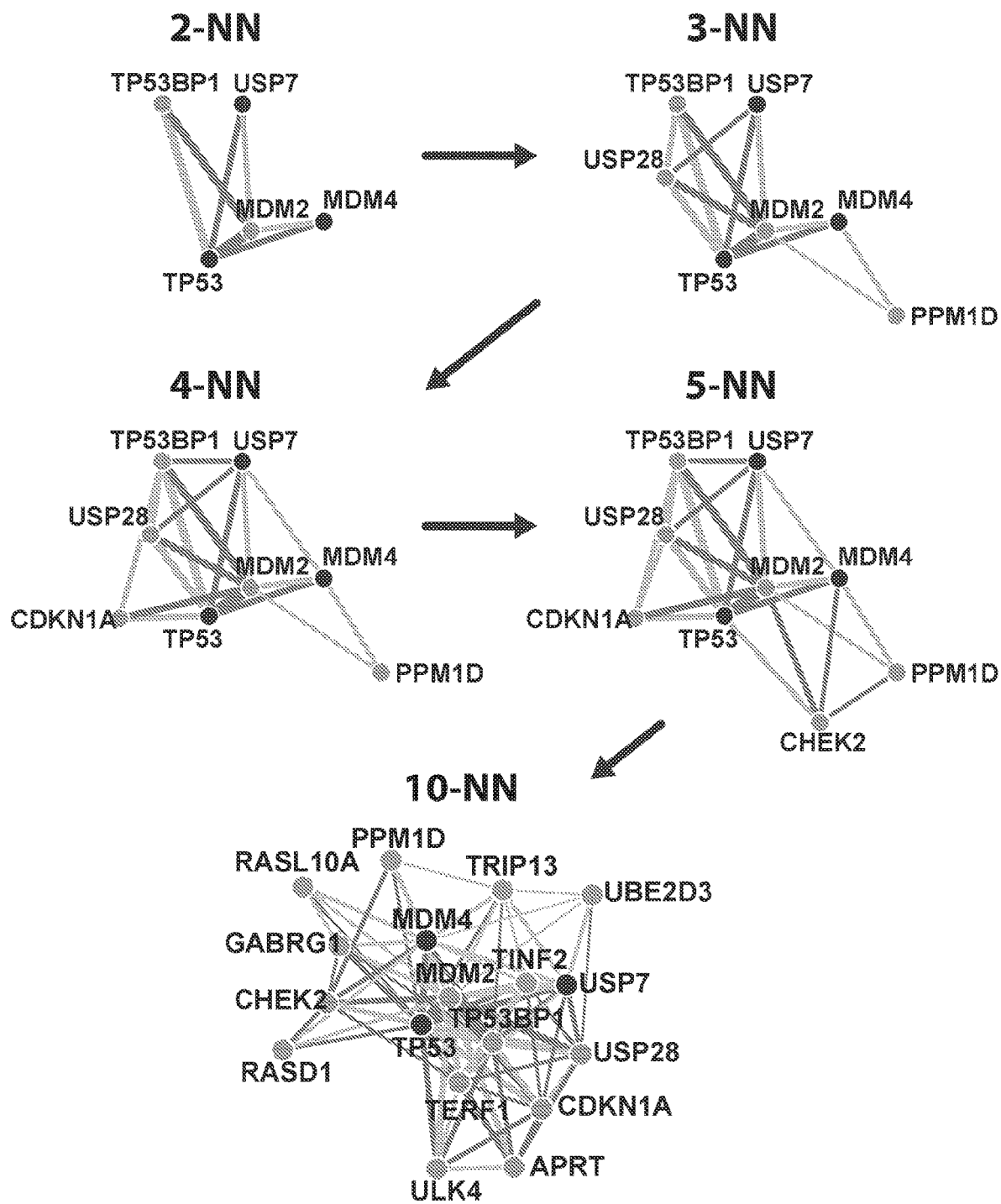
FIG. 13 depicts p53 DSN nearest neighbor (NN) analysis. Seed genes (p53, MDM4 and USP7; shown in orange) are used to nucleate the p53 neighborhood using the DSN interactive tool with a variable number of edges per gene (2, 3, 4, 5, and 10). All the edges from non-seed genes are also shown whenever they are part of their respective top N neighbors (2, 3, 4, 5, and 10 respectively). Positive correlations and negative correlations are shown while the thickness of the lines between two genes represents the strength of the correlation.

The recapitulation of the p53 pathway is robust in DRIVE. Known negative regulators (e.g. MDM2, MDM4, USP7, PPM1D) all show dependence effects in the WT p53 setting. Conversely, knockdown of p53 or positive regulators (e.g. TP53BP1, USP28, and CDKN1A) promote the growth of cells harboring WT p53. Nearly all known key regulators of p53 were discovered in this unbiased network. As an illustration of progressive cluster build using the DSN interactive tool, we show the p53 network when a range of 2-10 nearest neighbors (NN) is used (FIG. 13). Here, as the neighborhood is grown from 2 NN to 10, the absolute correlation coefficients (ranging from 0.35 to 0.86) decrease as indicated by the thickness of the lines between genes. As such, all members of the 2, 3, 4 and 5 NN networks are known components of the p53 pathway whereas new associations seen in the 10 NN network are less robust (by definition) and are not known p53 pathway members.

A network relationship between genes that appear to have similar functional consequences when depleted from cells was also observed. For instance, the PRC2 complex members form a tight interaction network suggesting very similar functional consequences of EZH2, EED and SUZ12 knockdown consistent with their function as a unit. In addition, the nearby neighborhood location of the MLL/menin (MEN1) and ASH1L methyltransferase complexes suggests a functional concordance between these proteins and the PRC2 complex. Interestingly, the histone acetyltransferases p300 and the MOZ complex, comprised in part by KAT6A (MYST3, MOZ) and BRPF1, is located nearby to all three methyltransferases suggesting an interplay of acetylation and methylation with likely similar effects on cancer dependence.

Two cell cycle neighborhoods were observed within the DSN. The CCNE1/CDK2 axis is active in cell lines with low RB expression or high CCNE1 expression. Here, E2F3 appeared uniquely required for CDK2-mediated cell cycle progression along with SKP2 and CKS1B. These proteins collaborate to degrade p27 (CDKN2B) (Ganoth et al., 2001), hence their knockdown would likely stabilize p27 leading to CDK2 inhibition. Interestingly, an E2 enzyme, UBE2Q1, was found in the CDK2 node suggesting that it may take part in p27 degradation. Not surprisingly, anti-correlations with CDKN2A and RB1 were also observed. A second sub-network of cell-cycle control genes regulating G2/M was observed in the DSN. This included Cyclin A2 and B1 along with FOXM1 that controls transcriptional events required for this transition including upregulation of CDC25B that controls activation of CDK1. Interference with the timely activation of the anaphase promoting complex (FBXO5) or the mitotic spindle checkpoint (BUB1B, MAD2L1) had apparently deleterious effects on a similar group of cell lines. BTG1, a G0/G1 cell cycle inhibitor, is anti-correlated within this network consistent with its role in inhibiting early cell cycle progression.

The critical balance between BCL2 family members has been highlighted as both MCL1 and BCL2L1 (BCLXL) demonstrate complex dependency profiles that contain expression of both pro- and anti-apoptotic family members in order to maintain cell survival. WSB2 (WD40 repeat and SOCS box protein) has an outlier profile but one that does not contain robust features predictive of dependence yet does demonstrate multiple connections to the apoptosis pathway in the DSN. The most robust association is anti-correlation of WSB2 and BAX. WSB2 positive correlations include MCL1 and C8orf33. WSB2 is thought to be a component of DDB1/CUL4 E3 ligase complexes (He et al., 2006). The anti-correlation between WSB2 and BAX raises the possibility that WSB2 acts as a negative regulator of BAX protein levels through ubiquitin-mediated degradation.

In addition to pathway and protein complex networks, genes with lineage specific activity can be detected as DSN neighborhoods. In the melanoma sub-network, nodes were observed that highlight both TF dependencies (MITF and SOX10) but also oncogenic signaling pathways. The MAPK node was robust (BRAF, MAPK1) likely due to the prevalence of mutant BRAF. However, the importance of fine tuning this pathway was also highlighted as inhibition of the negative pathway regulators, PEA15 and DUSP4, was similarly detrimental. The colon neighborhood, likely dominated by APC mutation, included the obligate CTNNB1 partner, TCF7L2, as well as a collection of transcription factors including GATA6, SMAD4 and YAP1.

DISCUSSION

Figure 14:
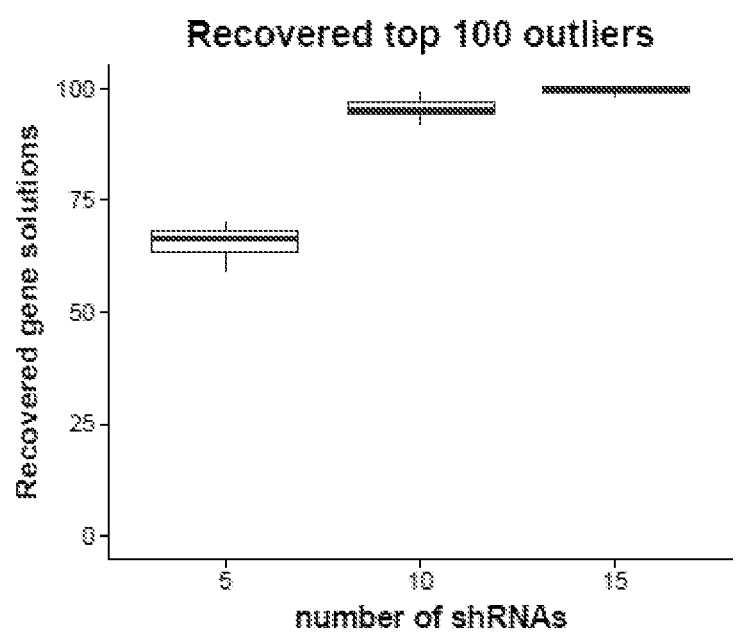
FIG. 14 depicts shRNA power analysis. The top 100 Outliers (by Normality LRT) were determined using the ATARiS solutions of 1381 genes containing 20 shRNAs per gene from the BGPD pool. 5, 10, or 15 shRNAs per gene were then randomly sampled for these top 100 outlier genes to generate ATARiS solutions. This process was repeated 10 times and the ability to generate an ATARiS solution using only 5, 10 or 15 shRNA reagents per gene is shown on the Y axis.

In Project DRIVE, a high-density shRNA library was used to assess the consequences of gene inactivation for half of the expressed genome of the CCLE in 398 cancer cell lines. The data and tools for interrogation as a resource for the further elucidation of therapeutic targets in cancer is provided herein. The breadth of cell line coverage allowed for a diversity of genomic backgrounds to be probed and for relationships with similar functional consequences to be identified. In addition, network relationships for essential genes were assembled due to incomplete gene depletion by RNA interference. The robustness of the dependence data and in particular the nodal relationship of known protein complexes and pathways in the DRIVE Sensitivity Network, suggested that the drawbacks of RNAi, namely off-target effects and inefficient target knockdown, were addressed by the use of appropriate deep coverage libraries and computational methods. We retrospectively conducted a power analysis to compare our ability to detect outliers with a decreasing number of shRNAs/gene (FIG. 14) allowing us to estimate the optimal number of shRNA/gene to recover the majority of the outliers for a dataset of this size. In this case, 15 shRNAs captured most of the observations seen with 20. This is consistent with a previous estimate made from one experimental system (Bassik et al., 2013). RNAi-mediated discovery of synthetic lethal relationships with partial reduction of essential genes, such as in the case of PRMT5, demonstrate that hypomorphs are needed in some circumstances (Kryukov et al., 2016; Marjon et al., 2016; Mavrakis et al., 2016). As such, large scale RNA interference and CRISPR datasets are likely to be complimentary.

Figure 15:
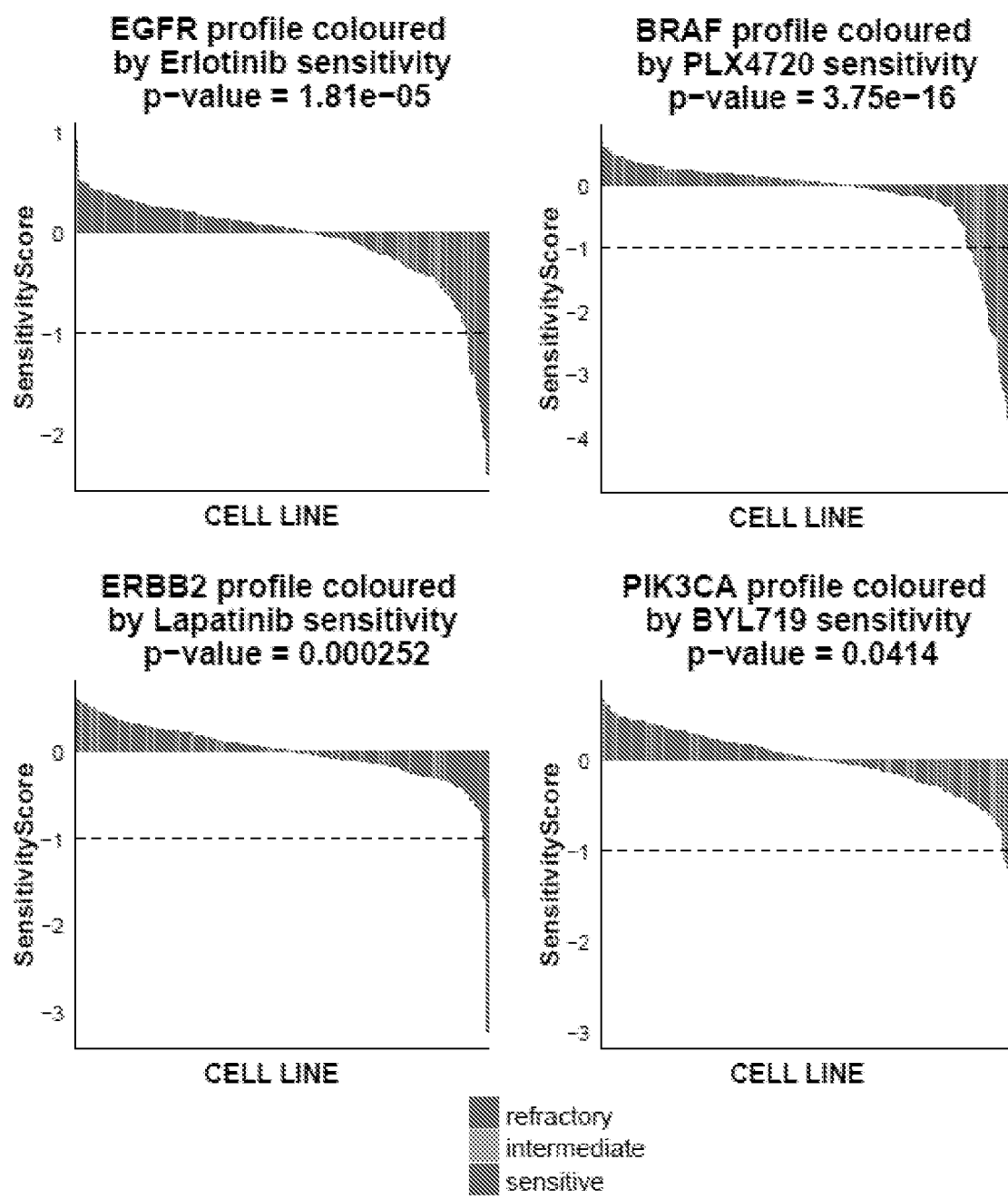
FIG. 15 depicts compound sensitivity coloring of DRIVE profiles. A fisher test was performed comparing the compound sensitivity call and the DRIVE sensitivity call based on a value <−1.

To further consider the robustness of this shRNA screen, we compared small data sets generated by CRISPR studies to the results seen in DRIVE (Munoz et al., 2016). Here, we found a consistent and significant overlap of selective dependencies when comparing shRNA and CRISPR screens across 5 models with libraries of comparable content and depth. Note that the shRNA library used in that study (2722 genes, with an average coverage of 20 reagents per gene) is a subset of the BGPD pool used in DRIVE. While CRISPR did uncover more essential genes, every essential gene scored by shRNA was also found by CRISPR, resulting in zero shRNA false-positives. As further orthogonal validation of the DRIVE dataset, we have also intersected selected DRIVE profiles with sensitivity calls from pharmacological treatment with a number of small molecule inhibitors with clinically validated modes of action, namely EGFR (erlotinib), ERBB2 (lapatinib), BRAF (PLX4720) and PIK3CA (BYL719, alpelisib). We observed an association of models sensitive to genetic target modulation (DRIVE) and sensitive to small molecule inhibitor treatment across the respective pairs (FIG. 15). Taken together, the technical performance of deep shRNA screening has been validated by several orthogonal means and provides clear evidence for the robustness of DRIVE.

The molecular characterization of the CCLE allows for the exploration of correlations between gene dependence and genetic, expression or other features of the cell line set. By analyzing feature correlations to ATARIS scores, all responses can be categorized as either self or non-self (synthetic lethal). Two out of our three defined outlier classes (genetic drivers, expression based drivers) are self-associations meaning they are driven by characteristics of the target of the shRNA itself. The synthetic lethal class represents relationships in which a non-self association is most highly correlated with the shRNA knockdown phenotype. These can be further broken down by the specific relationships uncovered by DRIVE: pathway, paralog or collateral lethality. The metabolism class also likely represents synthetic lethal relationships but the molecular features to explain the sensitivity are not yet characterized or are unclear. Two metabolic neighborhoods found in the network analysis (SCAP/SCD/SREBF1 and ASNS/ATF4/EIF2AK4) represent known biological pathways yet no currently available molecular feature explains sensitivity to these nodes. Similarly, dependence on WSB2 did not correlate with definable genetic or expression features yet the DRIVE network correlations with BCL2 family members form the basis of a testable hypothesis. Since our outlier approach is agnostic to the direction of the population skew, tumor suppressors CDKN2A and p53 are both detected. Knockdown of these tumor suppressors results in growth enhancement in cell lines that are wild-type for their respective genes. Some of the most robust DRIVE/DRIVE correlations and anti-correlations were seen with p53 and its pathway components (FIG. 12). Hence, these interactions can help robustly define the biology of the pathway rather than a specific therapeutic target.

Ultimately the goal of this project was to define drug targets for treating cancers within defined patient populations. The combination of the ATARiS gene summary and sensitivity feature prediction pipeline coupled with the outlier approach identified robust and selective cancer dependencies and outlined a biological hypothesis for the phenotype. It allowed for relationships to be discovered beyond those that could be predicted a priori, such as by hotspot mutational analysis. In Project DRIVE, we observed both known and novel mutation dependencies that begin to assign functional significance to the cancer mutational landscape. This dataset also helped to ascribe function (or not) to mutated genes unearthed by cancer genome sequencing efforts that have lacked functional validation, assuming they are present in the screening set. Additionally, DRIVE further refined what we know about some of the most prevalent lesions in cancer. The search for KRAS synthetic lethal interactions has been stymied by false discovery and the data here raise the likelihood that no single synthetic lethal gene may be found across all KRAS mutant tumors. While we affirm that the majority of KRAS mutant cancer cell lines are indeed dependent on continued expression of KRAS, we observed that some of the most commonly used KRAS mutant models are not KRAS dependent, when interrogated as monolayer cell cultures. Hence, studies of therapeutic approaches aiming at ablating KRAS dependence will need to carefully consider these findings.

The DRIVE dataset added significantly to our understanding of cancer dependencies and synthetic lethal relationships, including those for the most prevalent tumor suppressors. The homozygous and heterozygous deletion of p53, homozygous deletion of CDKN2A and homozygous deletion of SMAD4 all result in specific collateral synthetic lethality involving a diverse set of genes (UBC, POLR2A, AURKB, MED11, PRMT5 and VPS4A). For ARID1A/ARID1B, RPL22/RPL22L1 and SMARCA4/SMARCA2, inactivating mutations in the first paralog resulted in dependence on the second. For CDK4, YAP, and ARF4, lack of expression of their paralogs predicted dependence. Given the sub-genome nature of our library and our focus on the top outliers coupled with the expansion of the mammalian genome, this class of paralog relationships is only likely to grow. The identification of synthetic lethal relationships for most major tumor suppressors (FIG. 7D) has created the opportunity for novel therapeutics for these defined patient populations.

We have created for project DRIVE, a public portal of gene dependence profiles (oncologynibr.shinyapps.io/drive/) that affords the cancer community a resource to validate or de-validate experimental findings across nearly 400 cell lines rapidly by interactive query. Furthermore, the DRIVE network associations can be used in combination with emerging large scale datasets (e.g. proteomic, transcriptional) to confirm the discovery of novel complex and pathway components. The functional genomics now provided by project DRIVE complements the molecular characterization by TCGA and ICGC to bring us closer to an understanding of the molecular drivers of cancer.

EMBODIMENTS

1. A method for reducing, e.g., inhibiting, proliferation of cancer cells, e.g., cancer cells of a cancer disclosed in Tables 1 or 2, comprising administering to a subject in need thereof, an inhibitor, e.g., an inhibitor of a target disclosed in Tables 1 or 2, in an amount that is effective to inhibit proliferation of the cancer cells, wherein:
   i) the target is chosen from: MITF, MYB, FL11, ASNS, WRN, SOX10, ALDH18A1, FOXA1, HNF1B, RUNX1, CBFB, TP63, CDK2, VPS4A, TCF4, CEBPA, GATA3, ARID1B, PRKRA, HSPA8, IRF4, SPI1, MTHFD1, ADAR, and NFE2L2; and ii) the cancer is chosen from: hematopoietic cancer (e.g., ALL, AML, MM or DLBCL), skin cancer, lung cancer, colorectal cancer (CRC), stomach cancer, thyroid cancer, melanoma, uveal melanoma, pancreatic cancer, endometrial cancer, Ewing's sarcoma, breast cancer, CNS cancer, kidney cancer, bladder cancer, esophageal cancer, upper aerodigestive cancer, neuroblastoma, ovarian cancer, liver cancer, and colon cancer.

2. A composition comprising an inhibitor, e.g., an inhibitor of any of the targets disclosed in Tables 1 or 2, for use in treating a cancer e.g., a cancer disclosed in Tables 1 or 2, in a subject, wherein:

i) the target is chosen from: MITF, MYB, FL11, ASNS, WRN, SOX10, ALDH18A1, FOXA1, HNF1B, RUNX1, CBFB, TP63, CDK2, VPS4A, TCF4, CEBPA, GATA3, ARID1B, PRKRA, HSPA8, IRF4, SPI1, MTHFD1, ADAR, and NFE2L2; and ii) the cancer is chosen from: hematopoietic cancer (e.g., ALL, AML, MM or DLBCL), skin cancer, lung cancer, colorectal cancer (CRC), stomach cancer, thyroid cancer, melanoma, uveal melanoma, pancreatic cancer, endometrial cancer, Ewing's sarcoma, breast cancer, CNS cancer, kidney cancer, bladder cancer, esophageal cancer, upper aerodigestive cancer, neuroblastoma, ovarian cancer, liver cancer, and colon cancer.

3. The method of embodiment 1 or the composition for use of embodiment 2, wherein the inhibitor is a compound capable of inhibiting the expression, e.g., mRNA or protein expression, of the target.

4. The method of embodiment 1 or the composition for use of embodiment 2, wherein the inhibitor is a compound capable of inhibiting a normal cellular function of the target protein.

5. The method of embodiment 1 or the composition for use of embodiment 2, wherein the inhibitor is selected from the group consisting of: an RNAi agent, a CRISPR, a TALEN, a zinc finger nuclease, a mRNA, an antibody or derivative thereof, a chimeric antigen receptor T cell (CART) or a low molecular weight compound.

6. The method of embodiment 1 or the composition for use of embodiment 2, wherein the inhibitor is a low molecular weight compound, such as a low molecular weight compound disclosed herein.

7. The method of embodiment 1 or the composition for use of embodiment 2, wherein the inhibitor is an RNAi agent, such as a shRNA, or siRNA disclosed herein.

8. The method of embodiment 1 or the composition for use of embodiment 2, wherein the inhibitor is an antibody or derivative thereof, such as an antibody or derivative thereof targeting a HLA-peptide complex comprising a peptide of any of the targets disclosed herein.

9. The method of embodiment 1 or the composition for use of embodiment 2, wherein the method comprises administering to a subject in need thereof, an inhibitor, e.g., an inhibitor of any of the targets disclosed in Tables 1 or 2, in combination with a second therapeutic agent.

10. The method or the composition for use of embodiment 9, wherein the second therapeutic agent is an anti-cancer agent, anti-allergic agent, anti-nausea agent (or anti-emetic), pain reliever, or cytoprotective agent.

11. The method or the composition for use of any one of embodiments 1-10, wherein the target is MITF and the cancer is a skin cancer or uveal cancer.

12. The method or the composition for use of any one of embodiments 1-10, wherein the target is MYB and the cancer is a hematopoietic cancer (e.g., ALL or AML) or colorectal cancer (CRC).

13. The method or the composition for use of any one of embodiments 1-10, wherein the target is FLI1 and the cancer is a hematopoietic cancer (e.g., ALL, AML, MM or DLBCL) or Ewing's sarcoma.

14. The method or the composition for use of any one of embodiments 1-10, wherein the target is ASNS and the cancer is a breast, colorectal, pancreatic or skin cancer.

15. The method or the composition for use of any one of embodiments 1-10, wherein the target is WRN and the cancer displays microsatellite instability (MSI+).

16. The method or the composition for use of any of embodiments 1-15, wherein the cancer is a colorectal (CRC), an endometrial cancer or a stomach cancer.

17. The method or the composition for use of any one of embodiments 1-10, wherein the target is SOX10 and the cancer is a melanoma (e.g., a skin or uveal melanoma) or a central nervous system (CNS) cancer.

18. The method or the composition for use of any one of embodiments 1-10, wherein the target is ALDH18A1 and the cancer is a breast, lung, pancreatic or skin cancer.

19. The method or the composition for use of any one of embodiments 1-10, wherein the target is FOXA1 and the cancer is a breast, or prostate cancer.

20. The method or the composition for use of any one of embodiments 1-10, wherein the target is HNF1 B and the cancer is a kidney or a lung cancer.

21. The method or the composition for use of any one of embodiments 1-10, wherein the target is RUNX1 and the cancer is a hematopoietic cancer (e.g., ALL or AML).

22. The method or the composition for use of any one of embodiments 1-10, wherein the target is CBFB and the cancer is a hematopoietic cancer (e.g., ALL or AML).

23. The method or the composition for use of any one of embodiments 1-10, wherein the target is TP63 and the cancer is a squamous cancer (e.g., bladder, esophageal or upper aerodigestive cancer).

24. The method or the composition for use of any one of embodiments 1-10, wherein the target is CDK2 and the cancer is a breast, endometrial, ovarian or lung cancer.

25. The method or the composition for use of any one of embodiments 1-10, wherein the target is VPS4A and the cancer is a breast, CRC, lung, stomach, pancreatic or upper aerodigestive cancer.

26. The method or the composition for use of any one of embodiments 1-10, wherein the target is TCF4 and the cancer is a hematopoietic cancer or a neuroblastoma.

27. The method or the composition for use of any one of embodiments 1-10, wherein the target is CEBPA and the cancer is a liver cancer or AML.

28. The method or the composition for use of any one of embodiments 1-10, wherein the target is GATA3 and the cancer is a breast cancer or neuroblastoma.

29. The method or the composition for use of any one of embodiments 1-10, wherein the target is ARID1B and the cancer is a cancer as described in Table 1 or 2.

30. The method or the composition for use of any one of embodiments 1-10, wherein the target is PRKRA and the cancer is a cancer as described in Table 1 or 2.

31. The method or the composition for use of any one of embodiments 1-10, wherein the target is HSPA8 and the cancer is a colorectal cancer (CRC) or skin cancer.

32. The method or the composition for use of any one of embodiments 1-10, wherein the target is IRF4 and the cancer is multiple myeloma (MM).

33. The method or the composition for use of any one of embodiments 1-10, wherein the target is SPI1 and the cancer is a hematopoietic cancer, (e.g., AML or ALL).

34. The method or the composition for use of any one of embodiments 1-10, wherein the target is MTHFD1 and the cancer is a breast cancer, colorectal cancer, lung cancer, pancreatic cancer or hematopoietic cancer (e.g., AML or ALL).

35. The method or the composition for use of any one of embodiments 1-10, wherein the target is ADAR and the cancer is a breast cancer, a lung cancer, an esophageal cancer, an upper aerodigestive cancer, a pancreatic cancer or a skin cancer.

36. The method or the composition for use of any one of embodiments 1-10, wherein the target is NFE2L2 and the cancer is a lung cancer, an esophageal cancer or a kidney cancer.

37. A method of evaluating or predicting the responsiveness of a subject having a cancer (e.g., any of the cancers disclosed in Tables 1 or 2), to a therapeutic treatment (e.g., a treatment with an inhibitor, e.g., an inhibitor of any of the targets disclosed in Tables 1 or 2), wherein the method comprises:
  evaluating the presence or absence of a genetic alteration (e.g., a genetic alteration as described in Table 2), e.g., gene amplification, copy number deletion, duplication or presence of microsatellite instability, wherein:
  (i) the presence of the alteration is indicative that the subject is likely to respond to the therapeutic treatment; or
  (ii) the absence of the alteration is indicative that the subject is less likely to respond to the therapeutic treatment;
  for at least one time point, e.g., prior to administration of the therapeutic treatment, thereby evaluating the subject, or predicting the responsiveness of the subject to a therapeutic treatment.

38. The method of embodiment 37, wherein responsive to said evaluation or prediction, the method further comprises selecting the subject for administration in an amount effective to treat the cancer, an inhibitor (e.g., an inhibitor of any of the targets disclosed in Tables 1 or 2) to treat the cancer (e.g., any of the cancers disclosed in Tables 1 or 2) in the subject.

39. The method of embodiment 37, wherein responsive to said evaluation or prediction, the method further comprises administering an inhibitor (e.g., an inhibitor of any of the targets disclosed in Tables 1 or 2) in an amount effective to treat the cancer (e.g., any of the cancers disclosed in Tables 1 or 2) in the subject.

40. A method of evaluating or predicting the responsiveness of a subject having a cancer (e.g., any of the cancers disclosed in Tables 1 or 2), to a therapeutic treatment (e.g., a treatment with an inhibitor, e.g., an inhibitor of any of the targets disclosed in Tables 1 or 2), wherein the method comprises:
  evaluating the expression level (e.g., high or low expression of, e.g., mRNA or protein) or activity, of a target (e.g., a target disclosed in Tables 1 or 2) or a downstream target of a target (e.g., one or more downstream targets of a target disclosed in Table 2), comprising:
  (i) measuring the expression level or activity of the target or a target-associated molecule (e.g., a downstream effector disclosed in Table 2), in the subject for at least one time point (e.g., prior to administration of the therapeutic treatment), e.g., using a method described herein, and
  (ii) (optionally) comparing the expression level or activity of the target or a target-associated molecule (e.g., a downstream effector disclosed in Table 2) ("sample value") at least one time point with a reference level or activity ("reference value"), wherein:
  a) a higher sample value compared to the reference value is indicative that the subject is likely to respond to the therapeutic treatment; and
  b) a sample value that is the same or lower compared to the reference value is indicative that the subject is less likely to respond to the therapeutic treatment;
  thereby evaluating the subject, or predicting the responsiveness of the subject to a therapeutic treatment.

41. The method of embodiment 40, wherein, the reference value is the expression level or activity of a target (e.g., a target disclosed in Tables 1 or 2) or a target-associated molecule (e.g., a downstream effector disclosed in Table 2), of a sample taken from a healthy, e.g., normal, subject.

42. The method of embodiment 40, wherein responsive to said evaluation or prediction, the method further comprises selecting the subject for administration in an amount effective to treat the cancer, an inhibitor (e.g., an inhibitor of any of the targets disclosed in Tables 1 or 2) to treat the cancer (e.g., any of the cancers disclosed in Tables 1 or 2) in the subject.

43. The method of embodiment 40, wherein responsive to said evaluation or prediction, the method further comprises administering an inhibitor (e.g., an inhibitor of any of the targets disclosed in Tables 1 or 2) in an amount effective to treat the cancer (e.g., any of the cancers disclosed in Tables 1 or 2) in the subject.

44. The method of any of embodiments 37-43, wherein the subject has a skin cancer or a uveal cancer, which cancer has or is identified as having high MITF expression, and the therapeutic treatment is a MITF inhibitor.

45. The method of any of embodiments 37-43, wherein the subject has a hematopoietic cancer (e.g., ALL or AML) or colorectal cancer (CRC), which cancer has or is identified as having high MYB expression, and the therapeutic treatment is a MYB inhibitor.

46. The method of any of embodiments 37-43, wherein the subject has a hematopoietic cancer (e.g., ALL, AML, MM or DLBCL) or Ewing's sarcoma, which cancer has or is identified as having high FLI1 expression, and the therapeutic treatment is a FL11 inhibitor.

47. The method of any of embodiments 37-43, wherein the subject has a breast, colorectal, pancreatic or skin cancer, which cancer has or is identified as having high ASNS expression, and the therapeutic treatment is an ASNS inhibitor.

48. The method of any of embodiments 37-43, wherein the subject has a breast, colorectal, pancreatic or skin cancer, which cancer has or is identified as having low ASNS expression, and the therapeutic treatment is an ASNS agonist.

49. The method of any of embodiments 37-43, wherein the subject has a colorectal (CRC), endometrial or stomach cancer, which cancer has or is identified as having a microsatellite instability (MSI+), and the therapeutic treatment is a WRN inhibitor.

50. The method of any of embodiments 37-43, wherein the subject has a melanoma (e.g., a skin or uveal melanoma) or a central nervous system (CNS) cancer, which cancer has or is identified as having high SOX10 expression, and the therapeutic treatment is a SOX10 inhibitor.

51. The method of any of embodiments 37-43, wherein the subject has a breast, lung, pancreatic or skin cancer, which cancer has or is identified as having high ALDH18A1 expression, and the therapeutic treatment is an ALDH18A1 inhibitor.

52. The method of any of embodiments 37-43, wherein the subject has a breast, lung, pancreatic or skin cancer, which cancer has or is identified as having low ALDH18A1 expression, and the therapeutic treatment is an ALDH18A1 agonist.

53. The method of any of embodiments 37-43, wherein the subject has a breast, or prostate cancer, which cancer has or is identified as having high FOXA1 expression, and the therapeutic treatment is a FOXA1 inhibitor.

54. The method of any of embodiments 37-43, wherein the subject has a kidney or a lung cancer, which cancer has or is identified as having high HNF1B expression, and the therapeutic treatment is a HNF1B inhibitor.

55. The method of any of embodiments 37-43, wherein the subject has a hematopoietic cancer (e.g., ALL or AML), which cancer has or is identified as having high RUNX1 expression, and the therapeutic treatment is a RUNX1 inhibitor.

56. The method of any of embodiments 37-43, wherein the subject has a hematopoietic cancer (e.g., ALL or AML), which cancer has or is identified as having high RUNX1 or IKZF1 expression, and the therapeutic treatment is a CBFB inhibitor.

57. The method of any of embodiments 37-43, wherein the subject has a squamous cancer (e.g., bladder, esophageal or upper aerodigestive cancer), which cancer has or is identified as having high TP63 expression, and the therapeutic treatment is a TP63 inhibitor.

58. The method of any of embodiments 37-43, wherein the subject has a breast, endometrial, ovarian or lung cancer, which cancer has or is identified as having high CCNE1 expression or gene amplification, and the therapeutic treatment is a CDK2 inhibitor.

59. The method of any of embodiments 37-43, wherein the subject has a breast, CRC, lung, stomach, pancreatic or upper aerodigestive cancer, which cancer has or is identified as having a copy number deletion of VPS4B, and the therapeutic treatment is a VPS4A inhibitor.

60. The method of any of embodiments 37-43, wherein the subject has a hematopoietic cancer or a neuroblastoma, which cancer has or is identified as having high TCF4 expression, and the therapeutic treatment is a TCF4 inhibitor.

61. The method of any of embodiments 37-43, wherein the subject has a liver cancer or AML, which cancer has or is identified as having high CEBPA expression, and the therapeutic treatment is a CEBPA inhibitor.

62. The method of any of embodiments 37-43, wherein the subject has a breast cancer or neuroblastoma, which cancer has or is identified as having high GATA3 expression, and the therapeutic treatment is a GATA3 inhibitor.

63. The method of any of embodiments 37-43, wherein the subject has a cancer, which has or is identified as having an ARID1A mutation or low expression, and the inhibitor is an ARID1B inhibitor.

64. The method of any of embodiments 37-43, wherein the subject has a cancer, which has or is identified as having high EIF2AK2 expression, and the therapeutic treatment is a PRKRA inhibitor.

65. The method of any of embodiments 37-43, wherein the subject has a colorectal cancer (CRC) or skin cancer, which cancer has or is identified as having low HSP1A1 expression, and the therapeutic treatment is an HSPA8 inhibitor.

66. The method of any of embodiments 37-43, wherein the subject has multiple myeloma (MM), which cancer has or is identified as having high IRF4 expression, and the therapeutic treatment is an IRF4 inhibitor.

67. The method of any of embodiments 37-43, wherein the subject has a hematopoietic cancer (e.g., AML or ALL), which cancer has or is identified as having high SPI1 expression and the therapeutic treatment is an SPI1 inhibitor.

68. The method of any of embodiments 37-43, wherein the subject has a breast cancer, colorectal cancer, lung cancer, pancreatic cancer or hematopoietic cancer (e.g., AML or ALL), which cancer has or is identified as having high MTHFD1 expression, and the therapeutic treatment is a MTHFD1 inhibitor.

69. The method of any of embodiments 37-43, wherein the subject has a breast cancer, colorectal cancer, lung cancer, pancreatic cancer or hematopoietic cancer (e.g., AML or ALL), which cancer has or is identified as having low MTHFD1 expression, and the therapeutic treatment is a MTHFD1 agonist.

70. The method of any of embodiments 37-43, wherein the subject has a breast cancer, a lung cancer, an esophageal cancer, an upper aerodigestive cancer, a pancreatic cancer or a skin cancer, which cancer has or is identified as being positive for interferon stimulated gene (ISG) signature, and the therapeutic treatment is an ADAR inhibitor.

71. The method of any of embodiments 37-43, wherein the subject has a lung cancer, an esophageal cancer or a kidney cancer, which cancer has or is identified as having a KEAP1 mutation, an NFE2L2 mutation, high SQSTM1 expression, or positive for an NFE2L2 gene signature, and the therapeutic treatment is an NFE2L2 inhibitor.

72. A method of evaluating the effectiveness of a therapeutic treatment (e.g., a treatment with an inhibitor, e.g., an inhibitor of any of the targets disclosed in Tables 1 or 2), in a subject having a cancer (e.g., any of the cancers disclosed in Tables 1 or 2), comprising measuring the level (e.g., mRNA or protein) or activity (e.g., enzyme activity) of a target (e.g., a target of the inhibitor administered), in the subject (e.g., in a sample from the subject) for at least two time points, e.g., a first time point (e.g., prior to administration of the therapeutic treatment) and a second time point (e.g., after administration of the therapeutic treatment), e.g., using a method described herein, wherein:

(i) a decrease in the expression or activity of the target or a target-associated molecule (e.g., a downstream effector disclosed in Table 2) between the first time point and the second time point is indicative that the subject is responding to the therapeutic treatment; and (ii) an increase, or no change in the expression or activity of the target or a target-associated molecule (e.g., a downstream effector disclosed in Table 2) between the first time point and the second time point is indicative that the subject is not responding to the therapeutic treatment thereby evaluating the effectiveness of the therapeutic treatment in the subject.

73. The method of embodiment 72, wherein responsive to said evaluation, the method further comprises administering an inhibitor, e.g., the same inhibitor, at a higher dose, e.g., at a dose at least 1-fold, 2-fold, 3-fold, 4-fold, 5-fold, or 10-fold higher, compared to the first administration of the inhibitor to treat the disease.

74. The method of embodiment 72, wherein responsive to said evaluation, the method further comprising administering a second therapy, e.g., a therapy disclosed herein, to the subject, thereby treating the cancer.

75. A method of monitoring cancer relapse in a subject having a cancer (e.g., any of the cancers disclosed in Tables 1 or 2), who has responded or partially responded to a therapeutic treatment (e.g., a treatment with an inhibitor, e.g., an inhibitor of any of the targets disclosed in Tables 1 or 2), comprising measuring the level (e.g., mRNA or protein) or activity (e.g., enzyme activity) of a target (e.g., a target of the inhibitor administered), in the subject (e.g., in a sample from the subject) for at least two time points, e.g., a first time point (e.g., prior to administration of the therapeutic treatment) and a second time point (e.g., after administration of the therapeutic treatment), e.g., using a method described herein, wherein:
  (i) an increase in the expression or activity of the target or a target-associated molecule (e.g., a downstream effector disclosed in Table 2) between the first time point and the second time point is indicative that the cancer is relapsing; and
  (ii) the absence of an increase, e.g., a decrease, in the expression or activity of the target or a target-associated molecule (e.g., a downstream effector disclosed in Table 2) between the first time point and the second time point is indicative that the cancer is not relapsing.

76. The method of embodiment 75, wherein:
  (i) an increase in the expression or activity of the target or a target-associated molecule (e.g., a downstream effector disclosed in Table 2) at a subsequent (e.g., second, third, fourth, fifth, sixth, or seventh or later) time point relative to a prior (e.g., first, second, third, fourth, fifth, or sixth or later) time point, among the at least two time points, indicates that the cancer is relapsing; and
  (ii) the absence of an increase in the expression or activity of the target or a target-associated molecule (e.g., a downstream effector disclosed in Table 2) at a subsequent (e.g., second, third, fourth, fifth, sixth, or seventh or later) time point relative to a prior (e.g., first, second, third, fourth, fifth, or sixth or later) time point, among the at least two time points, indicates that the cancer is not relapsing.

77. A method of treating a subject having a cancer, e.g., a cancer disclosed in Tables 1 or 2, comprising in response to a determination that the subject, after having responded or partially responded to a first therapeutic treatment, (e.g., a treatment with an inhibitor, e.g., an inhibitor of any of the targets disclosed in Tables 1 or 2), has experienced, or has been identified as having experienced an increase in expression or activity of the target or a target-associated molecule (e.g., a downstream effector disclosed in Table 2), administering a second therapy, e.g., a second therapy disclosed herein, thereby treating the cancer.

78. A kit for predicting the sensitivity of a subject having a cancer associated with reduced, e.g., defective, activity of any of the targets disclosed in Tables 1 or 2, wherein the reduced activity of the target is due to gene inactivation mechanisms (e.g. epigenetic mechanisms), for treatment with an inhibitor, e.g., an inhibitor for the target, comprising:
  i) reagents capable of:
    a) detecting human cancer cells harboring genetic abnormalities, e.g., one or more of mutations, deletions, insertions, translocations, or microsatellite instability, or other gene inactivation mechanisms (e.g. epigenetic mechanisms); or
    b) detecting expression level (e.g., mRNA or protein), or activity (e.g., enzyme activity), of a target (e.g., a target of the inhibitor administered) or a target-associated molecule (e.g., a downstream effector disclosed in Table 2) in human cancer cells from a subject; and
  ii) instructions for how to use said kit.

The invention claimed is:

1. A method of treating microsatellite instable (MSI+) cancer in a subject in need thereof, comprising administering to the subject a therapeutically effective amount of a WRN inhibitor wherein the cancer is selected from a group consisting of hematopoietic cancer, skin cancer, lung cancer, colorectal cancer, stomach cancer, thyroid cancer, melanoma, uveal melanoma, pancreatic cancer, endometrial cancer, Ewing's sarcoma, breast cancer, CNS cancer, kidney cancer, bladder cancer, esophageal cancer, upper aerodigestive cancer, neuroblastoma, ovarian cancer, liver cancer, and colon cancer.

2. The method of claim 1, wherein the WRN inhibitor is selected from the group consisting of an RNAi agent, a CRISPR, a TALEN, a zinc finger nuclease, a mRNA, an antibody or derivative thereof, a chimeric antigen receptor T cell (CART), and a low molecular weight compound.

3. The method of claim 1, further comprising administering a second therapeutic agent.

4. The method of claim 3, wherein the second therapeutic agent is an anti-cancer agent, anti-allergic agent, anti-nausea agent, anti-emetic agent, pain reliever, or cytoprotective agent.

5. The method of claim 1, wherein the cancer is microsatellite instable colorectal cancer, microsatellite instable endometrial cancer or microsatellite instable stomach cancer.

6. The method of claim 2, wherein the low molecular weight compound is 1-[4-Fluoro-3-(trifluoromethyl)phenyl]-3-(5-pyridin-4-yl-1,3,4-thiadiazol-2-yl)urea.

* * * * *